United States Patent
Eijkelkamp et al.

(10) Patent No.: US 12,365,713 B2
(45) Date of Patent: Jul. 22, 2025

(54) FUSION PROTEIN COMPRISING IL13

(71) Applicant: Synerkine Pharma B.V., Naarden (NL)

(72) Inventors: Niels Eijkelkamp, Utrecht (NL);
Cornelis Erik Hack, Diemen (NL);
Judith Prado Sanchez, Utrecht (NL);
Jelena Popov-Čeleketić, Utrecht (NL);
Sabine Versteeg, Tiel (NL)

(73) Assignee: Synerkine Pharma B.V., Naarden (NL)

( * ) Notice: Subject to any disclaimer, the term of this patent is extended or adjusted under 35 U.S.C. 154(b) by 437 days.

(21) Appl. No.: 17/693,956

(22) Filed: Mar. 14, 2022

(65) Prior Publication Data

US 2022/0220179 A1    Jul. 14, 2022

Related U.S. Application Data

(60) Division of application No. 17/158,785, filed on Jan. 26, 2021, now Pat. No. 11,312,757, which is a continuation of application No. PCT/EP2020/060910, filed on Apr. 17, 2020.

(30) Foreign Application Priority Data

Apr. 19, 2019    (NL) ..................................... 2022982
Apr. 19, 2019    (NL) ..................................... 2022984

(51) Int. Cl.
| | | |
|---|---|---|
| *C07K 14/54* | (2006.01) | |
| *A61K 38/20* | (2006.01) | |
| *A61P 25/02* | (2006.01) | |
| *A61P 25/04* | (2006.01) | |
| *A61K 38/00* | (2006.01) | |

(52) U.S. Cl.
CPC ...... *C07K 14/5437* (2013.01); *A61K 38/2026* (2013.01); *A61P 25/02* (2018.01); *A61P 25/04* (2018.01); *C07K 14/5406* (2013.01); *C07K 14/5428* (2013.01); *A61K 38/00* (2013.01); *C07K 2319/00* (2013.01)

(58) Field of Classification Search
CPC ................................................. C07K 14/5437
See application file for complete search history.

(56) References Cited

U.S. PATENT DOCUMENTS

| | | |
|---|---|---|
| 4,399,216 A | 8/1983 | Axel et al. |
| 4,634,665 A | 1/1987 | Axel et al. |
| 5,179,017 A | 1/1993 | Axel et al. |
| 5,567,611 A | 10/1996 | Ralph et al. |
| 5,601,815 A | 2/1997 | Powrie et al. |
| 5,951,973 A | 9/1999 | Lee et al. |
| 5,986,059 A | 11/1999 | Shanafelt et al. |
| 6,428,985 B1 | 8/2002 | Bromberg et al. |
| 6,630,576 B2 | 10/2003 | Debinski |
| 7,261,882 B2 | 8/2007 | Watkins |
| 7,749,490 B2 | 7/2010 | Sommer et al. |
| 8,247,385 B2 | 8/2012 | Yoo |
| 8,349,332 B2 | 1/2013 | Chang et al. |
| 8,404,814 B2 | 3/2013 | Neri et al. |
| 9,738,696 B2 | 8/2017 | Garcia et al. |
| 10,851,143 B2 | 12/2020 | Van Roon et al. |
| 10,946,043 B2 | 3/2021 | Woodell-May et al. |
| 10,981,964 B2 | 4/2021 | Van Roon et al. |
| 11,002,735 B2 | 5/2021 | Cohen et al. |
| 11,110,122 B2 | 9/2021 | Bar-Sagi et al. |
| 11,312,757 B2 | 4/2022 | Eijkelkamp et al. |
| 11,357,826 B2 | 6/2022 | Xu et al. |
| 11,401,324 B2 | 8/2022 | Wong |
| 11,873,349 B1 | 1/2024 | Kastelein et al. |
| 2004/0072299 A1 | 4/2004 | Gillies et al. |
| 2005/0053579 A1 | 3/2005 | Galipeau et al. |
| 2005/0191730 A1 | 9/2005 | Karow et al. |
| 2006/0246032 A1 | 11/2006 | Strom et al. |
| 2010/0021421 A1 | 1/2010 | Galipeau et al. |
| 2010/0028296 A1 | 2/2010 | Chavez et al. |
| 2011/0124552 A1 | 5/2011 | Galipeau et al. |
| 2011/0150828 A1 | 6/2011 | Galipeau et al. |

(Continued)

FOREIGN PATENT DOCUMENTS

| | | |
|---|---|---|
| CN | 1074243 A | 7/1993 |
| CN | 1382158 A | 11/2002 |

(Continued)

OTHER PUBLICATIONS

Bork. Powers and Pitfalls in Sequence Analysis: The 70% Hurdle. Genome Research, 2000, 10:398-400 (Year: 2000).*
Greenspan et al. 1999. Defining epitopes: It's not as easy as it seems; Nature Biotechnology, 17:936-937 (Year: 1999).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine ResidueJ. Cell Biol. 111:2129-2138, 1990 (Year: 1990).*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*

(Continued)

*Primary Examiner* — Prema M Mertz
(74) *Attorney, Agent, or Firm* — Wilson Sonsini Goodrich & Rosati

(57) ABSTRACT

The invention is concerned with a fusion protein comprising interleukin 13 and a regulatory cytokine, for example, an interleukin chosen from interleukin 4, interleukin 10, interleukin 27, interleukin 33, transforming growth factor beta 1, transforming growth factor beta 2, and interleukin 13, a nucleic acid molecule encoding such fusion protein, a vector comprising such nucleic acid molecule, and a host cell comprising such nucleic acid molecule or such vector. The invention further pertains to a method for producing such fusion protein. The fusion protein or a gene therapy vector encoding the fusion protein may be used in the prevention or treatment of a condition characterized by pathological pain, chronic pain, neuro-inflammation and/or or neurodegeneration.

25 Claims, 15 Drawing Sheets

Figure 1:
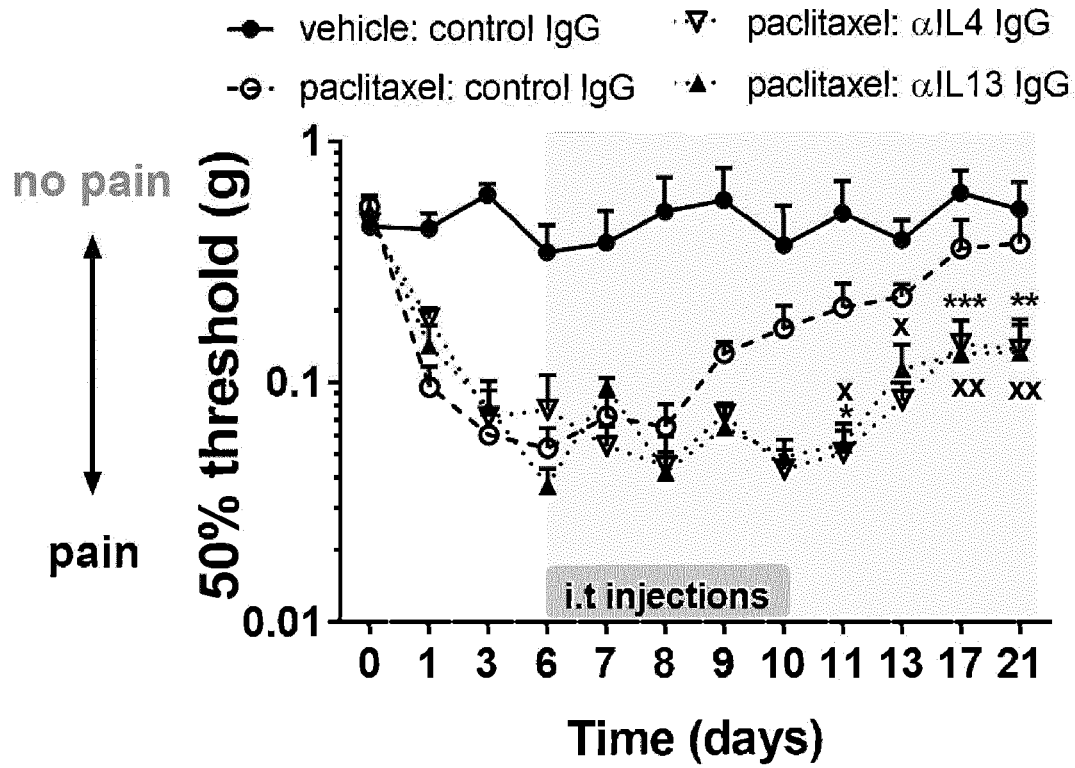

Specification includes a Sequence Listing.

(56) References Cited

U.S. PATENT DOCUMENTS

| | | |
|---|---|---|
| 2012/0164101 A1 | 6/2012 | Galipeau et al. |
| 2013/0096058 A1 | 4/2013 | Baca et al. |
| 2013/0316404 A1 | 11/2013 | Roers et al. |
| 2014/0314712 A1 | 10/2014 | Van Roon et al. |
| 2014/0369956 A1 | 12/2014 | Galipeau et al. |
| 2016/0046687 A1 | 2/2016 | Galipeau et al. |
| 2017/0073387 A1 | 3/2017 | Galipeau et al. |
| 2018/0094037 A1 | 4/2018 | Van Roon et al. |
| 2018/0155439 A1 | 6/2018 | Galipeau et al. |
| 2020/0095301 A1 | 3/2020 | Garcia et al. |
| 2020/0147178 A1 | 5/2020 | Van Roon et al. |
| 2020/0158716 A1 | 5/2020 | Shalek et al. |
| 2020/0283488 A1 | 9/2020 | Mumm |
| 2020/0377568 A1 | 12/2020 | Vogelaar et al. |
| 2021/0024631 A1 | 1/2021 | Kley et al. |
| 2021/0205427 A1 | 7/2021 | Grouard-Vogel et al. |
| 2021/0214410 A1 | 7/2021 | Garcia et al. |
| 2021/0261639 A1 | 8/2021 | Van Roon et al. |
| 2022/0106373 A1 | 4/2022 | Mumm |
| 2022/0118089 A1 | 4/2022 | Hubbell et al. |
| 2022/0143145 A1 | 5/2022 | Eijkelkamp et al. |
| 2022/0372096 A1 | 11/2022 | Merchant et al. |
| 2022/0378877 A1 | 12/2022 | Petri, Jr. et al. |
| 2022/0380428 A1 | 12/2022 | Mumm |
| 2022/0403026 A1 | 12/2022 | Butte et al. |
| 2023/0203117 A1 | 6/2023 | Gorby et al. |
| 2023/0210953 A1 | 7/2023 | Mumm |
| 2023/0242615 A1 | 8/2023 | Li et al. |
| 2023/0272088 A1 | 8/2023 | Kastelein et al. |
| 2023/0272090 A1 | 8/2023 | Kastelein et al. |
| 2023/0272091 A1 | 8/2023 | Kastelein et al. |
| 2023/0272094 A1 | 8/2023 | Kastelein et al. |
| 2023/0272095 A1 | 8/2023 | Kastelein et al. |
| 2023/0279125 A1 | 9/2023 | Kastelein et al. |
| 2023/0279126 A1 | 9/2023 | Kastelein et al. |
| 2023/0279127 A1 | 9/2023 | Kastelein et al. |
| 2023/0279128 A1 | 9/2023 | Kastelein et al. |
| 2023/0287075 A1 | 9/2023 | Mumm |
| 2023/0295314 A1 | 9/2023 | Kastelein et al. |
| 2023/0295315 A1 | 9/2023 | Kastelein et al. |
| 2023/0322936 A1 | 10/2023 | Kastelein et al. |
| 2023/0340052 A1 | 10/2023 | Mumm |
| 2023/0357414 A1 | 11/2023 | Vivona et al. |
| 2023/0365696 A1 | 11/2023 | Kastelein et al. |
| 2023/0391891 A1 | 12/2023 | Kastelein et al. |
| 2024/0026014 A1 | 1/2024 | Kastelein et al. |
| 2024/0052006 A1 | 2/2024 | Hubbell et al. |
| 2024/0076331 A1 | 3/2024 | Lu |
| 2024/0166754 A1 | 5/2024 | Kastelein et al. |
| 2024/0181009 A1 | 6/2024 | Gonzalez et al. |
| 2024/0197832 A1 | 6/2024 | Hu et al. |

FOREIGN PATENT DOCUMENTS

| | | |
|---|---|---|
| CN | 1922204 A | 2/2007 |
| CN | 101557817 A | 10/2009 |
| CN | 104136457 A | 11/2014 |
| CN | 106139125 A | 11/2016 |
| CN | 107683289 A | 2/2018 |
| CN | 108129574 A | 6/2018 |
| EP | 0923387 A2 | 6/1999 |
| EP | 1731531 A2 | 12/2006 |
| EP | 2776460 B1 | 5/2018 |
| JP | 6284482 B2 | 2/2018 |
| JP | 6527925 B2 | 6/2019 |
| WO | WO-9319770 A1 | 10/1993 |
| WO | WO-9404680 A1 | 3/1994 |
| WO | WO-9503411 A1 | 2/1995 |
| WO | WO-9749434 A2 | 12/1997 |
| WO | WO-9833516 A1 | 8/1998 |
| WO | WO-0027881 A3 | 8/2000 |
| WO | WO-0110912 A1 | 2/2001 |
| WO | WO-2006079169 A1 | 8/2006 |
| WO | WO-2010040105 A2 | 4/2010 |
| WO | WO-2011108937 A1 | 9/2011 |
| WO | WO-2013070076 A1 | 5/2013 |
| WO | WO-2014074186 A2 | 5/2014 |
| WO | WO-2018112266 A1 | 6/2018 |
| WO | WO-2018182935 A1 | 10/2018 |
| WO | WO-2018202876 A1 | 11/2018 |
| WO | WO-2019232523 A1 | 12/2019 |
| WO | WO-2020181235 A1 | 9/2020 |
| WO | WO-2020212602 A1 | 10/2020 |
| WO | WO-2022025643 A1 | 2/2022 |
| WO | WO-2022223001 A1 | 10/2022 |
| WO | WO-2023030489 A1 | 3/2023 |
| WO | WO-2023075623 A1 | 5/2023 |
| WO | WO-2023144393 A1 | 8/2023 |
| WO | WO-2023172868 A1 | 9/2023 |
| WO | WO-2023183816 A2 | 9/2023 |
| WO | WO-2023230163 A1 | 11/2023 |
| WO | WO-2024094755 A1 | 5/2024 |

OTHER PUBLICATIONS

Castillo-Guzman et al.: Complex regional pain syndrome (CRPS), a review. Medicina Universitaria. 17(67):114-121 (2015).
EP20722497.3 European Communication dated Apr. 8, 2024.
U.S. Appl. No. 17/192,183 Office Action dated Nov. 7, 2023.
Abrahamsen, B. et al., "The cell and molecular basis of mechanical, cold, and inflammatory pain," Science, 2008;321(5889):702-5.
Anders, S. et al., "HTSeq—a Python framework to work with high-throughput sequencing data," Bioinformatics, 2015;31(2):166-9.
Sasaguri, Tomoko, et al. "Interleukin-27 controls basal pain threshold in physiological and pathological conditions." Scientific reports 8.1 (2018): 1-13.
Sasaki, K. et al. "IL-4 inhibits VLA-4 expression on Tc1 cells resulting in poor tumor infiltration and reduced therapy benefit," European Journal of Immunology, 2008, vol. 38, No. 10, pp. 2865-2873.
Atkins, M. B. et al., "Phase I evaluation of thrice-daily intravenous bolus interleukin-4 in patients with refractory malignancy," J Clin Oncol, 1992, vol. 10, pp. 1802-1809.
Backonja, M.M. et al., "Altered cytokine levels in the blood and cerebrospinal fluid of chronic pain patients," J Neuroimmunol., 2008;195(1-2):157-163.
Bottros, MM, et al., "Current perspectives on intrathecal drug delivery," J Pain Res, 2014;7:615-26.
Breivik, H, et al., "Survey of chronic pain in Europe: prevalence, impact on daily life, and treatment," Eur J Pain 2006;10:287-333.
Breivik, H, et al., "The individual and societal burden of chronic pain in Europe: the case for strategic prioritization and action to improve knowledge and availability of appropriate care," BMC Public Health, 2013;13:1229.
Busch-Dienstfertig M., et al., "IL-4, JAK-STAT signaling, and pain," JAKSTAT, 2013;2(4):e27638.
Cavaillon, J., "PRO-versus Anti-Inflammatory Cytokines: Myth or Reality", Cellular and Molecular Biology, 2001, vol. 47, No. 4, pp. 1-8.
Chaplan, S.R. et al. "Quantitative assessment of tactile allodynia in the rat paw," J Neurosci Methods, 1994;53:55-63.
Chen G, et al., "Microglia in Pain: Detrimental and Protective Roles in Pathogenesis and Resolution of Pain," Neuron 2018;100:1292-311.
Chen H, et al., "IL-10 Promotes Neurite Outgrowth and Synapse Formation in Cultured Cortical Neurons after the Oxygen-Glucose Deprivation via JAK1/STAT3 Pathway," Sci Rep. 2016;6:30459.
Chomarat, P. et al., "Differential effects of interleukins 10 and 4 on the production of interleukin-6 by blood and synovium monocytes in rheumatoid arthritis," Arthritis Rheum, 1995, 38:1046-54.
Cunningham, F. et al., "Ensembl 2015." Nucleic acids research, 2015;43:D662-9.
Dahlhammer J, et al., "Prevalence of Chronic Pain and High-Impact Chronic Pain Among Adults—United States, 206," Morbidity and Mortality Weekly Report (MMWR), 2018;67:1001-6.
De Jong, et al., "Pan-DR-Binding Hsp60 Self Epitopes Induce and Interleukin-10-Mediated Immune Response in Rheumatoid Arthritis", Arthritis & Rheumatism, 2009, vol. 60, No. 7, pp. 1966-1976.

(56) References Cited

OTHER PUBLICATIONS

De Oliveira, et al. "Cytokines and Pain," Rev Bras Anestesiol, 2011;61(2):255-265.
Ding, et al., "A Single Amino Acid Determines the Immunostimulatory Activity of Interleukin 10", J. Exp. Med., 2000, vol. 191, No. 2, pp. 213-223.
Durocher, et al., "High-level an high-throughput recombinant protein production by transient transfection of suspension-growing human 293-EBNA1 cells", Nucleic Acids Research, 2002, vol. 30, No. 2e9, pp. 1-9.
Echeverry, S. et al. "Transforming growth factor-β1 impairs neuropathic pain through pleiotropic effects." Molecular pain, 2009;1744-8069.
Eijkelkamp, N. et al., "IL4-10 Fusion Protein is a Novel Drug to Treat Persistent Inflammatory Pain" The Journal of Neuroscience, 2016;36(28):7353-7363.
Eijkelkamp, N. et al., "A role for Piezo2 in EPAC1-dependent mechanical allodynia," Nat Commun, 2013;4(1682).
Eijkelkamp, N. et al., "GRK2: a novel cell-specific regulator of severity and duration of inflammatory pain," J Neurosci., 2010;30(6):2138-49.
Feldmann, M. et al., "Anti-TNF alpha therapy of rheumatoid arthritis: what have we learned?" Annu Rev Immunol., 2001;19:163-196.
Gillies, S. et al., "Bi-functional cytokine fusion proteins for gene therapy and antibody-targeted treatment of cancer," Cancer Immunol Immunother, 2002, vol. 51, pp. 449-460.
Grace, P.M. et al., "Pathological pain and the neuroimmune interface," Nat Rev Immunol, 2014;14(4):217-231.
Guichelaar, et al., "Cartilage proteoglycan-specific T cells as vectors of immunomodulatory biologicals in chronic proteoglycan-induced arthritis", Molecular Immunology, 2008;45:3526-3535.
Hagenacker, T. et al., "Sensitization of voltage activated calcium channel currents for capsaicin in nociceptive neurons by tumor-necrosis-factor-alpha," Brain Res Bull, 2010;81(1):157-163.
Shanafelt, A.B. et al. "An immune cell-selective interleukin 4 agonist." Proceedings of the National Academy of Sciences, 1998;95(16): 9454-9458.
Hao, S. et al., "HSV-mediated expression of interleukin-4 in dorsal root ganglion neurons reduces neuropathic pain," Mol Pain, 2006;2:6.
Hargreaves et al., "A new and sensitive method for measuring thermal nociception incutaneous hyperalgesia," Pain, 1988;32(1):77-88.
Hartgring, S.A.Y., "Role of IL-7 and TSLP in immunopathology of (rheumatoid) arthritis", University Medical Center Utrecht, 2009, pp. 1-185.
Hemmati, S. et al., "Polypharmacological Cell-Penetrating Peptides from Venomous Marine Animals Based on Immunomodulating, Antimicrobial, and Anticancer Properties," Mar Drugs. 2022;20(12):763.
Shen, K.F, et al., "Interleukin-10 down-regulates voltage gated sodium channels in rat dorsal root ganglion neurons," Exp Neurol, 2013;247:466-475.
Henikoff, et al., "Amino acid substitution matrices from protein blocks", PNAS, 1992, vol. 89, pp. 10915-10919.
Hernangomez, M. et al., "CD200R1 agonist attenuates glial activation, inflammatory reactions, and hypersensitivity immediately after its intrathecal application in a rat neuropathic pain model," J Neuroinflammation, 2016;13:43.
Shi, et al., "Interleukin-4 protects from chemotherapy-induced peripheral neuropathy in mice modal via the stimulation of IL-4/STAT6 signaling" Acta Cir Bras, 2018;33(6): 491-498.
Huhn, R. D. et al., "Pharmacodynamics of subcutaneous recombinant human interleukin-10 in healthy volunteers," Clin Pharmacol Ther, 1997, vol. 62, No. 2, pp. 171-180.
Hwang, S.Y. et al., "IL-17 induces production of IL-6 and IL-8 in rheumatoid arthritis synovial fibroblasts via VF-kB-and PI3-kinase/Akt-dependent pathways" Arthritis Research & Therapy, 2004, vol. 6, No. 2, pp. R120-R128.
International Search Report, PCT/EP2020/060910, issued Jun. 30, 2020.
International Search Report, PCT/EP2020/060914, issued Jul. 10, 2020.
International Search Report, PCT/NL2012/050790, issued Mar. 8, 2013.
Jansen, et al., "Protective Abilities of Interleukin-10 in Case of Blood-Induced Joint Damage" University Medical Center Utrecht, 2008, pp. S27.
Jansen, et al., "Interleukin-10 Projects Against Blood-Induced Joint Damage", Rheumatology & Clinical Immunology, University Medical Center Utrecht, 2007, pp. C116.
Jansen, et al., "Protective Abilities of Interleukin-10 in Blood-Induced Cartilage Damage," University Medical Center Utrecht, 2006, pp. S96.
Jansen, N.W.D. et al., "Interleukin-10 protects against blood-induced joint damage", British Journal of Haematology, 2008, vol. 142, pp. 953-961.
Ji, R.R. et al., "Pain regulation by non-neuronal cells and inflammation," Science, 2016;354(6312):572-577.
Ji, R.R. et al., "Glia and pain: is chronic pain a gliopathy?," Pain, 2013; 154(Suppl 1):S10-28.
Johannes, C.B. et al., "The prevalence of chronic pain in United States adults: results of an Internet-based survey," J Pain, 2010;11:1230-9.
Joosten, L. et al., "Role of interleukin-4 and interleukin-10 in murine collagen-induced arthritis. Protective effect of interleukin-4 and interleukin-10 treatment on cartilage destruction," Arthritis Rheum, 1997, vol. 40, No. 2, pp. 249-260.
Junttila, et al., "Redirecting cell-type specific cytokine responses with engineered interleukin-4 superkines" Nat Chem Bio., 2012;8(12): 990-998.
Khoonsari, P.E. et al., "The human CSF pain proteome," J Proteomics, 2019;190:67-76.
Kiguchi, et al., "Peripheral administration of interleukin-13 reverses inflammatory macrophage and tactile allodynia in mice with partial sciatic nerve ligation" Journal of Pharmacology Sciences, 2017;133:S53-S56.
Kim, H. et al., "The current state of the osteoarthritis drug development pipeline: a comprehensive narrative review of the present challenges and future opportunities," Ther Adv Musculoskelet Dis., 2022;14:1-28.
Kraus, J. et al., "Regulation of mu-opioid receptor gene transcription by interleukin-4 and influence of an allelic variation within a STAT6 transcription factor binding site," J Biol Chem, 2001;276(47):43901-43908.
Kreitman, et al., "Site-Specific Conjugation to Interleukin 4 Containing Mutated Cysteine Residues Produces Inerleukin 4-Toxin Conjugates with Improved Binding an Activity" Biochemistry, 1994;33:11637-11644.
Krukowski, K et al., "CD8+ T Cells and Endogenous IL-10 Are Required for Resolution of Chemotherapy-Induced Neuropathic Pain," J Neurosci, 2016;36(43):11074-11083.
Kruse, et al., "Site-directed mutagenesis reveals the importance of disulfide bridges and aromatic residues for structure and prolifeative activity of human Interleukin-4," Federation of European Biochemical Societies, 1991, vol. 286, No. 1,2, pp. 58-60.
Kruse, et al., "Two distinct functional sites of human interleukin 4 are identified by variants impaired in either receptor binding or receptor activation" The EMBO Journal, 1993, vol. 12, No. 13, pp. 5121-5129.
Lauw, et al., "Proinflammatory Effects of IL-10 During Human Endotoxemia", The Journal of Immunology, 2000, 165:2783-2789.
Ledeboer, A. et al., "Intrathecal interleukin-10 gene therapy attenuates paclitaxel-induced mechanical allodynia and proinflammatory cytokine expression in dorsal root ganglia in rats," Brain Behav Immun., 2007;21(5):686-698.
Lee, M. et al., "Prevention of autoimmune insulitis by delivery of a chimeric plasmid encoding interleukin-4 and interleukin-10," Journal of Controlled Release, 2003;88(2):333-342.
Lees, J.G. et al., "Immunotherapy targeting cytokines in neuropathic pain," Frontiers in pharmacology, 2013;4(142):1-4.
Lemmer, S, et al., "Enhanced spinal neuronal responses as a mechanism for the increased nociceptive sensitivity of interleukin-4 deficient mice," Exp Neurol., 2015;271:198-204.

(56) References Cited

OTHER PUBLICATIONS

Letzelter, F. et al., "The interleukin-4 site-2 epitope determining binding of the common receptor γ chain." Eur. J. Biochem., 1998;257:11-20.
Li, P. et al., "A fusion cytokine coupling GMCSF to IL9 induces heterologous receptor clustering and STAT1 hyperactivation through JAK2 promiscuity," PLoS One, 2013;8(7):e69405.
Lima, R. et al., "Systemic Interleukin-4 Administration after Spinal Cord Injury Modulates Inflammation and Promotes Neuroprotection," Pharmaceuticals, 2017;10(4):1-16.
Love, M.I. et al., "Moderated estimation of fold change and dispersion for RNA-seq data with DESeq2," Genome Biol., 2014;15(12):550.
Maini, R.N. et al., "rHuIL-10 in subjects with active rheumatoid arthritis: a phase I and cytokine response study [abstract]," Arthritis Rheum, 1997;40(Suppl. 9):S224.
Marie, C. et al., "IL-10 and IL-4 synergize with TNF-alpha to induce IL-1ra production by human neutrophils," Cytokine, 1996;8:147-51.
McKelvey, R. et al., "Neuropathic pain is constitutively suppressed in early life by anti-inflammatory neuroimmune regulation," J Neurosci, 2015;35(2):457-466.
Mika, J. et al., "Importance of glial activation in neuropathic pain," Eur J Pharmacol, 2013;716(1-3):106-119.
Milligan, E.D. et al., "Spinal interleukin-10 therapy to treat peripheral neuropathic pain," Neuromodulation, 2012;15(6):520-526.
Moraga, I. et al., "Synthekines are surrogate cytokine and growth factor agonists that compel signaling through non-natural receptor dimers," Elife, 2017;6:e22882.
Moraga, I. et al., "Multifarious determinants of cytokine receptor signaling specificity," Adv Immunol, 2014;121:1-39.
Morrison, B.W. et al., "A Receptor Binding Domain of Mouse Interleukin-4 Defined by a Solid-phase Binding Assay in in Vitro Mutagenesis", The Journal of Biological Chemistry, 1992, vol. 267, No. 17, Issue of Jun. 15, pp. 11957-11963.
Nassar, M.A. et al., "Nociceptor-specific gene deletion reveals a major role for Nav1.7 (PN1) in acute and inflammatory pain," PNAS, 2004;101(34):12706-11.
Ng, S. et al., "Concise review: engineering the fusion of cytokines for the modulation of immune cellular responses in cancer and autoimmune disorders," Stem Cells Transl Med, 2015;4(1):66-73.
Nicola, N. A. et al., "General Classes and Functions of Four-Helix Bundle Cytokines", Advanced in Protein Chemistry, 1999, vol. 52, pp. 1-65.
Nie, B, et al., "AKAP150 involved in paclitaxel-induced neuropathic pain via inhibiting CN/NFAT2 pathway and downregulating IL-4," Brain Behav Immun., 2017;68:158-168.
Old, E.A, et al., "The role of glia in the spinal cord in neuropathic and inflammatory pain," Handb Exp Pharmacol., 2015;227:145-70.
Spangler, J.B. et al., "A strategy for the selection of monovalent antibodies that span protein dimer interfaces," Journal of Biological Chemistry, 2019;294(38):13876-13886.
Pils, M.C. et al., "Monocytes/macrophages and/or neutrophils are the target of IL-10 in the LPS endotoxemia model," Eur J Immunol, 2010;40(2):443-448.
Popov-Celeketic, J. et al., "Local and Slow Release of IL4-10 Synerkine as a Disease Modifying Therapy for Osteoarthritis," Osteoarthritis and Cartilage, 2016;24:S532.
Powrie, F. et al., "Interleukin-4 and interleukin-10 synergize to inhibit cell-mediated immunity in vivo," Eur J Immunol, 1993, vol. 23, pp. 2223-2229.
Prado, J. et al., "A fusion protein of IL4 and IL10 resolves chronic inflammatory pain" Abstracts of the 5th European Congress of Immunology—ECI (2018) p. 357.
Prado, J. et al., "Fusion Proteins of Anti-Inflammatory cytokines to Treat Chemotherapy-Induced Neuropathy" Pain In Europe XI, 11th Congress of The European Pain Federation EFIC Abstract Book (2019) p. 312.
Prado, J. et al., "Development of Recombinant Proteins to Treat Chronic Pain," J Vis Exp., 2018;134(e57071).
Prado, J. et al., "Fusion Proteins of Anti-Inflammatory cytokines to Treat Chemotherapy-Induced Neuropathy" EFIC ePoster, University Medical Center Utrecht, 2016.
Prasad, P. et al., "Rheumatoid arthritis: advances in treatment strategies," Mol Cell Biochem. 2023;478(1):69-88.
Pricop, L. et al., "Differential modulation of stimulatory and inhibitory Fc gamma receptors on human monocytes by Th1 and Th2 cytokines," J Immunol, 2001, vol. 166, pp. 531-537.
Pulles, A.E., et al. "A fusion protein of interleukin-4 and interleukin-10 protects against blood-induced cartilage damage in vitro and in vivo." Osteoarthritis and Cartilage, 2016;24:S505.
Punnonen, J. et al., "IL-10 and viral IL-10 prevent IL-4-induced IgE synthesis by inhibiting the accessory cell function of monocytes," J Immunol, 1993, vol. 151, pp. 1280-1289.
Pustjens, M.F., et al. "IL4-10 synerkine induces direct and indirect structural cartilage repair in osteoarthritis." Osteoarthritis and Cartilage, 2016;24:S532.
Rafei, M. et al., "A granulocyte-macrophage colony-stimulating factor and interleukin-15 fusokine induces a regulatory B cell population with immune suppressive properties," Nature medicine, 2009;15(9):1038-1045.
Raoof, R. et al., "Divergent roles of immune cells and their mediators in pain," Rheumatology (Oxford), 2018;57(3):429-440.
Ray, P. et al., "Comparative transcriptome profiling of the human and mouse dorsal root ganglia: an RNA-seq-based resource for pain and sensory neuroscience research," Pain, 2018;159(7):1325-1345.
Ren, Y. et al., "Therapeutic effects of histone deacetylase inhibitors in a murine asthma model," Inflammation Research, 2016;65:995-1008.
Ren, K. et al., "Interactions between the immune and nervous systems in pain," Nat Med, 2010;16(11):1267-1276.
Rijsdijk, M. et al., "The effects of glucocorticoids on neuropathic pain: a review with emphasis on intrathecal methylprednisolone acetate delivery," Anesth Analg, 2014;118:1097-112.
Rijsdijk, M. et al., "No beneficial effect of intrathecal methylprednisolone acetate in postherpetic neuralgia patients," Eur J Pain, 2013;17:714-23.
Ripple, M.J. et al., "Immunomodulation with IL-4R alpha antisense oligonucleotide prevents respiratory syncytial virus-mediated pulmonary disease," J Immunol., 2010;185(8):4804-11.
Risso, D. et al., "Normalization of RNA-seq data using factor analysis of control genes or samples." Nature biotechnology, 2014, vol. 32, No. 9, pp. 896-902.
Sauer, B. et al., "Site-specific DNA recombination in mammalian cells by the Cre recombinase of bacteriophage P1," PNAS, 1988;85(14):5166-70.
Schaible, H.G. et al., "Nociceptive neurons detect cytokines in arthritis," Arthritis Res Ther., 2014;16:470.
Scholz J, et al., "The neuropathic pain triad: neurons, immune cells and glia," Nat Neurosci, 2007;10:1361-8.
Söderberg, O. et al., "Characterizing proteins and their interactions in cells and tissues using the in situ proximity ligation assay," Methods, 2008;45(3):227-32.
Search Report and Written Opinion for Dutch Patent Application No. NL/2022982 issued Apr. 19, 2019.
Search Report and Written Opinion for Dutch Patent Application No. NL/2022984 issued Apr. 19, 2019.
Serhan, C.N. et al., "Resolution of inflammation: state of the art, definitions and terms," FASEB J, 2007;21:325-32.
Shao, Q. et al., "IL-10 and IL-1beta mediate neuropathic-pain like behavior in the ventrolateral orbital cortex," Neurochem Res, 2015;40(4):733-739.
Shields, S.D, et al., "Nav1.8 expression is not restricted to nociceptors in mouse peripheral nervous system," Pain, 2012;153(10):2017-2030.
Soderquist, R.G. et al., "Release of plasmid DNA-encoding IL-10 from PLGA microparticles facilitates long-term reversal of neuropathic pain following a single intrathecal administration," Pharm Res, 2010;27(5):841-854.
Steen-Louws, C, et al., "IL4-10 fusion protein has chondroprotective, anti-inflammatory and potentially analgesic effects in the treatment of osteoarthritis," Osteoarthritis Cartilage, 2018, vol. 26, pp. 1127-1135.

(56) References Cited

OTHER PUBLICATIONS

Stone, L.S. et al., "The pain of antisense: in vivo application of antisense oligonucleotides for functional genomics in pain and analgesia," Adv Drug Deliv Rev, 2003;55(8):1081-1112.
Te Velde, A.A. et al., "IL-10 stimulates monocyte Fc gamma R surface expression and cytotoxic activity. Distinct regulation of antibody-dependent cellular cytotoxicity by IFN-gamma, IL-4, and IL-10," J Immunol, 1992, vol. 149, No. 12, pp. 4048-4052.
Steen-Louws, et al., "IL4-10 fusion protein: a novel immunoregulatroy drug combining activities of interleukin 4 and interleukin 10," Clinical & Experimental Immunology, The Journal of Translational Immunology, 2018;195: 1-9.
Thom, G. et al., "Probing a protein-protein interaction by in vitro evolution," PNAS, 2006;103:7619-24.
Toma, W. et al., "Effects of paclitaxel on the development of neuropathy and affective behaviors in the mouse," Neuropharmacology, 2017;117:305-15.
Uceyler, N. et al., "Differential expression patterns of cytokines in complex regional pain syndrome," Pain, 2007;132(1-2):195-205.
Uceyler, N. et al., "Reduced levels of antiinflammatory cytokines in patients with chronic widespread pain," Arthritis Rheum, 2006;54(8):2656-2664.
Urlaub, G. et al., "Isolation of Chinese hamster cell mutants deficient in dihydrofolate reductase activity," PNAS, 1980, vol. 77, No. 7, pp. 4216-4220.
Usoskin, D. et al., "Unbiased classification of sensory neuron types by large-scale single-cell RNA sequencing," Nat Neurosci., 2015;18:145-53.
Suthaus, J. et al., "Forced homo- and heterodimerization of all gp130-type receptor complexes leads to constitutive ligand-independent signaling and cytokine-independent growth," Mol Biol Cell, 2010;21(15):2797-2807.
Vale, M. et al., "Antinociceptive Effects of Interleukin-4, -10, and -13 on the Writhing Response in Mice and Zymosan-Induced Knee Joint Incapacitation in Rats", The Journal of Pharmacology and Experimental Therapeutics, 2003, vol. 301, No. 1. pp. 102-108.
Van De Loo, F.A.J. et al., "Gene therapy for rheumatoid arthritis. Lessons from animal models, including studies on interleukin-4, interleukin-10, and interleukin-1 receptor antagonist as potential disease modulators," Rheum Dis Clin North Am., 2002;28(1):127-149.
Van den Bosch, F. et al., "rHuIL-4 in subjects with active rheumatoid arthritis: a phase I dose escalating safety study [abstract]," Arthritis Rheum, 1998;41(Suppl. 9):S56.
Van Hecke O, et al. Chronic pain epidemiology and its clinical relevance. Br J Anaesth 2013;111:13-8.
Van Helvoort, E.M. et al., "Canine IL4-10 fusion protein provides disease modifying activity in a canine model of OA; an exploratory study," PLoS One. 2019;14(7):e0219587.
Van Helvoort, E.M. et al., "The Role of Interleukin-4 and Interleukin-10 in Osteoarthritic Joint Disease: A Systematic Narrative Review," Cartilage. 2022;13(2):19476035221098167.
Van Helvoort, E.M. et al., "Effects of the Human IL4-10 Fusion Protein in the Canine Groove Model of Osteoarthritis," Osteoarthritis and Cartilage, 2017;25:S76-S444.
Van Meegeren, M.E.R. et al., "IL-4 alone and in combination with IL-10 protects against blood-induced cartilage damage," Osteoarthritis and Cartilage, 2012;20:764-772.
Van Meegeren, M.E.R. et al., "A single intra-articular injection with IL-4 plus IL-10ameliorates blood-induced cartilage degeneration in haemophilic mice", British Journal of Haematology, 2013, vol. 160, 515-520.
Van Meegeren, M.E.R. et al., "Blood-induced joint damage: novel targets for therapy," Chapter 8, 2012, pp. 118-131.
Van Meegeren, M.E.R. et al., "The Combination of IL-4 and IL-10 and IL-10 protects against blood cartilage damage," Osteoarthritis and Cartilage, 2010, vol. 18, Supplement 2, pp. S45-S256.
Van Meegeren, M.E.R., "Blood-induced joint damage: novel targets for therapy", 2012;1-180.

Van Roon, J.A.G. et al., "Suppression of inflammation and joint destruction in rheumatoid arthritis may require a concerted action of Th2 cytokines," Current opinion in investigational drugs, 2002;3(7):1011-1016.
Van Roon, J.A.G. et al., "Interleukin 10 treatment of patients with rheumatoid arthritis enhances Fc gamma receptor expression on monocytes and responsiveness to immune complex stimulation," The Journal of rheumatology, 2003;30(4):648-651.
Van Roon, J.A.G. et al., "Decrease in Peripheral type 1 over type 2 T ell cytokine production in patients with rheumatoid arthritis correlates with an increase in severity of disease", Annals of the Rheumatic Diseases, 1997;56:656-660.
Van Roon, J.A.G. et al., "Differentiation of naïve CD4+ T cells towards T helper 2 cells is not impaired in rheumatoid arthritis patients", Arthritis Res Ther, 2003;5:R269-R276.
Van Roon, J.A.G. et al., "Prevention and Reversal of Cartilage Degradation in Rheumatoid Arthritis by Interleukin-10 and Interleukin-4", Arthritis & Rheumatism, 1996, vol. 39, No. 5, pp. 829-835.
Van Roon, J.A.G. et al. "Proinflammatory cytokine production and cartilage damage due to rheumatoid synovial T helper-1 activation is inhibited by interleukin-4", Annals of the Rheumatic Disease, 1995;54:836-840.
Van Roon, J.A.G. et al., "Stimulation of Suppressive T Cell Response by Human but not Bacterial 60-kD Heat-shock Protein in Synovial Fluid of Patients with Rheumatoid Arthritis", The American Society for Clinical Investigation, Inc., 1997, vol. 100, No. 2, 459-463.
Van Roon, J.A.G. et al., "Synergistic Activity of Interleukin-4 and Interleukin-10 in Suppression of Inflammation and Joint Destruction in Rheumatoid Arthritis", Arthritis & Rheumatish, 2001, vol. 44, No. 1, pp. 3-12.
Van Vulpen, L.F.D. et al., "A Fusion Protein ofInterleukin-4 and Interleukin-10 Protects Against Blood-Induced Cartilage Damage In Vitro and In Vivo," Journal of Thrombosis and Haemostasis, 2017;15(9): 1788-1798.
Vanderwall, A.G, et al., "Effects of spinal non-viral interleukin-10 gene therapy formulated with d-mannose in neuropathic interleukin-10 deficient mice: Behavioral characterization, mRNA and protein analysis in pain relevant tissues," Brain Behav Immun., 2017;69:91-112.
Verhoef, C. M., et al., "Interleukin 10 (IL-10), not IL-4 or interferon-gamma production, correlates with progression of joint destruction in rheumatoid arthritis," The Journal of rheumatology, 2001;28(9):1960-1966.
Verhoef, C.M. et al., "The immune suppressive effect of dexamethasone in rheumatoid arthritis is accompanied by upregulation of interleukin 10 and by differential changes in interferon and interleukin 4 production", Ann Rheum Dis., 1999;58:49-54.
Wang, Y. et al., "A mixed-charge pair in human interleukin 4 dominates high-affinity interaction with the receptor α chain" PNAS, 1997, vol. 94, pp. 1657-1662.
Westerhof, L.B. et al., "3D Domain Swapping Causes Extensive Multimerisation of Human Interleukin-10 When Expressed In Planta," PLoSONE, 2012, vol. 7, Issue 10, pp. 1-10.
Wijngaarden, S. et al., "A Shift in the Balance of Inhibitory and Activating FCγ Receptors on Monocytes Toward the Inhibitory FCγ Receptor Iib Is Associated with Prevention of Monocyte Activation in Rheumatoid Arthritis", Arthritis & Rheumatism, vol. 50, No. 12, 2004, pp. 3878-3887.
Willemen, H.L.D.M. et al., "Monocytes/Macrophages control resolution of transient inflammatory pain," J Pain, 2014;15(5):496-506.
Woolf, C.J. et al., "Neuronal plasticity: increasing the gain in pain," Science, 2000;288:1765-9.
Yoo, T.J. "Anti-Inflammatory Gene Therapy Improves Spatial Memory Performance in a Mouse Model of Alzheimer's Disease," J Alzheimers Dis., 2022;85(3):1001-1008.
Yoon, S. et al., "Conformational Changes Mediate Interleukin-10 Receptor 2 (IL-10R2) Binding to IL-10 and Assembly of the Signaling Complex" The Journal of Biological Chemistry, 2006, vol. 281, No. 46, pp. 35088-35096.
Zdanov, A., "Structural analysis of cytokines comprising the IL-10 family," Cytokine & Growth Factor Reviews, 2010;21:325-330.

(56) References Cited

OTHER PUBLICATIONS

Zhang, J. M., et al, "Cytokines, Inflammation, and Pain", Department of Anesthesiology and Department of Anesthesiology and Pain Medicine, 2007, vol. 45, No. 2, pp. 26-37.
Pani, G. et al.: MorphoNeuroNet: An automated method for dense neurite network analysis, Cytom Part A. 85(2):188-99 (2014).
Alexander, Guillermo M. et al. Changes in cerebrospinal fluid levels of pro-inflammatory cytokines in CRPS. Pain 116(3):213-219 (2005).
Alexander, Guillermo M. et al. Changes in immune and glial markers in the CSF of patients with complex regional pain syndrome. Brain, behavior, and immunity 21(5):668-676 (2007).
Azari, Pari. et al. Efficacy and safety of ketamine in patients with complex regional pain syndrome: a systematic review. CNS drugs 26:215-228 (2012).
Bean, D. J. et al. Extent of recovery in the first 12 months of complex regional pain syndrome type-1: A prospective study. European journal of pain 20(6):884-894 (2016).
Beerthuizen, Annemerle. et al. Demographic and medical parameters in the development of complex regional pain syndrome type 1 (CRPS1): prospective study on 596 patients with a fracture. Pain 153(6):1187-1192 (2012).
Bharwani, Krishna D. et al. Complex regional pain syndrome: diagnosis and treatment. BJA Education 17(8):262-268 (2017).
Coderre, Terence J. et al. Chronic post-ischemia pain (CPIP): a novel animal model of complex regional pain syndrome-type I (CRPS-I; reflex sympathetic dystrophy) produced by prolonged hindpaw ischemia and reperfusion in the rat. Pain 112(1-2):94-105 (2004).
De Mos, Marieke. et al. Medical history and the onset of complex regional pain syndrome (CRPS). Pain 139(2):458-466 (2008).
De Mos, Marissa. et al. The incidence of complex regional pain syndrome: a population-based study. Pain 129(1-2):12-20 (2007).
Goebel, Andreas. et al. Standards for the diagnosis and management of complex regional pain syndrome: Results of a European Pain Federation task force. European Journal of Pain 23(4):641-651 (2019).
Goebel, Andreas. et al. The Valencia consensus-based adaptation of the IASP complex regional pain syndrome diagnostic criteria. Pain 162(9):2346-2348 (2021).
Goh, En Lin. et al. Complex regional pain syndrome: a recent update. Burns and trauma 5:2, 1-11 (2017).
Goldberg, Michael E. et al. Pharmacodynamic profiles of ketamine (R−) And (S+) with five day inpatient infusion for the treatment of complex regional pain syndrome. Pain physician 13(4):379-387 (2010).
Harden, R. Norman. et al. Complex regional pain syndrome: practical diagnostic and treatment guidelines. Pain medicine 14(2):180-229 (2013).
Harden, R. Norman. et al. Complex regional pain syndrome: practical diagnostic and treatment guidelines. Pain medicine 23(Supplement_1):S1-S53 (2022).
Harden, R. Norman. et al. Validation of proposed diagnostic criteria (the "Budapest Criteria") for complex regional pain syndrome. Pain 150(2):268-274 (2010).
Hoikkanen, Tomas. et al. Long-term outcome of spinal cord stimulation in complex regional pain syndrome. Neurosurgery 89(4):597-609 (2021).
Lloyd, Emilia C.O. et al. Complex Regional Pain Syndrome. American Family Physician 104(1):49-55 (2021).
Mangnus, Thomas JP. et al. Different types of pain in complex regional pain syndrome require a personalized treatment strategy. Journal of Pain Research:4379-4391 (2023).
Mangnus, Thomas JP. et al. From a symptom-based to a mechanism-based pharmacotherapeutic treatment in complex regional pain syndrome. Drugs 82(5):511-531 (2022).
Milligan, Erin D. et al. Controlling pathological pain by adenovirally driven spinal production of the anti-inflammatory cytokine, interleukin-10. European Journal of Neuroscience 21(8):2136-2148 (2005).
Mogil, Jeffrey S. Animal models of pain: progress and challenges. Nature Reviews Neuroscience 10(4): 283-294 (2009).
Ott, Stephan, and Christian Maihofner. Signs and symptoms in 1,043 patients with complex regional pain syndrome. The Journal of Pain 19(6):599-611 (2018).
Prado, Judith. et al. Cytokine receptor clustering in sensory neurons with an engineered cytokine fusion protein triggers unique pain resolution pathways. Proceedings of the National Academy of Sciences 118(11):e2009647118, 1-12 (2021).
Price, Theodore J. et al. Transition to chronic pain: opportunities for novel therapeutics. Nature Reviews Neuroscience 19(7):383-384 (2018).
Raja, Srinivasa N. et al. Complex regional pain syndrome: a comprehensive qualitative research study on unmet needs in the "patient journey". Journal of Pain Research:2391-2401 (2021).
Sadler, Katelyn E. et al. Innovations and advances in modelling and measuring pain in animals. Nature Reviews Neuroscience 23(2):70-85 (2022).
Sandroni, Paola. et al. Complex regional pain syndrome type I: incidence and prevalence in Olmsted county, a population-based study. Pain 103(1-2):199-207 (2003).
Steen-Louws, Cristine. et al. Sialic Acid-Engineered IL4-10 Fusion Protein is Bioactive and Rapidly Cleared from the Circulation. Pharmaceutical Research 37:1-10 (2020).
Van Velzen, Gijsbrecht AJ. et al. Health-related quality of life in 975 patients with complex regional pain syndrome type 1. Pain 155(3):629-634 (2014).
Zdanov, Alexander. et al. Crystal structure of interleukin-10 reveals the functional dimer with an unexpected topological similarity to interferon γ. Structure 3(6):591-601 (1995).
Dispenza, Melanie C. Classification of Hypersensitivity Reactions. Allergy & Asthma Proceedings 40(6):470-473 (2019).
Intrathecal. National Cancer Institute. Oct. 5, 2024 [retrieved on Oct. 16, 2024]. Available at URL:https://www.cancer.gov/publications/dictionaries/cancer-terms/def/intrathecal pp. 1-2.
Kumar, Krishna. et al. Continuous intrathecal morphine treatment for chronic pain of nonmalignant etiology: long-term benefits and efficacy. Surgical Neurology 55(2):79-86 (2001).
Ma, Jun, and Jun Tang. A Review for Dynamics in Neuron and Neuronal Network. Nonlinear Dynamics 89:1569-1578 (2017).
Ursin, Holger. Brain Sensitization to External and Internal Stimuli. Psychoneuroendocrinology 42:134-145 (2014).
U.S. Appl. No. 17/192,183 Office Action dated Jun. 20, 2024.
U.S. Appl. No. 17/504,045 Office Action dated May 14, 2024.
U.S. Appl. No. 17/504,045 Office Action dated Oct. 10, 2024.

\* cited by examiner

** $p<0.01$ IL4/IL13 vs IL13
** $p<0.01$ IL4/IL13$_{SKP}$ vs IL13
$p<0.05$ IL4/IL13 vs IL4 + IL13
$p<0.05$ IL4/IL13$_{SKP}$ vs IL4 + IL13

* $p<0.05$; IL13/IL13 vs IL13
$p<0.05$; IL13/IL27-A$_{pool2}$ vs IL13

SEQUENCE LISTING

<160> NUMBER OF SEQ ID NOS: 45

<210> SEQ ID NO 1
<211> LENGTH: 129
<212> TYPE: PRT
<213> ORGANISM: Homo sapiens

<400> SEQUENCE: 1

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 2
<211> LENGTH: 113
<212> TYPE: PRT
<213> ORGANISM: Homo sapiens

<400> SEQUENCE: 2

Pro Gly Pro Val Pro Pro Ser Thr Ala Leu Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Asp Thr Lys Ile Glu Val Ala Gln Phe Val
                85                  90                  95

Lys Asp Leu Leu Leu His Leu Lys Lys Leu Phe Arg Glu Gly Gln Phe
            100                 105                 110

Asn

<210> SEQ ID NO 3
<211> LENGTH: 9
<212> TYPE: PRT
<213> ORGANISM: Homo sapiens

<400> SEQUENCE: 3

Gly Ser Gly Gly Gly Gly Ser Gly Thr
1               5

<210> SEQ ID NO 4
<211> LENGTH: 251
<212> TYPE: PRT
<213> ORGANISM: Homo sapiens

<400> SEQUENCE: 4

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser Gly Ser Gly Gly Gly Gly Ser Gly Thr Pro Gly Pro Val Pro Pro
    130                 135                 140

Ser Thr Ala Leu Arg Glu Leu Ile Glu Glu Leu Val Asn Ile Thr Gln
145                 150                 155                 160

Asn Gln Lys Ala Pro Leu Cys Asn Gly Ser Met Val Trp Ser Ile Asn
                165                 170                 175

Leu Thr Ala Gly Met Tyr Cys Ala Ala Leu Glu Ser Leu Ile Asn Val
            180                 185                 190

Ser Gly Cys Ser Ala Ile Glu Lys Thr Gln Arg Met Leu Ser Gly Phe
        195                 200                 205

Cys Pro His Lys Val Ser Ala Gly Gln Phe Ser Ser Leu His Val Arg
    210                 215                 220

Asp Thr Lys Ile Glu Val Ala Gln Phe Val Lys Asp Leu Leu Leu His
225                 230                 235                 240

Leu Lys Lys Leu Phe Arg Glu Gly Gln Phe Asn
                245                 250

<210> SEQ ID NO 5
<211> LENGTH: 160
<212> TYPE: PRT
<213> ORGANISM: Homo sapiens

<400> SEQUENCE: 5

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
                20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
 50                  55                  60

Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

<210> SEQ ID NO 6
<211> LENGTH: 270
<212> TYPE: PRT
<213> ORGANISM: Homo sapiens

<400> SEQUENCE: 6

Met Lys Pro Lys Met Lys Tyr Ser Thr Asn Lys Ile Ser Thr Ala Lys
 1               5                  10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
 50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                        245                 250                 255

Asn Leu Cys Thr Glu Asn Ile Leu Phe Lys Leu Ser Glu Thr
            260                 265                 270

<210> SEQ ID NO 7
<211> LENGTH: 390
<212> TYPE: PRT
<213> ORGANISM: Homo sapiens

<400> SEQUENCE: 7

Met Pro Pro Ser Gly Leu Arg Leu Leu Pro Leu Leu Pro Leu Leu
1               5                   10                  15

Trp Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala

```
                340                 345                 350
Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
            370                 375                 380

Arg Ser Cys Lys Cys Ser
385                 390

<210> SEQ ID NO 8
<211> LENGTH: 442
<212> TYPE: PRT
<213> ORGANISM: Homo sapiens

<400> SEQUENCE: 8

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
            35                  40                  45

Lys Leu Thr Ser Pro Pro Glu Asp Tyr Pro Glu Pro Glu Glu Val Pro
50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Thr Val Cys Pro Val Val Thr Thr Pro Ser Gly Ser Val
            115                 120                 125

Gly Ser Leu Cys Ser Arg Gln Ser Gln Val Leu Cys Gly Tyr Leu Asp
130                 135                 140

Ala Ile Pro Pro Thr Phe Tyr Arg Pro Tyr Phe Arg Ile Val Arg Phe
145                 150                 155                 160

Asp Val Ser Ala Met Glu Lys Asn Ala Ser Asn Leu Val Lys Ala Glu
                165                 170                 175

Phe Arg Val Phe Arg Leu Gln Asn Pro Lys Ala Arg Val Pro Glu Gln
            180                 185                 190

Arg Ile Glu Leu Tyr Gln Ile Leu Lys Ser Lys Asp Leu Thr Ser Pro
            195                 200                 205

Thr Gln Arg Tyr Ile Asp Ser Lys Val Val Lys Thr Arg Ala Glu Gly
            210                 215                 220

Glu Trp Leu Ser Phe Asp Val Thr Asp Ala Val His Glu Trp Leu His
225                 230                 235                 240

His Lys Asp Arg Asn Leu Gly Phe Lys Ile Ser Leu His Cys Pro Cys
                245                 250                 255

Cys Thr Phe Val Pro Ser Asn Asn Tyr Ile Ile Pro Asn Lys Ser Glu
            260                 265                 270

Glu Leu Glu Ala Arg Phe Ala Gly Ile Asp Gly Thr Ser Thr Tyr Thr
            275                 280                 285

Ser Gly Asp Gln Lys Thr Ile Lys Ser Thr Arg Lys Lys Asn Ser Gly
            290                 295                 300

Lys Thr Pro His Leu Leu Leu Met Leu Leu Pro Ser Tyr Arg Leu Glu
305                 310                 315                 320
```

```
Ser Gln Gln Thr Asn Arg Arg Lys Lys Arg Ala Leu Asp Ala Ala Tyr
            325                 330                 335

Cys Phe Arg Asn Val Gln Asp Asn Cys Cys Leu Arg Pro Leu Tyr Ile
        340                 345                 350

Asp Phe Lys Arg Asp Leu Gly Trp Lys Trp Ile His Glu Pro Lys Gly
            355                 360                 365

Tyr Asn Ala Asn Phe Cys Ala Gly Ala Cys Pro Tyr Leu Trp Ser Ser
        370                 375                 380

Asp Thr Gln His Ser Arg Val Leu Ser Leu Tyr Asn Thr Ile Asn Pro
385                 390                 395                 400

Glu Ala Ser Ala Ser Pro Cys Cys Val Ser Gln Asp Leu Glu Pro Leu
                405                 410                 415

Thr Ile Leu Tyr Tyr Ile Gly Lys Thr Pro Lys Ile Glu Gln Leu Ser
                420                 425                 430

Asn Met Ile Val Lys Ser Cys Lys Cys Ser
                435                 440
```

<210> SEQ ID NO 9
<211> LENGTH: 112
<212> TYPE: PRT
<213> ORGANISM: Homo sapiens

<400> SEQUENCE: 9

```
Gly Pro Val Pro Pro Ser Thr Ala Leu Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu Leu His Leu Lys Lys Leu Phe Arg Glu Gly Gln Phe Asn
                100                 105                 110
```

<210> SEQ ID NO 10
<211> LENGTH: 114
<212> TYPE: PRT
<213> ORGANISM: Homo sapiens

<400> SEQUENCE: 10

```
Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95
```

```
Val Lys Asp Leu Leu His Leu Lys Lys Leu Phe Arg Glu Gly Gln
            100                 105                 110
Phe Asn

<210> SEQ ID NO 11
<211> LENGTH: 122
<212> TYPE: PRT
<213> ORGANISM: Homo sapiens

<400> SEQUENCE: 11

Leu Thr Cys Leu Gly Gly Phe Ala Ser Pro Gly Pro Val Pro Pro Ser
1               5                   10                  15

Thr Ala Leu Arg Glu Leu Ile Glu Glu Leu Val Asn Ile Thr Gln Asn
                20                  25                  30

Gln Lys Ala Pro Leu Cys Asn Gly Ser Met Val Trp Ser Ile Asn Leu
            35                  40                  45

Thr Ala Gly Met Tyr Cys Ala Ala Leu Glu Ser Leu Ile Asn Val Ser
        50                  55                  60

Gly Cys Ser Ala Ile Glu Lys Thr Gln Arg Met Leu Ser Gly Phe Cys
65                  70                  75                  80

Pro His Lys Val Ser Ala Gly Gln Phe Ser Ser Leu His Val Arg Asp
                85                  90                  95

Thr Lys Ile Glu Val Ala Gln Phe Val Lys Asp Leu Leu Leu His Leu
            100                 105                 110

Lys Lys Leu Phe Arg Glu Gly Gln Phe Asn
            115                 120

<210> SEQ ID NO 12
<211> LENGTH: 113
<212> TYPE: PRT
<213> ORGANISM: Homo sapiens

<400> SEQUENCE: 12

Pro Gly Pro Val Pro Pro Ser Thr Ala Leu Arg Glu Leu Ile Glu Glu
1               5                   10                  15

Leu Val Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60

Arg Met Leu Ser Gly Phe Cys Pro His Lys Val Ser Ala Gly Gln Phe
65                  70                  75                  80

Ser Ser Leu His Val Arg Asp Thr Lys Ile Glu Val Ala Gln Phe Val
                85                  90                  95

Lys Asp Leu Leu Leu His Leu Lys Lys Leu Phe Arg Glu Gly Arg Phe
            100                 105                 110

Asn

<210> SEQ ID NO 13
<211> LENGTH: 112
<212> TYPE: PRT
<213> ORGANISM: Homo sapiens

<400> SEQUENCE: 13

Gly Pro Val Pro Pro Ser Thr Ala Leu Arg Glu Leu Ile Glu Glu Leu
1               5                   10                  15
```

```
Val Asn Ile Thr Gln Asn Gln Lys Ala Pro Leu Cys Asn Gly Ser Met
                20                  25                  30

Val Trp Ser Ile Asn Leu Thr Ala Gly Met Tyr Cys Ala Ala Leu Glu
        35                  40                  45

Ser Leu Ile Asn Val Ser Gly Cys Ser Ala Ile Glu Lys Thr Gln Arg
50                  55                  60

Met Leu Ser Gly Phe Cys Pro His Lys Val Ser Ala Gly Gln Phe Ser
65                  70                  75                  80

Ser Leu His Val Arg Asp Thr Lys Ile Glu Val Ala Gln Phe Val Lys
                85                  90                  95

Asp Leu Leu His Leu Lys Lys Leu Phe Arg Glu Gly Arg Phe Asn
                100                 105                 110
```

<210> SEQ ID NO 14
<211> LENGTH: 114
<212> TYPE: PRT
<213> ORGANISM: Homo sapiens

<400> SEQUENCE: 14

```
Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
                20                  25                  30

Ser Met Val Trp Ser Ile Asn Leu Thr Ala Gly Met Tyr Cys Ala Ala
            35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu His Leu Lys Lys Leu Phe Arg Glu Gly Arg
                100                 105                 110

Phe Asn
```

<210> SEQ ID NO 15
<211> LENGTH: 122
<212> TYPE: PRT
<213> ORGANISM: Homo sapiens

<400> SEQUENCE: 15

```
Leu Thr Cys Leu Gly Gly Phe Ala Ser Pro Gly Pro Val Pro Pro Ser
1               5                   10                  15

Thr Ala Leu Arg Glu Leu Ile Glu Glu Leu Val Asn Ile Thr Gln Asn
                20                  25                  30

Gln Lys Ala Pro Leu Cys Asn Gly Ser Met Val Trp Ser Ile Asn Leu
                35                  40                  45

Thr Ala Gly Met Tyr Cys Ala Ala Leu Glu Ser Leu Ile Asn Val Ser
        50                  55                  60

Gly Cys Ser Ala Ile Glu Lys Thr Gln Arg Met Leu Ser Gly Phe Cys
65                  70                  75                  80

Pro His Lys Val Ser Ala Gly Gln Phe Ser Ser Leu His Val Arg Asp
                85                  90                  95

Thr Lys Ile Glu Val Ala Gln Phe Val Lys Asp Leu Leu His Leu
                100                 105                 110

Lys Lys Leu Phe Arg Glu Gly Arg Phe Asn
```

<210> SEQ ID NO 16
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser Gly Ser Gly Gly Gly Ser Gly Thr Ser Pro Gly Pro Val Pro
    130                 135                 140

Pro Ser Thr Ala Leu Arg Glu Leu Ile Glu Glu Leu Val Asn Ile Thr
145                 150                 155                 160

Gln Asn Gln Lys Ala Pro Leu Cys Asn Gly Ser Met Val Trp Ser Ile
                165                 170                 175

Asn Leu Thr Ala Gly Met Tyr Cys Ala Ala Leu Glu Ser Leu Ile Asn
            180                 185                 190

Val Ser Gly Cys Ser Ala Ile Glu Lys Thr Gln Arg Met Leu Ser Gly
        195                 200                 205

Phe Cys Pro His Lys Val Ser Ala Gly Gln Phe Ser Ser Leu His Val
    210                 215                 220

Arg Asp Thr Lys Ile Glu Val Ala Gln Phe Val Lys Asp Leu Leu Leu
225                 230                 235                 240

His Leu Lys Lys Leu Phe Arg Glu Gly Arg Phe Asn
                245                 250

<210> SEQ ID NO 17
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala

```
                35                  40                  45
Leu Glu Ser Leu Ile Asn Val Ser Gly Cys Ser Ala Ile Glu Lys Thr
 50                  55                  60

Gln Arg Met Leu Ser Gly Phe Cys Pro His Lys Val Ser Ala Gly Gln
 65                  70                  75                  80

Phe Ser Ser Leu His Val Arg Asp Thr Lys Ile Glu Val Ala Gln Phe
                 85                  90                  95

Val Lys Asp Leu Leu Leu His Leu Lys Lys Leu Phe Arg Glu Gly Arg
            100                 105                 110

Phe Asn Gly Ser Gly Gly Gly Ser Gly Thr Ser Pro Gly Gln Gly
            115                 120                 125

Thr Gln Ser Glu Asn Ser Cys Thr His Phe Pro Gly Asn Leu Pro Asn
        130                 135                 140

Met Leu Arg Asp Leu Arg Asp Ala Phe Ser Arg Val Lys Thr Phe Phe
145                 150                 155                 160

Gln Met Lys Asp Gln Leu Asp Asn Leu Leu Leu Lys Glu Ser Leu Leu
                165                 170                 175

Glu Asp Phe Lys Gly Tyr Leu Gly Cys Gln Ala Leu Ser Glu Met Ile
            180                 185                 190

Gln Phe Tyr Leu Glu Glu Val Met Pro Gln Ala Glu Asn Gln Asp Pro
        195                 200                 205

Asp Ile Lys Ala His Val Asn Ser Leu Gly Glu Asn Leu Lys Thr Leu
210                 215                 220

Arg Leu Arg Leu Arg Arg Cys His Arg Phe Leu Pro Cys Glu Asn Lys
225                 230                 235                 240

Ser Lys Ala Val Glu Gln Val Lys Asn Ala Phe Asn Lys Leu Gln Glu
                245                 250                 255

Lys Gly Ile Tyr Lys Ala Met Ser Glu Phe Asp Ile Phe Ile Asn Tyr
            260                 265                 270

Ile Glu Ala Tyr Met Thr Met Lys Ile Arg Asn
        275                 280

<210> SEQ ID NO 18
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Phe Pro Arg Pro Pro Gly Arg Pro Gln Leu Ser Leu Gln Glu Leu Arg
 1               5                  10                  15

Arg Glu Phe Thr Val Ser Leu His Leu Ala Arg Lys Leu Leu Ser Glu
                20                  25                  30

Val Arg Gly Gln Ala His Arg Phe Ala Glu Ser His Leu Pro Gly Val
            35                  40                  45

Asn Leu Tyr Leu Leu Pro Leu Gly Glu Gln Leu Pro Asp Val Ser Leu
        50                  55                  60

Thr Phe Gln Ala Trp Arg Arg Leu Ser Asp Pro Glu Arg Leu Cys Phe
 65                  70                  75                  80

Ile Ser Thr Thr Leu Gln Pro Phe His Ala Leu Leu Gly Gly Leu Gly
                 85                  90                  95

Thr Gln Gly Arg Trp Thr Asn Met Glu Arg Met Gln Leu Trp Ala Met
            100                 105                 110
```

```
Arg Leu Asp Leu Arg Asp Leu Gln Arg His Leu Arg Phe Gln Val Leu
            115                 120                 125

Ala Ala Gly Phe Asn Cys Pro Glu Glu Glu Glu Glu Glu Glu Glu Glu
130                 135                 140

Glu Glu Glu Glu Arg Lys Gly Leu Leu Pro Gly Ala Leu Gly Ser Ala
145                 150                 155                 160

Leu Gln Gly Pro Ala Gln Val Ser Trp Pro Gln Leu Leu Ser Thr Tyr
                165                 170                 175

Arg Leu Leu His Ser Leu Glu Leu Val Leu Ser Arg Ala Val Arg Glu
            180                 185                 190

Leu Leu Leu Leu Ser Lys Ala Gly His Ser Val Trp Pro Leu Gly Phe
            195                 200                 205

Pro Thr Leu Ser Pro Gln Pro
    210                 215

<210> SEQ ID NO 19
<211> LENGTH: 338
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Arg
            100                 105                 110

Phe Asn Gly Ser Gly Gly Gly Ser Gly Thr Phe Pro Arg Pro Pro
            115                 120                 125

Gly Arg Pro Gln Leu Ser Leu Gln Glu Leu Arg Arg Glu Phe Thr Val
130                 135                 140

Ser Leu His Leu Ala Arg Lys Leu Leu Ser Glu Val Arg Gly Gln Ala
145                 150                 155                 160

His Arg Phe Ala Glu Ser His Leu Pro Gly Val Asn Leu Tyr Leu Leu
                165                 170                 175

Pro Leu Gly Glu Gln Leu Pro Asp Val Ser Leu Thr Phe Gln Ala Trp
            180                 185                 190

Arg Arg Leu Ser Asp Pro Glu Arg Leu Cys Phe Ile Ser Thr Thr Leu
            195                 200                 205

Gln Pro Phe His Ala Leu Leu Gly Gly Leu Gly Thr Gln Gly Arg Trp
210                 215                 220

Thr Asn Met Glu Arg Met Gln Leu Trp Ala Met Arg Leu Asp Leu Arg
225                 230                 235                 240

Asp Leu Gln Arg His Leu Arg Phe Gln Val Leu Ala Ala Gly Phe Asn
                245                 250                 255
```

Cys Pro Glu Glu Glu Glu Glu Glu Glu Glu Glu Arg
            260                 265                 270

Lys Gly Leu Leu Pro Gly Ala Leu Gly Ser Ala Leu Gln Gly Pro Ala
        275                 280                 285

Gln Val Ser Trp Pro Gln Leu Leu Ser Thr Tyr Arg Leu Leu His Ser
    290                 295                 300

Leu Glu Leu Val Leu Ser Arg Ala Val Arg Glu Leu Leu Leu Ser
305                 310                 315                 320

Lys Ala Gly His Ser Val Trp Pro Leu Gly Phe Pro Thr Leu Ser Pro
                325                 330                 335

Gln Pro

<210> SEQ ID NO 20
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Arg
            100                 105                 110

Phe Asn Gly Ser Gly Gly Gly Ser Gly Thr Ser Pro Gly Pro Val
        115                 120                 125

Pro Pro Ser Thr Ala Leu Arg Glu Leu Ile Glu Glu Leu Val Asn Ile
    130                 135                 140

Thr Gln Asn Gln Lys Ala Pro Leu Cys Asn Gly Ser Met Val Trp Ser
145                 150                 155                 160

Ile Asn Leu Thr Ala Gly Met Tyr Cys Ala Ala Leu Glu Ser Leu Ile
                165                 170                 175

Asn Val Ser Gly Cys Ser Ala Ile Glu Lys Thr Gln Arg Met Leu Ser
            180                 185                 190

Gly Phe Cys Pro His Lys Val Ser Ala Gly Gln Phe Ser Ser Leu His
        195                 200                 205

Val Arg Asp Thr Lys Ile Glu Val Ala Gln Phe Val Lys Asp Leu Leu
    210                 215                 220

Leu His Leu Lys Lys Leu Phe Arg Glu Gly Arg Phe Asn
225                 230                 235

<210> SEQ ID NO 21
<211> LENGTH: 112
<212> TYPE: PRT
<213> ORGANISM: Homo sapiens

<400> SEQUENCE: 21

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 22
<211> LENGTH: 112
<212> TYPE: PRT
<213> ORGANISM: Homo sapiens

<400> SEQUENCE: 22

```
Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110
```

<210> SEQ ID NO 23
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80
```

Val Leu Ala Ala Cys Gln Gln Gln Ser Thr Val Glu Cys Phe Ala Phe
                85                  90                  95
Gly Ile Ser Gly Val Gln Lys Tyr Thr Arg Ala Leu His Asp Ser Ser
            100                 105                 110
Ile Thr Gly Ile Ser Pro Ile Thr Glu Tyr Leu Ala Ser Leu Ser Thr
        115                 120                 125
Tyr Asn Asp Gln Ser Ile Thr Phe Ala Leu Glu Asp Glu Ser Tyr Glu
    130                 135                 140
Ile Tyr Val Glu Asp Leu Lys Lys Asp Glu Lys Asp Lys Val Leu
145                 150                 155                 160
Leu Ser Tyr Tyr Glu Ser Gln His Pro Ser Asn Glu Ser Gly Asp Gly
                165                 170                 175
Val Asp Gly Lys Met Leu Met Val Thr Leu Ser Pro Thr Lys Asp Phe
            180                 185                 190
Trp Leu His Ala Asn Asn Lys Glu His Ser Val Glu Leu His Lys Cys
        195                 200                 205
Glu Lys Pro Leu Pro Asp Gln Ala Phe Phe Val Leu His Asn Met His
    210                 215                 220
Ser Asn Cys Val Ser Phe Glu Cys Lys Thr Asp Pro Gly Val Phe Ile
225                 230                 235                 240
Gly Val Lys Asp Asn His Leu Ala Leu Ile Lys Val Asp Ser Ser Glu
                245                 250                 255
Asn Leu Cys Thr Glu Asn Ile Leu Phe Lys Leu Ser Glu Thr Gly Ser
            260                 265                 270
Gly Gly Gly Gly Ser Gly Thr Ser Pro Gly Pro Val Pro Pro Ser Thr
        275                 280                 285
Ala Leu Arg Glu Leu Ile Glu Glu Leu Val Asn Ile Thr Gln Asn Gln
    290                 295                 300
Lys Ala Pro Leu Cys Asn Gly Ser Met Val Trp Ser Ile Asn Leu Thr
305                 310                 315                 320
Ala Gly Met Tyr Cys Ala Ala Leu Glu Ser Leu Ile Asn Val Ser Gly
                325                 330                 335
Cys Ser Ala Ile Glu Lys Thr Gln Arg Met Leu Ser Gly Phe Cys Pro
            340                 345                 350
His Lys Val Ser Ala Gly Gln Phe Ser Ser Leu His Val Arg Asp Thr
        355                 360                 365
Lys Ile Glu Val Ala Gln Phe Val Lys Asp Leu Leu Leu His Leu Lys
    370                 375                 380
Lys Leu Phe Arg Glu Gly Arg Phe Asn
385                 390

<210> SEQ ID NO 24
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Leu Asp Thr Asn Tyr Cys Phe Ser Ser Thr Glu Lys Asn Cys Cys
1               5                   10                  15
Val Arg Gln Leu Tyr Ile Asp Phe Arg Lys Asp Leu Gly Trp Lys Trp
            20                  25                  30
Ile His Glu Pro Lys Gly Tyr His Ala Asn Phe Cys Leu Gly Pro Cys
        35                  40                  45

```
Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Lys Cys Ser
            100                 105                 110

Gly Ser Gly Gly Gly Ser Gly Thr Ser Pro Gly Pro Val Pro Pro
            115                 120                 125

Ser Thr Ala Leu Arg Glu Leu Ile Glu Glu Leu Val Asn Ile Thr Gln
130                 135                 140

Asn Gln Lys Ala Pro Leu Cys Asn Gly Ser Met Val Trp Ser Ile Asn
145                 150                 155                 160

Leu Thr Ala Gly Met Tyr Cys Ala Ala Leu Glu Ser Leu Ile Asn Val
                165                 170                 175

Ser Gly Cys Ser Ala Ile Glu Lys Thr Gln Arg Met Leu Ser Gly Phe
            180                 185                 190

Cys Pro His Lys Val Ser Ala Gly Gln Phe Ser Ser Leu His Val Arg
        195                 200                 205

Asp Thr Lys Ile Glu Val Ala Gln Phe Val Lys Asp Leu Leu Leu His
210                 215                 220

Leu Lys Lys Leu Phe Arg Glu Gly Arg Phe Asn
225                 230                 235

<210> SEQ ID NO 25
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

Gly Ser Gly Gly Gly Ser Gly Thr Ser Pro Gly Pro Val Pro Pro
            115                 120                 125

Ser Thr Ala Leu Arg Glu Leu Ile Glu Glu Leu Val Asn Ile Thr Gln
130                 135                 140

Asn Gln Lys Ala Pro Leu Cys Asn Gly Ser Met Val Trp Ser Ile Asn
145                 150                 155                 160

Leu Thr Ala Gly Met Tyr Cys Ala Ala Leu Glu Ser Leu Ile Asn Val
```

```
                165                 170                 175
Ser Gly Cys Ser Ala Ile Glu Lys Thr Gln Arg Met Leu Ser Gly Phe
            180                 185                 190

Cys Pro His Lys Val Ser Ala Gly Gln Phe Ser Ser Leu His Val Arg
            195                 200                 205

Asp Thr Lys Ile Glu Val Ala Gln Phe Val Lys Asp Leu Leu Leu His
            210                 215                 220

Leu Lys Lys Leu Phe Arg Glu Gly Arg Phe Asn
225                 230                 235

<210> SEQ ID NO 26
<211> LENGTH: 113
<212> TYPE: PRT
<213> ORGANISM: Homo sapiens

<400> SEQUENCE: 26

His Lys Cys Asp Ile Thr Leu Gln Glu Ile Ile Lys Thr Leu Asn Ser
1               5                   10                  15

Leu Thr Glu Gln Lys Asn Thr Thr Glu Lys Glu Thr Phe Cys Arg Ala
            20                  25                  30

Ala Thr Val Leu Arg Gln Phe Tyr Ser His His Glu Lys Asp Thr Arg
        35                  40                  45

Cys Leu Gly Ala Thr Ala Gln Gln Phe His Arg His Lys Gln Leu Ile
    50                  55                  60

Arg Phe Leu Lys Arg Leu Asp Arg Asn Leu Trp Gly Leu Ala Gly Leu
65                  70                  75                  80

Asn Ser Cys Pro Val Lys Glu Ala Asn Gln Ser Thr Leu Glu Asn Phe
                85                  90                  95

Leu Glu Arg Leu Lys Thr Ile Met Arg Glu Lys Tyr Ser Lys Cys Ser
            100                 105                 110

Ser

<210> SEQ ID NO 27
<211> LENGTH: 129
<212> TYPE: PRT
<213> ORGANISM: Homo sapiens

<400> SEQUENCE: 27

His Lys Arg Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser
```

<210> SEQ ID NO 28
<211> LENGTH: 113
<212> TYPE: PRT
<213> ORGANISM: Homo sapiens

<400> SEQUENCE: 28

His Lys Arg Asp Ile Thr Leu Gln Glu Ile Lys Thr Leu Asn Ser
1               5                   10                  15

Leu Thr Glu Gln Lys Asn Thr Thr Glu Lys Glu Thr Phe Cys Arg Ala
            20                  25                  30

Ala Thr Val Leu Arg Gln Phe Tyr Ser His His Glu Lys Asp Thr Arg
        35                  40                  45

Cys Leu Gly Ala Thr Ala Gln Gln Phe His Arg His Lys Gln Leu Ile
    50                  55                  60

Arg Phe Leu Lys Arg Leu Asp Arg Asn Leu Trp Gly Leu Ala Gly Leu
65                  70                  75                  80

Asn Ser Cys Pro Val Lys Glu Ala Asn Gln Ser Thr Leu Glu Asn Phe
                85                  90                  95

Leu Glu Arg Leu Lys Thr Ile Met Arg Glu Lys Tyr Ser Lys Cys Ser
            100                 105                 110

Ser

<210> SEQ ID NO 29
<211> LENGTH: 176
<212> TYPE: PRT
<213> ORGANISM: Homo sapiens

<400> SEQUENCE: 29

Ala Phe Gly Ile Ser Gly Val Gln Lys Tyr Thr Arg Ala Leu His Asp
1               5                   10                  15

Ser Ser Ile Thr Gly Ile Ser Pro Ile Thr Glu Tyr Leu Ala Ser Leu
            20                  25                  30

Ser Thr Tyr Asn Asp Gln Ser Ile Thr Phe Ala Leu Glu Asp Glu Ser
        35                  40                  45

Tyr Glu Ile Tyr Val Glu Asp Leu Lys Lys Asp Glu Lys Lys Asp Lys
    50                  55                  60

Val Leu Leu Ser Tyr Tyr Glu Ser Gln His Pro Ser Asn Glu Ser Gly
65                  70                  75                  80

Asp Gly Val Asp Gly Lys Met Leu Met Val Thr Leu Ser Pro Thr Lys
                85                  90                  95

Asp Phe Trp Leu His Ala Asn Asn Lys Glu His Ser Val Glu Leu His
            100                 105                 110

Lys Cys Glu Lys Pro Leu Pro Asp Gln Ala Phe Phe Val Leu His Asn
        115                 120                 125

Met His Ser Asn Cys Val Ser Phe Glu Cys Lys Thr Asp Pro Gly Val
    130                 135                 140

Phe Ile Gly Val Lys Asp Asn His Leu Ala Leu Ile Lys Val Asp Ser
145                 150                 155                 160

Ser Glu Asn Leu Cys Thr Glu Asn Ile Leu Phe Lys Leu Ser Glu Thr
                165                 170                 175

<210> SEQ ID NO 30
<211> LENGTH: 172
<212> TYPE: PRT
<213> ORGANISM: Homo sapiens

<400> SEQUENCE: 30

```
Ser Gly Val Gln Lys Tyr Thr Arg Ala Leu His Asp Ser Ser Ile Thr
1               5                   10                  15

Gly Ile Ser Pro Ile Thr Glu Tyr Leu Ala Ser Leu Ser Thr Tyr Asn
                20                  25                  30

Asp Gln Ser Ile Thr Phe Ala Leu Glu Asp Glu Ser Tyr Glu Ile Tyr
            35                  40                  45

Val Glu Asp Leu Lys Lys Asp Glu Lys Lys Asp Lys Val Leu Leu Ser
    50                  55                  60

Tyr Tyr Glu Ser Gln His Pro Ser Asn Glu Ser Gly Asp Gly Val Asp
65                  70                  75                  80

Gly Lys Met Leu Met Val Thr Leu Ser Pro Thr Lys Asp Phe Trp Leu
                85                  90                  95

His Ala Asn Asn Lys Glu His Ser Val Glu Leu His Lys Cys Glu Lys
                100                 105                 110

Pro Leu Pro Asp Gln Ala Phe Phe Val Leu His Asn Met His Ser Asn
            115                 120                 125

Cys Val Ser Phe Glu Cys Lys Thr Asp Pro Gly Val Phe Ile Gly Val
    130                 135                 140

Lys Asp Asn His Leu Ala Leu Ile Lys Val Asp Ser Ser Glu Asn Leu
145                 150                 155                 160

Cys Thr Glu Asn Ile Leu Phe Lys Leu Ser Glu Thr
                165                 170

<210> SEQ ID NO 31
<211> LENGTH: 162
<212> TYPE: PRT
<213> ORGANISM: Homo sapiens

<400> SEQUENCE: 31

His Asp Ser Ser Ile Thr Gly Ile Ser Pro Ile Thr Glu Tyr Leu Ala
1               5                   10                  15

Ser Leu Ser Thr Tyr Asn Asp Gln Ser Ile Thr Phe Ala Leu Glu Asp
                20                  25                  30

Glu Ser Tyr Glu Ile Tyr Val Glu Asp Leu Lys Lys Asp Glu Lys Lys
            35                  40                  45

Asp Lys Val Leu Leu Ser Tyr Tyr Glu Ser Gln His Pro Ser Asn Glu
    50                  55                  60

Ser Gly Asp Gly Val Asp Gly Lys Met Leu Met Val Thr Leu Ser Pro
65                  70                  75                  80

Thr Lys Asp Phe Trp Leu His Ala Asn Asn Lys Glu His Ser Val Glu
                85                  90                  95

Leu His Lys Cys Glu Lys Pro Leu Pro Asp Gln Ala Phe Phe Val Leu
                100                 105                 110

His Asn Met His Ser Asn Cys Val Ser Phe Glu Cys Lys Thr Asp Pro
            115                 120                 125

Gly Val Phe Ile Gly Val Lys Asp Asn His Leu Ala Leu Ile Lys Val
    130                 135                 140

Asp Ser Ser Glu Asn Leu Cys Thr Glu Asn Ile Leu Phe Lys Leu Ser
145                 150                 155                 160

Glu Thr

<210> SEQ ID NO 32
<211> LENGTH: 228
<212> TYPE: PRT
<213> ORGANISM: Homo sapiens
```

<400> SEQUENCE: 32

```
Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
                100                 105                 110

Ile Thr Asp Lys Val Leu Leu Ser Tyr Tyr Glu Ser Gln His Pro Ser
            115                 120                 125

Asn Glu Ser Gly Asp Gly Val Asp Gly Lys Met Leu Met Val Thr Leu
130                 135                 140

Ser Pro Thr Lys Asp Phe Trp Leu His Ala Asn Asn Lys Glu His Ser
145                 150                 155                 160

Val Glu Leu His Lys Cys Glu Lys Pro Leu Pro Asp Gln Ala Phe Phe
                165                 170                 175

Val Leu His Asn Met His Ser Asn Cys Val Ser Phe Glu Cys Lys Thr
            180                 185                 190

Asp Pro Gly Val Phe Ile Gly Val Lys Asp Asn His Leu Ala Leu Ile
            195                 200                 205

Lys Val Asp Ser Ser Glu Asn Leu Cys Thr Glu Asn Ile Leu Phe Lys
210                 215                 220

Leu Ser Glu Thr
225
```

<210> SEQ ID NO 33
<211> LENGTH: 228
<212> TYPE: PRT
<213> ORGANISM: Homo sapiens

<400> SEQUENCE: 33

```
Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Ile Ser Pro Ile Thr Glu Tyr
65                  70                  75                  80

Leu Ala Ser Leu Ser Thr Tyr Asn Asp Gln Ser Ile Thr Phe Ala Leu
                85                  90                  95

Glu Asp Glu Ser Tyr Glu Ile Tyr Val Glu Asp Leu Lys Lys Asp Glu
                100                 105                 110

Lys Lys Asp Lys Val Leu Leu Ser Tyr Tyr Glu Ser Gln His Pro Ser
            115                 120                 125
```

```
Asn Glu Ser Gly Asp Gly Val Asp Gly Lys Met Leu Met Val Thr Leu
    130                 135                 140

Ser Pro Thr Lys Asp Phe Trp Leu His Ala Asn Asn Lys Glu His Ser
145                 150                 155                 160

Val Glu Leu His Lys Cys Glu Lys Pro Leu Pro Asp Gln Ala Phe Phe
                165                 170                 175

Val Leu His Asn Met His Ser Asn Cys Val Ser Phe Glu Cys Lys Thr
                180                 185                 190

Asp Pro Gly Val Phe Ile Gly Val Lys Asp Asn His Leu Ala Leu Ile
            195                 200                 205

Lys Val Asp Ser Ser Glu Asn Leu Cys Thr Glu Asn Ile Leu Phe Lys
    210                 215                 220

Leu Ser Glu Thr
225

<210> SEQ ID NO 34
<211> LENGTH: 144
<212> TYPE: PRT
<213> ORGANISM: Homo sapiens

<400> SEQUENCE: 34

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Asn Lys
                20                  25                  30

Val Leu Leu Ser Tyr Tyr Glu Ser Gln His Pro Ser Asn Glu Ser Gly
            35                  40                  45

Asp Gly Val Asp Gly Lys Met Leu Met Val Thr Leu Ser Pro Thr Lys
        50                  55                  60

Asp Phe Trp Leu His Ala Asn Asn Lys Glu His Ser Val Glu Leu His
65                  70                  75                  80

Lys Cys Glu Lys Pro Leu Pro Asp Gln Ala Phe Phe Val Leu His Asn
                85                  90                  95

Met His Ser Asn Cys Val Ser Phe Glu Cys Lys Thr Asp Pro Gly Val
            100                 105                 110

Phe Ile Gly Val Lys Asp Asn His Leu Ala Leu Ile Lys Val Asp Ser
        115                 120                 125

Ser Glu Asn Leu Cys Thr Glu Asn Ile Leu Phe Lys Leu Ser Glu Thr
    130                 135                 140

<210> SEQ ID NO 35
<211> LENGTH: 414
<212> TYPE: PRT
<213> ORGANISM: Homo sapiens

<400> SEQUENCE: 35

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
                20                  25                  30

Met Arg Lys Arg Ile Glu Ala Ile Arg Gly Gln Ile Leu Ser Lys Leu
            35                  40                  45

Lys Leu Thr Ser Pro Pro Glu Asp Tyr Pro Glu Pro Glu Glu Val Pro
        50                  55                  60

Pro Glu Val Ile Ser Ile Tyr Asn Ser Thr Arg Asp Leu Leu Gln Glu
65                  70                  75                  80
```

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Asn Ala Ile Pro Pro Thr Phe Tyr Arg Pro Tyr Phe Arg
        115                 120                 125

Ile Val Arg Phe Asp Val Ser Ala Met Glu Lys Asn Ala Ser Asn Leu
    130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
        195                 200                 205

Glu Trp Leu His His Lys Asp Arg Asn Leu Gly Phe Lys Ile Ser Leu
    210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Thr Ser Gly Asp Gln Lys Thr Ile Lys Ser Thr Arg Lys
            260                 265                 270

Lys Asn Ser Gly Lys Thr Pro His Leu Leu Leu Met Leu Leu Pro Ser
        275                 280                 285

Tyr Arg Leu Glu Ser Gln Gln Thr Asn Arg Arg Lys Lys Arg Ala Leu
    290                 295                 300

Asp Ala Ala Tyr Cys Phe Arg Asn Val Gln Asp Asn Cys Cys Leu Arg
305                 310                 315                 320

Pro Leu Tyr Ile Asp Phe Lys Arg Asp Leu Gly Trp Lys Trp Ile His
                325                 330                 335

Glu Pro Lys Gly Tyr Asn Ala Asn Phe Cys Ala Gly Ala Cys Pro Tyr
            340                 345                 350

Leu Trp Ser Ser Asp Thr Gln His Ser Arg Val Leu Ser Leu Tyr Asn
        355                 360                 365

Thr Ile Asn Pro Glu Ala Ser Ala Ser Pro Cys Cys Val Ser Gln Asp
    370                 375                 380

Leu Glu Pro Leu Thr Ile Leu Tyr Tyr Ile Gly Lys Thr Pro Lys Ile
385                 390                 395                 400

Glu Gln Leu Ser Asn Met Ile Val Lys Ser Cys Lys Cys Ser
                405                 410

<210> SEQ ID NO 36
<211> LENGTH: 215
<212> TYPE: PRT
<213> ORGANISM: Homo sapiens

<400> SEQUENCE: 36

Phe Pro Arg Pro Pro Gly Arg Pro Gln Leu Ser Leu Gln Glu Leu Arg
1               5                   10                  15

Arg Glu Phe Thr Val Ser Leu His Leu Ala Arg Lys Leu Leu Ser Glu
            20                  25                  30

Val Arg Gly Gln Ala His Arg Phe Ala Glu Ser His Leu Pro Gly Val

```
                35                  40                  45
Asn Leu Tyr Leu Leu Pro Leu Gly Glu Gln Leu Pro Asp Val Ser Leu
 50                  55                  60

Thr Phe Gln Ala Trp Arg Arg Leu Ser Asp Pro Glu Arg Leu Cys Phe
 65                  70                  75                  80

Ile Ser Thr Thr Leu Gln Pro Phe His Ala Leu Leu Gly Gly Leu Gly
                 85                  90                  95

Thr Gln Gly Arg Trp Thr Asn Met Glu Arg Met Gln Leu Trp Ala Met
                100                 105                 110

Arg Leu Asp Leu Arg Asp Leu Gln Arg His Leu Arg Phe Gln Val Leu
                115                 120                 125

Ala Ala Gly Phe Asn Leu Pro Glu Glu Glu Glu Glu Glu Glu Glu Glu
130                 135                 140

Glu Glu Glu Glu Arg Lys Gly Leu Leu Pro Gly Ala Leu Gly Ser Ala
145                 150                 155                 160

Leu Gln Gly Pro Ala Gln Val Ser Trp Pro Gln Leu Leu Ser Thr Tyr
                165                 170                 175

Arg Leu Leu His Ser Leu Glu Leu Val Leu Ser Arg Ala Val Arg Glu
                180                 185                 190

Leu Leu Leu Leu Ser Lys Ala Gly His Ser Val Trp Pro Leu Gly Phe
                195                 200                 205

Pro Thr Leu Ser Pro Gln Pro
                210                 215

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Ser
1

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Gly Gly Ser
1               5

<210> SEQ ID NO 39

<400> SEQUENCE: 39

000

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 40

Lys Glu Ser Gly Ser Val Ser Ser Glu Gln Leu Ala Gln Phe Arg Ser
1               5                   10                  15

Leu Asp

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Gly Lys Ser Ser Gly Ser Gly Ser Glu Ser Lys Ser Thr
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Ser Ala Gly Ser Ala Ala Gly Ser Gly Glu Phe
1               5                   10

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Ala Ala Ala Lys
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Ala Ala Ala Arg
1               5

<210> SEQ ID NO 45
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Arg Lys Gly Pro Pro Ala Ala Leu Thr Leu Pro Arg Val Gln Cys Arg
1               5                   10                  15

Ala Ser Arg Tyr Pro Ile Ala Val Asp Cys Ser Trp Thr Leu Pro Pro
                20                  25                  30
```

```
Ala Pro Asn Ser Thr Ser Pro Val Ser Phe Ile Ala Thr Tyr Arg Leu
        35                  40                  45

Gly Met Ala Ala Arg Gly His Ser Trp Pro Cys Leu Gln Gln Thr Pro
    50                  55                  60

Thr Ser Thr Ser Cys Thr Ile Thr Asp Val Gln Leu Phe Ser Met Ala
65                  70                  75                  80

Pro Tyr Val Leu Asn Val Thr Ala Val His Pro Trp Gly Ser Ser Ser
                85                  90                  95

Ser Phe Val Pro Phe Ile Thr Glu His Ile Ile Lys Pro Asp Pro Pro
                100                 105                 110

Glu Gly Val Arg Leu Ser Pro Leu Ala Glu Arg Gln Leu Gln Val Gln
            115                 120                 125

Trp Glu Pro Pro Gly Ser Trp Pro Phe Pro Glu Ile Phe Ser Leu Lys
        130                 135                 140

Tyr Trp Ile Arg Tyr Lys Arg Gln Gly Ala Ala Arg Phe His Arg Val
145                 150                 155                 160

Gly Pro Ile Glu Ala Thr Ser Phe Ile Leu Arg Ala Val Arg Pro Arg
                165                 170                 175

Ala Arg Tyr Tyr Val Gln Val Ala Ala Gln Asp Leu Thr Asp Tyr Gly
            180                 185                 190

Glu Leu Ser Asp Trp Ser Leu Pro Ala Thr Ala Thr Met Ser Leu Gly
        195                 200                 205

Lys
```

FUSION PROTEIN COMPRISING IL13

CROSS REFERENCE

This application is a divisional of U.S. patent application Ser. No. 17/158,785 filed Jan. 26, 2021, which is a continuation of International Application No. PCT/EP2020/060910, filed Apr. 17, 2020, which claims the benefit of Dutch Patent Application No. 2022982, filed Apr. 19, 2019, and Dutch Patent Application No. 2022984, filed Apr. 19, 2019, each of which is incorporated herein by reference in its entirety.

SEQUENCE LISTING STATEMENT

The instant application contains a Sequence Listing which has been submitted electronically in ASCII format and is hereby incorporated by reference in its entirety. Said ASCII copy, created on Jan. 22, 2021, is named 56780-702_401_SL.txt and is 67,224 bytes in size.

FIELD OF THE INVENTION

The present invention is in the field of neuro-immunology and pharmacology, particularly for treatment of chronic pain, neuro-inflammatory and neurodegenerative diseases, and inflammatory disorders. The invention particularly relates to a novel fusion protein comprising interleukin 13 (IL13) and a regulatory cytokine, for example, without limitation, an interleukin chosen from interleukin 4 (IL4), interleukin 10 (IL10), interleukin 27 (IL27), interleukin 33 (IL33), transforming growth factor beta 1 (TGFβ1), transforming growth factor beta 2 (TGFβ2), and IL13 itself, either or not physically fused together through a linker sequence. Particularly, the present invention provides an IL4/IL13, IL10/IL13, IL27/IL13, IL33/IL13, TGFβ1/IL13, TGFβ2/IL13, or IL13/IL13 fusion protein endowed with a superior analgesic, neuro-protective, and anti-inflammatory activity over a combination of the individual cytokines, or over a fusion protein of IL4 and IL10. The present invention also provides nucleic acid sequences encoding a fusion protein, for example, an IL4/IL13 fusion protein, IL10/IL13 fusion protein, IL27/IL13 fusion protein, IL33/IL13 fusion protein, TGFβ1/IL13 fusion protein, TGFβ2/IL13 fusion protein, or IL13/IL13 fusion protein, expression vectors comprising such nucleic acid sequences, host cells or host organisms altered to harbour the nucleic acid sequence encoding the IL4/IL13 fusion protein, IL10/IL13 fusion protein, IL27/IL13 fusion protein, IL33/IL13 fusion protein, TGFβ1/IL13 fusion protein, TGFβ2/IL13 fusion protein, IL/13/IL13 fusion protein, and the fusion protein itself. The invention further provides methods for producing an IL4/IL13, IL10/IL13, IL27/IL13, IL33/IL13, TGFβ1/IL13, TGFβ2/IL13, or IL13/IL13 fusion protein using a cell or organism harbouring such nucleic acid sequences. Transgenic organisms comprising the nucleic acid sequence of the invention are also provided. The present invention also relates to pharmaceutical compositions comprising for example, the IL4/IL13 or IL10/IL13 or IL27/IL13 or IL33/IL13 or TGFβ1/IL13 or TGFβ2/IL13 or IL13/IL13 fusion protein. Finally, the use of the IL4/IL13 or IL10/IL13 or IL27/IL13 or IL33/IL13 or TGFβ1/IL13 or TGFβ2/IL13 or IL13/IL13 fusion protein as a medicament, in particular for the prevention and/or treatment of chronic pain and of conditions characterized by neuro-inflammation, neuro-degeneration, or inflammation is taught herein.

BACKGROUND OF THE INVENTION

Chronic pain affects millions of people and constitutes the largest unmet need of modern medicine[1-4]. In 2016, an estimated 20.4% of U.S. adults (50.0 million) had chronic pain and 8.0% of U.S. adults (19.6 million) had high-impact chronic pain[5]. Opioids and non-steroidal anti-inflammatory drugs (NSAIDs) constitute the main classes of drugs to combat pain. However, these analgesics ("pain-killers") are often ineffective and have severe side effects (addiction, gastrointestinal bleeding, cardiovascular, other). It is estimated that ~50% of chronic pain patients (~5-10% of the total population) do not receive adequate pain relief[6].

People with chronic pain suffer from spontaneous pain, hyperalgesia (a heightened experience of pain to a noxious stimulus) and allodynia (pain caused by a normally non-painful stimulus). Pain has multiple causes and results from biological processes at various anatomic levels[7-10]: the generation of stimuli that trigger sensory nerve endings in the periphery; the stimulation, sensitization, and dysfunction of peripheral sensory neurons that transmit action potentials to the spinal cord; neurons and glial cells in the dorsal horn of the spinal cord where action potentials from peripheral neurons are transmitted to spinal pain neurons via synapses; and finally central mechanisms in the brain. The contribution of all of these processes to different types of chronic pain varies. Depending on this contribution pain is discriminated in several types, including nociceptive pain, peripheral and central neuropathic pain, and mixed types of pain. Analgesic drugs used in the clinic, target pain at only one level: NSAIDs reduce the generation of nociceptive stimuli in the periphery, whereas opioids inhibit central mechanisms. Together with their notorious toxic side effects, this explains the limited clinical efficacy of these analgesics.

Last decade it has become increasingly clear that pain signals are not straightforwardly transferred to the brain but rather are modulated by neuro-inflammatory processes involving glial cells in the spinal cord as well as sensory neurons. Cytokines are well-known to orchestrate immune and inflammatory processes, and also are crucial in the control of pain. Pro-inflammatory cytokines enhance inflammation and promote pain whilst regulatory (e.g., anti-inflammatory) cytokines dampen inflammation. The balance between proinflammatory and regulatory cytokines determines the outcome of inflammatory reactions in vivo[11]. Although pain promoting effects of pro-inflammatory cytokines are well-known[12], knowledge on the role of regulatory cytokines in pain is limited[13]. Blocking of regulatory cytokines such as TGFβ, IL10, IL4, and IL13, severely impairs the resolution of transient inflammatory hyperalgesia[14] and chemotherapy-induced allodynia[15], demonstrating a critical role for endogenous regulatory cytokines in pain resolution. This role of cytokines goes far beyond reducing inflammation and is fundamentally different from that of anti-inflammatory drugs such as corticosteroids which only have limited analgesic effects[16,17]. Notably, not only glial cells are modulated by cytokines, but also sensory neurons themselves can directly respond to cytokines. Indeed, sensory neurons express receptors for all regulatory cytokines, though expression differs among neuronal subsets[18]. Pain resulting from peripheral inflammation or nerve damage is associated with the activation of spinal microglia and astrocytes that promote pain by enhancing spinal pain signal transmission[19-22].

Considering the role of neuro-inflammation in chronic pain, regulatory cytokines potentially can target pain at multiple levels. Indeed, they dampen stimulation of nociceptors by reducing inflammation, they suppress sensitization and dysfunction of sensory neurons, and they prevent activation of pain pathways in the spinal cord by attenuating the production of pro-inflammatory mediators by glial cells[21,22].

However, the analgesic effects of therapy with stand-alone regulatory (e.g., IL10 or IL13) or anti-inflammatory cytokines (IL1-receptor antagonist) are limited[19], presumably because optimal analgesic activity requires synergy of various regulatory cytokines, and because of their relatively poor bioavailability due to rapid clearance by the kidney. Therefore, a new strategy to resolve chronic pain with regulatory cytokines has been proposed using a fusion-protein of IL4 and IL10[19,23]. Intrathecal administration of analgesics is common practice in pain treatment as this reduces the dose and decreases toxicity of an analgesic drug[24]. Intrathecal injection of IL4/IL10 fusion protein reduces pain in mouse models for a variety of different types of pain[19]. Remarkably, three repeated intrathecal administrations of IL4/IL10 fusion protein results in a sustained alleviation of pain (e.g., completely and permanently resolves chronic pain, such as nociceptive pain) induced by inflammation in the paw, without modulating peripheral inflammation itself[19]. Interestingly, the efficacy of IL4/IL10 fusion protein is superior to that of stand-alone wild-type cytokines, and even to that of the combination of these cytokines[19].

Resolution of pain by IL4/IL10 fusion protein was also observed in neuropathic[19] and osteoarthritis pain models[25]. However, the effect of IL4/IL10 fusion protein on neuropathic and osteoarthritis pain can be transient, even after multiple injections. Therefore, there is a need for providing a molecule for prevention or treatment of neuropathic pain and osteoarthritis pain that has a long-lasting analgesic effect.

SUMMARY

The present disclosure provides a single molecule that targets neuro-inflammation and -degeneration and has a long-lasting effect on chronic neuropathic pain. This molecule can be used for the treatment of various diseases or disorders with different etiology, in which chronic pain, neuro-inflammation and/or neuro-degeneration play a role. The present disclosure provides fusion proteins that comprise an interleukin 13 (IL13) directly or indirectly linked to an a regulatory cytokine.

Disclosed herein, in some aspects, is a fusion protein comprising an interleukin 13 (IL13) amino acid sequence and a regulatory cytokine amino acid sequence, for use in treatment of neuropathy in a subject in need thereof.

Disclosed herein, in some aspects, is a fusion protein comprising an interleukin 13 (IL13) amino acid sequence and a regulatory cytokine amino acid sequence, for use in treatment of pain in a subject in need thereof.

Disclosed herein, in some aspects, is a fusion protein comprising an interleukin 13 (IL13) amino acid sequence and a regulatory cytokine amino acid sequence, for use in treatment of neurodegeneration or neuroinflammation in a subject in need thereof.

Disclosed herein, in some aspects, is a fusion protein comprising an interleukin 13 (IL13) amino acid sequence and a regulatory cytokine amino acid sequence, for use in treatment of inflammation in a subject in need thereof.

Disclosed herein, in some aspects, is a fusion protein comprising an interleukin 13 (IL13) amino acid sequence and a regulatory cytokine amino acid sequence, for use in promoting neuroprotection in a subject in need thereof.

Disclosed herein, in some aspects, is a fusion protein comprising an interleukin 13 (IL13) amino acid sequence and a regulatory cytokine amino acid sequence, for use in modulating activity of a signaling pathway in a nervous system cell.

In some embodiments, the regulatory cytokine is selected from the group consisting of an interleukin 4 (IL4), an interleukin 10 (IL10), an interleukin 33 (IL33), a transforming growth factor beta 1 (TGFβ1), a transforming growth factor beta 2 (TGFβ2), and an additional interleukin 13 (IL13). In some embodiments, the regulatory cytokine is IL4. In some embodiments, the regulatory cytokine is IL10. In some embodiments, the regulatory cytokine is IL33. In some embodiments, the regulatory cytokine is an interleukin 27 (IL27). In some embodiments, the regulatory cytokine is TGFβ1. In some embodiments, the regulatory cytokine is TGFβ2. In some embodiments, the regulatory cytokine is an additional IL13. In some embodiments, the IL13 comprises a wild type IL13. In some embodiments, the IL13 is a mammalian IL13. In some embodiments, the IL13 is a human IL13. In some embodiments, the regulatory cytokine comprises a wild type regulatory cytokine. In some embodiments, the regulatory cytokine is a mammalian regulatory cytokine. In some embodiments, the regulatory cytokine is a human regulatory cytokine. In some embodiments, the interleukin 27 comprises an interleukin 27 alpha (IL27A). In some embodiments, the IL27A comprises an L134C substitution relative to SEQ ID NO: 36. In some embodiments, the IL13 binds to interleukin 13 receptor alpha 1 (IL-13Rα1) with an affinity that is less than two fold increased and less than two fold decreased compared to a wild type IL13. In some embodiments, the IL13 binds to interleukin 13 receptor alpha 2 (IL-13Rα2) with an affinity that is less than two fold increased and less than two fold decreased compared to a wild type IL13. In some embodiments, the IL13 binds to an interleukin 4 receptor alpha (IL-4Rα) with an affinity that is less than two fold increased and less than two fold decreased compared to a wild type IL13. In some embodiments, the regulatory cytokine amino acid sequence is a derivative sequence that binds to all subunits of a receptor of the regulatory cytokine with a comparable affinity as a wild type regulatory cytokine. In some embodiments, the regulatory cytokine amino acid sequence is a derivative sequence that activates a native receptor of the regulatory cytokine. In some embodiments, the IL13 comprises an amino acid sequence with at least 90% sequence identity to a sequence selected from the group consisting of SEQ ID NO: 2 and any one of SEQ ID NOs: 9-15. In some embodiments, the IL13 comprises an amino acid sequence that is selected from the group consisting of SEQ ID NO: 2 and any one of SEQ ID NOs: 9-15. In some embodiments, the IL13 comprises an amino acid sequence with between 1 and 10 amino acid deletions, insertions, substitutions, or a combination thereof relative to a sequence selected from the group consisting of SEQ ID NO: 2 and any one of SEQ ID NOs: 9-15. In some embodiments, the regulatory cytokine comprises an amino acid sequence with at least 90% sequence identity to a sequence selected from the group consisting of SEQ ID NO: 1, any one of SEQ ID NOs: 26-28, SEQ ID NO: 5, SEQ ID NO: 6, any one of SEQ ID NO: 29-34, SEQ ID NO: 7, SEQ ID NO: 21, SEQ ID NO: 8, SEQ ID NO: 22, SEQ ID No: 35, SEQ ID NO: 18, SEQ ID NO: 36, and SEQ ID NO: 45. In some embodiments, the regulatory cytokine comprises an amino acid sequence that is selected from the group consisting of SEQ ID NO: 1, any one of SEQ ID NOs: 26-28, SEQ ID NO: 5, SEQ ID NO: 6, any one of SEQ ID NO: 29-34, SEQ ID NO: 7, SEQ ID NO: 21, SEQ ID NO: 8, SEQ ID NO: 22, SEQ ID No: 35, SEQ ID NO: 18, SEQ ID NO: 36, and SEQ ID NO: 45. In some embodiments, the regulatory cytokine comprises an amino acid sequence with between 1 and 10 amino acid deletions, insertions, substitutions, or a combination thereof relative to a sequence selected from the group consisting SEQ ID NO: 1, any one of SEQ ID NOs: 26-28, SEQ ID NO: 5, SEQ ID NO: 6, any one of SEQ ID NO: 29-34, SEQ ID NO: 7, SEQ ID NO: 21, SEQ ID NO: 8, SEQ ID NO: 22, SEQ ID No: 35, SEQ ID NO: 18, SEQ ID NO: 36, and SEQ ID NO: 45. In some embodiments, the IL13 and the regulatory cytokine are covalently linked. In some embodiments, the IL13 and the regulatory cytokine are joined by a linker. In some embodiments, a C terminus of the IL13 is joined to an N-terminus of the cytokine, optionally via a linker. In some embodiments, an N terminus of the IL13 is joined to a C-terminus of the cytokine, optionally via a linker. In some embodiments, the fusion protein further comprises one or more chemical modifications. In some embodiments, the one or more chemical modifications are selected from the group consisting of glycosylation, fucosylation, sialylation, and pegylation. In some embodiments, the protein construct comprises an affinity tag. In some embodiments, the neuropathy is post-traumatic peripheral neuropathy, post-operative peripheral neuropathy, diabetic peripheral neuropathy, inflammatory peripheral neuropathy, HIV-associated neuropathy, chemotherapy-induced neuropathy, polyneuropathy, mononeuropathy, multiple mononeuropathy, cranial neuropathy, predominantly motor neuropathy, predominantly sensory neuropathy, sensory-motor neuropathy, autonomic neuropathy, idiopathic neuropathy, post-herpetic neuralgia, trigeminal neuralgia, glossopharyngeal neuralgia, occipital neuralgia, pudenal neuralgia, atypical trigeminal neuralgia, sciatica, brachial plexopathy, or intercostal neuralgia. In some embodiments, the neuropathy is associated with pain, numbness, weakness, burning, atrophy, tingling, twitching, or a combination thereof. In some embodiments, the pain is chronic pain. In some embodiments, the pain is pathological pain, inflammatory pain, neuropathic pain, nociceptive pain, or mixed nociceptive-neuropathic pain. In some embodiments, the pain is visceral nociceptive pain, non-visceral nociceptive pain, peripheral neuropathic pain, central neuropathic pain, or a combination thereof. In some embodiments, the pain is post-operative orthopedic surgery pain, musculoskeletal pain, chemotherapy-associated pain, chemotherapy-induced allodynia, post-spinal cord injury pain, post-stroke pain, low back pain, cancer pain, or chronic visceral pain. In some embodiments, the pain is associated with irritable bowel syndrome, inflammatory bowel disease, rheumatoid arthritis, ankylosing spondylitis, post-herpetic neuralgia, trigeminal neuralgia, post-traumatic peripheral neuropathy, post-operative peripheral neuropathy, diabetic peripheral neuropathy, inflammatory peripheral neuropathy, HIV-associated neuropathy, peripheral neuropathy, nerve entrapment syndrome, chemotherapy-induced neuropathy, multiple sclerosis, chemotherapy-induced neurodegeneration, complex regional pain syndrome, osteoarthritis, fibromyalgia, polymyalgia rheumatica, myofascial pain syndrome, Alzheimer's disease, Parkinson's disease, Huntington's disease, polyneuropathy, or amyotrophic lateral sclerosis. In some embodiments, the pain is associated with Alpers' Disease, Arachnoiditis, Arthrofibrosis, Ataxic Cerebral Palsy, Autoimmune Atrophic Gastritis, Amyloidosis, hATTR Amyloidosis, Avascular Necrosis, Back Pain, Batten Disease, Behçet's Disease (Syndrome), Breakthrough Pain, Burning Mouth Syndrome, Bursitis, Central Autosomal Dominant Arteriopathy with Subcortical Infarcts and Leukoencephalopathy (Cadasil), Cerebral ischemia, Cerebro-Oculo-Facio-Skeletal Syndrome (COFS), Carpal Tunnel syndrome, Cauda Equina Syndrome, Central Pain Syndrome, Cerebral Palsy, Cerebrospinal Fluid (CSF) Leaks, Cervical Stenosis, Charcot-Marie-Tooth (CMT) Disease, Chronic Functional Abdominal Pain (CFAP), Chronic Pancreatitis, Collapsed Lung (Pneumothorax), Corticobasal Degeneration, Compression injury, Corneal Neuropathic Pain, Crush syndrome, Degenerative Disc Disease, Dermatomyositis, Dementia, Dystonia, Ehlers-Danlos Syndrome (EDS), Endometriosis, Eosinophilia-Myalgia Syndrome (EMS), Erythromelalgia, Failed Back Surgery Syndrome (FBSS), Fibromyalgia, Friedreich's Ataxia, Frontotemporal dementia, Glossopharyngeal neuralgia, Growing Pains, Herniated disc, Hydrocephalus, Intercostal Neuraligia, Interstitial Cystitis, Juvenile Dermatositis, Knee Injury, Leg Pain, Lewy Body Dementia, Loin Pain-Haematuria Syndrome, Lyme Disease, Meralgia Paresthetica, Mitochondrial Disorders, Mixed dementia, Motor neurone diseases (MND), Monomelic Amyotrophy, Multiple system atrophy (MSA), Myositis, Neck Pain, Occipital Neuralgia, Osteoporosis, Rhabdomyolysis, Paget's Disease, Parsonage Turner Syndrome, Pelvic Pain, Peripheral Neuropathy, Phantom Limb Pain, Pinched Nerve, Plantar Fasciitis, Polymyalgia Rhuematica, Polymyositis, Post Herniorraphy Pain Syndrome, Post Mastectomy Pain Syndrome, Post Stroke Pain, Post Thorocotomy Pain Syndrome, Post-Polio Syndrome, Primary Lateral Sclerosis, Psoriatic Arthritis, Pudendal Neuralgia, Radiculopathy, Restless Leg Syndrome, Rheumatoid Arthritis (RA), Sacroiliac Joint Dysfunction, Sarcoidosis, Scheuemann's Kyphosis Disease, Sciatica, Spinocerebellar ataxia (SCA), Spinal muscular atrophy (SMA), Herpes Zoster Shingles, Spasmodic Torticollis, Sphincter of Oddi Dysfunction, Spinal Cord Injury, Spinal Stenosis, Syringomyelia, Tarlov Cysts, Tethered Cord Syndrome, Thoracic Outlet Syndrome (TOS), TMJ disorders, Transverse Myelitis, Traumatic Brain Injuries, Vascular Pain, Vulvodynia, Whiplash, or a combination thereof. In some embodiments, the neurodegeneration or neuroinflammation comprises Alzheimer's disease, Parkinson's disease, Huntington's disease, amyotrophic lateral sclerosis, multiple sclerosis, spinocerebellar ataxia, or spinal muscular atrophy. In some embodiments, the inflammation comprises chronic inflammation. In some embodiments, the inflammation comprises local inflammation or systemic inflammation. In some embodiments, the inflammation is associated with inflammatory bowel disease, irritable bowel syndrome, osteoarthritis, rheumatoid arthritis, glomerulonephritis, sepsis, adult respiratory distress syndrome, dermatitis, sarcoidosis, allergic inflammation, psoriasis, ankylosing spondylarthritis, systemic lupus erythematosus, vasculitis, gout, allotransplantation, xenotransplantation, an autoimmune disease, Sjogren's disease, a burn injury, trauma, stroke, myocardial infarction, atherosclerosis, diabetes mellitus, extracorporeal dialysis and blood oxygenation, ischemia-reperfusion injuries, and toxicity induced by the in vivo administration of cytokines or other therapeutic monoclonal antibodies. In some embodiments, nerve fiber degeneration is reduced. In some embodiments, nerve fiber loss is reduced. In some embodiments, maintenance of nerve fiber density is promoted. In some embodiments, nerve fiber regrowth is promoted. In some embodiments, neuroprotection in the central nervous system is promoted. In some embodiments, neuroprotection in the peripheral nervous system is promoted. In some embodiments, intraepidermal nerve fiber loss is reduced. In some embodiments, the neuronal dysfunction is reduced. In some embodiments, the fusion protein elicits a therapeutic effect of greater magnitude than equivalent amounts of the IL13, the regulatory cytokine, or a combination thereof. In some embodiments, the fusion protein elicits a therapeutic effect of greater duration than equivalent amounts of the IL13, the regulatory cytokine, or a combination thereof. In some embodiments, the fusion protein is present in a pharmaceutical composition comprising the fusion protein and one or more pharmaceutically-acceptable excipients. In some embodiments, the pharmaceutical composition is in a unit dosage form. In some embodiments, the fusion protein is present in the pharmaceutical composition at a concentration of about 50 μg per mL to about 100 mg per mL. In some embodiments, the fusion protein is formulated for administration in a dose of between about 0.5 μg per kg of body weight to about 1 mg per kg of body weight. In some embodiments, the fusion protein is formulated for administration in a controlled release formulation. In some embodiments, the fusion protein is formulated for administration by a parenteral, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intrasternal, intracerebral, intraocular, intralesional, intracerebroventricular, intracisternal, or intraparenchymal route. In some embodiments, the nervous system cell is a neuron. In some embodiments, the nervous system cell is a central nervous system cell. In some embodiments, the nervous system cell is a peripheral nervous system cell. In some embodiments, the neuron is a sensory neuron. In some embodiments, the neuron is a somatosensory neuron. In some embodiments, the neuron is a visceral sensory neuron. In some embodiments, the neuron is a nociceptor. In some embodiments, the neuron is an autonomic neuron. In some embodiments, the nervous system cell is a glial cell. In some embodiments, the nervous system cell is a microglial cell. In some embodiments, the nervous system cell is an infiltrating cell. In some embodiments, the nervous system cell is an infiltrating macrophage. In some embodiments, the signaling pathway is modulated in a presence of a pro-inflammatory mediator.

Disclosed herein, in some aspects, is a method of treating neuropathy in a subject in need thereof, comprising administering to the subject an effective amount of a fusion protein that comprises an interleukin 13 (IL13) amino acid sequence and a regulatory cytokine amino acid sequence.

Disclosed herein, in some aspects, is a method of treating pain in a subject in need thereof, comprising administering to the subject an effective amount of a fusion protein that comprises an interleukin 13 (IL13) amino acid sequence and a regulatory cytokine amino acid sequence.

Disclosed herein, in some aspects, is a method of treating neurodegeneration or neuroinflammation in a subject in need thereof, comprising administering to the subject an effective amount of a fusion protein that comprises an interleukin 13 (IL13) amino acid sequence and a regulatory cytokine amino acid sequence.

Disclosed herein, in some aspects, is a method of treating inflammation in a subject in need thereof, comprising administering to the subject an effective amount of a fusion protein that comprises an interleukin 13 (IL13) amino acid sequence and a regulatory cytokine amino acid sequence.

Disclosed herein, in some aspects, is a method of promoting neuroprotection in a subject in need thereof, comprising administering to the subject an effective amount of a fusion protein that comprises an interleukin 13 (IL13) amino acid sequence and a regulatory cytokine amino acid sequence.

Disclosed herein, in some aspects, is a method of modulating activity of a signaling pathway in nervous system cell, comprising contacting the nervous system cell with a fusion protein that comprises an interleukin 13 (IL13) amino acid sequence and a regulatory cytokine amino acid sequence.

In some embodiments, the regulatory cytokine is selected from the group consisting of an interleukin 4 (IL4), an interleukin 10 (IL10), an interleukin 33 (IL33), a transforming growth factor beta 1 (TGFβ1), a transforming growth factor beta 2 (TGFβ2), and an additional interleukin 13 (aIL13). In some embodiments, the regulatory cytokine is IL4. In some embodiments, the regulatory cytokine is IL10. In some embodiments, the regulatory cytokine is IL33. In some embodiments, the regulatory cytokine is an interleukin 27 (IL27). In some embodiments, the regulatory cytokine is TGFβ1. In some embodiments, the regulatory cytokine is TGFβ2. In some embodiments, the regulatory cytokine is an aIL13. In some embodiments, the IL13 comprises a wild type IL13. In some embodiments, the IL13 is a mammalian IL13. In some embodiments, the IL13 is a human IL13. In some embodiments, the regulatory cytokine comprises a wild type regulatory cytokine. In some embodiments, the regulatory cytokine is a mammalian regulatory cytokine. In some embodiments, the regulatory cytokine is a human regulatory cytokine. In some embodiments, the interleukin 27 comprises an interleukin 27 alpha (IL27A). In some embodiments, the IL27A comprises an L134C substitution relative to SEQ ID NO: 36. In some embodiments, the IL13 binds to interleukin 13 receptor alpha 1 (IL-13Rα1) with an affinity that is less than two fold increased and less than two fold decreased compared to a wild type IL13. In some embodiments, the IL13 binds to interleukin 13 receptor alpha 2 (IL-13Rα2) with an affinity that is less than two fold increased and less than two fold decreased compared to a wild type IL13. In some embodiments, the IL13 binds to an interleukin 4 receptor alpha (IL-4Rα) with an affinity that is less than two fold increased and less than two fold decreased compared to a wild type IL13. In some embodiments, the regulatory cytokine amino acid sequence is a derivative sequence that binds to all subunits of a receptor of the regulatory cytokine with a comparable affinity as a wild type regulatory cytokine. In some embodiments, the regulatory cytokine amino acid sequence is a derivative sequence that activates a native receptor of the regulatory cytokine. In some embodiments, the IL13 comprises an amino acid sequence with at least 90% sequence identity to a sequence selected from the group consisting of SEQ ID NO: 2 and any one of SEQ ID NOs: 9-15. In some embodiments, the IL13 comprises an amino acid sequence that is selected from the group consisting of SEQ ID NO: 2 and any one of SEQ ID NOs: 9-15. In some embodiments, the IL13 comprises an amino acid sequence with between 1 and 10 amino acid deletions, insertions, substitutions, or a combination thereof relative to a sequence selected from the group consisting of SEQ ID NO: 2 and any one of SEQ ID NOs: 9-15. In some embodiments, the regulatory cytokine comprises an amino acid sequence with at least 90% sequence identity to a sequence selected from the group consisting of SEQ ID NO: 1, any one of SEQ ID NOs: 26-28, SEQ ID NO: 5, SEQ ID NO: 6, any one of SEQ ID NO: 29-34, SEQ ID NO: 7, SEQ ID NO: 21, SEQ ID NO: 8, SEQ ID NO: 22, SEQ ID No: 35, SEQ ID NO: 18, SEQ ID NO: 36, and SEQ ID NO: 45. In some embodiments, the regulatory cytokine comprises an amino acid sequence that is selected from the group consisting of SEQ ID NO: 1, any one of SEQ ID NOs: 26-28, SEQ ID NO: 5, SEQ ID NO: 6, any one of SEQ ID NO: 29-34, SEQ ID NO: 7, SEQ ID NO: 21, SEQ ID NO: 8, SEQ ID NO: 22, SEQ ID No: 35, SEQ ID NO: 18, SEQ ID NO: 36, and SEQ ID NO: 45. In some embodiments, the regulatory cytokine comprises an amino acid sequence with between 1 and 10 amino acid deletions, insertions, substitutions, or a combination thereof relative to a sequence selected from the group consisting SEQ ID NO: 1, any one of SEQ ID NOs: 26-28, SEQ ID NO: 5, SEQ ID NO: 6, any one of SEQ ID NO: 29-34, SEQ ID NO: 7, SEQ ID NO: 21, SEQ ID NO: 8, SEQ ID NO: 22, SEQ ID No: 35, SEQ ID NO: 18, SEQ ID NO: 36, and SEQ ID NO: 45. In some embodiments, the IL13 and the regulatory cytokine are covalently linked. In some embodiments, the IL13 and the regulatory cytokine are joined by a linker. In some embodiments, a C terminus of the IL13 is joined to an N-terminus of the cytokine, optionally via a linker. In some embodiments, an N terminus of the IL13 is joined to a C-terminus of the cytokine, optionally via a linker. In some embodiments, the fusion protein further comprises one or more chemical modifications. In some embodiments, the one or more chemical modifications are selected from the group consisting of glycosylation, fucosylation, sialylation, and pegylation. In some embodiments, the protein construct comprises an affinity tag. In some embodiments, the neuropathy is post-traumatic peripheral neuropathy, post-operative peripheral neuropathy, diabetic peripheral neuropathy, inflammatory peripheral neuropathy, HIV-associated neuropathy, chemotherapy-induced neuropathy, polyneuropathy, mononeuropathy, multiple mononeuropathy, cranial neuropathy, predominantly motor neuropathy, predominantly sensory neuropathy, sensory-motor neuropathy, autonomic neuropathy, idiopathic neuropathy, post-herpetic neuralgia, trigeminal neuralgia, glossopharyngeal neuralgia, occipital neuralgia, pudenal neuralgia, atypical trigeminal neuralgia, sciatica, brachial plexopathy, or intercostal neuralgia. In some embodiments, the neuropathy is associated with pain, numbness, weakness, burning, atrophy, tingling, twitching, or a combination thereof. In some embodiments, the pain is chronic pain. In some embodiments, the pain is neuropathic pain, nociceptive pain, or mixed nociceptive-neuropathic pain. In some embodiments, the pain is visceral nociceptive pain, non-visceral nociceptive pain, peripheral neuropathic pain, central neuropathic pain, or a combination thereof. In some embodiments, the pain is post-operative orthopedic surgery pain, musculoskeletal pain, chemotherapy-associated pain, chemotherapy-induced allodynia, post-spinal cord injury pain, post-stroke pain, low back pain, cancer pain, or chronic visceral pain. In some embodiments, the pain is associated with irritable bowel syndrome, inflammatory bowel disease, rheumatoid arthritis, ankylosing spondylitis, post-herpetic neuralgia, trigeminal neuralgia, post-traumatic peripheral neuropathy, post-operative peripheral neuropathy, diabetic peripheral neuropathy, inflammatory peripheral neuropathy, HIV-associated neuropathy, peripheral neuropathy, nerve entrapment syndrome, chemotherapy-induced neuropathy, multiple sclerosis, chemotherapy-induced neurodegeneration, complex regional pain syndrome, osteoarthritis, fibromyalgia, polymyalgia rheumatica, myofascial pain syndrome, Alzheimer's disease, Parkinson's disease, Huntington's disease, polyneuropathy, or amyotrophic lateral sclerosis. In some embodiments, the pain is associated with Alpers' Disease, Arachnoiditis, Arthrofibrosis, Ataxic Cerebral Palsy, Autoimmune Atrophic Gastritis, Amyloidosis, hATTR Amyloidosis, Avascular Necrosis, Back Pain, Batten Disease, Behçet's Disease (Syndrome), Breakthrough Pain, Burning Mouth Syndrome, Bursitis, Central Autosomal Dominant Arteriopathy with Subcortical Infarcts and Leukoencephalopathy (Cadasil), Cerebral ischemia, Cerebro-Oculo-Facio-Skeletal Syndrome (COFS), Carpal Tunnel syndrome, Cauda Equina Syndrome, Central Pain Syndrome, Cerebral Palsy, Cerebrospinal Fluid (CSF) Leaks, Cervical Stenosis, Charcot-Marie-Tooth (CMT) Disease, Chronic Functional Abdominal Pain (CFAP), Chronic Pancreatitis, Collapsed Lung (Pneumothorax), Corticobasal Degeneration, Compression injury, Corneal Neuropathic Pain, Crush syndrome, Degenerative Disc Disease, Dermatomyositis, Dementia, Dystonia, Ehlers-Danlos Syndrome (EDS), Endometriosis, Eosinophilia-Myalgia Syndrome (EMS), Erythromelalgia, Failed Back Surgery Syndrome (FBSS), Fibromyalgia, Friedreich's Ataxia, Frontotemporal dementia, Glossopharyngeal neuralgia, Growing Pains, Herniated disc, Hydrocephalus, Intercostal Neuraligia, Interstitial Cystitis, Juvenile Dermatositis, Knee Injury, Leg Pain, Lewy Body Dementia, Loin Pain-Haematuria Syndrome, Lyme Disease, Meralgia Paresthetica, Mitochondrial Disorders, Mixed dementia, Motor neurone diseases (MND), Monomelic Amyotrophy, Multiple system atrophy (MSA), Myositis, Neck Pain, Occipital Neuralgia, Osteoporosis, Rhabdomyolysis, Paget's Disease, Parsonage Turner Syndrome, Pelvic Pain, Peripheral Neuropathy, Phantom Limb Pain, Pinched Nerve, Plantar Fasciitis, Polymyalgia Rhuematica, Polymyositis, Post Herniorraphy Pain Syndrome, Post Mastectomy Pain Syndrome, Post Stroke Pain, Post Thorocotomy Pain Syndrome, Post-Polio Syndrome, Primary Lateral Sclerosis, Psoriatic Arthritis, Pudendal Neuralgia, Radiculopathy, Restless Leg Syndrome, Rheumatoid Arthritis (RA), Sacroiliac Joint Dysfunction, Sarcoidosis, Scheuemann's Kyphosis Disease, Sciatica, Spinocerebellar ataxia (SCA), Spinal muscular atrophy (SMA), Herpes Zoster Shingles, Spasmodic Torticollis, Sphincter of Oddi Dysfunction, Spinal Cord Injury, Spinal Stenosis, Syringomyelia, Tarlov Cysts, Tethered Cord Syndrome, Thoracic Outlet Syndrome (TOS), TMJ disorders, Transverse Myelitis, Traumatic Brain Injuries, Vascular Pain, Vulvodynia, Whiplash, or a combination thereof. In some embodiments, the neurodegeneration or neuroinflammation comprises Alzheimer's disease, Parkinson's disease, Huntington's disease, amyotrophic lateral sclerosis, multiple sclerosis, spinocerebellar ataxia, or spinal muscular atrophy. In some embodiments, the inflammation comprises chronic inflammation. In some embodiments, the inflammation comprises local inflammation or systemic inflammation. In some embodiments, the inflammation is associated with inflammatory bowel disease, irritable bowel syndrome, osteoarthritis, rheumatoid arthritis, glomerulonephritis, sepsis, adult respiratory distress syndrome, dermatitis, sarcoidosis, allergic inflammation, psoriasis, ankylosing spondylarthritis, systemic lupus erythematosus, vasculitis, gout, allotransplantation, xenotransplantation, an autoimmune disease, Sjogren's disease, a burn injury, trauma, stroke, myocardial infarction, atherosclerosis, diabetes mellitus, extracorporeal dialysis and blood oxygenation, ischemia-reperfusion injuries, and toxicity induced by the in vivo administration of cytokines or other therapeutic monoclonal antibodies. In some embodiments, IL13 treatment is indicated. In some embodiments, IL4, IL10, IL27, IL33, TGFβ1, or TGFβ2 treatment is indicated. In some embodiments, the method reduces nerve fiber degeneration. In some embodiments, the method reduces nerve fiber loss. In some embodiments, the method promotes maintenance of nerve fiber density. In some embodiments, the method promotes nerve fiber regrowth. In some embodiments, the method promotes neuroprotection in the central nervous system. In some embodiments, the method promotes neuroprotection in the peripheral nervous system. In some embodiments, the method reduces intraepidermal nerve fiber loss. In some embodiments, the method reduces neuronal dysfunction. In some embodiments, administering the fusion protein elicits a therapeutic effect of greater magnitude than administering equivalent amounts of the IL13, the regulatory cytokine, or a combination thereof. In some embodiments, administering the fusion protein elicits a therapeutic effect of greater duration than administering equivalent amounts of the IL13, the regulatory cytokine, or a combination thereof. In some embodiments, administering results in a higher magnitude of pain alleviation as compared to a comparable amount of IL13 and the regulatory cytokine administered individually or in combination as measured by mechanical sensitivity to von Frey hairs in a paclitaxel-induced mouse model of neuropathy. In some embodiments, the fusion protein is present in a pharmaceutical composition comprising the fusion protein and one or more pharmaceutically-acceptable excipients. In some embodiments, the composition is in a unit dosage form. In some embodiments, the fusion protein is present in the pharmaceutical composition at a concentration of about 50 μg to about 100 mg per mL. In some embodiments, the fusion protein is administered in a dose of between about 0.5 μg to 1 mg per kg of body weight. In some embodiments, the fusion protein is administered in a controlled release formulation. In some embodiments, the fusion protein is administered by a parenteral, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intrasternal, intracerebral, intraocular, intralesional, intracerebroventricular, intracisternal, or intraparenchymal route. In some embodiments, the nervous system cell is a neuron. In some embodiments, the nervous system cell is a central nervous system cell. In some embodiments, the nervous system cell is a peripheral nervous system cell. In some embodiments, the neuron is a sensory neuron. In some embodiments, the neuron is a somatosensory neuron. In some embodiments, the neuron is a visceral sensory neuron. In some embodiments, the neuron is a nociceptor. In some embodiments, the neuron is an autonomic neuron. In some embodiments, the nervous system cell is a glial cell. In some embodiments, the nervous system cell is a microglial cell. In some embodiments, the nervous system cell is an infiltrating cell. In some embodiments, the nervous system cell is an infiltrating macrophage. In some embodiments, the signaling pathway is modulated in a presence of a pro-inflammatory mediator.

Disclosed herein, in some aspects, is a fusion protein comprising an interleukin 13 (IL13) amino acid sequence that is a wild type IL13 sequence and a regulatory cytokine amino acid sequence.

Disclosed herein, in some aspects, is a fusion protein comprising an interleukin 13 (IL13) amino acid sequence and a regulatory cytokine amino acid sequence that is a wild type sequence.

Disclosed herein, in some aspects, is a fusion protein comprising an interleukin 13 (IL13) amino acid sequence and a regulatory cytokine amino acid sequence, wherein the IL13 amino acid sequence is an IL13 derivative sequence that binds to interleukin 13 receptor alpha 1 (IL-13Rα1), interleukin 13 receptor alpha 2 (IL-13Rα2), and interleukin 4 receptor alpha (IL-4Rα) with a comparable affinity as a wild type interleukin 13 sequence.

Disclosed herein, in some aspects, is a fusion protein comprising an interleukin 13 (IL13) amino acid sequence and a regulatory cytokine amino acid sequence, wherein the regulatory cytokine amino acid sequence is a derivative sequence that binds to all receptor subunits that a wild type version of the regulatory cytokine binds with a comparable affinity as the wild type regulatory cytokine.

In some embodiments, the regulatory cytokine is selected from the group consisting of an interleukin 4 (IL4), an interleukin 10 (IL10), an interleukin 33 (IL33), a transforming growth factor beta 1 (TGFβ1), a transforming growth factor beta 2 (TGFβ2), and an additional interleukin 13 (aIL13). In some embodiments, the regulatory cytokine is IL4. In some embodiments, the regulatory cytokine is IL10. In some embodiments, the regulatory cytokine is IL33. In some embodiments, the regulatory cytokine is an interleukin 27 (IL27). In some embodiments, the regulatory cytokine is TGFβ1. In some embodiments, the regulatory cytokine is TGFβ2. In some embodiments, the regulatory cytokine is an additional interleukin 13 (aIL13). In some embodiments, the IL13 is a mammalian IL13. In some embodiments, the IL13 is a human IL13. In some embodiments, the IL13 comprises a wild type IL13. In some embodiments, the regulatory cytokine comprises a wild type regulatory cytokine. In some embodiments, the regulatory cytokine is a mammalian regulatory cytokine. In some embodiments, the regulatory cytokine is a human regulatory cytokine. In some embodiments, the interleukin 27 comprises an interleukin 27 alpha (IL27A). In some embodiments, the IL27A comprises an L134C substitution relative to SEQ ID NO: 36. In some embodiments, the IL13 binds to interleukin 13 receptor alpha 1 (IL-13Rα1) with an affinity that is less than two fold increased and less than two fold decreased compared to a wild type IL13. In some embodiments, the IL13 binds to interleukin 13 receptor alpha 2 (IL-13Rα2) with an affinity that is less than two fold increased and less than two fold decreased compared to a wild type IL13. In some embodiments, the IL13 binds to an interleukin 4 receptor alpha (IL-4Rα) with an affinity that is less than two fold increased and less than two fold decreased compared to a wild type IL13. In some embodiments, the regulatory cytokine amino acid sequence is a derivative sequence that binds to all subunits of a receptor of the regulatory cytokine with a comparable affinity as a wild type regulatory cytokine. In some embodiments, the regulatory cytokine amino acid sequence is a derivative sequence that activates a native receptor of the regulatory cytokine. In some embodiments, the IL13 comprises an amino acid sequence with at least 90% sequence identity to a sequence selected from the group consisting of SEQ ID NO: 2 and any one of SEQ ID NOs: 9-15. In some embodiments, the IL13 comprises an amino acid sequence that is selected from the group consisting of SEQ ID NO: 2 and any one of SEQ ID NOs: 9-15. In some embodiments, the IL13 comprises an amino acid sequence with between 1 and 10 amino acid deletions, insertions, substitutions, or a combination thereof relative to a sequence selected from the group consisting of SEQ ID NO: 2 and any one of SEQ ID NOs: 9-15. In some embodiments, the regulatory cytokine comprises an amino acid sequence with at least 90% sequence identity to a sequence selected from the group consisting of SEQ ID NO: 1, any one of SEQ ID NOs: 26-28, SEQ ID NO: 5, SEQ ID NO: 6, any one of SEQ ID NO: 29-34, SEQ ID NO: 7, SEQ ID NO: 21, SEQ ID NO: 8, SEQ ID NO: 22, SEQ ID No: 35, SEQ ID NO: 18, SEQ ID NO: 36, and SEQ ID NO: 45. In some embodiments, the regulatory cytokine comprises an amino acid sequence that is selected from the group consisting of SEQ ID NO: 1, any one of SEQ ID NOs: 26-28, SEQ ID NO: 5, SEQ ID NO: 6, any one of SEQ ID NO: 29-34, SEQ ID NO: 7, SEQ ID NO: 21, SEQ ID NO: 8, SEQ ID NO: 22, SEQ ID No: 35, SEQ ID NO: 18, SEQ ID NO: 36, and SEQ ID NO: 45. In some embodiments, the regulatory cytokine comprises an amino acid sequence with between 1 and 10 amino acid deletions, insertions, substitutions, or a combination thereof relative to a sequence selected from the group consisting SEQ ID NO: 1, any one of SEQ ID NOs: 26-28, SEQ ID NO: 5, SEQ ID NO: 6, any one of SEQ ID NO: 29-34, SEQ ID NO: 7, SEQ ID NO: 21, SEQ ID NO: 8, SEQ ID NO: 22, SEQ ID NO: 35, SEQ ID NO: 18, SEQ ID NO: 36, and SEQ ID NO: 45. In some embodiments, the IL13 and the regulatory cytokine are covalently linked. In some embodiments, the IL13 and the regulatory cytokine are joined by a linker. In some embodiments, a C terminus of the IL13 is joined to an N-terminus of the cytokine, optionally via a linker. In some embodiments, an N terminus of the IL13 is joined to a C-terminus of the cytokine, optionally via a linker. In some embodiments, the fusion protein further comprises one or more chemical modifications. In some embodiments, the one or more chemical modifications are selected from the group consisting of glycosylation, fucosylation, sialylation, and pegylation. In some embodiments, the protein construct comprises an affinity tag. In some embodiments, a nucleic acid molecule is provided that encodes the fusion protein. In some embodiments, the nucleic acid molecule is codon optimized for expression in the cell. In some embodiments, the nucleic acid molecule is a vector. In some embodiments, a cell comprises the nucleic acid. In some embodiments, the fusion protein is present in a pharmaceutical composition that also comprises a pharmaceutically-acceptable excipient. In some embodiments, the nucleic acid vectors is present in a pharmaceutical composition that also comprises a pharmaceutically-acceptable excipient. In some embodiments, the pharmaceutical composition is in a unit dosage form. In some embodiments, the fusion protein is present in the pharmaceutical composition at about 50 μg to about 100 mg per mL. In some embodiments, the fusion protein is formulated for administration as a dose of between about 0.5 μg to 1 mg per kg of body weight. In some embodiments, the fusion protein formulated for administration as a controlled release formulation. In some embodiments, the pharmaceutical composition is formulated for administration by a parenteral, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intrasternal, intracerebral, intraocular, intralesional, intracerebroventricular, intracisternal, or intraparenchymal route. In some embodiments, an effective amount of the pharmaceutical composition is administered to a subject in need thereof. In some embodiments, the fusion protein is produced by comprising culturing a cell under conditions that permit the production of the fusion protein, wherein the cell comprises the polynucleotide sequence. In some embodiments, the fusion protein is harvested. In some embodiments, the fusion protein is purified from harvested culture medium. In some embodiments, the fusion protein is used for crosslinking an interleukin 13 receptor with a regulatory cytokine receptor.

Disclosed herein, in some aspects, is a fusion protein comprising an interleukin 13 and an interleukin chosen from interleukin 4, interleukin 10, interleukin 33, transforming growth factor beta 1, transforming growth factor beta 2, and interleukin 13.

In some embodiments, the interleukin 13 and said interleukin chosen from interleukin 4, interleukin 10, interleukin 33, transforming growth factor beta 1, transforming growth factor beta 2, and interleukin 13, are linked by a linker sequence. In some embodiments, the interleukin 13 is fused N-terminal of the interleukin chosen from interleukin 4, interleukin 10, interleukin 33, transforming growth factor beta 1, transforming growth factor beta 2, and interleukin 13. In some embodiments, the interleukin chosen from interleukin 4, interleukin 10, interleukin 33, transforming growth factor beta 1, transforming growth factor beta 2, and interleukin 13, is fused N-terminal of the interleukin 13. In some embodiments, the fusion protein further comprises one or more chemical modification(s). In some embodiments, the chemical modification is selected from the group consisting of glycosylation, fucosylation, sialylation, and pegylation. In some embodiments, the interleukin 13 is human interleukin 13. In some embodiments, the interleukin 4 is human interleukin 4, and/or said interleukin 10 is human interleukin 10, and/or said interleukin 33 is human interleukin 33, and/or said transforming growth factor beta 1 is human transforming growth factor beta 1, and/or said transforming growth factor beta 2 is human transforming growth factor beta 2. In some embodiments, the fusion protein is encoded by a polynucleotide present in a nucleic acid molecule. In some embodiments, the nucleic acid molecule is present in a vector. In some embodiments, the nucleic acid molecule is present in a host cell. In some embodiments, the fusion protein is made by a method comprising the steps of: culturing the host cell under conditions permitting the production of the fusion protein, optionally, purifying the fusion protein from the conditioned culture medium. In some embodiments, the fusion protein is present in a pharmaceutical composition that also comprises a pharmaceutically acceptable carrier. In some embodiments, the fusion protein is used as a medicament. In some embodiments, the fusion protein is used in the prevention or treatment of a condition characterized by chronic pain, neuro-inflammation or neuro-degeneration. In some embodiments, the condition is further characterized by visceral or non-visceral nociceptive pain, peripheral or central neuropathic pain, or mixed nociceptive-neuropathic pain, neuro-inflammation, and/or neuro-degeneration. In some embodiments, the condition is selected from the group consisting of post-operative orthopedic surgery pain, musculoskeletal pain, irritable bowel syndrome, inflammatory bowel disease, rheumatoid arthritis, ankylosing spondylitis, post-herpetic neuralgia, trigeminal neuralgia, post-traumatic or post-operative peripheral neuropathy, diabetic peripheral neuropathy, inflammatory peripheral neuropathy, HIV-associated neuropathy, painful peripheral neuropathy, nerve entrapment syndrome, chemotherapy-associated pain, chemotherapy-induced allodynia, complex regional pain syndrome, post-spinal injury pain, post-stroke pain, multiple sclerosis, low back pain, osteoarthritis, cancer pain, chronic visceral pain, fibromyalgia, polymyalgia rheumatica, myofascial pain syndrome, Alzheimer's disease and Parkinson's disease, Huntington's disease, and/or amyotrophic lateral sclerosis, or multiple sclerosis. In some embodiments, the fusion protein is used in the prevention or treatment of a clinical condition in a mammal, such as a human, for which interleukin 13 is indicated. In some embodiments, the fusion protein is used in the prevention or treatment of a clinical condition in a mammal, such as a human, for which interleukin 4 and/or interleukin 10 and/or interleukin 33 and/or interleukin 27 and/or transforming growth factor beta 1 and/or transforming growth factor beta 2, is indicated.

Disclosed herein, in some aspects is a gene therapy vector containing nucleotide sequence(s) coding for interleukin 13 and an interleukin chosen from interleukin 4, interleukin 10, interleukin 27, interleukin 33, transforming growth factor beta 1, transforming growth factor beta 2, and interleukin 13, for use in the prevention or treatment of a condition characterized by chronic pain, neuro-inflammation and/or neuro-degeneration.

In some embodiments, the condition is further characterized by visceral or non-visceral nociceptive pain, peripheral or central neuropathic pain, or mixed nociceptive-neuropathic pain, neuro-inflammation, and/or neuro-degeneration. In some embodiments, the condition is selected from the group consisting of post-operative orthopedic surgery pain, musculoskeletal pain, irritable bowel syndrome, inflammatory bowel disease, rheumatoid arthritis, ankylosing spondylitis, post-herpetic neuralgia, trigeminal neuralgia, post-traumatic or post-operative peripheral neuropathy, diabetic peripheral neuropathy, inflammatory peripheral neuropathy, HIV-associated neuropathy, painful peripheral neuropathy, nerve entrapment syndrome, chemotherapy-associated pain, chemotherapy-induced allodynia, complex regional pain syndrome, post-spinal injury pain, post-stroke pain, multiple sclerosis, low back pain, osteoarthritis, cancer pain, chronic visceral pain, fibromyalgia, polymyalgia rheumatica, myofascial pain syndrome, Alzheimer's disease and Parkinson's disease, Huntington's disease, and/or amyotrophic lateral sclerosis, or multiple sclerosis.

In a some aspects, the present invention relates to a fusion protein comprising at least 2, 3, 4, preferably 2 regulatory (e.g., anti-inflammatory) interleukins chosen from the group consisting of interleukin 13 (IL13), interleukin 4 (IL4), interleukin 10 (IL10), interleukin 27 (IL27), interleukin 33 (IL33), transforming growth factor beta 1 (TGFβ1), and transforming growth factor beta 2 (TGFβ2).

Preferably, the present invention relates to a fusion protein comprising an IL13 and another, i.e. a second, interleukin/cytokine, preferably chosen from IL4, IL10, IL27, IL33, TGFβ1, TGFβ2, and IL13 itself.

In an embodiment, said IL13 and said interleukin chosen from IL4, IL10, IL27, IL33, TGFβ1, TGFβ2, or IL13 itself are connected by a linker.

In an embodiment, the interleukin chosen from IL4, IL10, IL27, IL33, TGFβ1, TGFβ2, or IL13 itself is fused N-terminal of the IL13.

In another embodiment, the IL13 is fused N-terminal of the interleukin chosen from IL4, IL10, IL27, IL33, TGFβ1, TGFβ2, or IL13 itself.

In an embodiment, said fusion protein further comprises one or more chemical modifications. Said chemical modifications may be selected from the group consisting of glycosylation, fucosylation, sialylation, and pegylation.

In an embodiment, said IL13 is human IL13.
In an embodiment said IL4 is human IL4.
In an embodiment, said IL10 is human IL10.
In an embodiment, said IL27 is human IL27.
In an embodiment, said IL33 is human IL33.
In an embodiment, said TGFβ1 is human TGFβ1.
In an embodiment, said TGFβ2 is human TGFβ2.

In a second aspect, the present invention pertains to a nucleic acid molecule comprising a polynucleotide encoding the fusion protein taught herein.

In another aspect, the present invention is directed to a vector comprising the nucleic acid molecule taught herein.

In an aspect, the present invention is concerned with a host cell comprising the nucleic acid molecule taught herein or the vector taught herein.

In an aspect, the present invention provides a method for producing a fusion protein as taught herein, said method comprising the steps of: culturing a host cell as taught herein under conditions permitting the production of the fusion protein as taught herein; and optionally, recovering the fusion protein.

In yet another aspect, the present invention provides for a pharmaceutical composition comprising the fusion protein as taught herein, and a pharmaceutically acceptable carrier or excipient.

The invention also pertains to a fusion protein as taught herein for use as a medicament, such as for use in the prevention or treatment of a condition characterized by pathological pain, chronic pain, neuroinflammation, neurodegeneration, and/or local or systemic inflammation. In this regard, "chronic" can be regarded as persisting at least 1, 2, 3, 4, 5, 6, 10, or 12 months, or even at least 1, 2, 3, 4, or 5 years. Said condition may be characterized by visceral or non-visceral inflammatory pain, visceral or non-visceral nociceptive pain, peripheral or central neuropathic pain, mixed nociceptive-neuropathic pain, neuro-inflammation, and/or neuro-degeneration, and/or may be selected from the group consisting of post-operative orthopedic surgery pain, musculoskeletal pain, irritable bowel syndrome, inflammatory bowel disease, rheumatoid arthritis, ankylosing spondylitis, post-herpetic neuralgia, trigeminal neuralgia, post-traumatic or post-operative peripheral neuropathy, diabetic peripheral neuropathy, inflammatory peripheral neuropathy, HIV-associated neuropathy, painful peripheral neuropathy, nerve entrapment syndrome, chemotherapy-associated pain, chemotherapy-induced allodynia, chemotherapy-induced peripheral neuropathy, complex regional pain syndrome, post-spinal injury pain, post-stroke pain, multiple sclerosis, low back pain, osteoarthritis, cancer pain, chronic visceral pain, fibromyalgia, polymyalgia rheumatica, chronic widespread pain, myofascial pain syndrome, Alzheimer's disease and Parkinson's disease, Huntington's disease, and/or amyotrophic lateral sclerosis, or multiple sclerosis.

In an aspect, the invention relates to a fusion protein as taught herein for use in the prevention or treatment of a clinical condition in a mammal, such as a human, for which IL4 or IL13 is indicated.

The invention is also concerned with a fusion protein as taught herein for use in the prevention or treatment of a clinical condition in a mammal, such as a human, for which IL10 or IL27 or IL33 or TGFβ1 or TGFβ2 is indicated.

Finally, the invention teaches a vector for use in the prevention or treatment of a condition characterized by chronic pain, neuroinflammation, neurodegeneration, and/or local or systemic inflammation. Said condition may be characterized by visceral or non-visceral nociceptive pain, peripheral or central neuropathic pain, or mixed nociceptive-neuropathic pain, neuro-inflammation, and/or neuro-degeneration, and/or may be selected from the group consisting of post-operative orthopedic surgery pain, musculoskeletal pain, irritable bowel syndrome, inflammatory bowel disease, rheumatoid arthritis, ankylosing spondylitis, post-herpetic neuralgia, trigeminal neuralgia, post-traumatic or post-operative peripheral neuropathy, diabetic peripheral neuropathy, inflammatory peripheral neuropathy, HIV-associated neuropathy, painful peripheral neuropathy, nerve entrapment syndrome, chemotherapy-associated pain, complex regional pain syndrome, post-spinal injury pain, post-stroke pain, multiple sclerosis, low back pain, osteoarthritis, cancer pain, chronic visceral pain, fibromyalgia, polymyalgia rheumatica, myofascial pain syndromes, Alzheimer's disease and Parkinson's disease, Huntington's disease, and/or amyotrophic lateral sclerosis, or multiple sclerosis.

BRIEF DESCRIPTION OF THE FIGURES RELATED TO THE INVENTION

The features of the present disclosure are set forth with particularity in the appended claims. A better understanding of the features and advantages of the present disclosure can be obtained by reference to the following detailed description that sets forth illustrative embodiments, in which the principles of the disclosure are utilized, and the accompanying drawings of which:

FIG. 1. Regulatory (e.g., anti-inflammatory) cytokines are required for resolution of chemotherapy-induced pain. Mice were intraperitoneally injected with 2 mg/kg paclitaxel at day 0 and 2 to induce transient painful chemotherapy-induced polyneuropathy. From day 6 on, mice received daily intrathecal injections of neutralizing antibodies to endogenous IL4 (n=4; open downward triangles), or IL13 (n=4; closed upward triangles) for 5 days (5 µg antibody per injection). As a control, isotype IgG was injected intrathecally in mice treated with paclitaxel (n=3; dotted line with open circles). As another control, mice were pretreated with vehicle instead of paclitaxel and control IgG (n=3; closed line with closed circles). Pain-like behavior was followed over time by measuring mechanical sensitivity to touch using von Frey hairs. Note that a lower 50% threshold indicates increased sensitivity. Data represent mean and standard error of the mean. Statistical differences are indicated as $*p<0.05$, $p<0.01$, $*p<0.001$ between anti-IL13 IgG versus control IgG treated mice. x $p<0.05$, xx $p<0.01$ between anti-IL4 IgG versus control IgG treated mice.

Figure 2:
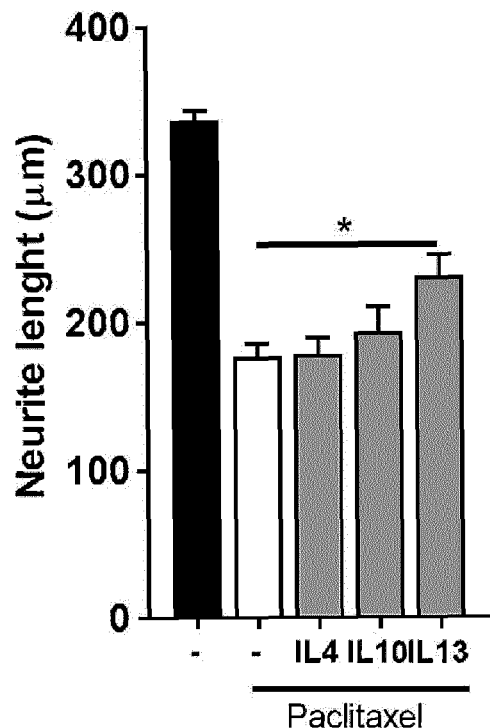

FIG. 2. IL13 attenuates paclitaxel-induced damage to neurons. Primary sensory neurons were cultured and treated overnight with Paclitaxel (1 µM) to induce neuronal damage that was quantified by measuring the neurite length after β3-tubulin staining. Vehicle (−) or individual cytokines (50 ng/ml) were added during treatment with the chemotherapeutic drug, and the average length of neurons was measured. Data represent mean and standard error of the mean of the neurite length in microns of >10 cells measured in at least 2 experiments.

Figure 3:
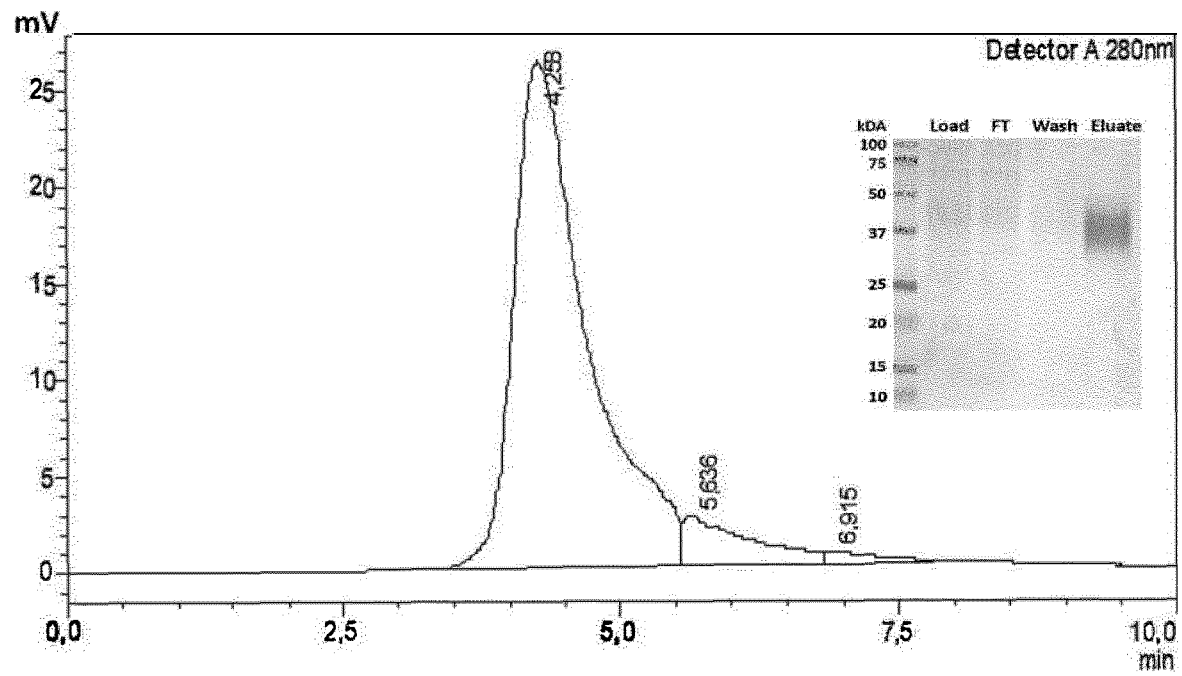

FIG. 3. Characterization of recombinant IL4/IL13 fusion protein. His-tagged IL4/IL13 fusion protein was expressed in HEK293 cells, purified using HIS-Select Nickel Affinity chromatography, and analyzed with High Pressure Size Exclusion Chromatography (HP-SEC). The HP-SEC profile indicates a homogenous monomeric preparation. Insert shows Sodium Dodecyl Sulfate Polyacrylamide Gel Electrophoresis (SDS-PAGE) analysis of starting material (load), flow through (FT), washing buffer (wash) and eluate of the His-tag purification column. The gel was stained with Coomassie Blue. Note that IL4/IL13 fusion protein migrates as a smear at 37 kDa.

Figure 4:
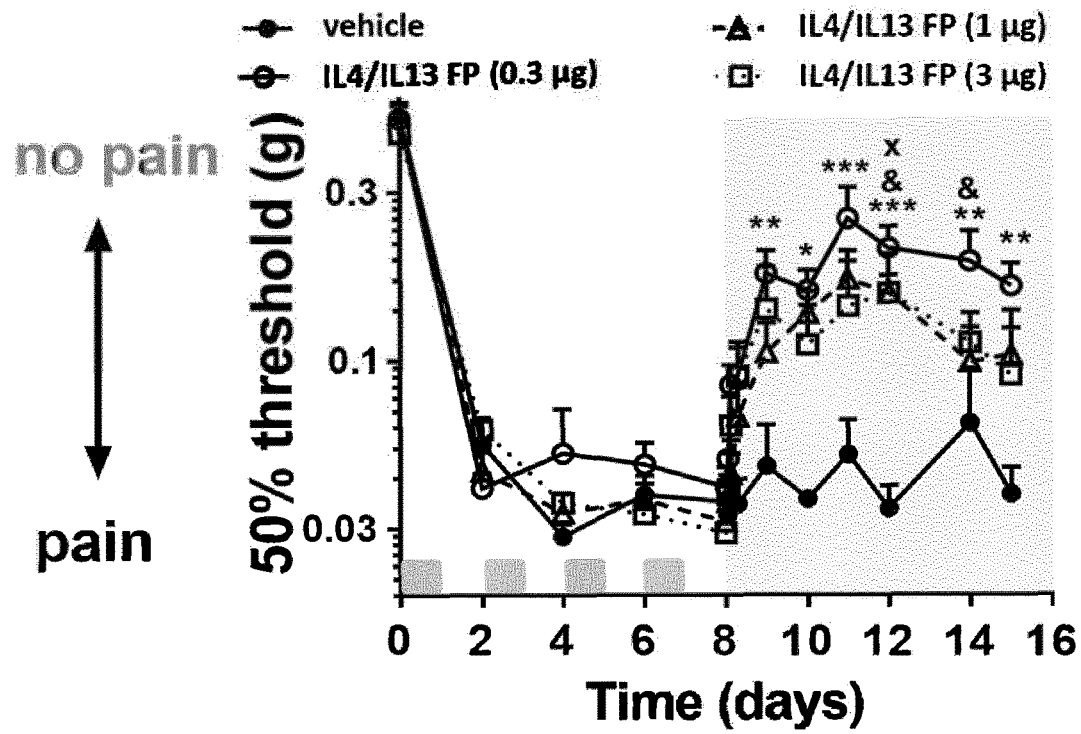

FIG. 4. IL4/IL13 fusion protein relieves paclitaxel-induced persistent mechanical allodynia. Paclitaxel (8 mg/kg) was administered intraperitoneally to C57BL/6 mice on days 0, 2, 4 and 6 (grey symbols on the X-axis) to induce persistent chemotherapy-induced polyneuropathy. IL4/IL13 fusion protein (0.3 [open circle], 1 [open triangle] or 3 µg/mouse [open square]; n=4/group) or vehicle (n=4) was administered intrathecally at day 8, and the course of mechanical allodynia was followed over time using von Frey hairs. Data is represented as mean±SEM. Statistics of the data were analysed with two-way ANOVA followed by Tukey's multiple comparisons test. *, , *=$p<0.05$, $p<0.01$, and $0.001$, 0.3 µg IL4/IL13 fusion protein versus vehicle respectively. &, =$p<0.05$, 3 µg IL4/IL13 fusion protein versus vehicle. x=$p<0.05$, 1 µg IL4/IL13 fusion protein versus vehicle.

Figure 5:
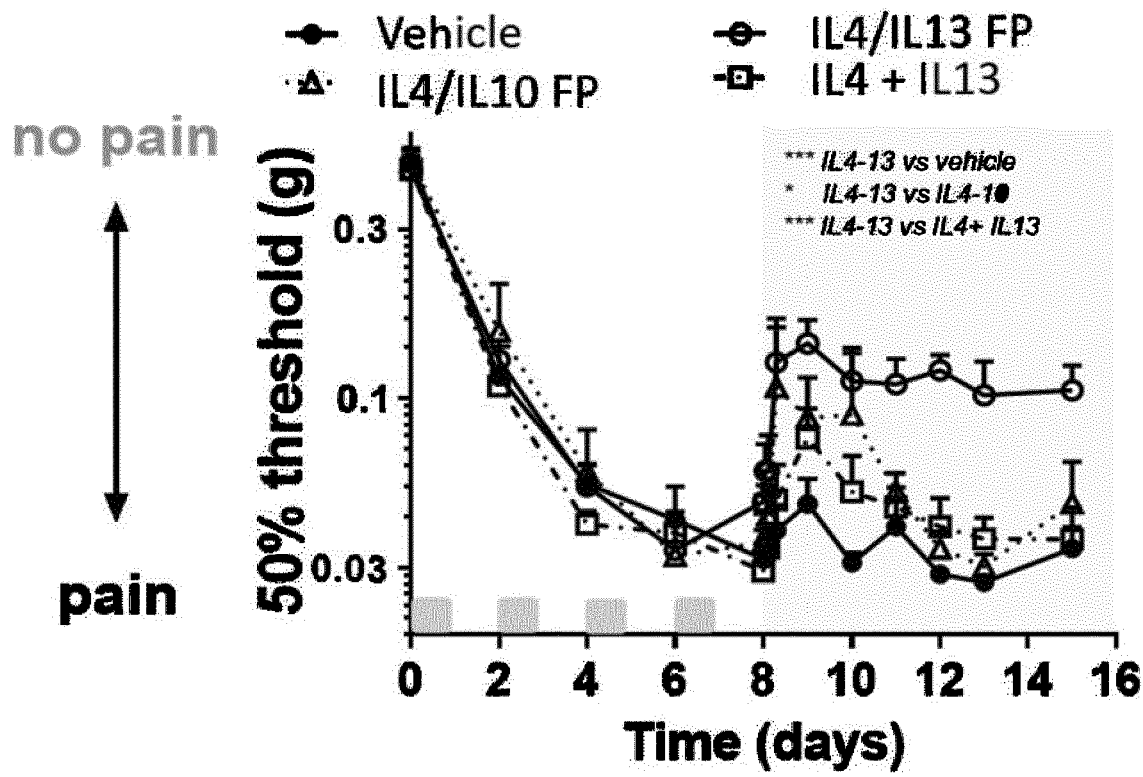

FIG. 5. IL4/IL13 fusion protein has a longer lasting effect on painful paclitaxel-induced neuropathy in mice than IL4/IL10 fusion protein. Mice received 4 intraperitoneal injections of 8 mg/kg paclitaxel every other day (grey symbols on X-axis) to induce persisting painful chemotherapy-induced polyneuropathy. At day 8, mice received a single intrathecal injection of IL4/IL13 fusion protein (0.7 µg; open circles, n=4), IL4/IL10 fusion protein (0.7 µg; open triangles, n=3), the combination of wildtype IL4 and IL13 (0.35 µg/cytokine; open squares, n=4) or vehicle (closed circles, n=4). Pain-like behavior was tested with von Frey hairs (see FIG. 1). Note that a single administration of IL4/IL13 fusion protein results in a sustained alleviation of pain (e.g., permanently resolves pain), whereas IL4/IL10 fusion protein has a temporary effect lasting 2 days in this experiment.

Figure 6:
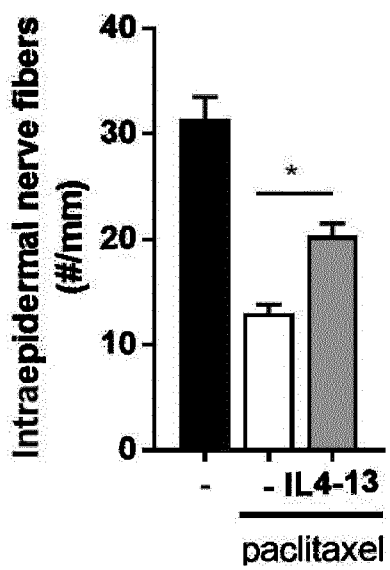

FIG. 6. IL4/IL13 fusion protein protects against paclitaxel-induced nerve damage in mice. Mice received 4 intraperitoneal injections of 8 mg/kg paclitaxel every other day to induce persisting painful chemotherapy-induced polyneuropathy. On day 8, they were treated with a single intrathecal injection of IL4/IL13 fusion protein (0.7 µg), or vehicle. On day 15, the length of intraepidermal nerve fibers in the paw skin was determined upon immunofluorescent visualization with the neuronal marker PGP9.5. The data of mice not treated with chemotherapeutic drug (black bar; n=4), or injected with paclitaxel and subsequently treated with vehicle (−; n=6) or IL4/IL3 fusion protein (IL4-13; n=4), are shown.

Figure 7:
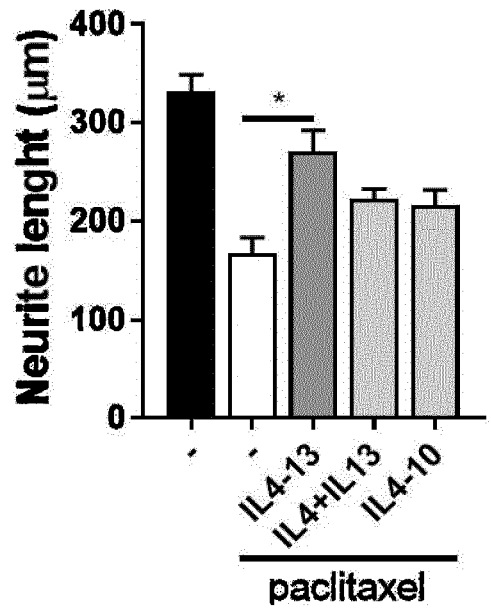

FIG. 7. IL4/IL13 fusion protein protects cultured neurons against chemotherapy induced damage better than IL4/IL10 fusion protein or the combination of IL4 and IL13. Primary sensory neurons were cultured overnight in presence of paclitaxel (1 µM) to induce neuronal damage that was quantified by measuring the neurite length upon β3-tubulin staining. Vehicle (−) or IL4/IL13 fusion protein (IL4-13), IL4/IL10 fusion protein (IL4-10) or the combination of IL4 and IL13 (IL4+IL13) were added at equimolar concentrations during incubation with the chemotherapeutic drug. Neurons cultured in absence of paclitaxel and cytokines are shown for comparison (black bar).

Figure 8:
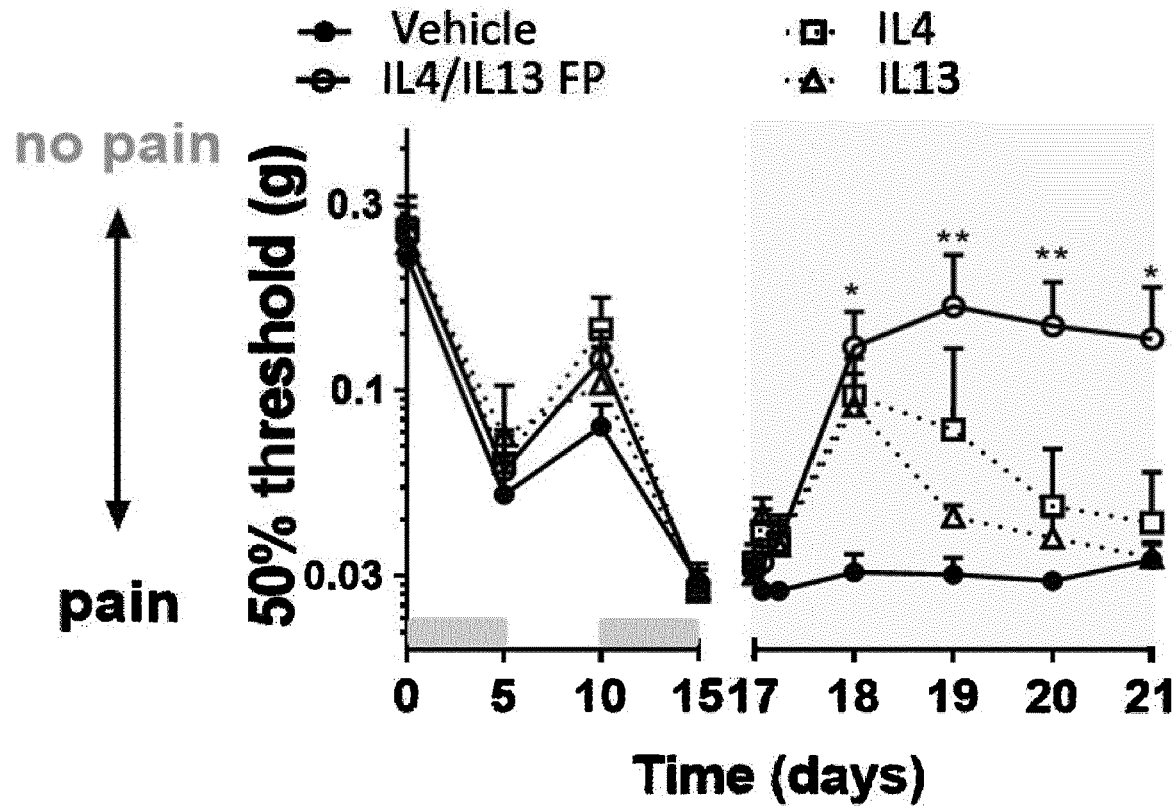

FIG. 8. IL4/IL13 cures oxaliplatin-induced polyneuropathy in mice whereas IL4 or IL13 only have a partial transient effect. Oxaliplatin (3 mg/kg) was daily injected intraperitoneally in mice for 5 days followed by 5 days no treatment and another 5 days of an oxaliplatin treatment cycle (grey symbols on X-axis). On the day after the last oxaliplatin injection animals received an intrathecal injection of IL4/IL13 fusion protein (0.3 µg; open circles, n=4) or the wild-type cytokines (0.15 µg; n=4, rectangles for IL4 and triangles for IL13); or vehicle only (closed circles). Pain was measured with von Frey test.

Figure 9:
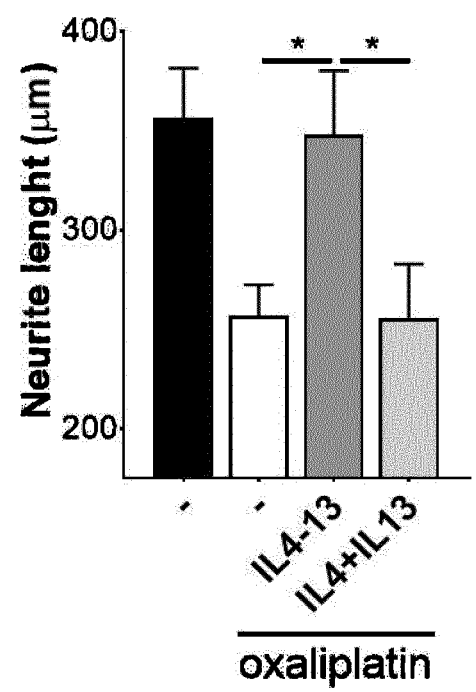

FIG. 9. IL4/IL13 fusion protein, but not the combination of IL4 and IL13, protects cultured neurons against oxaliplatin-induced damage. Primary sensory neurons were cultured and treated overnight with oxaliplatin (5 µg/ml). Neuronal damage was then quantified by measuring the neurite length upon β3-tubulin staining. Vehicle (−) or IL4/IL13 fusion protein or the combination of IL4 and IL13 (IL4+IL13) were added at equimolar concentrations during incubation with the chemotherapeutic drug. Neurons cultured in absence of oxaliplatin and cytokines are shown for comparison (black bar).

Figure 10:
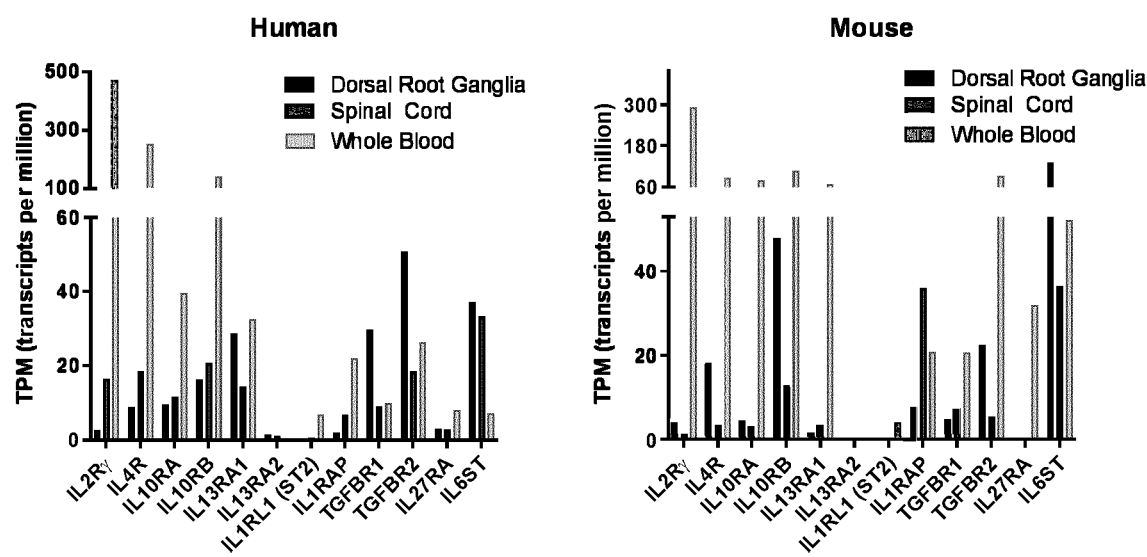

FIG. 10. Cytokine-receptor subunits of IL10, IL4, IL13, IL33, IL27, TGFβ1, and TGFβ2 are expressed in the dorsal root ganglia of human and mouse. To evaluate whether cytokine receptors targeted by fusion proteins of the present invention are expressed by the sensory system, RNAseq data of cytokine receptor subunits for IL10, IL4, IL13, IL33, IL27 TGFβ1, and TGFβ2 in the dorsal root ganglia and spinal cord were extracted from the data base by Ray et al. (Pain 2018; 159:1325-1345) as available on www_utdallas.edu/bbs/painneurosciencelab/sensoryomics/drgtxome/?go. RNA sequencing data are expressed as transcripts per million. For comparison, data for expression of the receptors in whole blood are also given.

Figure 11:
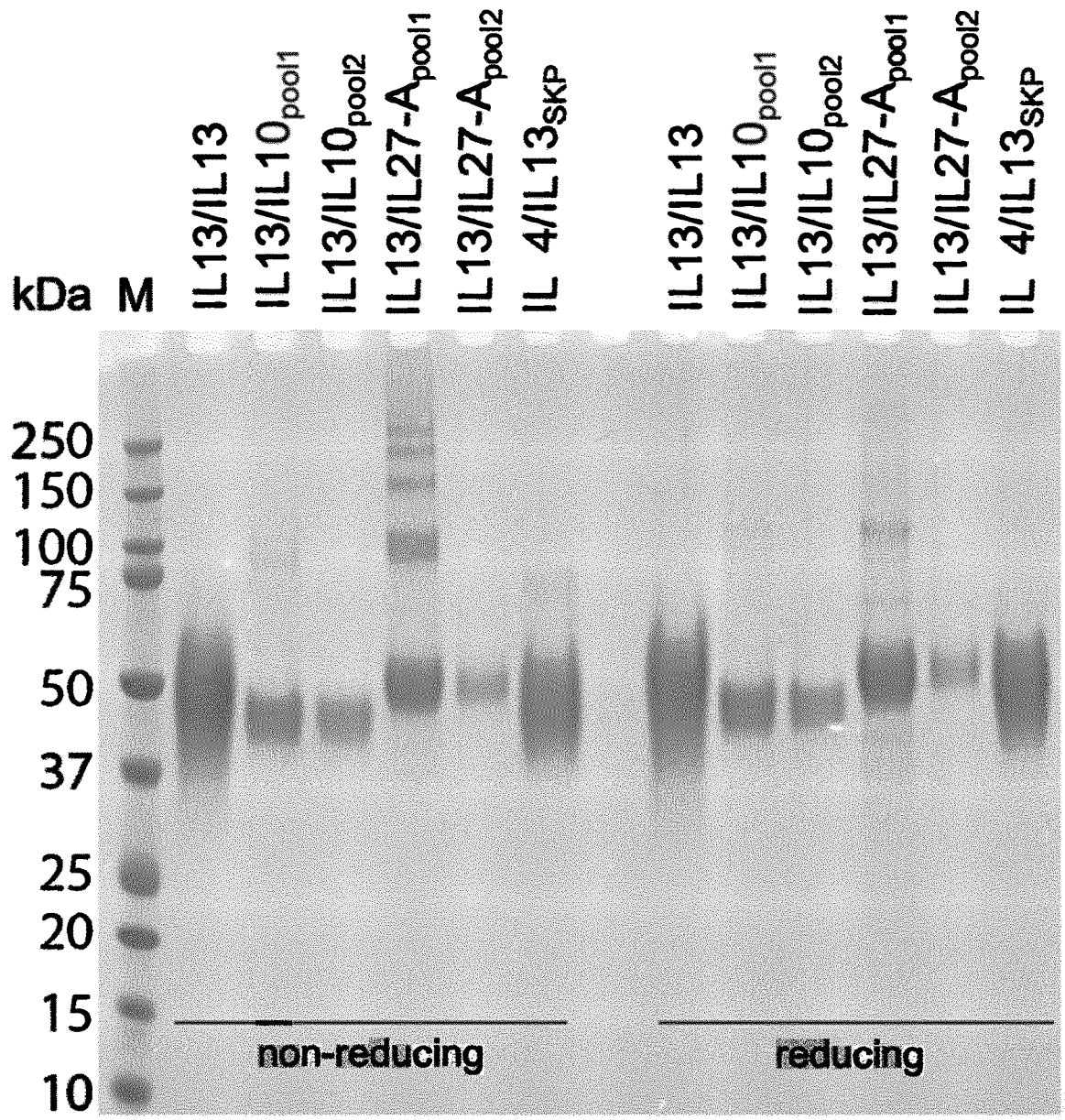

FIG. 11. Characterization of fusion proteins. Purified fusion proteins were analysed on a 4-12% gradient NuPage™ polyacrylamide gel under non-reducing and reducing conditions, and bands were visualized by Coomassie protein stain.

Figure 12:
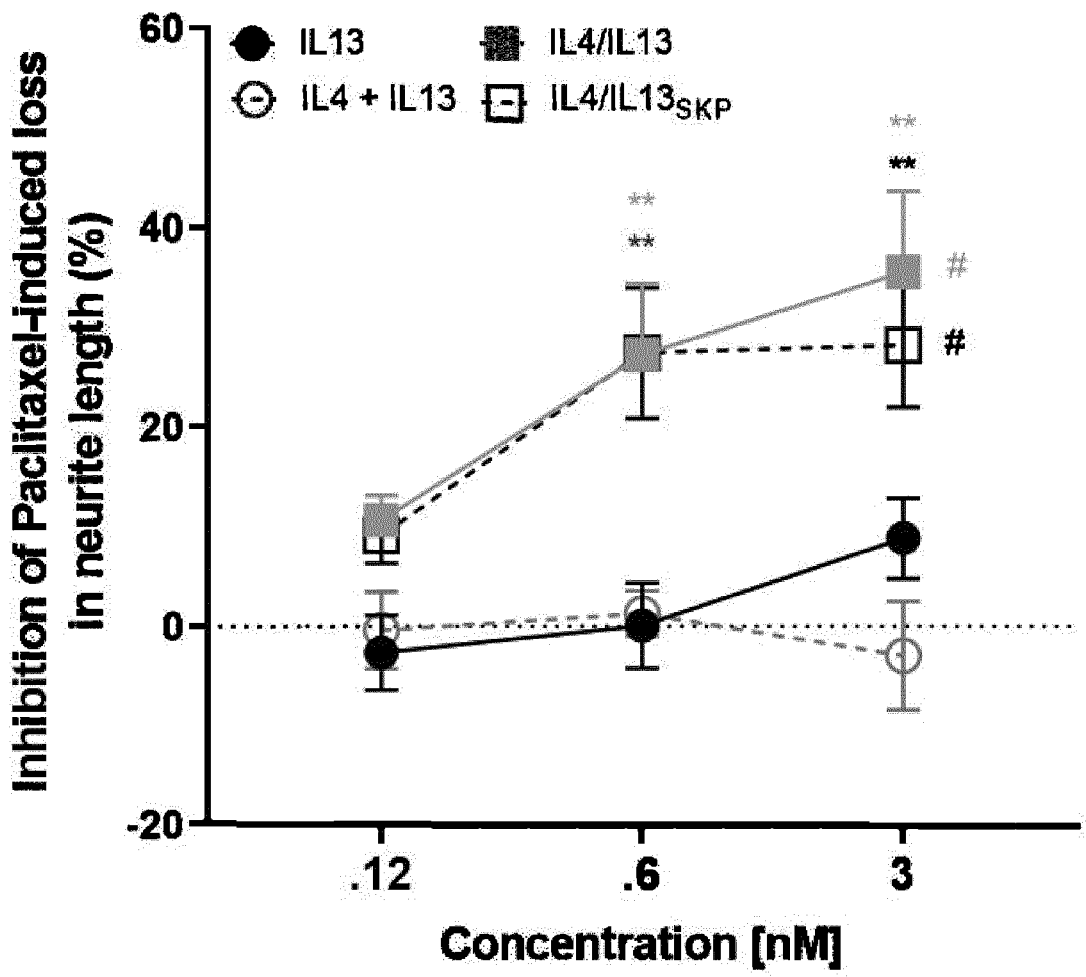

FIG. 12. Two IL4/IL13 fusion proteins of the disclosure protect neurons against chemotherapy induced neuron damage. Primary sensory neurons were cultured for 24 h in the presence of paclitaxel (1 µM), and different concentrations of each fusion protein or equimolar doses of IL13 or the combination of unlinked cytokines. The inhibition of paclitaxel-induced decrease in neurite length was calculated. The fusion protein labeled IL4/IL13 comprises SEQ ID NO: 4. The fusion protein labeled IL4/IL13$_{SKP}$ comprises SEQ ID NO: 16. Data are shown as mean±SEM. Data are analysed with a two-way ANOVA mixed-effects analysis followed by Tukey's multiple comparison test.

Figure 13:
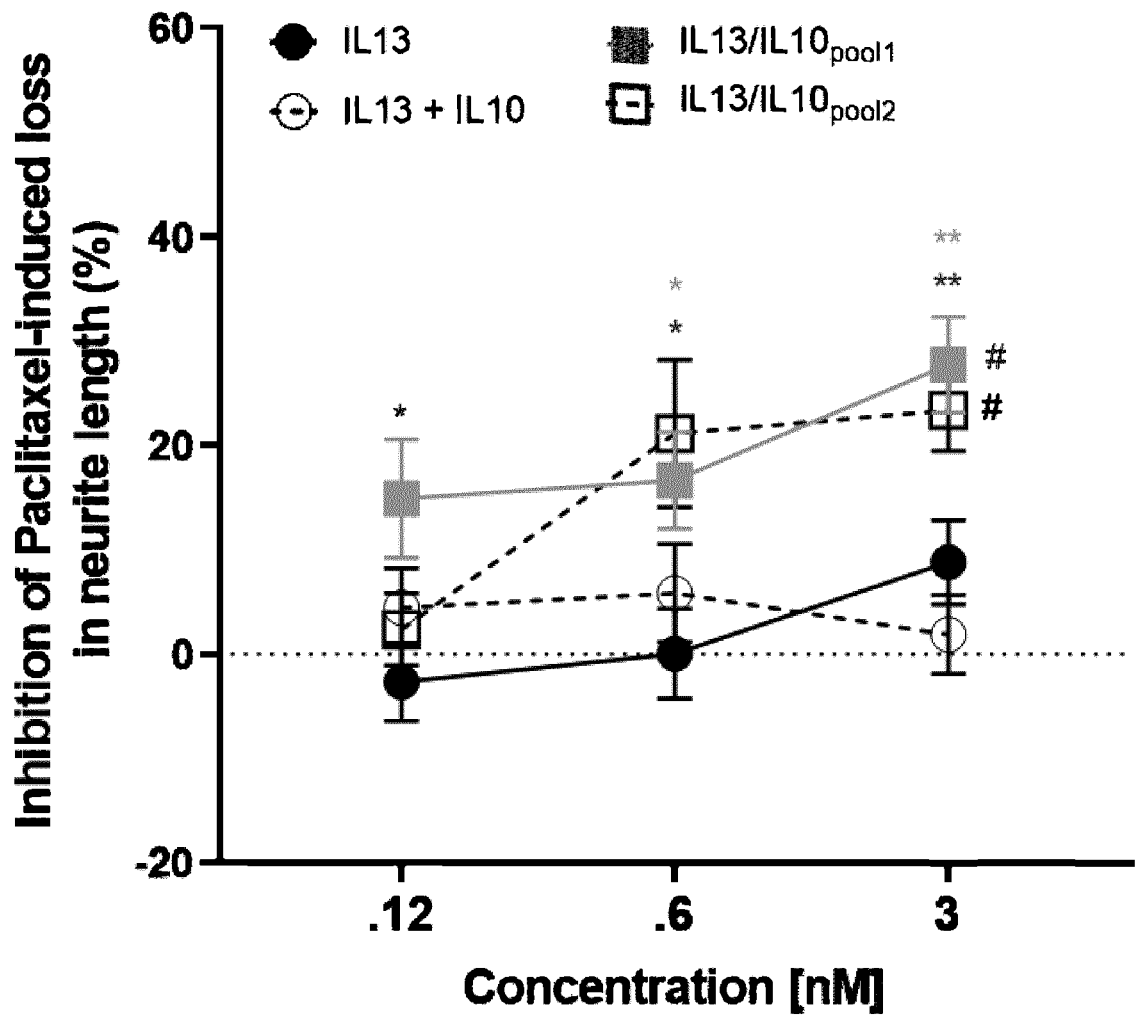

FIG. 13. IL10/IL13 protect neurons against chemotherapy induced neuron damage. Primary sensory neurons were cultured for 24 h in the presence of paclitaxel (1 µM), and different concentrations of each fusion protein or equimolar doses of IL13 or the combination of unlinked cytokines. The inhibition of paclitaxel-induced decrease in neurite length was calculated. Data are shown as mean±SEM. Data are analysed with a two-way ANOVA mixed-effects analysis followed by Tukey's multiple comparison test.

Figure 14:
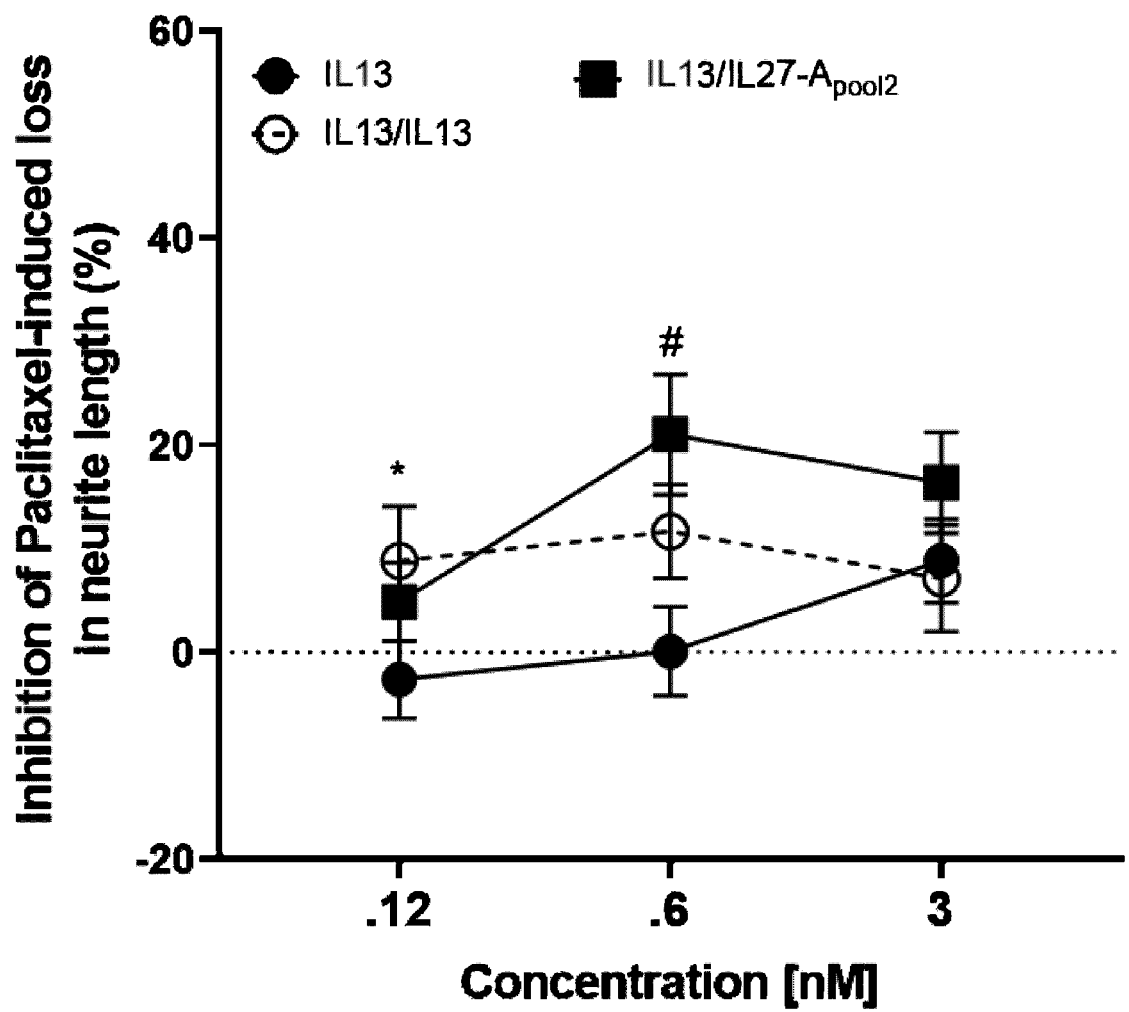

FIG. 14. Protective effects of IL13/IL13 and IL27/IL13 against chemotherapy induced neuron damage. Primary sensory neurons were cultured for 24 h in the presence of paclitaxel (1 µM), and different concentrations of each fusion protein or an equimolar dose of IL13. The inhibition of paclitaxel-induced decrease in neurite length was calculated. Data are shown as mean±SEM. Data are analysed with a two-way ANOVA mixed-effects analysis followed by Tukey's multiple comparison test.

Figure 15:
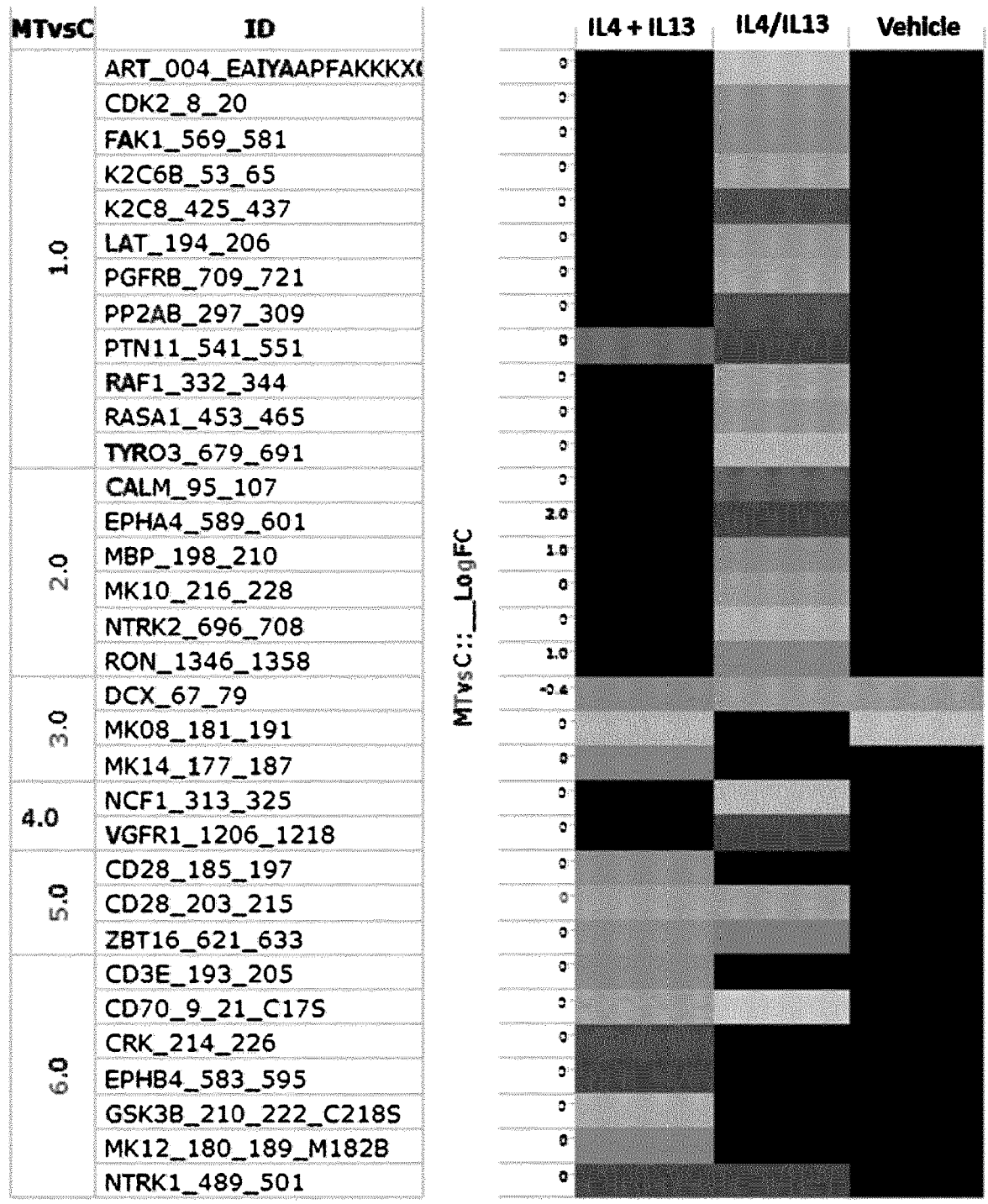

FIG. 15. An IL13-containing fusion protein of the disclosure elicits a distinct kinase activity profile in dorsal root ganglia (DRG) cells compared to a combination of unlinked cytokines. PamGene kinase activity profiling was performed to assess global protein tyrosine kinases (PTK) activity in homogenates of lumbar DRGs isolated from mice with persistent paclitaxel-induced peripheral neuropathy after IL4/IL13 fusion protein, IL4+IL13 (combination of unlinked cytokines), and vehicle administration. Kinomic profiles were assessed at 60 minutes after intrathecal administration of the IL4/IL13 fusion protein, the combination of cytokines, or vehicle (PBS). Peptides are shown that were differentially phosphorylated based on one-way ANOVA analysis between IL4/IL13, IL4+IL13, and vehicle-treated mice compared to naive mice (untreated; no paclitaxel, no intrathecal injection). Black indicates no significant changes, while color indicates decreased phosphorylation.

Figure 16:
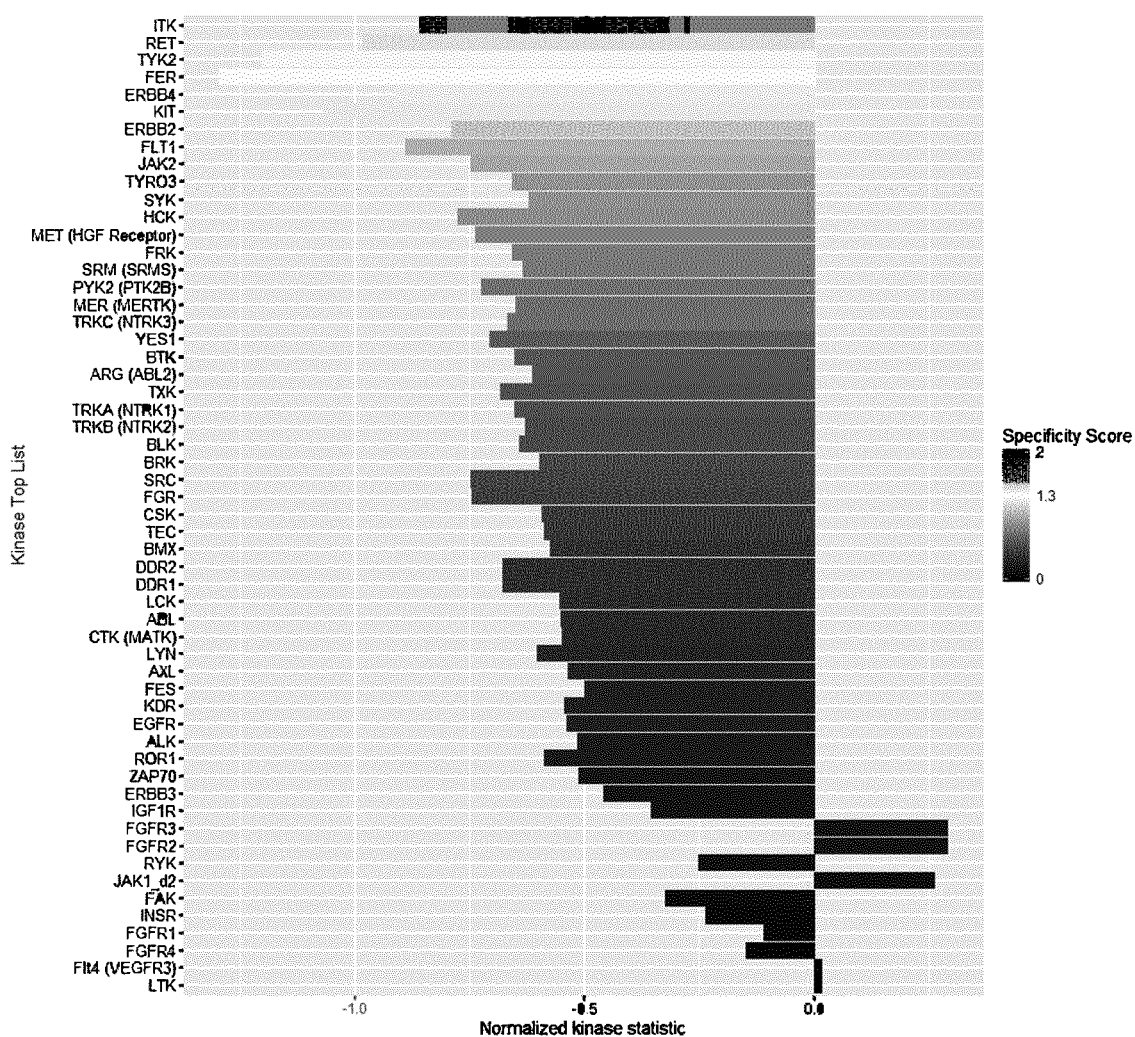

FIG. 16. Altered kinase activity in dorsal root ganglia (DRG) cells of female mice treated with IL4/IL13 compared to a combination of unlinked cytokines. PamGene kinase activity profiling was performed to assess global protein tyrosine kinases (PTK) activity in homogenates of lumbar DRGs isolated from female mice with persistent paclitaxel-induced CIPN after IL4/IL13 fusion protein or IL4+IL13 (combination of unlinked cytokines) administration. The graph shows the predicted upstream kinases inferred from the differentially phosphorylated peptide substrates identified by unpaired t-test comparison between samples from IL4/IL13 fusion protein-treated females and IL4+IL13-treated females (n=3 animals per group). The graph is sorted with the highest specificity scores at the top, and the lowest specificity scores at the bottom.

Figure 17:
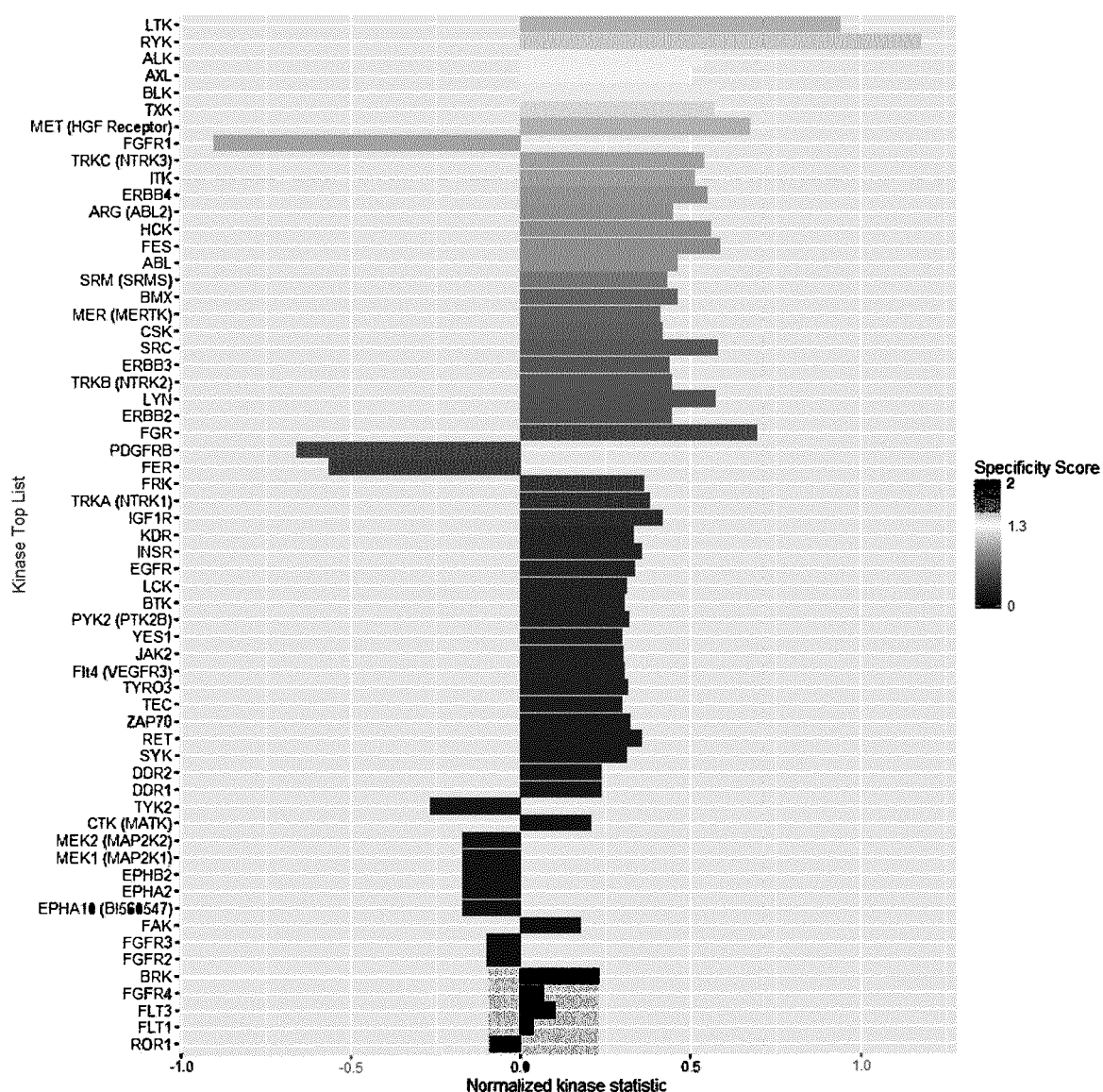

FIG. 17. Altered kinase activity in dorsal root ganglia (DRG) cells of male mice treated with IL4/IL13 compared to a combination of unlinked cytokines. PamGene kinase activity profiling was performed to assess global protein tyrosine kinases (PTK) activity in homogenates of lumbar DRGs isolated from male mice with persistent paclitaxel-induced CIPN after IL4/IL13 fusion protein or IL4+IL13 (combination of unlinked cytokines) administration. The graph shows the predicted upstream kinases inferred from the differentially phosphorylated peptide substrates identified by unpaired t test comparison between samples from IL4/IL13 fusion protein-treated males and IL4+IL13-treated males (n=3 animals per group). The graph is sorted with the highest specificity scores at the top, and the lowest specificity scores at the bottom.

Figure 18A:
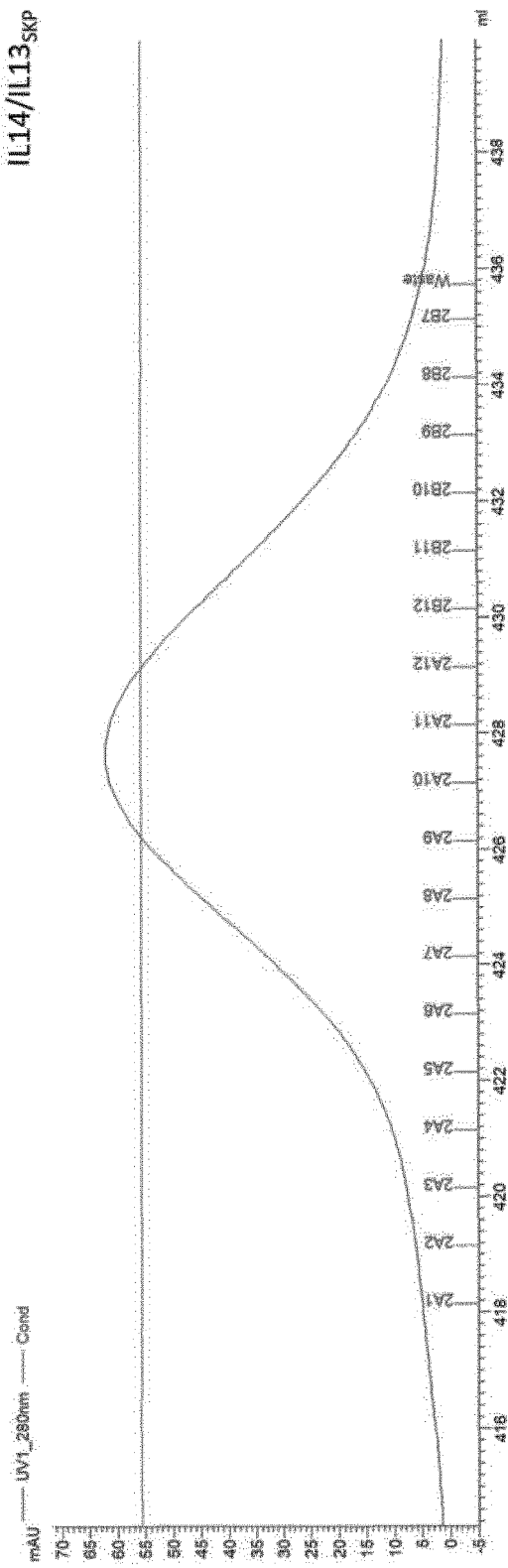
Figure 18B:
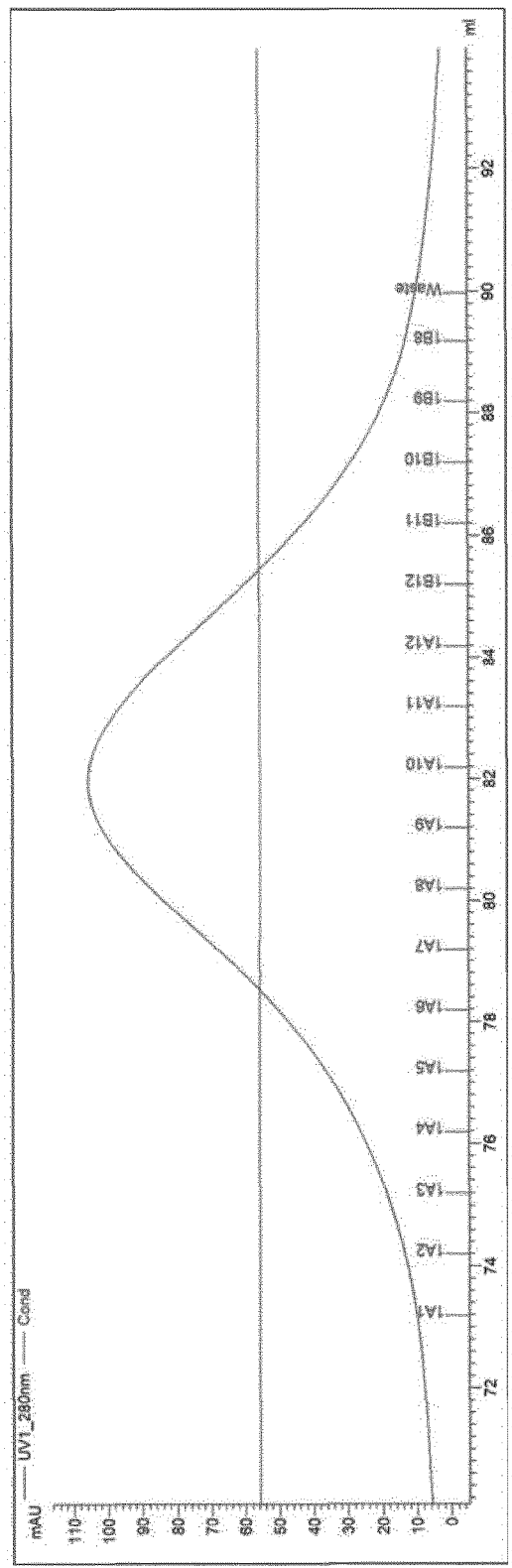
Figure 18C:
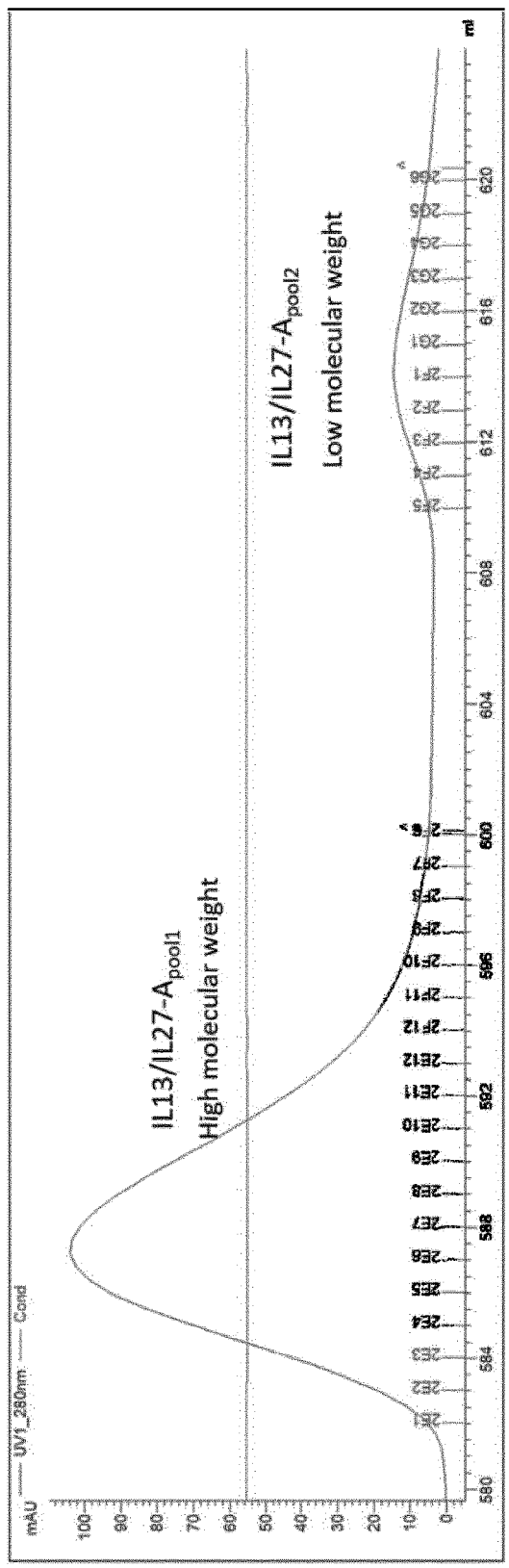
Figure 18D:
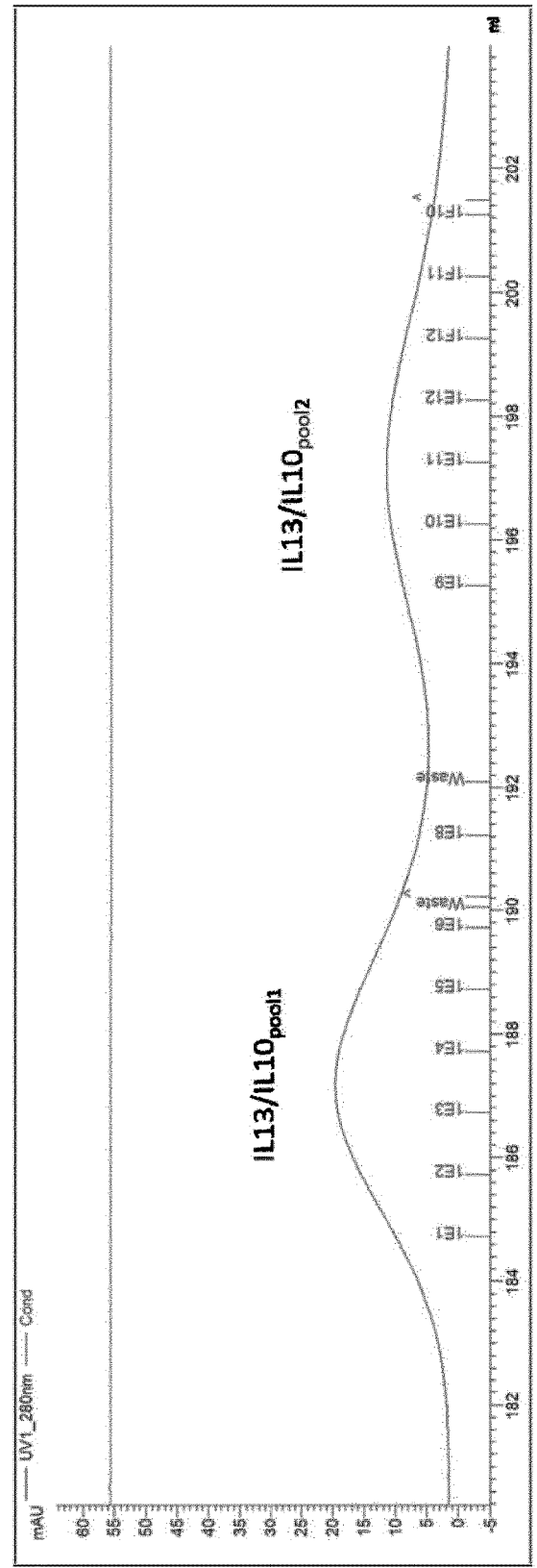

FIGS. 18A-18D. Size exclusion chromatography of IL4/IL13, IL10/IL13, IL27/IL13, and IL13/IL13 fusion proteins. Size exclusion chromatography was performed for IL4/IL13, IL10/IL13, IL27/IL13, and IL13/IL13 fusion proteins of the disclosure. FIG. 18A: Size exclusion chromatography of an IL4/IL13 fusion protein containing SEQ ID NO: 16. FIG. 18B: Size exclusion chromatography of an IL13/IL13 fusion protein containing SEQ ID NO: 20. FIG. 18C: Size exclusion chromatography of an IL27/IL13 fusion protein containing SEQ ID NO: 19. FIG. 18D: Size exclusion chromatography of an IL10/IL13 fusion protein containing SEQ ID NO: 17.

DETAILED DESCRIPTION OF THE INVENTION

General Definitions

The term "nucleic acid molecule" (or "nucleic acid sequence", "polynucleotide", or "nucleotide sequence") refers to a DNA or RNA molecule in single or double stranded form, particularly a DNA encoding a protein according to the invention. An "isolated nucleic acid sequence" refers to a nucleic acid sequence which is no longer in the natural environment from which it was isolated, e.g., the nucleic acid sequence in a bacterial host cell or in the plant nuclear or plastid genome.

The terms "protein" or "polypeptide" are used interchangeably and refer to molecules consisting of one or several chains of amino acids, without reference to a specific mode of action, size, three-dimensional structure or origin. An "isolated protein" is used to refer to a protein which is no longer in its natural environment, for example in vitro or in a recombinant mammalian, bacterial, or plant host cell.

The term "fusion protein" refers to a protein or polypeptide that has an amino acid sequence from or derived from two or more proteins. The fusion protein may also include linking regions or a linker of amino acids between amino acid portions from or derived from separate proteins. The fusion protein also refers to a molecule that has an amino acid sequence from or derived from two or more proteins which are non-covalently bound, or connected via chemical crosslinkers (e.g., covalently linked), with or without a spacer. A fusion protein can be a polypeptide construct.

The terms IL4, IL10, IL13, IL27, IL33, TGFβ1, and TGFβ2 preferably refer to the wild-type sequences of these respective cytokines, and/or to mutated variants thereof capable of binding to at least one of their respective cytokine receptors or receptor subunits (e.g., preferably at least two).

The terms "TGFβ", "TGFβ1/2" and "TGFβ(1 or 2)" are used to refer to TGFβ1 and/or TGFβ2. The term "IL4/IL13 fusion protein" refers to a fusion polypeptide comprising at least IL4 and IL13, optionally coupled to one another via a linker. The fusion protein may comprise additional polypeptide sequences, e.g., a signal sequence, a His-tag, targeting sequence(s), an antibody Fc fragment, an extracellular matrix-binding polypeptide, or any combination thereof.

The term "IL10/IL13 fusion protein" refers to a fusion polypeptide comprising at least IL10 and IL13, optionally coupled to one another via a linker. The fusion protein may comprise additional polypeptide sequences, e.g., a signal sequence, a His-tag, targeting sequence(s) or an antibody Fc fragment, an extracellular matrix-binding polypeptide, or any combination thereof.

The term "IL33/IL13 fusion protein" refers to a fusion polypeptide comprising at least IL33 and IL13, optionally coupled to one another via a linker. The fusion protein may comprise additional polypeptide sequences, e.g., a signal sequence, a His-tag, targeting sequence(s) or an antibody Fc fragment, an extracellular matrix-binding polypeptide, or any combination thereof.

The term "TGFβ1/IL13 fusion protein" refers to a fusion polypeptide comprising at least TGFβ1 and IL13, optionally coupled to one another via a linker. The fusion protein may comprise additional polypeptide sequences, e.g., a signal sequence, a His-tag, targeting sequence(s) or an antibody Fc fragment, an extracellular matrix-binding polypeptide, or any combination thereof.

The term "TGFβ2/IL13 fusion protein" refers to a fusion polypeptide comprising at least TGFβ2 and IL13, optionally coupled to one another via a linker. The fusion protein may comprise additional polypeptide sequences, e.g., a signal sequence, a His-tag, targeting sequence(s) or an antibody Fc fragment, an extracellular matrix-binding polypeptide, or any combination thereof.

The term "IL13/IL13 fusion protein" refers to a fusion polypeptide comprising at least two IL13 molecules, optionally coupled to one another via a linker. The fusion protein may comprise additional polypeptide sequences, e.g., a signal sequence, a His-tag, targeting sequence(s) or an antibody Fc fragment, an extracellular matrix-binding polypeptide, or any combination thereof.

As used herein, a "linker" means a polypeptide used to couple two proteins or polypeptides, in casu IL4 (or IL10 or IL27 or IL33 or TGFβ or IL13) and IL13. The linker typically is a stretch of amino acids, e.g., predominantly glycine and/or serine. In an embodiment, the linker is a stretch of amino acids having a length of up to 100 amino acids, such as from about 2, 5, 7, 10, 15 amino acids up to about 15, 20, 25, 30, 35, 50, 75, or 100 amino acids, preferably comprising predominantly serine and glycine residues.

As used herein, "interleukin-13" (IL13) preferably refers to any mammalian IL13, such as human IL13, mouse IL13, or an active species or variant (e.g., allelic variant), (functional) fragment or derivative thereof.

As used herein, "interleukin-4" (IL4) preferably refers to any mammalian IL4, such as human IL4, mouse IL4, or an active species or variant (e.g., allelic variant), (functional) fragment or derivative thereof.

As used herein, "interleukin-10" (IL10) preferably refers to any mammalian IL10, such as human IL10, mouse IL10, or an active species or variant (e.g., allelic variant), (functional) fragment or derivative thereof.

As used herein, "interleukin-27" (IL27) can refer to any mammalian IL27, such as human IL27, mouse IL27, or an active species or variant (e.g., allelic variant), (functional) fragment or derivative thereof. In some cases, IL27 refers to IL27 subunit alpha (IL27A), for example, human IL27A. In some cases, IL27 refers to IL27 subunit beta (IL27B), for example, human IL27B. In some cases, IL27 refers to IL27A and IL27B.

As used herein, "interleukin-33" (IL33) preferably refers to any mammalian IL33, such as human IL33, mouse IL33, or an active species or variant (e.g., allelic variant), (functional) fragment or derivative thereof.

As used herein, "transforming growth factor β1" (TGFβ1) preferably refers to any mammalian TGFβ1, such as human TGFβ1, mouse TGFβ1, or an active species or variant (e.g., allelic variant), (functional) fragment or derivative thereof.

As used herein, "transforming growth factor β2" (TGFβ2) preferably refers to any mammalian TGFβ2, such as human TGFβ2, mouse TGFβ2, or an active species or variant (e.g., allelic variant), (functional) fragment or derivative thereof.

When describing a cytokine, the term "wild type" refers to a cytokine with an amino acid sequence that is naturally occurring and encoded by a germline genome of a given species. A species can have one wild type sequence, or two or more wild type sequences (for example, with one canonical wild type sequence and one or more non-canonical wild type sequences). A wild type cytokine sequence can include a sequence that is truncated at the N and/or C terminus relative to the sequence encoded by an open reading frame. A wild type cytokine sequence can be a mature form of a cytokine that has been processed to remove N-terminal and/or C-terminal residues. A wild type cytokine can lack a signal peptide or can include a signal peptide (e.g., a signal peptide can be added to the N-terminus of the wild type cytokine). When describing a cytokine, the term "derivative" refers to a cytokine with an amino acid sequence that differs from a wild type sequence by one or more amino acids, for example, containing one or more amino acid insertions, deletions, or substitutions relative to a wild type sequence. A cytokine derivative binds to at least one subunit of the corresponding native receptor for the wild type cytokine and elicits signaling and/or cytokine activity. The binding affinity, signaling, and/or cytokine activity of a cytokine derivative can be the same or different than the corresponding wild type cytokine.

"Functional", in relation to the fusion proteins of the present invention (or variants or fragments thereof), refers to the capability to display both IL4 (or IL10 or IL27 or IL33 or TGFβ1 or TGFβ2 or other regulatory cytokine, e.g., anti-inflammatory cytokine) and IL13 functionality, for example, the ability to bind to at least one receptor subunit that a wild type version of the cytokine binds.

Assays to assess the functional activity of these cytokines are well known to those skilled in the art. For example, a functional assay for IL4 and IL10 is the lipopolysaccharide (LPS) induced TNF release in whole blood in presence of anti-IL10 antibody[26]. A functional assay for IL13 is the proliferation of TF1 human erythroleukemic cells[27]. An assay for IL33 function is IL6 production by the mast cell line MC/9. An assay for TGFβ1 or TGFβ2 is inhibition of IL4-dependent growth of mouse T-cell line HT-2. A functional assay for IL27 can comprise IL6 production by LPS-stimulated THP-1 macrophages.

The term "gene" means a DNA sequence comprising a region (transcribed region), which is transcribed into an RNA molecule (e.g. a mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA), introns, and a 3' non-translated sequence comprising e.g. transcription termination sites.

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment). "Expression of a polypeptide" additionally refers to a process wherein an mRNA is translated into a protein product, which may or may not be secreted.

As used herein, the term "promoter" refers to a nucleic acid sequence that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells. As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous.

A "nucleic acid construct" or "vector" is herein understood to mean a man-made nucleic acid molecule resulting from the use of recombinant DNA technology and which is used to deliver exogenous DNA into a host cell. Vectors usually comprise further genetic elements to facilitate their use in molecular cloning, such as e.g. selectable markers, or multiple cloning sites (see below).

"Sequence identity" and "sequence similarity" can be determined by alignment of two peptide or two nucleotide sequences using global or local alignment algorithms. Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or EmbossWin version 2.10.0 (using the program "needle"). Alternatively, percent similarity or identity may be determined by searching against databases, using algorithms such as FASTA, BLAST, etc. Preferably, the sequence identity refers to the sequence identity over the entire length of the sequence.

A "host cell" or a "recombinant host cell" or "transformed cell" are terms referring to a new individual cell (or organism) arising as a result of at least one nucleic acid molecule, especially comprising a nucleic acid molecule encoding a desired protein. The host cell is preferably a mammalian cell, plant cell or a bacterial cell. The host cell may contain the nucleic acid molecule or vector of the present invention as an extra-chromosomally (episomal) replicating molecule, or more preferably, comprises the nucleic acid molecule or vector of the present invention integrated in the genome of the host cell.

The term "selectable marker" is a term familiar to one of ordinary skill in the art and is used herein to describe any genetic entity which, when expressed, can be used to select for a cell or cells containing the selectable marker. Selectable marker gene products confer for example antibiotic resistance or nutritional requirements.

The term "nervous system cell" refers to a cell that is found within the central nervous system or peripheral nervous system. A nervous system cell can be a neuron, a central nervous system cell, a peripheral nervous system cell, a glial cell, a microglial cell, an astrocyte, a schwann cell, a satellite glial cell, an oligodendrocyte, an infiltrating cell, an infiltrating immune cell, an infiltrating myeloid cell, an infiltrating lymphoid cell, an infiltrating macrophage, an infiltrating neutrophil, an infiltrating lymphocyte, an infiltrating T cell, an infiltrating B cell, or an infiltrating natural killer cell. A neuron can be, for example, a sensory neuron, a somatosensory neuron, a visceral sensory neuron, a nociceptor, and/or an autonomic neuron.

In this document and in its claims, the verb "to comprise" and its conjugations is used in its non-limiting sense to mean that items following the word are included, but items not specifically mentioned are not excluded. It also encompasses the more limiting verb "to consist of". In addition, reference to an element by the indefinite article "a" or "an" does not exclude the possibility that more than one of the elements is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids) are referred to.

Proteins, Nucleic Acid Sequences, Vectors and Host Cells of the Invention

The present inventors provide a fusion protein comprising an IL13 protein and a regulatory cytokine, for example, a protein chosen from IL4, IL10, IL27, IL33, TGFβ1, TGFβ2, or IL13 itself, optionally physically fused together via a linker. Regulatory cytokines of the disclosure include, but are not limited to, IL4, IL10, IL13, IL27, IL33, TGFβ1, and TGFβ2. Particularly, the fusion protein of the present invention was found to have a superior activity in a treatment for a condition disclosed herein (e.g., neuropathic pain) over its individual counterparts, i.e., regulatory cytokine (e.g., IL4 or IL10 or IL27 or IL33 or TGFβ1 or TGFβ2) and IL13 separately. Specifically, it was found that, upon intrathecal administration, the fusion protein of the present invention has a long-lasting analgesic effect on neuropathic pain, and abrogates allodynia associated with chemotherapy-induced neuropathy. The inventors unexpectedly observed that this analgesic effect of the fusion protein of the present invention lasted longer than that of a previously described fusion protein of IL4 and IL10[19,23,26]. Surprisingly, the fusion protein of the present invention also improved chemotherapy-associated neuro-degeneration. It prevented the shortening of neurites in vitro upon incubation with chemotherapeutic drugs, and was more potent regarding this effect than a fusion protein of IL4 and IL10, or the combination of IL4 (or IL10 or IL27 or IL33 or TGFβ1 or TGFβ2) and IL13. The latter surprising finding indicates a unique effect of the fusion protein over its individual cytokines or the combination of these. In vivo, the fusion protein of the present invention attenuated the decrease of intraepidermal nerve fibers upon administration of chemotherapeutic drugs.

In one embodiment of the invention, nucleic acid sequences and amino acid sequences of IL4/IL13 fusion proteins or IL10/IL13 fusion proteins or IL27/IL13 fusion proteins or IL33/IL13 fusion proteins or TGFβ1/IL13 fusion proteins or TGFβ2/IL13 or IL13/IL13 fusion proteins are provided (including variants, derivatives, and fragments thereof). The IL4/IL13 fusion proteins or IL10/IL13 fusion proteins or IL27/IL13 fusion proteins or IL33/IL13 fusion proteins, as well as derivatives, functional fragments and variants thereof, display IL4 (or IL10 or IL27 or IL33 or TGFβ1 or TGFβ2) activity as well as IL13 activity.

In some cases, fusion proteins disclosed herein contain two cytokines, C1 and C2, and are referred to in the format C1/C2 or C1-C2. The order in which the cytokines are presented is not limiting and does not necessarily infer the orientation of the cytokines. For example, C1/C2 or C1-C2 can contain cytokine C1 on the C-terminal side of C2 or on the N-terminal side of C2. Similarly, a cytokine referred to as C1/C2 can be the same as a cytokine referred to as C2/C1 unless otherwise specified.

In one aspect, a fusion protein comprising IL4 (or IL10 or IL13 or IL27 or IL33 or TGFβ1 or TGFβ2) and IL13 is provided.

Interleukin 13

A fusion protein disclosed herein can comprise an IL13 protein, or a variant, derivative, or fragment thereof operably linked or directly or indirectly fused to a regulatory cytokine or a variant or derivative thereof. The IL13 protein is preferably a mammalian IL13 protein, such as a human IL13, or mouse IL13. Non-limiting examples of amino acid sequences representing human IL13 are set forth in SEQ ID NO:2 and SEQ ID NOs: 9-15. Variants of IL13 include, for example, proteins having at least 70%, 75%, 80%, 85%, 90%, 92%, 95%, 96%, 97%, 98%, 99% or more, such as 100%, amino acid sequence identity, to SEQ ID NO:2 or any one of SEQ ID NOs: 9-15, preferably over the entire length. Amino acid sequence identity is preferably determined by pairwise alignment using the Needleman and Wunsch algorithm and GAP default parameters as defined above. Variants, derivatives, and fragments thereof also include proteins having IL13 activity, which have been derived, by way of one or more amino acid substitutions, deletions or insertions, from the polypeptide having the amino acid sequence of SEQ ID NO:2 or any one of SEQ ID NOs: 9-15. Preferably, such proteins comprise from 1, 2, 3, 4, 5, 6, 7, 8, 9, 10 or more up to about 100, 90, 80, 70, 60, 50, 45, 40, 35, 30, 25, 20, 15 amino acid substitutions, deletions or insertions.

In some embodiments, an IL13 of the disclosure (e.g., an IL13 variant, derivative, or fragment thereof) can comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least or at least 50 amino acid substitutions, deletions, or insertions relative to an IL13 sequence disclosed herein (e.g., a wild type IL13 sequence).

In some embodiments, an IL13 of the disclosure (e.g., an IL13 variant, derivative, or fragment thereof) can comprise at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, at most 20, at most 25, at most 30, at most 35, at most 40, at most 45, or at most 50 amino acid substitutions, deletions, or insertions relative to an IL13 sequence disclosed herein (e.g., a wild type IL13 sequence).

In some embodiments, an IL13 sequence of the disclosure (e.g., an IL13 variant, derivative, or fragment thereof) can comprise 1-2, 1-3, 1-4, 1-5, 1-6, 1-7, 1-8, 1-9, 1-10, 1-15, 1-20, 1-30, 1-40, 2-3, 2-4, 2-5, 2-6, 2-7, 2-8, 2-9, 2-10, 2-15, 2-20, 2-30, 2-40, 3-3, 3-4, 3-5, 3-6, 3-7, 3-8, 3-9, 3-10, 3-15, 3-20, 3-30, 3-40, 5-6, 5-7, 5-8, 5-9, 5-10, 5-15, 5-20, 5-30, 5-40, 10-15, 15-20, or 20-25 amino acid substitutions, deletions, or insertions relative to an IL13 sequence disclosed herein (e.g., a wild type IL13 sequence).

In some embodiments, an IL13 sequence of the disclosure (e.g., an IL13 variant, derivative, or fragment thereof) can comprise 1, 2, 3, 4, 5, 6, 7, 8, 9, 10, 11, 12, 13, 14, 15, 16, 17, 18, 19, or 20 amino acid substitutions, deletions, or insertions relative to an IL13 sequence disclosed herein (e.g., a wild type IL13 sequence). An amino acid substitution can be a conservative or a non-conservative substitution. The one or more amino acid substitutions, deletions, or insertions can be at the N-terminus, the C-terminus, within the amino acid sequence, or a combination thereof. The amino acid substitutions, deletions, or insertions can be contiguous, non-contiguous, or a combination thereof.

An IL13 of the disclosure can comprise a wild type IL13 sequence. Non-limiting examples of wild type IL13 sequences include SEQ ID NOs: 2 and 9-15. SEQ ID NO: 12 can be a canonical wild type IL13 sequence of the disclosure.

An IL13 of the disclosure can comprise an IL13 variant, derivative, or fragment thereof with one or more amino acid substitutions. For example, an IL13 variant, derivative, or fragment thereof can comprise an amino acid substitution at position L10, E12, R11, I14, E15, E16, V18, R65, S68, R86, D87, T88, K89, D98, L101, L103, K104, K105 L106, F107, R108, R111, F114, N113, or a combination thereof of SEQ ID NO: 2 or SEQ ID NO: 12. In some embodiments, an IL13 variant, derivative, or fragment thereof comprises a substitution that is L10F; L10I; L10V; L10A; L10D; L10T; L10H; R11S; R11N; R11H; R11L; R11I; I14L; I14F; I14V; I14M; V18L; V18F; V18I; E12A; R65D; R86K; R86T; R86M; D87E; D87K; D87R; D87G; D87S; T88S; T88I; T88K; T88R; K89R; K89T; K89M; L101F; L101I; L101Y; L101H; L101N; K104R; K104T; K104M; K105T; K105A; K105R; K105E; F107L; F107I; F107V; F107M; R108K; R108T; R108M; E12K, E12I, E12C, E12S, E12R, E12Y, E12D, E15K, E16K, R65D, S68D, D98K, L101A, L103A, K104D, K105D, L106A, F107Y, R108D, R111D, F114D, N113D, or a combination thereof relative to SEQ ID NO: 2 or SEQ ID NO: 12. In some embodiments, an IL13 variant, derivative, or fragment thereof comprises the substitutions L10H, R86T, D87G, T88R, and R108K relative to SEQ ID NO: 2 or SEQ ID NO: 12. In some embodiments, an IL13 variant, derivative, or fragment thereof comprises the substitutions L10A, V18F, R86K, D87K, K89R, L101I, K104R, and R108K relative to SEQ ID NO: 2 or SEQ ID NO: 12. In some embodiments, an IL13 variant, derivative, or fragment thereof comprises the substitutions R11S, V18I, R86K, D87G, T88S, K89M, L101Y, K104R, and K105T relative to SEQ ID NO: 2 or SEQ ID NO: 12. In some embodiments, an IL13 variant, derivative, or fragment thereof comprises the substitutions L10V, K89R, L101 N, K105E, and R108T relative to SEQ ID NO: 2 or SEQ ID NO: 12. In some embodiments, an IL13 variant, derivative, or fragment thereof comprises the substitutions L10D, R11I, V18I, R86K, D87K, K89R, and R108K relative to SEQ ID NO: 2 or SEQ ID NO: 12. In some embodiments, an IL13 variant, derivative, or fragment thereof comprises the substitutions L10A, R86T, D87G, T88K, K89R, L101N, K104R, K105A, and R108K relative to SEQ ID NO: 2 or SEQ ID NO: 12. In some embodiments, an IL13 variant, derivative, or fragment thereof comprises the substitutions L10V, K89R, L101 N, K105E, and R108T relative to SEQ ID NO: 2 or SEQ ID NO: 12. In some embodiments, an IL13 variant, derivative, or fragment thereof comprises the substitutions R11S, I14M, T88S, L101 N, K105A, and R108K relative to SEQ ID NO: 2 or SEQ ID NO: 12. In some embodiments, an IL13 variant, derivative, or fragment thereof comprises the substitutions L10H, R11 L, V18I, R86K, D87E, K89R, L101N, K105T, and R108K relative to SEQ ID NO: 2 or SEQ ID NO: 12. In some embodiments, an IL13 variant, derivative, or fragment thereof comprises the substitutions L10H, R86T, D87G, T88R, and R108K relative to SEQ ID NO: 2 or SEQ ID NO: 12. In some embodiments, an IL13 variant, derivative, or fragment thereof comprises the substitutions L10A, V18F, R86K, D87K, K89R, L101I, K104R, and R108K relative to SEQ ID NO: 2 or SEQ ID NO: 12. In some embodiments, an IL13 variant, derivative, or fragment thereof comprises the substitutions L10T or L10D; R11I; V18I; R86K; D87K or D87G; T88S; K89R; L101Y; K104R; K105T; and R108K relative to SEQ ID NO: 2 or SEQ ID NO: 12. In some embodiments, an IL13 variant, derivative, or fragment thereof comprises the substitutions L10A or L10V; R86T; D87G; T88K; K89R; L101N; K104R; K105A or K105E; and R108K or R108T relative to SEQ ID NO: 2 or SEQ ID NO: 12. In some embodiments, an IL13 variant, derivative, or fragment thereof comprises the substitutions L10V, V18I, D87S, D88S, L101F, K104R, and K105T relative to SEQ ID NO: 2 or SEQ ID NO: 12. In some embodiments, an IL13 variant, derivative, or fragment thereof comprises the substitutions R11S, V18I, R86K, D87G, T88S, K89M, L101Y, K104R, and K105T relative to SEQ ID NO: 2 or SEQ ID NO: 12. In some embodiments, an IL13 variant, derivative, or fragment thereof comprises the substitutions L10V, V18I, D87S, T88S, L101F, K104R, and K105T relative to SEQ ID NO: 2 or SEQ ID NO: 12. In some embodiments, an IL13 variant, derivative, or fragment thereof comprises the substitutions L10V or L10I; D87S; T88S; K89R; L101H or L101F; K104R; and K105T relative to SEQ ID NO: 2 or SEQ ID NO: 12. In some embodiments, an IL13 variant, derivative, or fragment thereof comprises the substitutions L10I; V18I; R86T; D87G; T88S; K89R; L101Y, L101H; K104R; and K105A relative to SEQ ID NO: 2 or SEQ ID NO: 12. In some embodiments, an IL13 variant, derivative, or fragment thereof comprises the substitutions L10V; V18I; D87S; T88S; L101F; K104R; and K105T relative to SEQ ID NO: 2 or SEQ ID NO: 12. In some embodiments, an IL13 variant, derivative, or fragment thereof comprises the substitutions V18I, R86T, D87G, T88S, L101Y, K104R, and K105A relative to SEQ ID NO: 2 or SEQ ID NO: 12. In some embodiments, an IL13 variant, derivative, or fragment thereof comprises the substitutions R11I, V18I, R86K, D87G, T88S, L101H, K104R, K105A, and F107M relative to SEQ ID NO: 2 or SEQ ID NO: 12. In some embodiments, an IL13 variant, derivative, or fragment thereof comprises the substitutions E12K and S68D relative to SEQ ID NO: 2 or SEQ ID NO: 12. In some embodiments, an IL13 variant, derivative, or fragment thereof comprises the substitutions E12K and R108D relative to SEQ ID NO: 2 or SEQ ID NO: 12. In some embodiments, an IL13 variant, derivative, or fragment thereof comprises the substitutions E12K and R111D relative to SEQ ID NO: 2 or SEQ ID NO: 12. In some embodiments, an IL13 variant, derivative, or fragment thereof comprises the substitutions E12Y and R65D relative to SEQ ID NO: 2 or SEQ ID NO: 12. In some embodiments, an IL13 variant, derivative, or fragment thereof comprises the substitutions E12Y and S68D relative to SEQ ID NO: 2 or SEQ ID NO: 12. In some embodiments, an IL13 variant, derivative, or fragment thereof comprises the substitutions E12K, R65D and S68D relative to SEQ ID NO: 2 or SEQ ID NO: 12. In some embodiments, an IL13 variant, derivative, or fragment thereof comprises the substitutions E12Y, R65D and S68D relative to SEQ ID NO: 2 or SEQ ID NO: 12. In some embodiments, an IL13 variant, derivative, or fragment thereof comprises the substitutions E12K, R65D, S68D and R111D relative to SEQ ID NO: 2 or SEQ ID NO: 12.

In some embodiments, an IL13 variant, derivative, or fragment thereof does not contain a substitution at position L10, E12, R11, I14, E15, E16, V18, R65, S68, R86, D87, T88, K89, D98, L101, L103, K104, K105 L106, F107, R108, R111, F114, or N113 relative to SEQ ID NO: 2 or SEQ ID NO: 12. In some embodiments, an IL13 variant, derivative, or fragment thereof does not contain a L10F; L10I; L10V; L10A; L10D; L10T; L10H; R11S; R11N; R11H; R11L; R11I; I14L; I14F; I14V; I14M; V18L; V18F; V18I; E12A; R65D; R86K; R86T; R86M; D87E; D87K; D87R; D87G; D87S; T88S, T88I; T88K; T88R; K89R; K89T; K89M; L101F; L101I; L101Y; L101H; L101N; K104R; K104T; K104M; K105T; K105A; K105R; K105E; F107L; F107I; F107V; F107M; R108K; R108T; R108M; E12K, E12I, E12C, E12S, E12R, E12Y, E12D, E15K, E16K, R65D, S68D, D98K, L101A, L103A, K104D, K105D, L106A, F107Y, R108D, R111D, F114D, or N113D substitution.

In some embodiments, an IL13 or IL13 variant, derivative, or fragment thereof of the disclosure binds to an IL13 receptor subunit with about a comparable affinity as a wild type IL13 sequence. A comparable affinity can be, for example, less than about 10, less than about 5, less than about 2, less than about 1.9, less than about 1.8, less than about 1.7, less than about 1.6, less than about 1.5, less than about 1.4, less than about 1.3, less than about 1.2, or less than about 1.1 fold increased affinity compared to a wild type IL13 sequence. A comparable affinity can be, for example, less than about 10, less than about 5, less than about 2, less than about 1.9, less than about 1.8, less than about 1.7, less than about 1.6, less than about 1.5, less than about 1.4, less than about 1.3, less than about 1.2, or less than about 1.1 fold decreased affinity compared to a wild type IL13 sequence.

For example, an IL13 or IL13 variant, derivative, or fragment thereof of the disclosure can bind to an interleukin 13 receptor alpha 1 (IL-13Rα1), interleukin 13 receptor alpha 2 (IL-13Rα2), interleukin 4 receptor alpha (IL-4Rα), or a combination thereof with about a comparable affinity as a wild type IL13. In some embodiments, an IL13 or IL13 variant, derivative, or fragment thereof of the disclosure can bind to IL-13Rα1 with about a comparable affinity as a wild type IL13. In some embodiments, an IL13 or IL13 variant, derivative, or fragment thereof of the disclosure can bind to IL-13Rα2 with about a comparable affinity as a wild type IL13. In some embodiments, an IL13 or IL13 variant, derivative, or fragment thereof of the disclosure can bind to IL-4Rα with about a comparable affinity as a wild type IL13 sequence. In some embodiments, an IL13 or IL13 variant, derivative, or fragment thereof of the disclosure can bind to IL-13Rα1 and IL-13Rα2 with about a comparable affinity as a wild type IL13. In some embodiments, an IL13 or IL13 variant, derivative, or fragment thereof of the disclosure can bind to IL-13Rα1 and IL-4Rα with about a comparable affinity as a wild type IL13. In some embodiments, an IL13 or IL13 variant, derivative, or fragment thereof of the disclosure can bind to IL-13Rα2 and IL-4Rα with about a comparable affinity as a wild type IL13. In some embodiments, an IL13 or IL13 variant, derivative, or fragment thereof of the disclosure can bind to IL-13Rα1, IL-13Rα2, and IL-4Rα with about a comparable affinity as a wild type IL13.

In some embodiments, an IL13 or IL13 variant, derivative, or fragment thereof of the disclosure can bind to an IL13 receptor subunit with at least a comparable affinity as a wild type IL13. For example, an IL13 or IL13 variant, derivative, or fragment thereof of the disclosure can bind to an interleukin 13 receptor alpha 1 (IL-13Rα1), interleukin 13 receptor alpha 2 (IL-13Rα2), interleukin 4 receptor alpha (IL-4Rα), or a combination thereof with at least a comparable affinity as a wild type IL13. In some embodiments, an IL13 or IL13 variant, derivative, or fragment thereof of the disclosure can bind to IL-13Rα1 with at least a comparable affinity as a wild type IL13. In some embodiments, an IL13 or IL13 variant, derivative, or fragment thereof of the disclosure can bind to IL-13Rα2 with at least a comparable affinity as a wild type IL13. In some embodiments, an IL13 or IL13 variant, derivative, or fragment thereof of the disclosure can bind to IL-4Rα with at least a comparable affinity as a wild type IL13 sequence. In some embodiments, an IL13 or IL13 variant, derivative, or fragment thereof of the disclosure can bind to IL-13Rα1 and IL-13Rα2 with at least a comparable affinity as a wild type IL13. In some embodiments, an IL13 or IL13 variant, derivative, or fragment thereof of the disclosure can bind to IL-13Rα1 and IL-4Rα with at least a comparable affinity as a wild type IL13. In some embodiments, an IL13 or IL13 variant, derivative, or fragment thereof of the disclosure can bind to IL-13Rα2 and IL-4Rα with at least a comparable affinity as a wild type IL13. In some embodiments, an IL13 or IL13 variant, derivative, or fragment thereof of the disclosure can bind to IL-13Rα1, IL-13Rα2, and IL-4Rα with at least a comparable affinity as a wild type IL13.

In some embodiments, an IL13 or IL13 variant, derivative, or fragment thereof of the disclosure can bind to an IL13 receptor subunit with at most a comparable affinity as a wild type IL13. For example, an IL13 or IL13 variant, derivative, or fragment thereof of the disclosure can bind to an interleukin 13 receptor alpha 1 (IL-13Rα1), interleukin 13 receptor alpha 2 (IL-13Rα2), interleukin 4 receptor alpha (IL-4Rα), or a combination thereof with at most a comparable affinity as a wild type IL13. In some embodiments, an IL13 or IL13 variant, derivative, or fragment thereof of the disclosure can bind to IL-13Rα1 with at most a comparable affinity as a wild type IL13. In some embodiments, an IL13 or IL13 variant, derivative, or fragment thereof of the disclosure can bind to IL-13Rα2 with at most a comparable affinity as a wild type IL13. In some embodiments, an IL13 or IL13 variant, derivative, or fragment thereof of the disclosure can bind to IL-4Rα with at most a comparable affinity as a wild type IL13 sequence. In some embodiments, an IL13 or IL13 variant, derivative, or fragment thereof of the disclosure can bind to IL-13Rα1 and IL-13Rα2 with at most a comparable affinity as a wild type IL13. In some embodiments, an IL13 or IL13 variant, derivative, or fragment thereof of the disclosure can bind to IL-13Rα1 and IL-4Rα with at most a comparable affinity as a wild type IL13. In some embodiments, an IL13 or IL13 variant, derivative, or fragment thereof of the disclosure can bind to IL-13Rα2 and IL-4Rα with at most a comparable affinity as a wild type IL13. In some embodiments, an IL13 or IL13 variant, derivative, or fragment thereof of the disclosure can bind to IL-13Rα1, IL-13Rα2, and IL-4Rα with at most a comparable affinity as a wild type IL13.

In some embodiments, an IL13 or IL13 variant, derivative, or fragment thereof can bind to an IL-13Rα1 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type IL13 sequence. In some embodiments, an IL13 or IL13 variant, derivative, or fragment thereof can bind to an IL-13Rα1 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type IL13 sequence.

In some embodiments, an IL13 or IL13 variant, derivative, or fragment thereof can bind to an IL-13Rα2 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type IL13 sequence. In some embodiments, an IL13 or IL13 variant, derivative, or fragment thereof can bind to an IL-13Rα2 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type IL13 sequence.

In some embodiments, an IL13 or IL13 variant, derivative, or fragment thereof can bind to an IL-4Rα with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type IL13 sequence. In some embodiments, an IL13 or IL13 variant, derivative, or fragment thereof can bind to an IL-4Rα with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type IL13 sequence.

In some embodiments, an IL13 or IL13 variant, derivative, or fragment thereof of the disclosure can activate a native IL13 receptor. A native IL13 receptor can be, for example, a receptor comprising an IL-13Rα1 subunit and an IL-4Rα subunit.

Interleukin 4

A fusion protein disclosed herein may comprise an IL4 protein, or a variant, derivative, or fragment thereof operably linked or directly or indirectly fused to an interleukin 13 or a variant or derivative thereof. The IL4 protein is preferably a mammalian IL4 protein, such as a human IL4, or mouse IL4. Non-limiting examples of amino acid sequences of IL4 are set forth in SEQ ID NO:1 and SEQ ID NOs: 26-28. Variants of IL4 include, for example, proteins having at least 70%, 75%, 80%, 85%, 90%, 92%, 95%, 96%, 97%, 98%, 99% or more, such as 100%, amino acid sequence identity to SEQ ID NO:1 or any one of SEQ ID NOs: 26-28, preferably over the entire length. Amino acid sequence identity is preferably determined by pairwise alignment using the Needleman and Wunsch algorithm and GAP default parameters as defined above. Variants also include proteins having IL4 activity, which have been derived, by way of one or more amino acid substitutions, deletions or insertions, from the polypeptide having the amino acid sequence of SEQ ID NO:1 or any one of SEQ ID NOs: 26-28. Preferably, such proteins comprise from 1, 2, 3, 4, 5, 6, 7, 8, 9, 10 or more up to about 100, 90, 80, 70, 60, 50, 45, 40, 35, 30, 25, 20, 15 amino acid substitutions, deletions or insertions. In some embodiments, an IL4 of the disclosure (e.g., an IL4 variant, derivative, or fragment thereof) can comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least or at least 50 amino acid substitutions, deletions, or insertions relative to an IL4 sequence disclosed herein (e.g., a wild type IL4 sequence).

In some embodiments, an IL4 of the disclosure (e.g., an IL4 variant, derivative, or fragment thereof) can comprise at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, at most 20, at most 25, at most 30, at most 35, at most 40, at most 45, or at most 50 amino acid substitutions, deletions, or insertions relative to an IL4 sequence disclosed herein (e.g., a wild type IL4 sequence).

In some embodiments, an IL4 sequence of the disclosure (e.g., an IL4 variant, derivative, or fragment thereof) can comprise 1-2, 1-3, 1-4, 1-5, 1-6, 1-7, 1-8, 1-9, 1-10, 1-15, 1-20, 1-30, 1-40, 2-3, 2-4, 2-5, 2-6, 2-7, 2-8, 2-9, 2-10, 2-15, 2-20, 2-30, 2-40, 3-3, 3-4, 3-5, 3-6, 3-7, 3-8, 3-9, 3-10, 3-15, 3-20, 3-30, 3-40, 5-6, 5-7, 5-8, 5-9, 5-10, 5-15, 5-20, 5-30, 5-40, 10-15, 15-20, or 20-25 amino acid substitutions, deletions, or insertions relative to an IL4 sequence disclosed herein (e.g., a wild type IL4 sequence).

In some embodiments, an IL4 sequence of the disclosure (e.g., an IL4 variant, derivative, or fragment thereof) can comprise 1, 2, 3, 4, 5, 6, 7, 8, 9, 10, 11, 12, 13, 14, 15, 16, 17, 18, 19, or 20 amino acid substitutions, deletions, or insertions relative to an IL4 sequence disclosed herein (e.g., a wild type IL4 sequence). An amino acid substitution can be a conservative or a non-conservative substitution. The one or more amino acid substitutions, deletions, or insertions can be at the N-terminus, the C-terminus, within the amino acid sequence, or a combination thereof. The amino acid substitutions, deletions, or insertions can be contiguous, non-contiguous, or a combination thereof.

An IL4 of the disclosure can comprise a wild type IL4 sequence. Non-limiting examples of wild type IL4 sequences include SEQ ID NOs: 1 and 26-28. A canonical wild type IL4 sequence of the disclosure can be SEQ ID NO: 1.

An IL4 of the disclosure can comprise an IL4 variant, derivative, or fragment thereof with one or more amino acid substitutions. For example, an IL4 variant, derivative, or fragment thereof can comprise an amino acid substitution at position K117, T118, R121, E122, Y124, S125, S128, S129, or a combination thereof of SEQ ID NO: 1. In some embodiments, an IL4 variant, derivative, or fragment thereof comprises a substitution that is K117R, T118V, R121Q, R121D, R121K, R121E, E122S, Y124W, Y124F, Y124D, S125F, S128G, S125R, S129A, or a combination thereof relative to SEQ ID NO: 1. In some embodiments, an IL4 variant, derivative, or fragment thereof comprises the substitutions K117R, T118V, R121Q, E122S, Y124W, S125F, S128G, and S129A relative to SEQ ID NO: 1. In some embodiments, an IL4 variant, derivative, or fragment thereof comprises the substitutions R121D and Y124D relative to SEQ ID NO: 1.

In some embodiments, an IL4 variant, derivative, or fragment thereof does not contain a substitution at position K117, T118, R121, E122, Y124, S125, S128, or S129, relative to SEQ ID NO: 1. In some embodiments, an IL4 variant, derivative, or fragment thereof does not contain a K117R, T118V, R121Q, R121D, R121K, R121E, E122S, Y124W, Y124F, Y124D, S125F, S128G, S125R, or S129A substitution.

In some embodiments, an IL4 or IL4 variant, derivative, or fragment thereof of the disclosure binds to an IL4 receptor subunit with about a comparable affinity as a wild type IL4 sequence. A comparable affinity can be, for example, less than about 10, less than about 5, less than about 2, less than about 1.9, less than about 1.8, less than about 1.7, less than about 1.6, less than about 1.5, less than about 1.4, less than about 1.3, less than about 1.2, or less than about 1.1 fold increased affinity compared to a wild type IL4 sequence. A comparable affinity can be, for example, less than about 10, less than about 5, less than about 2, less than about 2, less than about 1.9, less than about 1.8, less than about 1.7, less than about 1.6, less than about 1.5, less than about 1.4, less than about 1.3, less than about 1.2, or less than about 1.1 fold decreased affinity compared to a wild type IL4 sequence.

For example, an IL4 or IL4 variant, derivative, or fragment thereof of the disclosure can bind to an interleukin 13 receptor alpha 1 (IL-13Rα1), common gamma chain, interleukin 4 receptor alpha (IL-4Rα), or a combination thereof, e.g. with about a comparable affinity as a wild type IL4. In some embodiments, an IL4 or IL4 variant, derivative, or fragment thereof of the disclosure can bind to IL-13Rα1 with about a comparable affinity as a wild type IL4. In some embodiments, an IL4 or IL4 variant, derivative, or fragment thereof of the disclosure can bind to common gamma chain with about a comparable affinity as a wild type IL4. In some embodiments, an IL4 or IL4 variant, derivative, or fragment thereof of the disclosure can bind to IL-4Rα with about a comparable affinity as a wild type IL4 sequence. In some embodiments, an IL4 or IL4 variant, derivative, or fragment thereof of the disclosure can bind to IL-13Rα1 and common gamma chain with about a comparable affinity as a wild type IL4. In some embodiments, an IL4 or IL4 variant, derivative, or fragment thereof of the disclosure can bind to IL-13Rα1 and IL-4Rα with about a comparable affinity as a wild type IL4. In some embodiments, an IL4 or IL4 variant, derivative, or fragment thereof of the disclosure can bind to common gamma chain and IL-4Rα with about a comparable affinity as a wild type IL4. In some embodiments, an IL4 or IL4 variant, derivative, or fragment thereof of the disclosure can bind to IL-13Rα1, common gamma chain, and IL-4Rα with about a comparable affinity as a wild type IL4.

In some embodiments, an IL4 or IL4 variant, derivative, or fragment thereof of the disclosure binds to an IL4 receptor subunit with at least a comparable affinity as a wild type IL4 sequence. For example, an IL4 or IL4 variant, derivative, or fragment thereof of the disclosure can bind to an interleukin 13 receptor alpha 1 (IL-13Rα1), common gamma chain, interleukin 4 receptor alpha (IL-4Rα), or a combination thereof with at least a comparable affinity as a wild type IL4. In some embodiments, an IL4 or IL4 variant, derivative, or fragment thereof of the disclosure can bind to IL-13Rα1 with at least a comparable affinity as a wild type IL4. In some embodiments, an IL4 or IL4 variant, derivative, or fragment thereof of the disclosure can bind to common gamma chain with at least a comparable affinity as a wild type IL4. In some embodiments, an IL4 or IL4 variant, derivative, or fragment thereof of the disclosure can bind to IL-4Rα with at least a comparable affinity as a wild type IL4 sequence. In some embodiments, an IL4 or IL4 variant, derivative, or fragment thereof of the disclosure can bind to IL-13Rα1 and common gamma chain with at least a comparable affinity as a wild type IL4. In some embodiments, an IL4 or IL4 variant, derivative, or fragment thereof of the disclosure can bind to IL-13Rα1 and IL-4Rα with at least a comparable affinity as a wild type IL4. In some embodiments, an IL4 or IL4 variant, derivative, or fragment thereof of the disclosure can bind to common gamma chain and IL-4Rα with at least a comparable affinity as a wild type IL4. In some embodiments, an IL4 or IL4 variant, derivative, or fragment thereof of the disclosure can bind to IL-13Rα1, common gamma chain, and IL-4Rα with at least a comparable affinity as a wild type IL4.

In some embodiments, an IL4 or IL4 variant, derivative, or fragment thereof of the disclosure binds to an IL4 receptor subunit with at most a comparable affinity as a wild type IL4 sequence. For example, an IL4 or IL4 variant, derivative, or fragment thereof of the disclosure can bind to an interleukin 13 receptor alpha 1 (IL-13Rα1), common gamma chain, interleukin 4 receptor alpha (IL-4Rα), or a combination thereof with at most a comparable affinity as a wild type IL4. In some embodiments, an IL4 or IL4 variant, derivative, or fragment thereof of the disclosure can bind to IL-13Rα1 with at most a comparable affinity as a wild type IL4. In some embodiments, an IL4 or IL4 variant, derivative, or fragment thereof of the disclosure can bind to common gamma chain with at most a comparable affinity as a wild type IL4. In some embodiments, an IL4 or IL4 variant, derivative, or fragment thereof of the disclosure can bind to IL-4Rα with at most a comparable affinity as a wild type IL4 sequence. In some embodiments, an IL4 or IL4 variant, derivative, or fragment thereof of the disclosure can bind to IL-13Rα1 and common gamma chain with at most a comparable affinity as a wild type IL4. In some embodiments, an IL4 or IL4 variant, derivative, or fragment thereof of the disclosure can bind to IL-13Rα1 and IL-4Rα with at most a comparable affinity as a wild type IL4. In some embodiments, an IL4 or IL4 variant, derivative, or fragment thereof of the disclosure can bind to common gamma chain and IL-4Rα with at most a comparable affinity as a wild type IL4. In some embodiments, an IL4 or IL4 variant, derivative, or fragment thereof of the disclosure can bind to IL-13Rα1, common gamma chain, and IL-4Rα with at most a comparable affinity as a wild type IL4.

In some embodiments, an IL4 or IL4 variant, derivative, or fragment thereof can bind to an IL-13Rα1 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type IL4 sequence. In some embodiments, an IL4 or IL4 variant, derivative, or fragment thereof can bind to an IL-13Rα1 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type IL4 sequence.

In some embodiments, an IL4 or IL4 variant, derivative, or fragment thereof can bind to a common gamma chain with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type IL4 sequence. In some embodiments, an IL4 or IL4 variant, derivative, or fragment thereof can bind to a common gamma chain with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type IL4 sequence.

In some embodiments, an IL4 or IL4 variant, derivative, or fragment thereof can bind to an IL-4Rα with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type IL4 sequence. In some embodiments, an IL4 or IL4 variant, derivative, or fragment thereof can bind to an IL-4Rα with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type IL4 sequence.

In some embodiments, an IL4 or IL4 variant, derivative, or fragment thereof of the disclosure can activate a native IL4 receptor. A native IL4 receptor can be, for example, a receptor comprising an IL-13Rα1 subunit and an IL-4Rα subunit, or a common gamma chain subunit and an IL-4Rα subunit. In some embodiments, an IL4 or IL4 variant, derivative, or fragment thereof of the disclosure can activate a native IL4 receptor when present in a fusion protein. In some embodiments, an IL4 or IL4 variant, derivative, or fragment thereof of the disclosure can activate a native IL4 receptor when present as a polypeptide that is not part of a fusion protein, but does not activate native IL4 receptor when present in a fusion protein.

In some embodiments, a polypeptide of the disclosure does not contain IL4. In some embodiments, a polypeptide of the disclosure does not contain SEQ ID NO: 1.

Interleukin 10

A fusion protein may comprise an IL10 protein, or a variant, derivative, or fragment thereof operably linked or directly or indirectly fused to an interleukin 10 or a variant or derivative thereof. The IL10 protein is preferably a mammalian IL10 protein, such as a human IL10, or mouse IL10. One amino acid sequence representing IL10 is set forth in SEQ ID NO:5. Variants of IL10 include, for example, proteins having at least 70%, 75%, 80%, 85%, 90%, 92%, 95%, 96%, 97%, 98%, 99% or more, such as 100%, amino acid sequence identity to SEQ ID NO:5, preferably over the entire length. Amino acid sequence identity is preferably determined by pairwise alignment using the Needleman and Wunsch algorithm and GAP default parameters as defined above. Variants, derivatives, and fragments thereof also include proteins having IL10 activity, which have been derived, by way of one or more amino acid substitutions, deletions or insertions, from the polypeptide having the amino acid sequence of SEQ ID NO:5. Preferably, such proteins comprise from 1, 2, 3, 4, 5, 6, 7, 8, 9, 10 or more up to about 100, 90, 80, 70, 60, 50, 45, 40, 35, 30, 25, 20, 15 amino acid substitutions, deletions or insertions.

In some embodiments, an IL10 of the disclosure (e.g., an IL10 variant, derivative, or fragment thereof) can comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least or at least 50 amino acid substitutions, deletions, or insertions relative to an IL10 sequence disclosed herein (e.g., a wild type IL10 sequence).

In some embodiments, an IL10 of the disclosure (e.g., an IL10 variant, derivative, or fragment thereof) can comprise at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, at most 20, at most 25, at most 30, at most 35, at most 40, at most 45, or at most 50 amino acid substitutions, deletions, or insertions relative to an IL10 sequence disclosed herein (e.g., a wild type IL10 sequence).

In some embodiments, an IL10 sequence of the disclosure (e.g., an IL10 variant, derivative, or fragment thereof) can comprise 1-2, 1-3, 1-4, 1-5, 1-6, 1-7, 1-8, 1-9, 1-10, 1-15, 1-20, 1-30, 1-40, 2-3, 2-4, 2-5, 2-6, 2-7, 2-8, 2-9, 2-10, 2-15, 2-20, 2-30, 2-40, 3-3, 3-4, 3-5, 3-6, 3-7, 3-8, 3-9, 3-10, 3-15, 3-20, 3-30, 3-40, 5-6, 5-7, 5-8, 5-9, 5-10, 5-15, 5-20, 5-30, 5-40, 10-15, 15-20, or 20-25 amino acid substitutions, deletions, or insertions relative to an IL10 sequence disclosed herein (e.g., a wild type IL10 sequence).

In some embodiments, an IL10 sequence of the disclosure (e.g., an IL10 variant, derivative, or fragment thereof) can comprise 1, 2, 3, 4, 5, 6, 7, 8, 9, 10, 11, 12, 13, 14, 15, 16, 17, 18, 19, or 20 amino acid substitutions, deletions, or insertions relative to an IL10 sequence disclosed herein (e.g., a wild type IL10 sequence). An amino acid substitution can be a conservative or a non-conservative substitution. The one or more amino acid substitutions, deletions, or insertions can be at the N-terminus, the C-terminus, within the amino acid sequence, or a combination thereof. The amino acid substitutions, deletions, or insertions can be contiguous, non-contiguous, or a combination thereof.

An IL10 of the disclosure can comprise a wild type IL10 sequence. A non-limiting examples of a wild type IL10 sequences is SEQ ID NO: 5. SEQ ID NO: 5 can be a canonical wild type IL10 sequence of the disclosure.

An IL10 of the disclosure can comprise an IL10 variant, derivative, or fragment thereof with one or more amino acid substitutions. For example, an IL10 variant, derivative, or fragment thereof can comprise an amino acid substitution at a position I87, A89, H109, R110, F111, Y153, M156, or a combination thereof of SEQ ID NO: 5. In some embodiments, an IL10 variant, derivative, or fragment thereof comprises a substitution that is M156, F111S, I87A, I87G, A89D, HI09D, R110D, YI53D, MI56D, A89D, HI09E, R110E, YI53E, MI56E, or a combination thereof relative to SEQ ID NO: 5.

In some embodiments, an IL10 variant, derivative, or fragment thereof does not contain a substitution at position I87, A89, H109, R110, F111, Y153, or M156 relative to SEQ ID NO: 5. In some embodiments, an IL10 variant, derivative, or fragment thereof does not contain a M156, F111S, I87A, I87G, A89D, HI09D, R110D, YI53D, MI56D, A89D, HI09E, R110E, YI53E, or MI56E substitution.

In some embodiments, an IL10 or IL10 variant, derivative, or fragment thereof of the disclosure binds to an IL10 receptor subunit with about a comparable affinity as a wild type IL10 sequence. A comparable affinity can be, for example, less than about 10, less than about 5, less than about 2, less than about 1.9, less than about 1.8, less than about 1.7, less than about 1.6, less than about 1.5, less than about 1.4, less than about 1.3, less than about 1.2, or less than about 1.1 fold increased affinity compared to a wild type IL10 sequence. A comparable affinity can be, for example, less than about 10, less than about 5, less than about 2, less than about 1.9, less than about 1.8, less than about 1.7, less than about 1.6, less than about 1.5, less than about 1.4, less than about 1.3, less than about 1.2, or less than about 1.1 fold decreased affinity compared to a wild type IL10 sequence.

For example, an IL10 or IL10 variant, derivative, or fragment thereof of the disclosure can bind to an interleukin 10 receptor 1 (IL-10R1), interleukin 10 receptor 2 (IL-10R2), or a combination thereof with about a comparable affinity as a wild type IL10. In some embodiments, an IL10 or IL10 variant, derivative, or fragment thereof of the disclosure can bind to IL-10R1 with about a comparable affinity as a wild type IL10. In some embodiments, an IL10 or IL10 variant, derivative, or fragment thereof of the disclosure can bind to IL-10R2 with about a comparable affinity as a wild type IL10. In some embodiments, an IL10 or IL10 variant, derivative, or fragment thereof of the disclosure can bind to IL-10R1 and IL-10R2 with about a comparable affinity as a wild type IL10.

In some embodiments, an IL10 or IL10 variant, derivative, or fragment thereof of the disclosure can bind to an IL10 receptor subunit with at least a comparable affinity as a wild type IL10. For example, an IL10 or IL10 variant, derivative, or fragment thereof of the disclosure can bind to IL-10R1, IL-10R2, or a combination thereof with at least a comparable affinity as a wild type IL10. In some embodiments, an IL10 or IL10 variant, derivative, or fragment thereof of the disclosure can bind to an IL-10R1 with at least a comparable affinity as a wild type IL10. In some embodiments, an IL10 or IL10 variant, derivative, or fragment thereof of the disclosure can bind to an IL-10R2 with at least a comparable affinity as a wild type IL10. In some embodiments, an IL10 or IL10 variant, derivative, or fragment thereof of the disclosure can bind to an IL-10R1 and an IL-10R2 with at least a comparable affinity as a wild type IL10.

In some embodiments, an IL10 or IL10 variant, derivative, or fragment thereof of the disclosure can bind to an IL10 receptor subunit with at most a comparable affinity as a wild type IL10. For example, an IL10 or IL10 variant, derivative, or fragment thereof of the disclosure can bind to IL-10R1, IL-10R2, or a combination thereof with at most a comparable affinity as a wild type IL10. In some embodiments, an IL10 or IL10 variant, derivative, or fragment thereof of the disclosure can bind to an IL-10R1 with at most a comparable affinity as a wild type IL10. In some embodiments, an IL10 or IL10 variant, derivative, or fragment thereof of the disclosure can bind to an IL-10R2 with at most a comparable affinity as a wild type IL10. In some embodiments, an IL10 or IL10 variant, derivative, or fragment thereof of the disclosure can bind to an IL-10R1 and an IL-10R2 with at most a comparable affinity as a wild type IL10.

In some embodiments, an IL10 or IL10 variant, derivative, or fragment thereof can bind to an IL-10R1 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type IL10 sequence. In some embodiments, an IL10 or IL10 variant, derivative, or fragment thereof can bind to an IL-10R1 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type IL10 sequence.

In some embodiments, an IL10 or IL10 variant, derivative, or fragment thereof can bind to an IL-10R2 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type IL10 sequence. In some embodiments, an IL10 or IL10 variant, derivative, or fragment thereof can bind to an IL-10R2 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type IL10 sequence.

In some embodiments, an IL10 or IL10 variant, derivative, or fragment thereof of the disclosure can activate a native IL10 receptor. A native IL10 receptor can be, for example, a receptor comprising an IL-10R1 subunit and an IL-10R2 subunit. In some embodiments, an IL10 or IL10 variant, derivative, or fragment thereof of the disclosure can activate a native IL10 receptor when present in a fusion protein. In some embodiments, an IL10 or IL10 variant, derivative, or fragment thereof of the disclosure can activate a native IL10 receptor when present as a polypeptide that is not part of a fusion protein, but does not activate native IL10 receptor when present in a fusion protein.

In some embodiments, a polypeptide of the disclosure does not contain IL10. In some embodiments, a polypeptide of the disclosure does not contain SEQ ID NO: 5.

Interleukin 33

A fusion protein may comprise an IL33 protein, or a variant, derivative, or fragment thereof operably linked or directly or indirectly fused to an interleukin 13 or a variant or derivative thereof. The IL33 protein is preferably a mammalian IL33 protein, such as a human IL33, or mouse IL33. Non-limiting examples of amino acid sequences representing IL33 include SEQ ID NO:6 and SEQ ID NOs: 29-34. Variants of IL33 include, for example, proteins having at least 70%, 75%, 80%, 85%, 90%, 92%, 95%, 96%, 97%, 98%, 99% or more, such as 100%, amino acid sequence identity to SEQ ID NO:6 or any one of SEQ ID NOs: 29-34, preferably over the entire length. Amino acid sequence identity is preferably determined by pairwise alignment using the Needleman and Wunsch algorithm and GAP default parameters as defined above. Variants, derivatives, and fragments thereof also include proteins having IL33 activity, which have been derived, by way of one or more amino acid substitutions, deletions or insertions, from the polypeptide having the amino acid sequence of SEQ ID NO:6 or any one of SEQ ID NOs: 29-34. Preferably, such proteins comprise from 1, 2, 3, 4, 5, 6, 7, 8, 9, 10 or more up to about 100, 90, 80, 70, 60, 50, 45, 40, 35, 30, 25, 20, 15 amino acid substitutions, deletions or insertions.

In some embodiments, an IL33 of the disclosure (e.g., an IL33 variant, derivative, or fragment thereof) can comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least or at least 50 amino acid substitutions, deletions, or insertions relative to an IL33 sequence disclosed herein (e.g., a wild type IL33 sequence).

In some embodiments, an IL33 of the disclosure (e.g., an IL33 variant, derivative, or fragment thereof) can comprise at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, at most 20, at most 25, at most 30, at most 35, at most 40, at most 45, or at most 50 amino acid substitutions, deletions, or insertions relative to an IL33 sequence disclosed herein (e.g., a wild type IL33 sequence).

In some embodiments, an IL33 sequence of the disclosure (e.g., an IL33 variant, derivative, or fragment thereof) can comprise 1-2, 1-3, 1-4, 1-5, 1-6, 1-7, 1-8, 1-9, 1-10, 1-15, 1-20, 1-30, 1-40, 2-3, 2-4, 2-5, 2-6, 2-7, 2-8, 2-9, 2-10, 2-15, 2-20, 2-30, 2-40, 3-3, 3-4, 3-5, 3-6, 3-7, 3-8, 3-9, 3-10, 3-15, 3-20, 3-30, 3-40, 5-6, 5-7, 5-8, 5-9, 5-10, 5-15, 5-20, 5-30, 5-40, 10-15, 15-20, or 20-25 amino acid substitutions, deletions, or insertions relative to an IL33 sequence disclosed herein (e.g., a wild type IL33 sequence).

In some embodiments, an IL33 sequence of the disclosure (e.g., an IL33 variant, derivative, or fragment thereof) can comprise 1, 2, 3, 4, 5, 6, 7, 8, 9, 10, 11, 12, 13, 14, 15, 16, 17, 18, 19, or 20 amino acid substitutions, deletions, or insertions relative to an IL33 sequence disclosed herein (e.g., a wild type IL33 sequence). An amino acid substitution can be a conservative or a non-conservative substitution. The one or more amino acid substitutions, deletions, or insertions can be at the N-terminus, the C-terminus, within the amino acid sequence, or a combination thereof. The amino acid substitutions, deletions, or insertions can be contiguous, non-contiguous, or a combination thereof.

An IL33 of the disclosure can comprise a wild type IL33 sequence. Non-limiting examples of wild type IL33 sequences include SEQ ID NOs: 6 and 29-34. SEQ ID NO: 6 can be a canonical wild type IL33 sequence.

An IL33 of the disclosure can comprise an IL33 variant, derivative, or fragment thereof with one or more amino acid substitutions. For example, an IL33 variant, derivative, or fragment thereof can comprise an amino acid substitution at position I263 of SEQ ID NO: 6. In some embodiments, an IL33 variant, derivative, or fragment thereof comprises a substitution that is I263M relative to SEQ ID NO: 6.

In some embodiments, an IL33 variant, derivative, or fragment thereof does not contain a substitution at position I263 relative to SEQ ID NO: 6. In some embodiments, an IL33 variant, derivative, or fragment thereof does not contain an I263M substitution.

In some embodiments, an IL33 or IL33 variant, derivative, or fragment thereof of the disclosure binds to an IL33 receptor subunit with about a comparable affinity as a wild type IL33 sequence. A comparable affinity can be, for example, less than about 10, less than about 5, less than about 2, less than about 1.9, less than about 1.8, less than about 1.7, less than about 1.6, less than about 1.5, less than about 1.4, less than about 1.3, less than about 1.2, or less than about 1.1 fold increased affinity compared to a wild type IL33 sequence. A comparable affinity can be, for example, less than about 10, less than about 5, less than about 2, less than about 1.9, less than about 1.8, less than about 1.7, less than about 1.6, less than about 1.5, less than about 1.4, less than about 1.3, less than about 1.2, or less than about 1.1 fold decreased affinity compared to a wild type IL33 sequence.

For example, an IL33 or IL33 variant, derivative, or fragment thereof of the disclosure can bind to ST2 (IL1 RL1), IL1RAP, or a combination thereof with about a comparable affinity as a wild type IL33. In some embodiments, an IL33 or IL33 variant, derivative, or fragment thereof of the disclosure can bind to ST2 with about a comparable affinity as a wild type IL33. In some embodiments, an IL33 or IL33 variant, derivative, or fragment thereof of the disclosure can bind to IL1RAP with about a comparable affinity as a wild type IL33. In some embodiments, an IL33 or IL33 variant, derivative, or fragment thereof of the disclosure can bind to ST2 and IL1RAP with about a comparable affinity as a wild type IL33.

In some embodiments, an IL33 or IL33 variant, derivative, or fragment thereof of the disclosure can bind to an IL33 receptor subunit with at least a comparable affinity as a wild type IL33. For example, an IL33 or IL33 variant, derivative, or fragment thereof of the disclosure can bind to ST2, IL1RAP, or a combination thereof with at least a comparable affinity as a wild type IL33. In some embodiments, an IL33 or IL33 variant, derivative, or fragment thereof of the disclosure can bind to an ST2 with at least a comparable affinity as a wild type IL33. In some embodiments, an IL33 or IL33 variant, derivative, or fragment thereof of the disclosure can bind to an IL1RAP with at least a comparable affinity as a wild type IL33. In some embodiments, an IL33 or IL33 variant, derivative, or fragment thereof of the disclosure can bind to an ST2 and an IL1RAP with at least a comparable affinity as a wild type IL33.

In some embodiments, an IL33 or IL33 variant, derivative, or fragment thereof of the disclosure can bind to an IL33 receptor subunit with at most a comparable affinity as a wild type IL33. For example, an IL33 or IL33 variant, derivative, or fragment thereof of the disclosure can bind to ST2, IL1RAP, or a combination thereof with at most a comparable affinity as a wild type IL33. In some embodiments, an IL33 or IL33 variant, derivative, or fragment thereof of the disclosure can bind to an ST2 with at most a comparable affinity as a wild type IL33. In some embodiments, an IL33 or IL33 variant, derivative, or fragment thereof of the disclosure can bind to an IL1RAP with at most a comparable affinity as a wild type IL33. In some embodiments, an IL33 or IL33 variant, derivative, or fragment thereof of the disclosure can bind to an ST2 and an IL1RAP with at most a comparable affinity as a wild type IL33.

In some embodiments, an IL33 or IL33 variant, derivative, or fragment thereof can bind to an ST2 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type IL33 sequence. In some embodiments, an IL33 or IL33 variant, derivative, or fragment thereof can bind to an ST2 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type IL33 sequence.

In some embodiments, an IL33 or IL33 variant, derivative, or fragment thereof can bind to an IL1RAP with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type IL33 sequence. In some embodiments, an IL33 or IL33 variant, derivative, or fragment thereof can bind to an IL1RAP with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type IL33 sequence.

In some embodiments, an IL33 or IL33 variant, derivative, or fragment thereof of the disclosure can activate a native IL33 receptor. A native IL33 receptor can be, for example, a receptor comprising an ST2 subunit and an IL1RAP subunit. In some embodiments, an IL33 or IL33 variant, derivative, or fragment thereof of the disclosure can activate a native IL33 receptor when present in a fusion protein. In some embodiments, an IL33 or IL33 variant, derivative, or fragment thereof of the disclosure can activate a native IL33 receptor when present as a polypeptide that is not part of a fusion protein, but does not activate native IL33 receptor when present in a fusion protein.

Transforming Growth Factor Beta 1

A fusion protein may comprise a TGFβ1 protein, or a variant, derivative, or fragment thereof operably linked or directly or indirectly fused to an interleukin 13 or a variant or derivative thereof. The TGFβ1 protein is preferably a mammalian TGFβ1 protein, such as a human TGFβ1, or mouse TGFβ1. Non-limiting examples of amino acid sequences representing TGFβ1 include SEQ ID NO:7 and SEQ ID NO: 21. Variants of TGFβ1 include, for example, proteins having at least 70%, 75%, 80%, 85%, 90%, 92%, 95%, 96%, 97%, 98%, 99% or more, such as 100%, amino acid sequence identity to SEQ ID NO:7 (whole or underlined part) or SEQ ID NO: 21, preferably over the entire length. Amino acid sequence identity is preferably determined by pairwise alignment using the Needleman and Wunsch algorithm and GAP default parameters as defined above. Variants, derivatives, or fragments thereof also include proteins having TGFβ1 activity, which have been derived, by way of one or more amino acid substitutions, deletions or insertions, from the polypeptide having the amino acid sequence of SEQ ID NO:7 or SEQ ID NO: 21. Preferably, such proteins comprise from 1, 2, 3, 4, 5, 6, 7, 8, 9, 10 or more up to about 100, 90, 80, 70, 60, 50, 45, 40, 35, 30, 25, 20, 15 amino acid substitutions, deletions or insertions.

In some embodiments, a TGFβ1 of the disclosure (e.g., a TGFβ1 variant, derivative, or fragment thereof) can comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least or at least 50 amino acid substitutions, deletions, or insertions relative to a TGFβ1 sequence disclosed herein (e.g., a wild type TGFβ1 sequence).

In some embodiments, a TGFβ1 of the disclosure (e.g., a TGFβ1 variant, derivative, or fragment thereof) can comprise at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, at most 20, at most 25, at most 30, at most 35, at most 40, at most 45, or at most 50 amino acid substitutions, deletions, or insertions relative to a TGFβ1 sequence disclosed herein (e.g., a wild type TGFβ1 sequence).

In some embodiments, a TGFβ1 sequence of the disclosure (e.g., a TGFβ1 variant, derivative, or fragment thereof) can comprise 1-2, 1-3, 1-4, 1-5, 1-6, 1-7, 1-8, 1-9, 1-10, 1-15, 1-20, 1-30, 1-40, 2-3, 2-4, 2-5, 2-6, 2-7, 2-8, 2-9, 2-10, 2-15, 2-20, 2-30, 2-40, 3-3, 3-4, 3-5, 3-6, 3-7, 3-8, 3-9, 3-10, 3-15, 3-20, 3-30, 3-40, 5-6, 5-7, 5-8, 5-9, 5-10, 5-15, 5-20, 5-30, 5-40, 10-15, 15-20, or 20-25 amino acid substitutions, deletions, or insertions relative to a TGFβ1 sequence disclosed herein (e.g., a wild type TGFβ1 sequence).

In some embodiments, a TGFβ1 sequence of the disclosure (e.g., a TGFβ1 variant, derivative, or fragment thereof) can comprise 1, 2, 3, 4, 5, 6, 7, 8, 9, 10, 11, 12, 13, 14, 15, 16, 17, 18, 19, or 20 amino acid substitutions, deletions, or insertions relative to a TGFβ1 sequence 10 disclosed herein (e.g., a wild type TGFβ1 sequence). An amino acid substitution can be a conservative or a non-conservative substitution. The one or more amino acid substitutions, deletions, or insertions can be at the N-terminus, the C-terminus, within the amino acid sequence, or a combination thereof.

The amino acid substitutions, deletions, or insertions can be contiguous, non-contiguous, or a combination thereof.

A TGFβ1 of the disclosure can comprise a wild type TGFβ1 sequence. Non-limiting examples of wild type TGFβ1 sequences include SEQ ID NOs: 7 and 21. A canonical TGFβ1 sequence can be SEQ ID NO: 21.

In some embodiments, a TGFβ1 or TGFβ1 variant, derivative, or fragment thereof of the disclosure binds to a TGFβ1 receptor subunit with about a comparable affinity as a wild type TGFβ1 sequence. A comparable affinity can be, for example, less than about 10, less than about 5, less than about 2, less than about 1.9, less than about 1.8, less than about 1.7, less than about 1.6, less than about 1.5, less than about 1.4, less than about 1.3, less than about 1.2, or less than about 1.1 fold increased affinity compared to a wild type TGFβ1 sequence. A comparable affinity can be, for example, less than about 10, less than about 5, less than about 2, less than about 1.9, less than about 1.8, less than about 1.7, less than about 1.6, less than about 1.5, less than about 1.4, less than about 1.3, less than about 1.2, or less than about 1.1 fold decreased affinity compared to a wild type TGFβ1 sequence.

For example, a TGFβ1 or TGFβ1 variant, derivative, or fragment thereof of the disclosure can bind to a transforming growth factor beta receptor 1 (TGFβR1), a transforming growth factor beta receptor 2 (TGFβR2), an activin receptor-like kinase 1 (ALK-1), an activin receptor-like kinase 2 (ALK-2), or a combination thereof with about a comparable affinity as a wild type TGFβ1. In some embodiments, a TGFβ1 or TGFβ1 variant, derivative, or fragment thereof of the disclosure can bind to TGFβR1 with about a comparable affinity as a wild type TGFβ1. In some embodiments, a TGFβ1 or TGFβ1 variant, derivative, or fragment thereof of the disclosure can bind to TGFβR2 with about a comparable affinity as a wild type TGFβ1. In some embodiments, a TGFβ1 or TGFβ1 variant, derivative, or fragment thereof of the disclosure can bind to ALK-1 with about a comparable affinity as a wild type TGFβ1 sequence. In some embodiments, a TGFβ1 or TGFβ1 variant, derivative, or fragment thereof of the disclosure can bind to ALK-2 with about a comparable affinity as a wild type TGFβ1 sequence. In some embodiments, a TGFβ1 or TGFβ1 variant, derivative, or fragment thereof of the disclosure can bind to a TGFβR1, TGFβR2, ALK-1, and ALK-2 with about a comparable affinity as a wild type TGFβ1 sequence.

In some embodiments, a TGFβ1 or TGFβ1 variant, derivative, or fragment thereof of the disclosure can bind to a transforming growth factor beta receptor 1 (TGFβR1), a transforming growth factor beta receptor 2 (TGFβR2), an activin receptor-like kinase 1 (ALK-1), an activin receptor-like kinase 2 (ALK-2), or a combination thereof with at least a comparable affinity as a wild type TGFβ1. In some embodiments, a TGFβ1 or TGFβ1 variant, derivative, or fragment thereof of the disclosure can bind to TGFβR1 with at least a comparable affinity as a wild type TGFβ1. In some embodiments, a TGFβ1 or TGFβ1 variant, derivative, or fragment thereof of the disclosure can bind to TGFβR2 with at least a comparable affinity as a wild type TGFβ1. In some embodiments, a TGFβ1 or TGFβ1 variant, derivative, or fragment thereof of the disclosure can bind to ALK-1 with at least a comparable affinity as a wild type TGFβ1 sequence. In some embodiments, a TGFβ1 or TGFβ1 variant, derivative, or fragment thereof of the disclosure can bind to ALK-2 with at least a comparable affinity as a wild type TGFβ1 sequence. In some embodiments, a TGFβ1 or TGFβ1 variant, derivative, or fragment thereof of the disclosure can bind to a TGFβR1, TGFβR2, ALK-1, and ALK-2 with at least a comparable affinity as a wild type TGFβ1 sequence.

In some embodiments, a TGFβ1 or TGFβ1 variant, derivative, or fragment thereof of the disclosure can bind to a transforming growth factor beta receptor 1 (TGFβR1), a transforming growth factor beta receptor 2 (TGFβR2), an activin receptor-like kinase 1 (ALK-1), an activin receptor-like kinase 2 (ALK-2), or a combination thereof with at most a comparable affinity as a wild type TGFβ1. In some embodiments, a TGFβ1 or TGFβ1 variant, derivative, or fragment thereof of the disclosure can bind to TGFβR1 with at most a comparable affinity as a wild type TGFβ1. In some embodiments, a TGFβ1 or TGFβ1 variant, derivative, or fragment thereof of the disclosure can bind to TGFβR2 with at most a comparable affinity as a wild type TGFβ1. In some embodiments, a TGFβ1 or TGFβ1 variant, derivative, or fragment thereof of the disclosure can bind to ALK-1 with at most a comparable affinity as a wild type TGFβ1 sequence. In some embodiments, a TGFβ1 or TGFβ1 variant, derivative, or fragment thereof of the disclosure can bind to ALK-2 with at most a comparable affinity as a wild type TGFβ1 sequence. In some embodiments, a TGFβ1 or TGFβ1 variant, derivative, or fragment thereof of the disclosure can bind to a TGFβR1, TGFβR2, ALK-1, and ALK-2 with at most a comparable affinity as a wild type TGFβ1 sequence.

In some embodiments, an TGFβ1 or TGFβ1 variant, derivative, or fragment thereof can bind to a TGFβR1, TGFβR2, ALK-1, or ALK-2 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type TGFβ1 sequence. In some embodiments, an TGFβ1 or TGFβ1 variant, derivative, or fragment thereof can bind to a TGFβR1, TGFβR2, ALK-1, or ALK-2 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type TGFβ1 sequence.

In some embodiments, a TGFβ1 or TGFβ1 variant, derivative, or fragment thereof of the disclosure can activate a native TGFβ1 receptor. A native TGFβ1 receptor can be, for example, a receptor comprising a TGFβR1 subunit and a TGFβR2 subunit. In some embodiments, an TGFβ1 or TGFβ1 variant, derivative, or fragment thereof of the disclosure can activate a native TGFβ1 receptor when present in a fusion protein. In some embodiments, an TGFβ1 or TGFβ1 variant, derivative, or fragment thereof of the disclosure can activate a native TGFβ1 receptor when present as a polypeptide that is not part of a fusion protein, but does not activate native TGFβ1 receptor when present in a fusion protein.

Transforming Growth Factor Beta 2

A fusion protein may comprise a TGFβ2 protein, or a variant, derivative, or fragment thereof operably linked or directly or indirectly fused to an interleukin 13 or a variant or derivative thereof. The TGFβ2 protein is preferably a mammalian TGFβ2 protein, such as a human TGFβ2, or mouse TGFβ2. Non-limiting examples of amino acid sequences representing TGFβ2 include SEQ ID NO:8, SEQ ID NO: 22, and SEQ ID NO: 35. Variants of TGFβ2 include, for example, proteins having at least 70%, 75%, 80%, 85%, 90%, 92%, 95%, 96%, 97%, 98%, 99% or more, such as 100%, amino acid sequence identity to SEQ ID NO:8 (whole or underlined part), SEQ ID NO: 22, or SEQ ID NO: 35, preferably over the entire length. Amino acid sequence identity is preferably determined by pairwise alignment using the Needleman and Wunsch algorithm and GAP default parameters as defined above. Variants, derivatives, and fragments thereof also include proteins having TGFβ2 activity, which have been derived, by way of one or more amino acid substitutions, deletions or insertions, from the polypeptide having the amino acid sequence of SEQ ID NO:8, SEQ ID NO: 22, or SEQ ID NO: 35. Preferably, such proteins comprise from 1, 2, 3, 4, 5, 6, 7, 8, 9, 10 or more up to about 100, 90, 80, 70, 60, 50, 45, 40, 35, 30, 25, 20, 15 amino acid substitutions, deletions or insertions.

In some embodiments, a TGFβ2 of the disclosure (e.g., a TGFβ2 variant, derivative, or fragment thereof) can comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least or at least 50 amino acid substitutions, deletions, or insertions relative to a TGFβ2 sequence disclosed herein (e.g., a wild type TGFβ2 sequence).

In some embodiments, a TGFβ2 of the disclosure (e.g., a TGFβ2 variant, derivative, or fragment thereof) can comprise at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, at most 20, at most 25, at most 30, at most 35, at most 40, at most 45, or at most 50 amino acid substitutions, deletions, or insertions relative to a TGFβ2 sequence disclosed herein (e.g., a wild type TGFβ2 sequence).

In some embodiments, a TGFβ2 sequence of the disclosure (e.g., a TGFβ2 variant, derivative, or fragment thereof) can comprise 1-2, 1-3, 1-4, 1-5, 1-6, 1-7, 1-8, 1-9, 1-10, 1-15, 1-20, 1-30, 1-40, 2-3, 2-4, 2-5, 2-6, 2-7, 2-8, 2-9, 2-10, 2-15, 2-20, 2-30, 2-40, 3-3, 3-4, 3-5, 3-6, 3-7, 3-8, 3-9, 3-10, 3-15, 3-20, 3-30, 3-40, 5-6, 5-7, 5-8, 5-9, 5-10, 5-15, 5-20, 5-30, 5-40, 10-15, 15-20, or 20-25 amino acid substitutions, deletions, or insertions relative to a TGFβ2 sequence disclosed herein (e.g., a wild type TGFβ2 sequence).

In some embodiments, a TGFβ2 sequence of the disclosure (e.g., a TGFβ2 variant, derivative, or fragment thereof) can comprise 1, 2, 3, 4, 5, 6, 7, 8, 9, 10, 11, 12, 13, 14, 15, 16, 17, 18, 19, or 20 amino acid substitutions, deletions, or insertions relative to a TGFβ2 sequence disclosed herein (e.g., a wild type TGFβ2 sequence). An amino acid substitution can be a conservative or a non-conservative substitution. The one or more amino acid substitutions, deletions, or insertions can be at the N-terminus, the C-terminus, within the amino acid sequence, or a combination thereof. The amino acid substitutions, deletions, or insertions can be contiguous, non-contiguous, or a combination thereof.

A TGFβ2 of the disclosure can comprise a wild type TGFβ2 sequence. Non-limiting examples of wild type TGFβ2 sequences include SEQ ID NOs: 8, 22, and 35. SEQ ID NO: 22 can be a canonical wild type TGFβ2 sequence of the disclosure.

A TGFβ2 of the disclosure can comprise an TGFβ2 variant, derivative, or fragment thereof with one or more amino acid substitutions. For example, a TGFβ2 variant, derivative, or fragment thereof can comprise an amino acid substitution at position R18, P36, or a combination thereof of SEQ ID NO: 22. In some embodiments, a TGFβ2 variant, derivative, or fragment thereof comprises a substitution that is R18C, P36H, or a combination thereof relative to SEQ ID NO: 22. In some embodiments, a TGFβ2, fragment, or derivative thereof comprises the substitutions R18C, and P36H relative to SEQ ID NO: 22.

In some embodiments, a TGFβ2 variant, derivative, or fragment thereof does not contain a substitution at position R18, or P36 relative to SEQ ID NO: 22. In some embodiments, a TGFβ2 variant, derivative, or fragment thereof does not contain a R18C or P36H substitution.

In some embodiments, a TGFβ2 or TGFβ2 variant, derivative, or fragment thereof of the disclosure binds to a TGFβ2 receptor subunit with about a comparable affinity as a wild type TGFβ2 sequence. A comparable affinity can be, for example, less than about 10, less than about 5, less than about 2, less than about 1.9, less than about 1.8, less than about 1.7, less than about 1.6, less than about 1.5, less than about 1.4, less than about 1.3, less than about 1.2, or less than about 1.1 fold increased affinity compared to a wild type TGFβ2 sequence. A comparable affinity can be, for example, less than about 10, less than about 5, less than about 2, less than about 1.9, less than about 1.8, less than about 1.7, less than about 1.6, less than about 1.5, less than about 1.4, less than about 1.3, less than about 1.2, or less than about 1.1 fold decreased affinity compared to a wild type TGFβ2 sequence.

For example, a TGFβ2 or TGFβ2 variant, derivative, or fragment thereof of the disclosure can bind to a transforming growth factor beta receptor 1 (TGFβR1), a transforming growth factor beta receptor 2 (TGFβR2), an activin receptor-like kinase 1 (ALK-1), an activin receptor-like kinase 2 (ALK-2), or a combination thereof with about a comparable affinity as a wild type TGFβ2. In some embodiments, a TGFβ2 or TGFβ2 variant, derivative, or fragment thereof of the disclosure can bind to TGFβR1 with about a comparable affinity as a wild type TGFβ2. In some embodiments, a TGFβ2 or TGFβ2 variant, derivative, or fragment thereof of the disclosure can bind to TGFβR2 with about a comparable affinity as a wild type TGFβ2. In some embodiments, a TGFβ2 or TGFβ2 variant, derivative, or fragment thereof of the disclosure can bind to ALK-1 with about a comparable affinity as a wild type TGFβ2 sequence. In some embodiments, a TGFβ2 or TGFβ2 variant, derivative, or fragment thereof of the disclosure can bind to ALK-2 with about a comparable affinity as a wild type TGFβ2 sequence. In some embodiments, a TGFβ2 or TGFβ2 variant, derivative, or fragment thereof of the disclosure can bind to a TGFβR1, TGFβR2, ALK-1, and ALK-2 with about a comparable affinity as a wild type TGFβ2 sequence.

In some embodiments, a TGFβ2 or TGFβ2 variant, derivative, or fragment thereof of the disclosure can bind to a transforming growth factor beta receptor 1 (TGFβR1), a transforming growth factor beta receptor 2 (TGFβR2), an activin receptor-like kinase 1 (ALK-1), an activin receptor-like kinase 2 (ALK-2), or a combination thereof with at least a comparable affinity as a wild type TGFβ2. In some embodiments, a TGFβ2 or TGFβ2 variant, derivative, or fragment thereof of the disclosure can bind to TGFβR1 with at least a comparable affinity as a wild type TGFβ2. In some embodiments, a TGFβ2 or TGFβ2 variant, derivative, or fragment thereof of the disclosure can bind to TGFβR2 with at least a comparable affinity as a wild type TGFβ2. In some embodiments, a TGFβ2 or TGFβ2 variant, derivative, or fragment thereof of the disclosure can bind to ALK-1 with at least a comparable affinity as a wild type TGFβ2 sequence. In some embodiments, a TGFβ2 or TGFβ2 variant, derivative, or fragment thereof of the disclosure can bind to ALK-2 with at least a comparable affinity as a wild type TGFβ2 sequence. In some embodiments, a TGFβ2 or TGFβ2 variant, derivative, or fragment thereof of the disclosure can bind to a TGFβR1, TGFβR2, ALK-1, and ALK-2 with at least a comparable affinity as a wild type TGFβ2 sequence.

In some embodiments, a TGFβ2 or TGFβ2 variant, derivative, or fragment thereof of the disclosure can bind to a transforming growth factor beta receptor 1 (TGFβR1), a transforming growth factor beta receptor 2 (TGFβR2), an activin receptor-like kinase 1 (ALK-1), an activin receptor-like kinase 2 (ALK-2), or a combination thereof with at most a comparable affinity as a wild type TGFβ2. In some embodiments, a TGFβ2 or TGFβ2 variant, derivative, or fragment thereof of the disclosure can bind to TGFβR1 with at most a comparable affinity as a wild type TGFβ2. In some embodiments, a TGFβ2 or TGFβ2 variant, derivative, or fragment thereof of the disclosure can bind to TGFβR2 with at most a comparable affinity as a wild type TGFβ2. In some embodiments, a TGFβ2 or TGFβ2 variant, derivative, or fragment thereof of the disclosure can bind to ALK-1 with at most a comparable affinity as a wild type TGFβ2 sequence. In some embodiments, a TGFβ2 or TGFβ2 variant, derivative, or fragment thereof of the disclosure can bind to ALK-2 with at most a comparable affinity as a wild type TGFβ2 sequence. In some embodiments, a TGFβ2 or TGFβ2 variant, derivative, or fragment thereof of the disclosure can bind to a TGFβR1, TGFβR2, ALK-1, and ALK-2 with at most a comparable affinity as a wild type TGFβ2 sequence.

In some embodiments, a TGFβ2 or TGFβ2 variant, derivative, or fragment thereof can bind to a TGFβR1, TGFβR2, ALK-1, or ALK-2 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type TGFβ2 sequence. In some embodiments, a TGFβ2 or TGFβ2 variant, derivative, or fragment thereof can bind to a TGFβR1, TGFβR2, ALK-1, or ALK-2 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type TGFβ2 sequence.

In some embodiments, a TGFβ2 or TGFβ2 variant, derivative, or fragment thereof of the disclosure can activate a native TGFβ2 receptor. A native TGFβ2 receptor can be, for example, a receptor comprising a TGFβR1 subunit and a TGFβR2 subunit. In some embodiments, an TGFβ2 or TGFβ2 variant, derivative, or fragment thereof of the disclosure can activate a native TGFβ2 receptor when present in a fusion protein. In some embodiments, an TGFβ2 or TGFβ2 variant, derivative, or fragment thereof of the disclosure can activate a native TGFβ2 receptor when present as a polypeptide that is not part of a fusion protein, but does not activate native TGFβ2 receptor when present in a fusion protein.

Interleukin 27

A fusion protein may comprise an IL27 protein, or a variant, derivative, or fragment thereof operably linked or directly or indirectly fused to an interleukin 13 or a variant or derivative thereof. The IL27 protein is preferably a mammalian IL27 protein, such as a human IL27, or mouse IL27, or a variant, derivative, or fragment thereof. An IL27 or an IL27 variant, derivative, or fragment thereof of the disclosure can comprise an IL27A subunit, an IL27B (EBI3) subunit, or a combination thereof. In some embodiments, an IL27 of the disclosure comprises an IL27A subunit. In some embodiments, an IL27 of the disclosure comprises a variant IL27A subunit as disclosed below (e.g., as provided in SEQ ID NO: 18). In some embodiments, an IL27 of the disclosure comprises an IL27B subunit.

An example of an amino acid sequence representing IL27A is set forth in SEQ ID NO:36. An example of an amino acid sequence representing IL27B is set forth in SEQ ID NO:45. Variants of IL27 include, for example, proteins having at least 70%, 75%, 80%, 85%, 90%, 92%, 95%, 96%, 97%, 98%, 99% or more, such as 100%, amino acid sequence identity to SEQ ID NO:36 or SEQ ID NO: 45, preferably over the entire length. Amino acid sequence identity is preferably determined by pairwise alignment using the Needleman and Wunsch algorithm and GAP default parameters as defined above. Variants, derivatives, and fragments thereof also include proteins having IL27 activity, which have been derived, by way of one or more amino acid substitutions, deletions or insertions, from the polypeptide having the amino acid sequence of SEQ ID NO:36 or SEQ ID NO: 45. Preferably, such proteins comprise from 1, 2, 3, 4, 5, 6, 7, 8, 9, 10 or more up to about 100, 90, 80, 70, 60, 50, 45, 40, 35, 30, 25, 20, 15 amino acid substitutions, deletions or insertions.

In some embodiments, an IL27 of the disclosure (e.g., an IL27 variant, derivative, or fragment thereof) can comprise at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least or at least 50 amino acid substitutions, deletions, or insertions relative to an IL27 sequence disclosed herein (e.g., a wild type IL27 sequence).

In some embodiments, an IL27 of the disclosure (e.g., an IL27 variant, derivative, or fragment thereof) can comprise at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, at most 20, at most 25, at most 30, at most 35, at most 40, at most 45, or at most 50 amino acid substitutions, deletions, or insertions relative to an IL27 sequence disclosed herein (e.g., a wild type IL27 sequence).

In some embodiments, an IL27 sequence of the disclosure (e.g., an IL27 variant, derivative, or fragment thereof) can comprise 1-2, 1-3, 1-4, 1-5, 1-6, 1-7, 1-8, 1-9, 1-10, 1-15, 1-20, 1-30, 1-40, 2-3, 2-4, 2-5, 2-6, 2-7, 2-8, 2-9, 2-10, 2-15, 2-20, 2-30, 2-40, 3-3, 3-4, 3-5, 3-6, 3-7, 3-8, 3-9, 3-10, 3-15, 3-20, 3-30, 3-40, 5-6, 5-7, 5-8, 5-9, 5-10, 5-15, 5-20, 5-30, 5-40, 10-15, 15-20, or 20-25 amino acid substitutions, deletions, or insertions relative to an IL27 sequence disclosed herein (e.g., a wild type IL27 sequence).

In some embodiments, an IL27 sequence of the disclosure (e.g., an IL27 variant, derivative, or fragment thereof) can comprise 1, 2, 3, 4, 5, 6, 7, 8, 9, 10, 11, 12, 13, 14, 15, 16, 17, 18, 19, or 20 amino acid substitutions, deletions, or insertions relative to an IL27 sequence disclosed herein (e.g., a wild type IL27 sequence). An amino acid substitution can be a conservative or a non-conservative substitution. The one or more amino acid substitutions, deletions, or insertions can be at the N-terminus, the C-terminus, within the amino acid sequence, or a combination thereof. The amino acid substitutions, deletions, or insertions can be contiguous, non-contiguous, or a combination thereof.

An IL27 of the disclosure can comprise a wild type IL27 sequence. Non-limiting examples of wild type IL27 sequences include SEQ ID NO: 36 (IL27A) and SEQ ID NO: 45 (IL27B). SEQ ID NO: 36 can be a canonical wild type IL27 sequence. In some embodiments, an IL27 sequence of the disclosure comprises one substitution relative to a wild type IL27 sequence.

An example of an IL27 variant, derivative, or fragment thereof of the disclosure is an IL27 variant sequence that can be secreted as a functional immune modulatory monomer protein, for example, an IL27A variant, derivative, or fragment thereof that can be secreted and function as a functional immune modulatory monomer protein without needing to associate with an IL27B (EBI3) subunit. One or more amino acid substitutions, deletions, or insertions can be introduced to generate such a molecule. SEQ ID NO: 18 is an example of an IL27 variant, derivative, or fragment thereof of the disclosure that comprises one amino acid substation L134C relative to SEQ ID NO: 36 (which is L162C in the sequence that includes the signal peptide), and can be secreted as a functional immune modulatory monomer protein.

An IL27 of the disclosure can comprise an IL27 variant, derivative, or fragment thereof with one or more amino acid substitutions. For example, an IL27 variant, derivative, or fragment thereof can comprise an amino acid substitution at position F132, N132, L134, P135, E136, E137, L152, L153, P154, or a combination thereof of SEQ ID NO: 36. In some embodiments, an IL27 variant, derivative, or fragment thereof comprises a substitution that is F132C, N132C, L134C, P135C, E136C, E137C, L152C, L153C, P154C, F132D, N132D, L134D, P135D, E136D, E137D, L152D, L153D, P154D, F132E, N132E, L134E, P135E, E136E, E137E, L152E, L153E, P154E, F132R, N132R, L134R, P135R, E136R, E137R, L152R, L153R, P154R, F132K, N132K, L134K, P135K, E136K, E137K, L152K, L153K, P154K, S31A, L91P, or a combination thereof relative to SEQ ID NO: 36.

In some embodiments, an IL27 variant, derivative, or fragment thereof does not contain a substitution at position F132, N132, L134, P135, E136, E137, L152, L153, or P154 relative to SEQ ID NO: 36. In some embodiments, an IL27 variant, derivative, or fragment thereof does not contain an F132C, N132C, L134C, P135C, E136C, E137C, L152C, L153C, P154C, F132D, N132D, L134D, P135D, E136D, E137D, L152D, L153D, P154D, F132E, N132E, L134E, P135E, E136E, E137E, L152E, L153E, P154E, F132R, N132R, L134R, P135R, E136R, E137R, L152R, L153R, P154R, F132K, N132K, L134K, P135K, E136K, E137K, L152K, L153K, P154K, S31A, or L91P substitution.

In some embodiments, an IL27 or IL27 variant, derivative, or fragment thereof of the disclosure binds to an IL27 receptor subunit with about a comparable affinity as a wild type IL27 sequence. A comparable affinity can be, for example, less than about 10, less than about 5, less than about 2, less than about 1.9, less than about 1.8, less than about 1.7, less than about 1.6, less than about 1.5, less than about 1.4, less than about 1.3, less than about 1.2, or less than about 1.1 fold increased affinity compared to a wild type IL27 sequence. A comparable affinity can be, for example, less than about 10, less than about 5, less than about 2, less than about 1.9, less than about 1.8, less than about 1.7, less than about 1.6, less than about 1.5, less than about 1.4, less than about 1.3, less than about 1.2, or less than about 1.1 fold decreased affinity compared to a wild type IL27 sequence.

For example, an IL27 or IL27 variant, derivative, or fragment thereof of the disclosure can bind to an interleukin 27 receptor alpha (IL-27RA), gp130, or a combination thereof with about a comparable affinity as a wild type IL27. In some embodiments, an IL27 or IL27 variant, derivative, or fragment thereof of the disclosure can bind to IL-27RA with about a comparable affinity as a wild type IL27. In some embodiments, an IL27 or IL27 variant, derivative, or fragment thereof of the disclosure can bind to gp130 with about a comparable affinity as a wild type IL27. In some embodiments, an IL27 or IL27 variant, derivative, or fragment thereof of the disclosure can bind to IL-27RA and gp130 with about a comparable affinity as a wild type IL27.

In some embodiments, an IL27 or IL27 variant, derivative, or fragment thereof of the disclosure can bind to an IL27 receptor subunit with at least a comparable affinity as a wild type IL27. For example, an IL27 or IL27 variant, derivative, or fragment thereof of the disclosure can bind to IL-27RA, gp130, or a combination thereof with at least a comparable affinity as a wild type IL27. In some embodiments, an IL27 or IL27 variant, derivative, or fragment thereof of the disclosure can bind to an IL-27RA with at least a comparable affinity as a wild type IL27. In some embodiments, an IL27 or IL27 variant, derivative, or fragment thereof of the disclosure can bind to an gp130 with at least a comparable affinity as a wild type IL27. In some embodiments, an IL27 or IL27 variant, derivative, or fragment thereof of the disclosure can bind to an IL-27RA and an gp130 with at least a comparable affinity as a wild type IL27.

In some embodiments, an IL27 or IL27 variant, derivative, or fragment thereof of the disclosure can bind to an IL27 receptor subunit with at most a comparable affinity as a wild type IL27. For example, an IL27 or IL27 variant, derivative, or fragment thereof of the disclosure can bind to IL-27RA, gp130, or a combination thereof with at most a comparable affinity as a wild type IL27. In some embodiments, an IL27 or IL27 variant, derivative, or fragment thereof of the disclosure can bind to an IL-27RA with at most a comparable affinity as a wild type IL27. In some embodiments, an IL27 or IL27 variant, derivative, or fragment thereof of the disclosure can bind to an gp130 with at most a comparable affinity as a wild type IL27. In some embodiments, an IL27 or IL27 variant, derivative, or fragment thereof of the disclosure can bind to an IL-27RA and an gp130 with at most a comparable affinity as a wild type IL27.

In some embodiments, an IL27 or IL27 variant, derivative, or fragment thereof can bind to an IL-27RA with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type IL27 sequence. In some embodiments, an IL27 or IL27 variant, derivative, or fragment thereof can bind to an IL-27RA with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type IL27 sequence.

In some embodiments, an IL27 or IL27 variant, derivative, or fragment thereof can bind to gp130 A with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold increased affinity relative to a wild type IL27 sequence. In some embodiments, an IL27 or IL27 variant, derivative, or fragment thereof can bind to gp130 with at least about 1.5 fold, 2 fold, 5 fold, 10 fold, 15 fold, 20 fold, 30 fold, 40 fold, 50 fold, 100 fold, 200 fold, 500 fold, 1000 fold, or 10,000 fold decreased affinity relative to a wild type IL27 sequence.

In some embodiments, an IL27 or IL27 variant, derivative, or fragment thereof of the disclosure can activate a native IL27 receptor. A native IL27 receptor can be, for example, a receptor comprising an IL-27RA subunit and a gp130 subunit. In some embodiments, an IL27 or IL27 variant, derivative, or fragment thereof of the disclosure can activate a native IL27 receptor when present in a fusion protein. In some embodiments, an IL27 or IL27 variant, derivative, or fragment thereof of the disclosure can activate a native IL27 receptor when present as a polypeptide that is not part of a fusion protein, but does not activate native IL27 receptor when present in a fusion protein.

Fusion Proteins

The present disclosure provides fusion proteins that comprise an interleukin 13 (IL13) directly or indirectly linked to a regulatory cytokine, for example, IL4, IL10, IL27, IL33, TGFβ1, TGFβ2, or another IL13.

In some embodiments, a fusion protein of the disclosure can bind to receptors present on the surface of a cell and form a complex with about 2, about 3, about 4, about 5, about 6, about 7, about 8, about 9, about 10, about 11, or about 12 receptor subunits (e.g., polypeptide chains). In some embodiments, a fusion protein of the disclosure can bind to receptors present on the surface of a cell and form a complex with at least 2, at least 3, at least 4, at least 5, at least 6, at least 7, at least 8, at least 9, at least 10, at least 11, or at least 12 receptor subunits (e.g., polypeptide chains). In some embodiments, a fusion protein of the disclosure can bind to receptors present on the surface of a cell and form a complex with at most 2, at most 3, at most 4, at most 5, at most 6, at most 7, at most 8, at most 9, at most 10, at most 11, or at most 12 receptor subunits (e.g., polypeptide chains).

The IL4 (or IL10 or IL13 or IL27 or IL33 or TGFβ1 or TGFβ2) and IL13 in the fusion protein may or may not be connected by a linker, e.g., a linker sequence, or by a chemical spacer.

A linker can be a peptide. A linker can comprise a linker sequence, for example, a linker peptide sequence. A linker sequence can be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 51, 53, 54, 55, 56, 57, 58, 59, 60, 61, 62, 63, 64, 65, 66, 67, 68, 69, or 70 amino acid residues in length.

A linker as described herein can include a flexible or rigid linker. A flexible linker can have a sequence containing stretches of glycine and serine residues. The small size of the glycine and serine residues provides flexibility, and allows for mobility of the connected functional domains. The incorporation of serine or threonine can maintain the stability of the linker in aqueous solutions by forming hydrogen bonds with the water molecules, thereby reducing unfavorable interactions between the linker and protein moieties. Flexible linkers can also contain additional amino acids such as threonine and alanine to maintain flexibility, as well as polar amino acids such as lysine and glutamine to improve solubility.

A flexible linker can comprise SEQ ID NO: 3. A flexible linker can comprise repeats of SEQ ID NO: 37 (GGGS), for example, 1, 2, 3, 4, 5, 6, 7, 8, 9, or 10 repeats of SEQ ID NO: 37. A flexible linker can comprise repeats of SEQ ID NO: 38 (GGGGS), for example, 1, 2, 3, 4, 5, 6, 7, 8, 9, or 10 repeats of SEQ ID NO: 38. Several other types of flexible linkers, including SEQ ID NO: 40 (KESGSVSSEQLAQFRSLD) and SEQ ID NO: 41 (EGKSSGSGSESKST), can also be used. The SEQ ID NO: 42 (GSAGSAAGSGEF) linker can also be used, in which large hydrophobic residues are minimized to maintain good solubility in aqueous solutions. The length of the flexible linkers can be adjusted to allow for proper folding or to achieve optimal biological activity of the fused proteins.

A rigid linker can have, for example, an alpha helix-structure. An alpha-helical rigid linker can act as a spacer between protein domains. A rigid linker can comprise repeats of SEQ ID NO: 43 (EAAAK), for example, 1, 2, 3, 4, 5, 6, 7, 8, 9, or 10 repeats of SEQ ID NO: 43. A rigid linker can comprise repeats of SEQ ID NO: 44 (EAAAR), for example, 1, 2, 3, 4, 5, 6, 7, 8, 9, or 10 repeats of SEQ ID NO: 44. A rigid linker can have a proline-rich sequence, (XP)n, with X designating alanine, lysine, glutamine, or any amino acid. The presence of proline in non-helical linkers can increase stiffness, and allow for effective separation of protein domains.

A linker of the disclosure can include a non-peptide linker, for example, a chemical linker. For example, two amino acid sequences of the disclosure can be connected by a chemical linker. Each chemical linker of the disclosure can be alkylene, alkenylene, alkynylene, heteroalkylene, cycloalkylene, heterocycloalkylene, arylene, or heteroarylene, any of which is optionally substituted. In some embodiments, a chemical linker of the disclosure can be an ester, ether, amide, thioether, or polyethyleneglycol (PEG). In some embodiments, a linker can reverse the order of the amino acids sequence in a compound, for example, so that the amino acid sequences linked by the linked are head-to-head, rather than head-to-tail. Non-limiting examples of such linkers include diesters of dicarboxylic acids, such as oxalyl diester, malonyl diester, succinyl diester, glutaryl diester, adipyl diester, pimetyl diester, fumaryl diester, maleyl diester, phthalyl diester, isophthalyl diester, and terephthalyl diester. Non-limiting examples of such linkers include diamides of dicarboxylic acids, such as oxalyl diamide, malonyl diamide, succinyl diamide, glutaryl diamide, adipyl diamide, pimetyl diamide, fumaryl diamide, maleyl diamide, phthalyl diamide, isophthalyl diamide, and terephthalyl diamide. Non-limiting examples of such linkers include diamides of diamino linkers, such as ethylene diamine, 1,2-di(methylamino)ethane, 1,3-diaminopropane, 1,3-di(methylamino)propane, 1,4-di(methylamino)butane, 1,5-di(methylamino)pentane, 1,6-di(methylamino)hexane, and pipyrizine. Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, epoxy groups, and ester groups.

In some embodiments, an N terminus of a polypeptide sequence can be linked to an N terminus of another polypeptide. In some embodiments, a C terminus of a polypeptide sequence can be linked to a C terminus of another polypeptide.

In some embodiments, a fusion protein of the disclosure does not contain a linker.

Amino acids can include genetically encoded and non-genetically encoded occurring amino acids. Amino acids can include naturally occurring and non-naturally occurring amino acids. Amino acids can be L forms or D forms. Substitutions can include conservative and/or non-conservative amino acid substitutions. A conservative amino acid substitution can be a substitution of one amino acid for another amino acid of similar biochemical properties (e.g., charge, size, and/or hydrophobicity). A non-conservative amino acid substitution can be a substitution of one amino acid for another amino acid with different biochemical properties (e.g., charge, size, and/or hydrophobicity). A conservative amino acid change can be, for example, substitution that has minimal effect on the secondary or tertiary structure of a polypeptide. A conservative amino acid change can be an amino acid change from one hydrophilic amino acid to another hydrophilic amino acid. Hydrophilic amino acids can include Thr (T), Ser (S), His (H), Glu (E), Asn (N), Gln (Q), Asp (D), Lys (K) and Arg (R). A conservative amino acid change can be an amino acid change from one hydrophobic amino acid to another hydrophilic amino acid. Hydrophobic amino acids can include Ile (I), Phe (F), Val (V), Leu (L), Trp (W), Met (M), Ala (A), Gly (G), Tyr (Y), and Pro (P). A conservative amino acid change can be an amino acid change from one acidic amino acid to another acidic amino acid. Acidic amino acids can include Glu (E) and Asp (D). A conservative amino acid change can be an amino acid change from one basic amino acid to another basic amino acid. Basic amino acids can include His (H), Arg (R) and Lys (K). A conservative amino acid change can be an amino acid change from one polar amino acid to another polar amino acid. Polar amino acids can include Asn (N), Gln (Q), Ser (S) and Thr (T). A conservative amino acid change can be an amino acid change from one nonpolar amino acid to another nonpolar amino acid. Nonpolar amino acids can include Leu (L), Val(V), Ile (I), Met (M), Gly (G) and Ala (A). A conservative amino acid change can be an amino acid change from one aromatic amino acid to another aromatic amino acid. Aromatic amino acids can include Phe (F), Tyr (Y) and Trp (W). A conservative amino acid change can be an amino acid change from one aliphatic amino acid to another aliphatic amino acid. Aliphatic amino acids can include Ala (A), Val (V), Leu (L) and Ile (I). In some embodiments, a conservative amino acid substitution is an amino acid change from one amino acid to another amino acid within one of the following groups: Group I: ala, pro, gly, gln, asn, ser, thr; Group II: cys, ser, tyr, thr; Group III: val, ile, leu, met, ala, phe; Group IV: lys, arg, his; Group V: phe, tyr, trp, his; and Group VI: asp, glu.

Additional amino acid sequences may present at the N- and/or C-terminus of the fusion protein of the present invention, e.g., an affinity tag to facilitate purification. For example, a poly-histidine-tag, GST-tag, FLAG-tag, CBP tag, HA tag, or Myc tag may be present at the C- or N-terminus to facilitate purification. In some embodiments, an affinity tag is removed from a fusion protein of the disclosure, e.g., after purification. In some embodiments, a fusion protein of the disclosure does not contain an affinity tag, (e.g., the fusion protein can be purified by other methods). Additionally or alternatively, the fusion protein of the invention may optionally comprise additional protein moieties, such as moieties capable of targeting, e.g., a protein moiety comprising one or more antibody Fc regions. In some embodiments, a fusion protein comprises an antibody Fc region. In some embodiments, a fusion protein comprises an extracellular matrix-binding polypeptide.

The IL4 (or IL10 or IL27 or IL33 or TGFβ1 or TGFβ2) may be located N-terminal of the IL13, or may be located C-terminal of the IL13. In a preferred embodiment, the IL4 (or IL10 or IL27 or IL33 or TGFβ1 or TGFβ2) molecule is located N-terminal of the IL13 molecule.

In an embodiment, the fusion protein of the invention consists essentially of IL4 (or IL10 or IL27 or IL33 or TGFβ1 or TGFβ2) and IL13, optionally linked by a linker sequence.

In an embodiment, the fusion protein of the present invention prevents or reduces neuronal damage to primary sensory neurons cultured overnight in presence of oxaliplatin or paclitaxel as quantified by measuring the neurite length after β3-tubulin staining.

In a suitable embodiment, the fusion protein of the present invention is present in, purified into, and/or used in a monomeric form. In one embodiment, it has a molecular weight of 30 to 37 kDa. In some embodiments, a fusion protein of the disclosure is present in, purified into, and/or used in a multimeric form, for example, a dimeric form or a tetrameric form. In some embodiments, a fusion protein of the disclosure is present as, purified into, and/or used as a monomer, a dimer, a trimer, a tetramer, a multimer, or any combination thereof. A dimer, trimer, tetramer, or multimer can comprise subunits that are covalently or non-covalently bound.

In some embodiments, an IL4/IL13 fusion protein of the disclosure is present as, purified into, and/or used as a monomer. In some embodiments, an IL4/IL13 fusion protein of the disclosure is present as, purified into, and/or used as a dimer. In some embodiments, an IL4/IL13 fusion protein of the disclosure is present as, purified into, and/or used as a trimer. In some embodiments, an IL4/IL13 fusion protein of the disclosure is present as, purified into, and/or used as a tetramer. In some embodiments, an IL4/IL13 fusion protein of the disclosure is present as, purified into, and/or used as a multimer. In some embodiments, an IL4/IL13 fusion protein is present as, purified into, and/or used as a monomer and a dimer. In some embodiments, an IL4/IL13 fusion protein is present as, purified into, and/or used as a monomer, a dimer, a trimer, a tetramer, a multimer, or any combination thereof.

In some embodiments, an IL10/IL13 fusion protein of the disclosure is present as, purified into, and/or used as monomer. In some embodiments, an IL10/IL13 fusion protein of the disclosure is present as, purified into, and/or used as dimer. In some embodiments, an IL10/IL13 fusion protein of the disclosure is present as, purified into, and/or used as trimer. In some embodiments, an IL10/IL13 fusion protein of the disclosure is present as, purified into, and/or used as tetramer. In some embodiments, an IL10/IL13 fusion protein of the disclosure is present as, purified into, and/or used as multimer. In some embodiments, an 10/IL13 fusion protein is present as, purified into, and/or used as monomer and a dimer. In some embodiments, an IL10/IL13 fusion protein is present as, purified into, and/or used as monomer, a dimer, a trimer, a tetramer, a multimer, or any combination thereof.

In some embodiments, an IL13/IL13 fusion protein of the disclosure is present as, purified into, and/or used as monomer. In some embodiments, an IL13/IL13 fusion protein of the disclosure is present as, purified into, and/or used as dimer. In some embodiments, an IL13/IL13 fusion protein of the disclosure is present as, purified into, and/or used as trimer. In some embodiments, an IL13/IL13 fusion protein of the disclosure is present as, purified into, and/or used as tetramer. In some embodiments, an IL13/IL13 fusion protein of the disclosure is present as, purified into, and/or used as multimer. In some embodiments, an IL10/IL13 fusion protein is present as, purified into, and/or used as monomer and a dimer. In some embodiments, an IL10/IL13 fusion protein is present as, purified into, and/or used as monomer, a dimer, a trimer, a tetramer, a multimer, or any combination thereof.

In some embodiments, an IL27/IL13 fusion protein of the disclosure is present as, purified into, and/or used as monomer. In some embodiments, an IL27/IL13 fusion protein of the disclosure is present as, purified into, and/or used as dimer. In some embodiments, an IL27/IL13 fusion protein of the disclosure is present as, purified into, and/or used as trimer. In some embodiments, an IL27/IL13 fusion protein of the disclosure is present as, purified into, and/or used as tetramer. In some embodiments, an IL27/IL13 fusion protein of the disclosure is present as, purified into, and/or used as multimer. In some embodiments, an IL27/IL13 fusion protein is present as, purified into, and/or used as monomer and a dimer. In some embodiments, an IL27/IL13 fusion protein is present as, purified into, and/or used as monomer, a dimer, a trimer, a tetramer, a multimer, or any combination thereof.

In some embodiments, an IL33/IL13 fusion protein of the disclosure is present as, purified into, and/or used as monomer. In some embodiments, an IL33/IL13 fusion protein of the disclosure is present as, purified into, and/or used as dimer. In some embodiments, an IL33/IL13 fusion protein of the disclosure is present as, purified into, and/or used as trimer. In some embodiments, an IL33/IL13 fusion protein of the disclosure is present as, purified into, and/or used as tetramer. In some embodiments, an IL33/IL13 fusion protein of the disclosure is present as, purified into, and/or used as multimer. In some embodiments, an IL33/IL13 fusion protein is present as, purified into, and/or used as monomer and a dimer. In some embodiments, an IL33/IL13 fusion protein is present as, purified into, and/or used as monomer, a dimer, a trimer, a tetramer, a multimer, or any combination thereof.

In some embodiments, an TGFβ1/IL13 fusion protein of the disclosure is present as, purified into, and/or used as monomer. In some embodiments, a TGFβ1/IL13 fusion protein of the disclosure is present as, purified into, and/or used as dimer. In some embodiments, a TGFβ1/IL13 fusion protein of the disclosure is present as, purified into, and/or used as trimer. In some embodiments, a TGFβ1/IL13 fusion protein of the disclosure is present as, purified into, and/or used as tetramer. In some embodiments, a TGFβ1/IL13 fusion protein of the disclosure is present as, purified into, and/or used as multimer. In some embodiments, a TGFβ1/IL13 fusion protein is present as, purified into, and/or used as monomer and a dimer. In some embodiments a TGFβ1/IL13 fusion protein is present as, purified into, and/or used as monomer, a dimer, a trimer, a tetramer, a multimer, or any combination thereof.

In some embodiments, a TGFβ2/IL13 fusion protein of the disclosure is present as, purified into, and/or used as monomer. In some embodiments, a TGFβ2/IL13 fusion protein of the disclosure is present as, purified into, and/or used as dimer. In some embodiments, a TGFβ2/IL13 fusion protein of the disclosure is present as, purified into, and/or used as trimer. In some embodiments, a TGFβ2/IL13 fusion protein of the disclosure is present as, purified into, and/or used as tetramer. In some embodiments, an TGFβ2/IL13 fusion protein of the disclosure is present as, purified into, and/or used as multimer. In some embodiments, a TGFβ2/IL13 fusion protein is present as, purified into, and/or used as monomer and a dimer. In some embodiments, a TGFβ2/IL13 fusion protein is present as, purified into, and/or used as monomer, a dimer, a trimer, a tetramer, a multimer, or any combination thereof.

Methods of Making

The fusion protein of the present invention may be prepared by techniques which are routine to the skilled person. For example, it may be prepared using a technique which provides for the production of recombinant fusion proteins by continuous cell lines in culture. For example, fusion proteins of the present invention can be produced in a host cell transfectoma using a combination of recombinant DNA techniques and gene transfection methods.

For example, to express the fusion proteins of the present invention, a nucleic acid molecule encoding the fusion proteins of the present invention can be prepared by standard molecular biology techniques. The nucleic acid molecule of the invention is preferably operably linked to transcription regulatory sequences such as a promoter, and optionally a 3' untranslated region. The nucleic acid molecule of the present invention may be inserted into a vector, such as an expression vector, such that the genes are operatively linked to transcriptional and translational control sequences. The expression vector and transcription regulatory sequences are selected to be compatible with the expression host cell used. The nucleic acid molecule encoding a fusion protein of the present invention may be inserted into the expression vector by routine methods. The nucleic acid molecule or vector of the present invention may further include a nucleotide sequence encoding a signal peptide, which may facilitate secretion of the fusion protein from the host cell. Said nucleotide sequence encoding a signal peptide may be operably linked to the nucleic acid molecule of the present invention. Preferably, said signal peptide is located at the amino terminus of the fusion protein of the present invention, and as such, the nucleotide sequence encoding said signal peptide may be located 5' of the nucleic acid molecule encoding the fusion protein of the present invention. The signal peptide may be a cytokine signal peptide or a signal peptide from a non-cytokine protein. The signal peptide can be absent on a mature form of fusion protein. The promoter may be constitutive or inducible. The vector may comprise a selectable marker for selection of a vector-carrying host cell. The vector may comprise an origin of replication when the vector is a replicable vector.

The fusion protein according to the invention may be synthesized de novo by chemical synthesis (using e.g. a peptide synthesizer such as supplied by Applied Biosystems) or may be produced by recombinant host cells by expressing the nucleic acid sequence encoding the fusion protein, fragment derivative, or variant. Variants and fragments are preferably functional, i.e., they bind at least to one, two, three, four, or all of the corresponding membrane-receptor(s) or receptor subunits and have IL4 (or IL10 or IL27 or IL33 or TGFβ1 or TGFβ2) and/or IL13 activity, preferably IL4 (or IL10 or IL27 or IL33 or TGFβ1 or TGFβ2) and IL13 activity.

The functional activity of IL4 (or IL10 or IL27 or IL33 or TGFβ1 or TGFβ2) and IL13, as well as the IL4 (or IL10 or IL27 or IL33 or TGFβ1 or TGFβ2) and IL13 comprising fusion protein can be determined using routine methods known for those skilled in the art. For example, a suitable assay for functionality of IL4, as well as the IL4 (or IL10) and IL13 comprising fusion protein, is the lipopolysaccharide (LPS) induced cytokine release (IL1, IL6, IL8, TNFα) in whole blood, optionally in the presence of anti-IL10 antibody. Functional activity may also be determined by assessing the activation of intracellular signalling pathways upon incubation of target cells with the fusion protein in presence or absence of blocking antibody against either cytokine moiety of the fusion protein or their receptors.

In another aspect, isolated nucleic acid sequences encoding any of the above fusion proteins are provided, such as cDNA, genomic DNA and RNA sequences. Due to the degeneracy of the genetic code various nucleic acid sequences may encode the same amino acid sequence. Any nucleic acid sequence encoding the fusion proteins of the invention are herein referred to as "IL4/IL13 (or IL10/IL13, IL27/IL13, IL33/IL13, TGFβ1/IL13, TGFβ2/IL13, IL13/IL13) encoding nucleic acid sequences". The nucleic acid sequences provided include recombinant, artificial or synthetic nucleic acid sequences. It is understood that when sequences are depicted as DNA sequences while RNA is referred to, the actual base sequence of the RNA molecule is identical with the difference that thymine (T) is replaced by uracil (U). The nucleic acid sequences of the invention are particularly useful for expression of the IL4/IL13 (or IL10/IL13, IL27/IL13, IL33/IL13, TGFβ1/IL13, TGFβ2/IL13, IL13/IL13) fusion protein of the invention, for either the production of these proteins, or for gene therapy purposes.

The nucleic acid sequence, particularly DNA sequence, encoding the IL4/IL13 (or IL10/IL13 or IL27/IL13 or IL33/13 or TGFβ1/IL13 or TGFβ2/IL13 or IL13/IL13) fusion protein of this invention can be inserted in expression vectors to produce (e.g., high amounts of) IL4/IL13 (or IL10/IL13 or IL27/IL13 or IL33/13 or TGFβ1/IL13 or TGFβ2/IL13, or IL13/IL13) fusion protein. Suitable vectors include, without limitation, linear nucleic acids, plasmids, phagemids, cosmids, RNA vectors, viral vectors and the like. Non-limiting examples of a viral vector include a retrovirus, an adenovirus, and an adeno-associated virus.

Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter.

In addition to the nucleic acid molecules encoding IL4/IL13 (or IL10/IL13 or IL27/IL13 or IL33/IL13 or TGFβ1/113 or TGFβ2/IL13 or IL13/IL13) fusion proteins and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection). Finally, the recombinant expression vector may contain a gene that codes for a glycosyl transferase in addition to the nucleic acid sequence encoding the fusion proteins of the present invention.

In another aspect, the present invention relates to a host cell comprising a nucleic acid sequence of the present invention, or a nucleic acid construct or vector comprising a nucleic acid sequence of the present invention. The host cell may be any host cell. The host cell may be selected from prokaryotic and eukaryotic cells. The host cell may also be a cell line, such as a prokaryotic or eukaryotic cell line. The host cell is preferably an animal cell or cell line, such as a mammalian cell or cell line.

In one embodiment the fusion proteins of the present invention are expressed in eukaryotic cells, such as mammalian host cells. Preferred mammalian host cells for expressing the fusion proteins of the invention include CHO cells (including dhfr-CHO cells, described in (Urlaub et al., 1980), used with a DHFR selectable marker, NS/0 myeloma cells, COS cells, HEK293 cells, PER.C6 cells, SP2.0 cells, or other cells. When recombinant expression vectors comprising nucleic acid sequences encoding a fusion protein according to the present invention are introduced into mammalian host cells, the fusion proteins of the present invention may be produced by culturing the host cells for a period of time sufficient to allow for expression of the fusion proteins in the host cells or, more preferably, secretion of the fusion proteins into the culture medium in which the host cells are grown. The fusion proteins of the present invention can be recovered from the culture medium using standard protein purification methods.

Alternatively, the nucleic acid sequences encoding the fusion proteins of the invention can be expressed in other expression systems, including prokaryotic cells, such as microorganisms, e.g. *E. coli*, or in algal expression systems, insect cell expression systems, or cell-free protein synthesis systems. Furthermore, the fusion proteins of the present invention can be produced in transgenic non-human animals, such as in milk from sheep and rabbits or eggs from hens, or in transgenic plants.

Introduction of the nucleic acid sequence of the present invention into a host cell may be carried out by any standard technique known in the art. For expression of the fusion proteins of the present invention, the expression vector(s) encoding the fusion protein may transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, lipofectamine transfection and freeze-dry method transfection, and the like. Cell lines that secrete fusion proteins of the present invention can be identified by assaying culture supernatants for the presence of the fusion protein. The preferred screening procedure comprises two sequential steps, the first being identification of cell lines that secrete the fusion protein, the second being determination of the quality of the fusion protein such as the ability of the fusion protein to inhibit cytokine production by blood cells stimulated with LPS or other Toll-like receptor agonists, glycosylation patterns, and other.

For optimal expression in a host cell, the DNA sequence encoding a fusion protein of the disclosure (e.g., an IL4/IL13 or IL10/IL13 or IL27/IL13 or IL33/13 or TGFβ1/IL13 or TGFβ2/IL13 or IL13/IL13 fusion protein can be codon-optimized by adapting the codon usage to that most preferred in host cell genes. Several techniques for modifying the codon usage to that preferred by the host cells can be found in patent and scientific literature. The exact method of codon usage modification is not critical for this invention.

In another embodiment of the invention PCR primers and/or probes and kits for detecting the IL4/IL13 (or IL10/IL13 or IL27/IL13 or IL33/IL13 or TGFβ1/IL13 or TGFβ2/IL13 or IL13/IL13) fusion protein encoding DNA or RNA sequences are provided. Degenerate or specific PCR primer pairs to amplify IL4/IL13 (or IL10/IL13 or IL27/IL13 or IL33/IL13 or TGFβ1/IL13 or TGFβ2/IL13 or IL13/IL13) fusion protein encoding DNA from samples can be synthesized (see Dieffenbach and Dveksler (1995) PCR Primer: A Laboratory Manual, Cold Spring Harbor Laboratory Press, and McPherson at al. (2000) PCR-Basics: From Background to Bench, First Edition, Springer Verlag, Germany). For example, any stretch of 9, 10, 11, 12, 13, 14, 15, 16, 18 or more contiguous nucleotides of an IL4/IL13 (or IL10/IL13 or IL27/IL13 or IL33/IL13 or TGFβ1/IL13 or TGFβ2/IL13 or IL13/IL13) fusion protein encoding nucleic acid sequence (or the complement strand) may be used as primer or probe. Likewise, DNA fragments of an IL4/IL13 (or IL10/IL13 or IL27/IL13 or IL33/IL13 or TGFβ1/IL13 or TGFβ2/IL13 or IL13/IL13) fusion protein encoding nucleic acid sequence can be used as hybridization probes. A detection kit for an IL4/IL13 (or IL10/IL13 or IL27/IL13 or IL33/IL13 or TGFβ1/IL13 or TGFβ2/IL13 or IL13/IL13) fusion protein encoding nucleic acid sequence may comprise primers specific for an IL4/IL13 (or IL10/IL13 or IL27/IL13 or IL33/IL13 or TGFβ1/IL13 or TGFβ2/IL13 or IL13/IL13) fusion protein encoding nucleic acid sequence and/or probes specific for an IL4/IL13 (or IL10/IL13 or IL27/IL13 or IL33/IL13 or TGFβ1/IL13 or TGFβ2/IL13 or IL13/IL13) fusion protein encoding nucleic acid sequences, and an associated protocol to use the primers or probe to detect specifically IL4/IL13 (or IL10/IL13 or IL27/IL13 or IL33/IL13 or TGFβ1/IL13 or TGFβ2/IL13 or IL13/IL13) fusion protein encoding nucleic acid sequence in a sample. Such a detection kit may, for example, be used to determine, whether a host cell has been transformed with a specific an IL4/IL13 (or IL10/IL13 or IL27/IL13 or IL33/IL13 or TGFβ1/IL13 or TGFβ2/113 or IL13/IL13) fusion protein encoding nucleic acid sequence of the invention. Because of the degeneracy of the genetic code, some amino acid codons can be replaced by others without changing the amino acid sequence of the protein.

In an aspect, the present invention is concerned with a method for producing a fusion protein of the disclosure (e.g., an IL4/IL13 or IL10/IL13 or IL27/IL13 or IL33/IL13 or TGFβ1/IL13 or TGFβ2/IL13 or IL13/IL13 fusion protein, said method comprising the steps of culturing a host cell of the present invention under conditions permitting the production of the fusion protein (e.g., IL4/IL13 or IL10/IL13 or IL27/IL13 or IL33/IL13 or TGFβ1/IL13 or TGFβ2/IL13 or IL13/IL13 fusion protein; and optionally, recovering the fusion protein. The skilled person will be capable of routinely selecting conditions permitting production of the IL4/IL13 (or IL10/IL13 or IL27/IL13 or IL33/IL13 or TGFβ1/IL13 or TGFβ2/IL13 or IL13/IL13) fusion protein. Additionally, a person skilled in the art will be capable of recovering the fusion protein produced using routine methods, which include, without limitation, chromatographic methods (including, without limitation, size exclusion chromatography, hydrophobic interaction chromatography, ion exchange chromatography, affinity chromatography, immunoaffinity chromatography, metal binding, and the like), immunoprecipitation, HPLC, ultracentrifugation, precipitation and differential solubilisation, and extraction. As said above, recovery or purification of the fusion protein may be facilitated by adding, for example, a His-tag to the fusion protein.

Pharmaceutical Composition

In an aspect, the invention relates to a pharmaceutical composition comprising the fusion protein of the present invention and a pharmaceutically acceptable carrier.

The pharmaceutical compositions may be formulated with pharmaceutically acceptable carriers or diluents as well as any other known adjuvants and excipients in accordance with conventional techniques (e.g., as described in Remington: The Science and Practice of Pharmacy, 19$^{th}$ Edition, Gennaro, Ed., Mack Publishing Co., Easton, PA, 1995).

The term "pharmaceutically acceptable carrier" relates to carriers or excipients, which are inherently nontoxic and nontherapeutic. Examples of such excipients are, but are not limited to, saline, Ringer's solution, dextrose solution and Hank's solution.

The pharmaceutical composition may be administered by any suitable route and mode. As will be appreciated by the skilled artisan, the route and/or mode of administration will vary depending upon the desired results.

The pharmaceutical compositions according to the invention may be formulated in accordance with routine procedures for administration by any route, preferably parenteral. The compositions may be in the form of liquid preparations, such as oral or sterile parenteral solutions or suspensions.

The pharmaceutical compositions of the present invention include those suitable for any form of parenteral administration.

In an embodiment, the pharmaceutical composition is administered parenterally.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural intrasternal, intracerebral, intraocular, intralesional, intracerebroventricular, intracisternal, and intraparenchymal, e.g., injection and infusion.

In an embodiment the pharmaceutical composition is administered by intravenous or subcutaneous injection or infusion.

In an embodiment the fusion proteins of the invention are administered in crystalline form by subcutaneous injection.

As used herein, "pharmaceutically acceptable carrier" includes any and all solvents, dispersion media, coatings, antibacterial and antifungal agents, isotonicity agents, antioxidants and absorption delaying agents, and the like that are physiologically compatible.

Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical composition of the invention is contemplated. Preferably, the carrier is suitable for parenteral administration, e.g. intravenous or subcutaneous injection or infusion.

Pharmaceutical compositions typically must be sterile and stable under the conditions of manufacture and storage. The composition can be formulated as a solution, microemulsion, liposome, or other ordered structure suitable to high drug concentration. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Sterile injectable solutions can be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Depending on the route of administration, the active compound, i.e., the IL4/IL13 (or IL10/IL13 or IL27/IL13 or IL33/IL13 or TGFβ1/IL13 or TGFβ2/IL13 or IL13/IL13) fusion protein, may be coated in a material to protect it from the action of acids and other natural conditions that may inactivate the compound. For example, the compound may be administered to a subject in an appropriate carrier, for example, liposomes. Liposomes include water-in-oil-in-water CGF emulsions as well as conventional liposomes (Strejan et al., 1984).

The fusion proteins of the present invention may also be prepared with carriers that will protect it against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

A pharmaceutical composition of the disclosure can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism.

Pharmaceutical formulations for administration can include aqueous solutions of the active compounds in water soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. The active ingredient can be in powder form for constitution with a suitable vehicle, for example, sterile pyrogen-free water, before use.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising compounds described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers, and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, dispersible granules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include liquid, powder, gel, nanosuspension, nanoparticle, microgel, aqueous or oily suspensions, emulsion, and any combination thereof.

Non-limiting examples of pharmaceutically-acceptable excipients suitable for use in the disclosure include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

Non-limiting examples of pharmaceutically-acceptable carriers include saline, Ringer's solution, and dextrose solution. In some embodiments, the pH of the solution can be from about 5 to about 8, and can be from about 7 to about 7.5. Further carriers include sustained release preparations such as semipermeable matrices of solid hydrophobic polymers containing the compound. The matrices can be in the form of shaped articles, for example, films, liposomes, microparticles, or microcapsules.

The pH of the disclosed composition can range from about 3 to about 12. The pH of the composition can be, for example, from about 3 to about 4, from about 4 to about 5, from about 5 to about 6, from about 6 to about 7, from about 7 to about 8, from about 8 to about 9, from about 9 to about 10, from about 10 to about 11, or from about 11 to about 12 pH units. The pH of the composition can be, for example, about 3, about 4, about 5, about 6, about 7, about 8, about 9, about 10, about 11, or about 12 pH units. The pH of the composition can be, for example, at least 3, at least 4, at least 5, at least 6, at least 6.2 at least 6.4, at least 6.6, at least 6.8, at least 7, at least 7.2, at least 7.4, at least 7.6, at least 7.8, at least 8, at least 9, at least 10, at least 11 or at least 12 pH units. The pH of the composition can be, for example, at most 3, at most 4, at most 5, at most 6, at most 6.2 at most 6.4, at most 6.6, at most 6.8, at most 7, at most 7.2, at most 7.4, at most 7.6, at most 7.8, at most 8, at most 9, at most 10, at most 11, or at most 12 pH units. A pharmaceutical formulation disclosed herein can have a pH of from about 5.5 to about 8.5.

Formulations of the disclosure can comprise sugars, alcohols, antioxidants, buffers, bacteriostats, solutes which render the formulation isotonic with the blood of the intended recipient or suspending or thickening agents. These compositions can also contain preservatives, wetting agents, emulsifying agents and dispersing agents. Prevention of the action of microorganisms upon the subject compounds can be achieved by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin. If desired, the formulation can be diluted prior to use with, for example, an isotonic saline solution or a dextrose solution.

In some embodiments, the pharmaceutical composition provided herein comprises a therapeutically effective amount of a compound (e.g., fusion protein) in admixture with a pharmaceutically-acceptable carrier and/or excipient, for example, saline, phosphate buffered saline, phosphate and amino acids, polymers, polyols, sugar, buffers, preservatives, and other proteins. Illustrative agents include octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene, and glycol.

In some embodiments, a pharmaceutical formulation disclosed herein can comprise: (i) a compound or fusion protein disclosed herein; (ii) a buffer; (iii) a non-ionic detergent; (iv) a tonicity agent; and (v) a stabilizer. In some embodiments, the pharmaceutical formulation disclosed herein is a stable liquid pharmaceutical formulation.

For solid compositions, solid carriers include, for example, pharmaceutical grades of mannitol, lactose, starch, magnesium stearate, sodium saccharin, talc, cellulose, glucose, sucrose, and magnesium carbonate.

A pharmaceutical carrier or excipient can be a solvent, dispersion media, coatings, antibacterial and antifungal agents, isotonic and absorption delaying agents, and the like that is physiologically compatible. The carrier can be suitable for administration by a route disclosed herein (e.g., parenteral).

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some embodiments, a formulation of the disclosure contains a thermal stabilizer, such as a sugar or sugar alcohol, for example, sucrose, sorbitol, glycerol, trehalose, or mannitol, or any combination thereof. In some embodiments, the stabilizer is a sugar. In some embodiments, the sugar is sucrose, mannitol or trehalose.

Non-limiting examples of pharmaceutically-acceptable excipients can be found, for example, in Remington: The Science and Practice of Pharmacy, Nineteenth Ed (Easton, Pa: Mack Publishing Company, 1995); Hoover, John E., Remington's Pharmaceutical Sciences, Mack Publishing Co., Easton, Pennsylvania. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), each of which is incorporated by reference in its entirety.

A pharmaceutical composition can be administered in a local manner, for example, via injection of the compound directly into an organ, optionally in a depot or sustained release formulation or implant. A pharmaceutical composition can be provided in the form of a rapid release formulation, in the form of an extended release formulation, or in the form of an intermediate release formulation. A rapid release form can provide an immediate release. An extended release formulation can provide a controlled release or a sustained delayed release.

In some embodiments, a pump can be used for delivery of the pharmaceutical composition. In some embodiments, a pen delivery device can be used, for example, for subcutaneous delivery of a composition of the disclosure. Such a pen delivery device can be reusable or disposable. A reusable pen delivery device can use a replaceable cartridge that contains a pharmaceutical composition disclosed herein. Once all of the pharmaceutical composition within the cartridge has been administered and the cartridge is empty, the empty cartridge can readily be discarded and replaced with a new cartridge that contains the pharmaceutical composition. The pen delivery device can then be reused. A disposable pen has no replaceable cartridge. Rather, the disposable pen delivery device comes prefilled with the pharmaceutical composition held in a reservoir within the device. Once the reservoir is emptied of the pharmaceutical composition, the entire device is discarded.

A pharmaceutical composition described herein can be in a unit dosage form suitable for a single administration of a precise dosage. In unit dosage form, the formulation can be divided into unit doses containing appropriate quantities of one or more compounds, fusion proteins, and/or therapeutic agents. The unit dosage can be in the form of a package containing discrete quantities of the formulation. Non-limiting examples are packaged injectables, vials, and ampoules. An aqueous suspension composition disclosed herein can be packaged in a single-dose non-reclosable container. Multiple-dose reclosable containers can be used, for example, in combination with or without a preservative. A formulation for injection disclosed herein can be present in a unit dosage form, for example, in ampoules, or in multi dose containers with a preservative.

In some embodiments, a pharmaceutical formulation disclosed herein is a liquid formulation that can comprise about 50 µg/mL to about 100 mg/mL of fusion protein. A formulation can comprise, for example, at least 50 µg/mL, at least 100 µg/mL, at least 200 µg/mL, at least 300 µg/mL, at least 400 µg/mL, at least 500 µg/mL, at least 600 µg/mL, at least 700 µg/mL, at least 800 µg/mL, at least 900 µg/mL, at least 1 mg/mL, at least 10 mg/mL, at least 20 mg/mL, or at least 50 mg/mL. In some embodiments, a formulation can comprise at most 100 µg/mL, at most 200 µg/mL, at most 300 µg/mL, at most 400 µg/mL, at most 500 µg/mL, at most 600 µg/mL, at most 700 µg/mL, at most 800 µg/mL, at most 900

µg/mL, at most 1 mg/mL, at most 10 mg/mL, at most 20 mg/mL, or at most 50 mg/mL.

Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the IL4/IL13 (or IL10/IL13 or IL27/IL13 or IL33/IL13 TGFβ1/IL13 or TGFβ2/IL13 or IL13/IL13) fusion proteins of the present invention may be varied so as to obtain an amount of the IL4/IL13 (or IL10/IL13 or IL27/IL13 or IL33/IL13 or TGFβ1/IL13 or TGFβ2/IL13 or IL13/IL13) fusion protein which is effective ("effective amount") to achieve the desired therapeutic response for a particular subject (e.g., patient), composition, and mode of administration, without being toxic to the subject (e.g., patient). The selected dosage level will depend upon a variety of pharmacokinetic factors including the activity of the particular compositions of the present invention employed, the route of administration, the time of administration, the rate of excretion, the duration of the treatment, other drugs, compounds and/or materials used in combination with the particular compositions employed, the age, sex, weight, condition, general health and prior medical history of the patient being treated, and like factors well known in the medical arts.

In one embodiment the IL4/IL13 (or IL10/IL13 or IL27/IL13 or IL33/IL13 or TGFβ1/IL13 or TGFβ2/IL13 or IL13/IL13) fusion proteins present invention can be given as intravenous injection or a short infusion, in another embodiment, they are administered by slow continuous infusion over a long period, such as more than 24 hours, in order to reduce toxic side effects.

In yet another embodiment, the IL4/IL13 (or IL10/IL13 or IL27/IL13 or IL33/IL13 or TGFβ1/IL13 or TGFβ2/IL13 or IL13/IL13) fusion proteins of the present invention can be administered as maintenance therapy, such as, e.g., once a week for a period of 6 months or more.

In another embodiment, the IL4/IL13 (or IL10/IL13 or IL27/IL13 or IL33/IL13 or TGFβ1/IL13 or TGFβ2/IL13 or IL13/IL13) fusion proteins of the present invention can be administered as an intrathecal injection. And in yet another embodiment they are administered through an intrathecal or intraspinal drug delivery system which allows continuous or repeated administration.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

A dose can be based on the amount of the fusion protein per kilogram of body weight of a subject. A dose a of a fusion protein can be at least about 0.5 µg/kg, 1 µg/kg, 25 µg/kg, 50 µg/kg, 75 µg/kg, 100 µµg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, or 1 mg/kg. A dose a of a fusion protein can be at most about 1 µg/kg, 25 µg/kg, 50 µg/kg, 75 µg/kg, 100 µµg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, or 1 mg/kg.

In some embodiments, a dose can be at least about 1 ng, at least 10 ng, at least 100 ng, at least 500 ng, at least at least 1 µg, at least 5 µg, at least at least 10 µg, at least 50 µg, at least at least 100 µg, at least 500 µg, at least at least 1 mg, at least 5 mg, at least 10 mg, at least 50 mg, or at least 100 mg. A dose can be at most about 1 ng, at most 10 ng, at most 100 ng, at most 500 ng, at most at most 1 µg, at most 5 µg, at most at most 10 µg, at most 50 µg, at most at most 100 µg, at most 500 µg, at most at most 1 mg, at most 5 mg, at most 10 mg, at most 50 mg, or at most 100 mg.

A dose can be determined by reference to a plasma concentration or a local concentration of the fusion protein. A target plasma concentration or local concentration of the fusion protein can be at least about 1 pM, at least about 10 pM, at least about 20 pM, at least about 30 pM, at least about 40 pM, at least about 50 pM, at least about 60 pM, at least about 70 pM, at least about 80 pM, at least about 90 pM, at least about 100 pM, at least about 200 pM, at least about 300 pM, at least about 400 pM, at least about 500 pM, at least about 600 pM, at least about 700 pM, at least about 800 pM, at least about 900 pM, at least about 1 nM, at least about 2 nM, at least about 3 nM, at least about 4 nM, at least about 5 nM, at least about 6 nM, at least about 7 nM, at least about 8 nM, at least about 9 nM, at least about 10 nM, at least about 20 nM, at least about 30 nM, at least about 40 nM, at least about 50 nM, at least about 60 nM, at least about 70 nM, at least about 80 nM, at least about 90 nM, at least about 100 nM, at least about 200 nM, at least about 300 nM, at least about 400 nM, at least about 500 nM, at least about 600 nM, at least about 700 nM, at least about 800 nM, at least about 900 nM, at least about 1 µM, at least about 10 µM, or at least about 100 µM. A target plasma concentration or local concentration of the fusion protein can be at most about 1 nM, at most about 10 nM, at most about 100 nM, at most about 1 µM, at most about 10 µM, at most about 100 µM, or at most about 1 mM.

Administration of the fusion protein can continue for as long as clinically necessary. In some embodiments, a fusion protein of the disclosure can be administered for more than 1 day, more than 1 week, more than 1 month, more than 2 months, more than 3 months, more than 4 months, more than 5 months, more than 6 months, more than 7 months, more than 8 months, more than 9 months, more than 10 months, more than 11 months, more than 12 months, more than 13 months, more than 14 months, more than 15 months, more than 16 months, more than 17 months, more than 18 months, more than 19 months, more than 20 months, more than 21 months, more than 22 months, more than 23 months, or more than 24 months. In some embodiments, a fusion protein of the disclosure is administered for less than 1 week, less than 1 month, less than 2 months, less than 3 months, less than 4 months, less than 5 months, less than 6 months, less than 7 months, less than 8 months, less than 9 months, less than 10 months, less than 11 months, less than 12 months, less than 13 months, less than 14 months, less than 15 months, less than 16 months, less than 17 months, less than 18 months, less than 19 months, less than 20 months, less than 21 months, less than 22 months, less than 23 months, or less than 24 months.

In some embodiments, a fusion protein can be administered to a subject 1, 2, 3, 4, 5, 6, 7, 8, 9, 10, 11, 12, 13, 14, 15, 16, 17, 18, 19, or 20 times over a treatment cycle. In some embodiments, a treatment cycle is 7 days, 14 days, 21 days, or 28 days long. In some embodiments, a treatment cycle is 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 11 months, 22 months, 23 months, 24 months, 25 months, 26 months, 27 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, 49 months, 50 months, 51 months, 52 months, 53 months, 54 months, 55 months, 56 months, 57 months, 58 months, 59 months, or 60 months.

In some embodiments, a fusion protein is administered to a subject once every 1, 2, 3, 4, 5, 6, 7, or 8 weeks.

Therapeutic Uses

In a further aspect, the present invention relates to the fusion protein of the present invention or a nucleic acid encoding the same for use as a medicament.

In an aspect, the present invention pertains to a fusion protein or a nucleic acid encoding the same for use in treating pain, for example, chronic pain. "Chronic" may mean that the pains persists/persisted over more than 2 weeks or more than 1, 3, 6, 12 months, or even more than 1, 2, 4, 6 years. Pain can include pain that is mediated by the central nervous system, the peripheral nervous system, or a combination thereof. Non-limiting types of pain include nociceptive pain, peripheral neuropathic pain, central neuropathic pain, and mixed types of pain.

Neuropathy can contribute to pain. In some embodiments, a fusion protein of the disclosure can be used for treating a neuropathy. A neuropathy can be associated with pain, numbness, weakness, or a combination thereof.

Particularly, it was found that the fusion protein of the present invention has a long-lasting analgesic effect against allodynia associated with chemotherapy-associated neuropathy and neurodegeneration in mice. In addition, the fusion protein prevents neurodegeneration induced by chemotherapy in vitro and in vivo. Therefore, the fusion protein of the invention or a nucleic acid encoding the same may be used for prevention and treatment neuropathic pain. As such, the fusion protein may be particularly useful for the treatment of neuropathy (e.g., chemotherapy induced neuropathy), and other forms of peripheral neuropathic pain such as post-herpetic neuralgia, trigeminal neuralgia, post-traumatic or post-operative peripheral neuropathy, diabetic peripheral neuropathy, inflammatory peripheral neuropathy, HIV-associated neuropathy, painful peripheral neuropathy, nerve entrapment syndrome, chemotherapy-associated pain, complex regional pain syndrome, and other. In some embodiments, a fusion protein of the disclosure can be used to treat postoperative cognitive dysfunction.

In some embodiments, a fusion protein of the disclosure can be used to treat a condition associated with cancer or chemotherapy, for example, chemotherapy-induced neuropathy, chemotherapy-associated pain, chemo brain, cancer-related cognitive impairment, cancer-related cognitive dysfunction. In some embodiments, the condition is associated with a chemotherapy that is being used to treat acute leukemia, astrocytomas, biliary cancer (cholangiocarcinoma), bone cancer, breast cancer, brain stem glioma, bronchioloalveolar cell lung cancer, cancer of the adrenal gland, cancer of the anal region, cancer of the bladder, cancer of the endocrine system, cancer of the esophagus, cancer of the head or neck, cancer of the kidney, cancer of the parathyroid gland, cancer of the penis, cancer of the pleural/peritoneal membranes, cancer of the salivary gland, cancer of the small intestine, cancer of the thyroid gland, cancer of the ureter, cancer of the urethra, carcinoma of the cervix, carcinoma of the endometrium, carcinoma of the fallopian tubes, carcinoma of the renal pelvis, carcinoma of the vagina, carcinoma of the vulva, cervical cancer, chronic leukemia, colon cancer, colorectal cancer, cutaneous melanoma, ependymoma, epidermoid tumors, Ewings sarcoma, gastric cancer, glioblastoma, glioblastoma multiforme, glioma, hematologic malignancies, hepatocellular (liver) carcinoma, hepatoma, Hodgkin's Disease, intraocular melanoma, Kaposi sarcoma, lung cancer, lymphomas, medulloblastoma, melanoma, meningioma, mesothelioma, multiple myeloma, muscle cancer, neoplasms of the central nervous system (CNS), neuronal cancer, small cell lung cancer, non-small cell lung cancer, osteosarcoma, ovarian cancer, pancreatic cancer, pediatric malignancies, pituitary adenoma, prostate cancer, rectal cancer, renal cell carcinoma, sarcoma of soft tissue, schwanoma, skin cancer, spinal axis tumors, squamous cell carcinomas, stomach cancer, synovial sarcoma, testicular cancer, uterine cancer, or tumors and their metastases, including refractory versions of any of the above cancers, or any combination thereof.

In a further embodiment, the fusion protein of the present invention or a nucleic acid encoding the same may be used to treat pain and neurodegeneration of central neuropathic disorders including spinal cord injury, post-stroke pain and multiple sclerosis. In some embodiments, a fusion protein of the disclosure can be used to treat postoperative cognitive dysfunction.

In a further aspect, the present invention pertains to a fusion protein of the present invention or a nucleic acid encoding the same for use in treatment of chronic mixed nociceptive and neuropathic pain such as low back pain, osteoarthritis, cancer pain, chronic visceral pain, fibromyalgia, polymyalgia rheumatica, myofascial pain syndromes, and other.

In yet a further aspect, the fusion protein of the present invention or a nucleic acid encoding the same may be used to treat post-operative orthopedic surgery pain, musculoskeletal pain, irritable bowel syndrome, inflammatory bowel disease, rheumatoid arthritis, ankylosing spondylitis, and other.

In an embodiment, the condition treated with the fusion protein of the present invention is characterized by pain and may be selected from nociceptive pain, neuropathic pain, or mixed nociceptive-neuropathic pain.

In another embodiment, the fusion protein of the present invention or a nucleic acid encoding the same may be used to prevent chronic pain. Particularly, the fusion protein may be used to prevent neuropathic pain and neurodegeneration in cancer patients treated with chemotherapy.

In another aspect, the invention is directed to a fusion protein of the present invention for use in the prevention or treatment of a clinical condition in a mammal, such as a human, for which interleukin 13 is indicated.

In a further aspect, the invention is directed to a fusion protein of the present invention for use in the prevention or treatment of a clinical condition in a mammal, such as a human, for which interleukin 4 or interleukin 10 or 27 or IL33 or TGFβ1 or TGFβ2 is indicated.

According to one embodiment the fusion proteins taught herein can be used for inhibiting neuro-inflammation due to activation of glial cells, and neuronal cells, infiltrating immune cells, or any combination thereof in the central nerve system.

As a result, the fusion proteins of the present invention can be used for the preparation of a medicament to attenuate neuro-inflammatory reactions by inhibiting the activation of glial cells and neuronal cells in vivo.

In an embodiment the fusion proteins of the present invention or nucleic acids encoding the same can be used as stand-alone drug. In another embodiment they are used in combination with other drugs. In some embodiments, a fusion protein of the disclosure is administered in combination with an analgesic, for example, acetaminophen/paracetamol, a non-steroidal anti-inflammatory drug (NSAID), or an opioid. In some embodiments, a fusion protein of the disclosure can be used in combination with NSAIDs, such as aspirin, ibuprofen, naproxen, celecoxib, ketorolac, or diclofenac. In some embodiments, a fusion protein of the disclosure can be used in combination with specific COX-2 inhibitors, such as celecoxib (Celebrex®), rofecoxib, or etoricoxib. In some embodiments, a fusion protein of the disclosure can be used in combination with corticosteroids, such as dexamethasone or glucosteroids (e.g., hydrocortisone and prednisone). In some embodiments, a fusion protein of the disclosure is administered in combination with an antagonist of a pro-inflammatory cytokine (e.g., and antibody derivative, or other molecule thereof that binds to TNF-α (e.g., adalimumab, etanercept), IL-17 (e.g., secukinumab), IL-23 (e.g., guselkumab, ildrakizumab), or IL-12 and IL-23 (e.g., ustekinumab). In some embodiments, a fusion protein is administered in combination with hyaluronic acid. Multiple therapeutic agents can be administered in any order or simultaneously. In some embodiments, a compound of the invention is administered in combination with, before, or after another drug.

In some embodiments, a fusion protein of the disclosure or a nucleic acid encoding the same can be used for treating Alpers' Disease, Arachnoiditis, Arthrofibrosis, Ataxic Cerebral Palsy, Autoimmune Atrophic Gastritis, Amyloidosis, hATTR Amyloidosis, Avascular Necrosis, Back Pain, Batten Disease, Behçet's Disease (Syndrome), Breakthrough Pain, Burning Mouth Syndrome, Bursitis, Central Autosomal Dominant Arteriopathy with Subcortical Infarcts and Leukoencephalopathy (Cadasil), Cerebral ischemia, Cerebro-Oculo-Facio-Skeletal Syndrome (COFS), Carpal Tunnel syndrome, Cauda Equina Syndrome, Central Pain Syndrome, Cerebral Palsy, Cerebrospinal Fluid (CSF) Leaks, Cervical Stenosis, Charcot-Marie-Tooth (CMT) Disease, Chronic Functional Abdominal Pain (CFAP), Chronic Pancreatitis, Collapsed Lung (Pneumothorax), Corticobasal Degeneration, Compression injury, Corneal Neuropathic Pain, Crush syndrome, Degenerative Disc Disease, Dermatomyositis, Dementia, Dystonia, Ehlers-Danlos Syndrome (EDS), Endometriosis, Eosinophilia-Myalgia Syndrome (EMS), Erythromelalgia, Failed Back Surgery Syndrome (FBSS), Fibromyalgia, Friedreich's Ataxia, Frontotemporal dementia, Glossopharyngeal neuralgia, Growing Pains, Herniated disc, Hydrocephalus, Intercostal Neuraligia, Interstitial Cystitis, Juvenile Dermatositis, Knee Injury, Leg Pain, Lewy Body Dementia, Loin Pain-Haematuria Syndrome, Lyme Disease, Meralgia Paresthetica, Mitochondrial Disorders, Mixed dementia, Motor neurone diseases (MND), Monomelic Amyotrophy, Multiple system atrophy (MSA), Myositis, Neck Pain, Occipital Neuralgia, Osteoporosis, Rhabdomyolysis, Paget's Disease, Parsonage Turner Syndrome, Pelvic Pain, Peripheral Neuropathy, Phantom Limb Pain, Pinched Nerve, Plantar Fasciitis, Polymyalgia Rhuematica, Polymyositis, Post Herniorraphy Pain Syndrome, Post Mastectomy Pain Syndrome, Post Stroke Pain, Post Thorocotomy Pain Syndrome, Post-Polio Syndrome, Primary Lateral Sclerosis, Psoriatic Arthritis, Pudendal Neuralgia, Radiculopathy, Restless Leg Syndrome, Rheumatoid Arthritis (RA), Sacroiliac Joint Dysfunction, Sarcoidosis, Scheuemann's Kyphosis Disease, Sciatica, Spinocerebellar ataxia (SCA), Spinal muscular atrophy (SMA), Herpes Zoster Shingles, Spasmodic Torticollis, Sphincter of Oddi Dysfunction, Spinal Cord Injury, Spinal Stenosis, Syringomyelia, Tarlov Cysts, Tethered Cord Syndrome, Thoracic Outlet Syndrome (TOS), TMJ disorders, Transverse Myelitis, Traumatic Brain Injuries, Vascular Pain, Vulvodynia, Whiplash, or a combination thereof.

A fusion protein of the disclosure of a nucleic acid encoding the same can be used to treat a neuropathy. Non-limiting examples of neuropathy include post-traumatic peripheral neuropathy, post-operative peripheral neuropathy, diabetic peripheral neuropathy, inflammatory peripheral neuropathy, HIV-associated neuropathy, chemotherapy-induced neuropathy, polyneuropathy, mononeuropathy, multiple mononeuropathy, cranial neuropathy, predominantly motor neuropathy, predominantly sensory neuropathy, sensory-motor neuropathy, autonomic neuropathy, idiopathic neuropathy, post-herpetic neuralgia, trigeminal neuralgia, glossopharyngeal neuralgia, occipital neuralgia, pudenal neuralgia, atypical trigeminal neuralgia, sciatica, brachial plexopathy, or intercostal neuralgia. A neuropathy can be associated with, for example, pain, numbness, weakness, burning, atrophy, tingling, twitching, or a combination thereof.

In some embodiments, a fusion protein of the disclosure or a nucleic acid encoding the same can be used to treat an autoimmune disease. Non-limiting examples of autoimmune diseases include Acute disseminated encephalomyelitis, Acute motor axonal neuropathy, Addison's disease, Adiposis dolorosa, Adult-onset Still's disease, Alopecia areata, Ankylosing Spondylitis, Anti-Glomerular Basement Membrane nephritis, Anti-neutrophil cytoplasmic antibody-associated vasculitis, Anti-N-Methyl-D-Aspartate Receptor Encephalitis, Antiphospholipid syndrome, Antisynthetase syndrome, Aplastic anemia, Autoimmune Angioedema, Autoimmune Encephalitis, Autoimmune enteropathy, Autoimmune hemolytic anemia, Autoimmune hepatitis, Autoimmune inner ear disease, Autoimmune lymphoproliferative syndrome, Autoimmune neutropenia, Autoimmune oophoritis, Autoimmune orchitis, Autoimmune pancreatitis, Autoimmune polyendocrine syndrome, Autoimmune polyendocrine syndrome type 2, Autoimmune polyendocrine syndrome type 3, Autoimmune progesterone dermatitis, Autoimmune retinopathy, Autoimmune thrombocytopenic purpura, Autoimmune thyroiditis, Autoimmune urticaria, Autoimmune uveitis, Balo concentric sclerosis, Behçet's disease, Bickerstaffs encephalitis, Bullous pemphigoid, Celiac disease, Chronic fatigue syndrome, Chronic inflammatory demyelinating polyneuropathy, Churg-Strauss syndrome, Cicatricial pemphigoid, Cogan syndrome, Cold agglutinin disease, Complex regional pain syndrome, CREST syndrome, Crohn's disease, Dermatitis herpetiformis, Dermatomyositis, Diabetes mellitus type 1, Discoid lupus erythematosus, Endometriosis, Enthesitis, Enthesitis-related arthritis, Eosinophilic esophagitis, Eosinophilic fasciitis, Epidermolysis bullosa acquisita, Erythema nodosum, Essential mixed cryoglobulinemia, Evans syndrome, Felty syndrome, Fibromyalgia, Gastritis, Gestational pemphigoid, Giant cell arteritis, Goodpasture syndrome, Graves' disease, Graves ophthalmopathy, Guillain-Barré syndrome, Hashimoto's Encephalopathy, Hashimoto Thyroiditis, Henoch-Schonlein purpura, Hidradenitis suppurativa, Idiopathic dilated cardiomyopathy, Idiopathic inflammatory demyelinating diseases, IgA nephropathy, IgG4-related systemic disease, Inclusion body myositis, Inflamatory Bowel Disease (IBD), Intermediate uveitis, Interstitial cystitis, Juvenile Arthritis, Kawasaki's disease, Lambert-Eaton myasthenic syndrome, Leukocytoclastic vasculitis, Lichen planus, Lichen sclerosus, Ligneous conjunctivitis, Linear IgA disease, Lupus nephritis, Lupus vasculitis, Lyme disease, Ménière's disease, Microscopic colitis, Microscopic polyangiitis, Mixed connective tissue disease, Mooren's ulcer, Morphea, Mucha-Habermann disease, Multiple sclerosis, Myasthenia gravis, Myocarditis, Myositis, Neuromyelitis optica, Neuromyotonia, Opsoclonus myoclonus syndrome, Optic neuritis, Ord's thyroiditis, Palindromic rheumatism, Paraneoplastic cerebellar degeneration, Parry Romberg syndrome, Parsonage-Turner syndrome, Pediatric Autoimmune Neuropsychiatric Disorder Associated with Streptococcus, Pemphigus vulgaris, Pernicious anemia, Pityriasis lichenoides et varioliformis acuta, POEMS syndrome, Polyarteritis nodosa, Polymyalgia rheumatica, Polymyositis, Postmyocardial infarction syndrome, Postpericardiotomy syndrome, Primary biliary cirrhosis, Primary immunodeficiency, Primary sclerosing cholangitis, Progressive inflammatory neuropathy, Psoriasis, Psoriatic arthritis, Pure red cell aplasia, Pyoderma gangrenosum, Raynaud's phenomenon, Reactive arthritis, Relapsing polychondritis, Restless leg syndrome, Retroperitoneal fibrosis, Rheumatic fever, Rheumatoid arthritis, Rheumatoid vasculitis, Sarcoidosis, Schnitzler syndrome, Scleroderma, Sjogren's syndrome, Stiff person syndrome, Subacute bacterial endocarditis, Susac's syndrome, Sydenham chorea, Sympathetic ophthalmia, Systemic Lupus Erythematosus, Systemic scleroderma, Thrombocytopenia, Tolosa-Hunt syndrome, Transverse myelitis, Ulcerative colitis, Undifferentiated connective tissue disease, Urticaria, Urticarial vasculitis, Vasculitis, and Vitiligo.

In some embodiments, a fusion protein of the disclosure or a nucleic acid encoding the same can be used to treat inflammation. In some embodiments, the inflammation is chronic inflammation. In some embodiments, a fusion protein of the disclosure can be used to treat inflammation that is associated with inflammatory bowel disease, irritable bowel syndrome, osteoarthritis, rheumatoid arthritis, glomerulonephritis, sepsis, adult respiratory distress syndrome, dermatitis, sarcoidosis, allergic inflammation, psoriasis, ankylosing spondylarthritis, systemic lupus erythematosus, vasculitis, gout, allotransplantation, xenotransplantation, an autoimmune disease, Sjogren's disease, a burn injury, trauma, stroke, myocardial infarction, atherosclerosis, diabetes mellitus, extracorporeal dialysis and blood oxygenation, ischemia-reperfusion injuries, and toxicity induced by the in vivo administration of cytokines or other therapeutic monoclonal antibodies. In some embodiments, the inflammation is chronic inflammation. In some embodiments, a fusion protein of the disclosure can be used to treat inflammatory bowel disease, irritable bowel syndrome, osteoarthritis, rheumatoid arthritis, glomerulonephritis, sepsis, adult respiratory distress syndrome, dermatitis, sarcoidosis, allergic inflammation, psoriasis, ankylosing spondylarthritis, systemic lupus erythematosus, vasculitis, gout, allotransplantation, xenotransplantation, an autoimmune disease, Sjogren's disease, a burn injury, trauma, stroke, myocardial infarction, atherosclerosis, diabetes mellitus, extracorporeal dialysis and blood oxygenation, ischemia-reperfusion injuries, and toxicity induced by the in vivo administration of cytokines or other therapeutic monoclonal antibodies.

In some embodiments, a fusion protein is used to treat a condition, wherein the condition is not a cancer.

Treatment (prophylactic or therapeutic) will generally consist of administering the fusion protein of the present invention or a nucleic acid encoding the same parenterally, preferably intrathecally, intraarticularly, intravenously, intramuscularly or subcutaneously. The dose and administration regimen will depend on the extent of inhibition of neuroinflammation and neurodegeneration aimed at. Typically, the amount of the fusion protein given will be in the range of 0.5 µg to 1 mg per kg of body weight. The dosage can be determined or adjusted by measuring cytokine levels (IL13, IL4 or IL10 or IL27 or IL33 or TGFβ1 or TGFβ2, or a combination thereof) in the body compartment targeted upon administration. The dose can also be determined by measuring neuro-inflammation in a patient for example by positron emission tomography (PET) imaging of microglia.

For parenteral administration, the fusion protein or a nucleic acid encoding the same is preferably formulated in an injectable form combined with a pharmaceutically acceptable parenteral vehicle. Such vehicles are well-known in the art and examples include saline, dextrose solution, Ringer's solution and solutions containing small amounts of human serum albumin.

Typically, the fusion proteins of the present invention may be formulated in such vehicles at a concentration of from about 50 µg to about 100 mg per ml.

Gene Therapy

The nucleic acid constructs or vectors of the present invention may be used as gene therapy agents for treatment of the conditions set forth above.

As such, in an aspect the invention is directed to a vector as described above for use in the prevention or treatment of a condition characterized by visceral or non-visceral nociceptive pain, peripheral or central neuropathic pain, or mixed nociceptive-neuropathic pain, neuroinflammation and/or neurodegeneration, preferably wherein said condition may be selected from the group consisting of post-operative orthopedic surgery pain, musculoskeletal pain, irritable bowel syndrome, inflammatory bowel disease, rheumatoid arthritis, ankylosing spondylitis, post-herpetic neuralgia, trigeminal neuralgia, post-traumatic or post-operative peripheral neuropathy, diabetic peripheral neuropathy, inflammatory peripheral neuropathy, HIV-associated neuropathy, painful peripheral neuropathy, nerve entrapment syndrome, chemotherapy-associated pain, complex regional pain syndrome, post-spinal injury pain, post-stroke pain, multiple sclerosis, low back pain, osteoarthritis, cancer pain, chronic visceral pain, fibromyalgia, polymyalgia rheumatica, myofascial pain syndrome, Alzheimer's disease and Parkinson's disease, Huntington's disease, and/or amyotrophic lateral sclerosis, or multiple sclerosis. In some embodiments, the condition can be Alpers' Disease, Arachnoiditis, Arthrofibrosis, Ataxic Cerebral Palsy, Autoimmune Atrophic Gastritis, Amyloidosis, hATTR Amyloidosis, Avascular Necrosis, Back Pain, Batten Disease, Behcet's Disease (Syndrome), Breakthrough Pain, Burning Mouth Syndrome, Bursitis, Central Autosomal Dominant Arteriopathy with Subcortical Infarcts and Leukoencephalopathy (Cadasil), Cerebral ischemia, Cerebro-Oculo-Facio-Skeletal Syndrome (COFS), Carpal Tunnel syndrome, Cauda Equina Syndrome, Central Pain Syndrome, Cerebral Palsy, Cerebrospinal Fluid (CSF) Leaks, Cervical Stenosis, Charcot-Marie-Tooth (CMT) Disease, Chronic Functional Abdominal Pain (CFAP), Chronic Pancreatitis, Collapsed Lung (Pneumothorax), Corticobasal Degeneration, Compression injury, Corneal Neuropathic Pain, Crush syndrome, Degenerative Disc Disease, Dermatomyositis, Dementia, Dystonia, Ehlers-Danlos Syndrome (EDS), Endometriosis, Eosinophilia-Myalgia Syndrome (EMS), Erythromelalgia, Failed Back Surgery Syndrome (FBSS), Fibromyalgia, Friedreich's Ataxia, Frontotemporal dementia, Glossopharyngeal neuralgia, Growing Pains, Herniated disc, Hydrocephalus, Intercostal Neuraligia, Interstitial Cystitis, Juvenile Dermatositis, Knee Injury, Leg Pain, Lewy Body Dementia, Loin Pain-Haematuria Syndrome, Lyme Disease, Meralgia Paresthetica, Mitochondrial Disorders, Mixed dementia, Motor neurone diseases (MND), Monomelic Amyotrophy, Multiple system atrophy (MSA), Myositis, Neck Pain, Occipital Neuralgia, Osteoporosis, Rhabdomyolysis, Paget's Disease, Parsonage Turner Syndrome, Pelvic Pain, Peripheral Neuropathy, Phantom Limb Pain, Pinched Nerve, Plantar Fasciitis, Polymyalgia Rhuematica, Polymyositis, Post Herniorraphy Pain Syndrome, Post Mastectomy Pain Syndrome, Post Stroke Pain, Post Thorocotomy Pain Syndrome, Post-Polio Syndrome, Primary Lateral Sclerosis, Psoriatic Arthritis, Pudendal Neuralgia, Radiculopathy, Restless Leg Syndrome, Rheumatoid Arthritis (RA), Sacroiliac Joint Dysfunction, Sarcoidosis, Scheuemann's Kyphosis Disease, Sciatica, Spinocerebellar ataxia (SCA), Spinal muscular atrophy (SMA), Herpes Zoster Shingles, Spasmodic Torticollis, Sphincter of Oddi Dysfunction, Spinal Cord Injury, Spinal Stenosis, Syringomyelia, Tarlov Cysts, Tethered Cord Syndrome, Thoracic Outlet Syndrome (TOS), TMJ disorders, Transverse Myelitis, Traumatic Brain Injuries, Vascular Pain, Vulvodynia, Acute disseminated encephalomyelitis, Accute Optic Neuritis, Transverse Myelitis, Neuromyelitis Optica, or Whiplash.

As described earlier herein, the present invention relates to a fusion protein comprising at least 2, 3, 4, preferably 2 regulatory (e.g., anti-inflammatory) interleukins chosen from the group consisting of interleukin 13 (IL13), interleukin 4 (IL4), interleukin 10 (IL10), interleukin 27 (IL27), interleukin 33 (IL33), transforming growth factor beta 1 (TGFβ1), and transforming growth factor beta 2 (TGFβ2). Accordingly, where reference is made in the present disclosure to "IL13", this may be replaced by transforming growth factor beta 1 (TGFβ1), or transforming growth factor beta 2 (TGFβ2). Similarly, where reference is made in the present disclosure to "IL4", this may be replaced by transforming growth factor beta 1 (TGFβ1), or transforming growth factor beta 2 (TGFβ2). The present disclosure thus also encompasses a fusion protein of IL13/TGFβ1 or IL13/TGFβ2. Further, the present disclosure encompasses a fusion protein of IL4/TGFβ1 or IL4/TGFβ2. Additionally, the present disclosure encompasses a fusion protein of IL10/TGFβ1 or IL10/TGFβ2.

The present invention will now be illustrated with reference to the following examples, which set forth particularly advantageous embodiments. However, it should be noted that these embodiments are illustrative and are not to be construed as restricting the invention in any way.

EXAMPLES

Animals.

All animal experiments were performed in agreement with international guidelines and with prior approval by the University Medical Centre Utrecht experimental animal committee. Experiments were conducted using both male and female C57BL/6 mice aged between 8 and 16 weeks. Observers carrying out behavioural experiments were blinded to treatment.

Material and Methods

Expression and purification of an IL4/IL13 fusion protein. IL4/13 fusion protein HEK293 cells were transiently transfected according to standard procedures with a vector containing a transgene (Y Derocher et al., Nucleic Acids Research 2002, vol 30, no 2, e9). Briefly, synthetic cDNA (GeneArt, ThermoFisher Scientific) coding for an IL4/IL13 fusion protein sequence of the present invention (see SEQ ID NO: 4, N-terminal of this sequence a 6-His tag was inserted) was cloned in an expression vector, containing a cystatin signal sequence. HEK293E cells were then transfected with the expression vector, and co-transfected with a vector carrying the transgene for beta-galactoside alpha-2, 3-sialyltransferase 5 (SIAT 9; Homo sapiens) to optimize capping of the glycans with sialic acid. Cells were cultured in FreeStyle medium (Invitrogen) with 0.9% primatone and ~0.04%, v/v, fetal calf serum as described before[19,26]. Cell suspension was collected on day 4 after transfection and centrifuged at 435×g for 5 minutes. The supernatant was passed through a HIS-Select Nickel Affinity gel (Sigma-Aldrich) to purify the recombinant IL4/IL13 fusion protein. Elution fraction was dialysed overnight at 4° C. against phosphate buffered saline, pH 7.4 (PBS).

Protein assays. Bradford (Bio-Rad), BCA (Thermo Scientific), and Qubit 1.0 (Thermo Scientific) were used to determine the amount of protein in the eluded & dialysed fractions. All protein assays were performed according to the manufacturer's protocols.

ELISAs. The amount of fusion protein was determined based on the amount of the individual cytokines, measured with ELISA (IL4 Pelipair ELISA kit, Sanquin; IL13, DuoSet ELISA, R&D Systems). ELISAs were performed according to the manufacturer's instructions. Concentrations were calculated based on the theoretical molecular weight of the fusion protein compared to the individual cytokines.

SDS-Page and Western Blot. Fractions of the HIS-Select Nickel affinity chromatography purification (load, flow-through, wash, elution/dialysis) were separated on 12% polyacrylamide SDS-Page gels (Bio-Rad) and transferred to polyvinylidene difluoride membranes. Membranes were stained with IL4 antibody (Santa Cruz, SC-13555).

High Performance Size Exclusion Chromatography (HP-SEC). To determine its molecular weight and homogeneity, IL4/IL13 fusion protein was analyzed with High Performance Size Exclusion Chromatography (HP-SEC). The gel filtration (BioSuite 125 4 μm UHR SEC Column; Waters; Cat #186002161) was performed on a High-Performance Liquid Chromatography System (Shimadzu) with 50 mM phosphate buffer containing 0.5 M NaCl as mobile phase. The column was calibrated prior to the run using a protein mix of thyroglobulin, bovine serum albumen, carbonic anhydrase, myoglobulin, and ribonuclease. Fifty μl of 20 μg/ml of purified IL4/IL13 fusion protein was injected and separated on the column at a flow rate of 0.35 ml/min and under a pressure of 35 bar.

Evaluation of chemotherapy-induced neurotoxicity in vitro. Dorsal root ganglion (DRG) neurons were cultured as described previously[27]. Briefly, adult mice DRG neurons were dissected out and subsequently digested in an enzyme mixture containing $Ca^{2+}$- and $Mg^{2+}$-free HBSS, 5 mM HEPES, 10 mM glucose, collagenase type XI (5 mg/ml) and dispase (10 mg/ml) for 1 hour before mechanical trituration in DMEM containing 10%, v/v, heat-inactivated fetal calf serum. Cells were centrifuged for 5 min at 800 rpm, resuspended in DMEM containing 4.5 g/L glucose, 4 mM L-glutamine, 110 mg/L sodium pyruvate, 10% fetal calf serum, 1% penicillin-streptomycin (10,000 IU/ml), 1% glutamax, and incubated in 24 wells plates for 24 hours in presence of paclitaxel (1 uM) or oxaliplatin (5 ug/ml) to induce neurotoxicity. IL4/IL10 fusion protein (100 ng/mL), IL4/IL13 fusion protein (100 ng/mL), IL4 an IL13 (50 ng/mL each), IL4 (50 ng/mL), IL10 (50 ng/mL), and IL13 (50 ng/mL) were added together with the chemotherapeutic agent. As controls cells were also cultured in absence of chemotherapeutic drugs or cytokines, and in presence of chemotherapeutic drugs only. After fixation with 4% paraformaldehyde, cells were stained with rabbit anti-mouse βIII-tubulin (ab18207, 1:1000; Abcam). Neurites were visualized with a Zeiss Axio Lab A1 microscope (Zeiss-Oberkochen, Germany) and using a random sampling method, at least 10 images per glass slide were made at a magnification of 10×. The length of neurites was measured with the ImageJ plugin Simple Neurite Tracer76. The averages of neurite length per neuron for a minimum of five neurons per condition were compared between groups for the three individual primary sensory cultures.

Chemotherapy-induced polyneuropathy and assessment of allodynia. To induce transient chemotherapy-induced polyneuropathy (CIPN), paclitaxel (2 mg/kg, Cayman Chemical Company) was injected intraperitoneally on days 0 and 2. To induce persistent paclitaxel-induced CIPN, paclitaxel (8 mg/kg, Cayman Chemical Company) was injected intraperitoneal on day 0, 2, 4 and 6. To induce persistent oxaliplatin-induced polyneuropathy, mice received two treatment cycles, each consisting of 5 daily intraperitoneal injections of 3 mg/kg oxaliplatin (Tocris) with a 5 days treatment-free interval.

Noxious mechanical sensitivity in the hind paws was measured using von Frey hairs (Stoelting, Wood Dale, USA). Results were expressed as the 50% paw-withdrawal threshold using the up-and-down method[29]. In some experiments the length of intraepidermal nerve fibers in the paw skin at day 15 was determined by immunofluorescent staining of skin biopsies with the neuronal marker PGP9.5. All experiments were performed in a blinded manner.

Statistical analysis. Unless indicated otherwise, all data are expressed as mean±SEM. Data were analysed for statistical significance by one-way or two-way ANOVA (with repeated measures if appropriate) followed by the appropriate post-hoc test. A p value of $p<0.05$ was considered significant.

Example 1

Endogenous IL4 and IL13 are Necessary for Normal Resolution of Paclitaxel-Induced Transient Hyperalgesia To investigate the possible role of regulatory (e.g., anti-inflammatory) cytokines on recovery from chemotherapy-induced polyneuropathy, the transient pain model of paclitaxel-induced pain[15] was used. Mice received 2 injections of low dose (2 mg/kg) of paclitaxel on days 0 and 2. From days 6 to 10 after start of chemotherapy treatment, mice received a daily intrathecal injection of neutralizing antibodies against IL4, IL13 or control IgG antibodies (5 μg antibody per injection; FIG. 1). Mice that received paclitaxel, developed mechanical hyperalgesia starting on the first day of chemotherapy, which resolved spontaneously after one week of treatment termination (FIG. 1). In animals intrathecally injected with neutralizing antibodies against IL4 or IL13, resolution of hyperalgesia was delayed and persisted for at least 2 weeks. These data indicate that endogenously produced IL4 and IL13 are necessary for normal pain resolution after chemotherapy treatment (FIG. 1).

Example 2

Neuroprotective Effects of IL4, IL10 and IL13

To assess whether regulatory (e.g., anti-inflammatory) cytokines possess neuroprotective properties sensory neurons isolated from the dorsal root ganglion were cultured overnight with paclitaxel in combination of either IL4, IL10 or IL13 as described in methods. Neurotoxicity was evaluated by measuring neurite length using βIII-tubulin staining. Paclitaxel (1 μM) reduced neurite length with ~50% indicating paclitaxel damaged sensory neurons. Addition of IL13 during the culture with paclitaxel prevented the paclitaxel-induced negative effect on neurite length, whilst IL10 and IL4 did not (FIG. 2).

Example 3

Characterization of Recombinant IL4/13 Fusion Protein

Human IL4/IL13 fusion protein (see SEQ ID NO: 4) with an N-terminal 6 His-tag was produced by transient transfection of HEK293 cells and purified as described in methods. On HP-SEC the purified IL4/IL13 fusion protein migrated as a single peak with an apparent mass of 40 kDa (FIG. 3). The preparation was also analyzed on SDS-PAGE and Coomassie staining. A homogenous preparation migrating as a smear with a molecular mass of ~37 kDa was detected (insert FIG. 3).

Example 4

IL4/IL13 Fusion Protein Cures Paclitaxel-Induced Persistent Polyneuropathy

The potential of IL4/IL13 fusion protein to inhibit chemotherapy-induced hyperalgesia was evaluated in model of persistent paclitaxel-induced painful neuropathy[30]. Mice received 4 injections of paclitaxel (8 mg/kg) every other day from day 0 to 6. Paclitaxel induced mechanical hyperalgesia that started on the first day after the first injection and that persisted at least 3 weeks after chemotherapy-treatment was stopped. Two days after the last paclitaxel injection, mice were injected intrathecally with 3 different doses of IL4/IL13 fusion protein comprising SEQ ID NO: 4 (0.3, 1 and 3 µg/mouse) (FIG. 4). All three doses of IL4/IL13 fusion protein markedly reduced paclitaxel-induced polyneuropathy. Importantly, the almost normalization of mechanical hyperalgesia lasted for at least a week, demonstrating the potential of the IL4/IL13 fusion protein for long-lasting resolution of chemotherapy-induced polyneuropathy.

Example 5

Potency of IL4/IL13 Fusion Protein is Superior Over IL4/IL10 Fusion Protein or IL4 and IL13 Combination Therapy to Cure Chemotherapy-Induced Polyneuropathy Next it was assessed whether IL4/IL13 fusion protein inhibits paclitaxel-induced polyneuropathy better than IL4/IL10 fusion protein, or the combination of IL4 and IL13. Mice developed paclitaxel-induced painful polyneuropathy after 4 injections of paclitaxel (8 mg/kg) every other day from day 0 to 6. IL4/IL13 fusion protein (comprising SEQ ID NO: 4) inhibited paclitaxel-induced mechanical hypersensitivity for at least 1 week, whilst the combination of wildtype IL4 and IL13, or IL4/IL10 fusion protein only inhibited paclitaxel-induced mechanical hypersensitivity for 1-2 days (FIG. 5). The inhibition of paclitaxel-induced persistent allodynia by IL4/IL13 fusion protein was associated with reduced paclitaxel-induced intra-epidermal nerve fibre loss in the paw skin (FIG. 6).

To evaluate whether IL4/IL13 fusion protein protects against neurotoxicity induced by paclitaxel in vitro we measured neurite length of mouse sensory neurons cultured in presence of paclitaxel with or without fusion protein. Paclitaxel had a significant negative effect on neurite length when compared to the control group (FIG. 7). Simultaneous presence of IL4/IL10 fusion protein or the combination of IL4 and IL13 had a moderate beneficial effect on neurite length. However, presence of IL4/IL13 fusion protein in the culture markedly prevented paclitaxel-induced neurotoxicity (FIG. 7). Thus, these data together demonstrated an unexpected superior effect of IL4/IL13 fusion protein over IL4/IL10 fusion protein or the combination of IL4 and IL13 to protect neurons against toxic effects of the chemotherapeutic drug paclitaxel. In particular the superiority of the fusion protein over the combination was surprising as the in vitro system is not affected by different clearance of the proteins from the site of action. Rather the data pointed to a unique effect of IL4/IL13 fusion protein regarding neuroprotection.

Example 6

IL4/IL13 Fusion Protein Also Cures Polyneuropathy Induced by Oxaliplatin

It was investigated whether neuroprotective effects of IL4/IL13 fusion protein are unique for paclitaxel-induced neurotoxicity or whether neuroprotective effects are against a broader spectrum of chemotherapy-induced polyneuropathy. Toxic neuropathy was induced in mice using a platinum-based chemotherapeutic drug, oxaliplatin. Two cycles of 5 times a daily injection of oxaliplatin, separated by 5 days without intraperitoneal injection, induced mechanical allodynia that persisted for at least 3 weeks (FIG. 8). Intrathecal injection of IL4/IL13 fusion protein (comprising SEQ ID NO: 4) on the second day after the last oxaliplatin injection reduced mechanical allodynia significantly for 4 days (FIG. 8). Intrathecal injection of either wild-type IL4 or wild-type IL13 transiently inhibited oxaliplatin-induced mechanical allodynia for ~1 day, which was significantly shorter than the effect of the IL4/IL13 fusion protein. Similarly, in vitro IL4/IL13 fusion protein protected against oxaliplatin-induced neurotoxicity, whilst the combination of IL4 and IL13 did not (FIG. 9). Thus, these data indicate that IL4/IL13 fusion protein protects against chemotherapy-induced neurotoxicity and chemotherapy-induced polyneuropathy.

Example 7

IL10/IL13 and IL33/IL13 Fusion Proteins

Further, it was considered whether an IL10/IL13 fusion protein or IL33/IL13 fusion protein would have a therapeutic effect in the medical indications as disclosed herein. Surprisingly, cross-linking of the IL10 receptor and the IL13 receptor by administration of an IL10/IL13 fusion protein, or the cross-linking of the IL33 receptor and the IL13 receptor by administration of an IL33/IL13 fusion protein, can lead to a stronger and prolonged therapeutic effect, in comparison to administration of an IL4/IL10 fusion protein, and in particular in the neuropathic pain model.

Example 8

Expression of Cytokine Receptors in Dorsal Root Ganglia and Spinal Cord

It was addressed whether cytokine receptors targeted by fusion proteins of the present invention are expressed by the sensory system. To analyze this, RNAseq data of receptors for IL10, IL4, IL13, IL27, TGFβ1, and TGFβ2 in the dorsal root ganglia and spinal cord were extracted from the data base by Ray et al. (Pain 2018; 159:1325-1345) as available on www_utdallas.edu/bbs/painneurosciencelab/sensoryomics/drgtxome/?go. RNA sequencing revealed expression of receptor chains for IL10, IL4, IL13, IL27, TGFβ1 and TGFβ2 in the dorsal root ganglia and spinal cord of human and mouse (FIG. 10; data are expressed as transcripts per million).

Example 9

Fusion Proteins of the Disclosure

This example demonstrates design and generation of non-limiting examples of IL13-containing fusion proteins of the disclosure.

An IL4/IL13 fusion protein of the disclosure comprising SEQ ID NO:1 and SEQ ID NO: 14 was designed. SEQ ID NO: 1 was joined to SEQ ID NO: 14 using the SEQ ID NO: 3 linker, resulting in SEQ ID NO: 16. A hexa-histidine tag was added to the N-terminus, and the fusion protein was produced by transient transfection of HEK293E cells as disclosed below. The fusion protein containing SEQ ID NO: 16, has IL4 located at the N-terminal end, and is labeled as IL4/IL13$_{SKP}$ in FIG. 11, FIG. 12, and FIG. 18A.

An IL10/IL13 fusion protein of the disclosure comprising SEQ ID NO:5 and SEQ ID NO: 14 was designed. SEQ ID NO: 5 was joined to SEQ ID NO: 14 using the SEQ ID NO: 3 linker, resulting in SEQ ID NO: 17. A hexa-histidine tag was added to the N-terminus, and the fusion protein was produced by transient transfection of HEK293E cells as disclosed below. The fusion protein containing SEQ ID NO: 17 contains IL13 at the N-terminal end and is labeled as IL13/IL10 in FIG. 11, FIG. 13, and FIG. 18D.

An IL27/IL13 fusion protein of the disclosure comprising SEQ ID NO:18 and SEQ ID NO: 14 was designed. SEQ ID NO: 18 was joined to SEQ ID NO: 14 using the SEQ ID NO: 3 linker, resulting in SEQ ID NO: 19. A hexa-histidine tag was added to the N-terminus, and the fusion protein was produced by transient transfection of HEK293E cells as disclosed below. The fusion protein containing SEQ ID NO: 19 contains IL13 at the N-terminal end and is labeled IL13/IL27-A in FIG. 11, FIG. 14, and FIG. 18C.

An IL13/IL13 fusion protein of the disclosure comprising two copies of SEQ ID NO: 14 was designed. SEQ ID NO: 14 was joined to a second copy of SEQ ID NO: 14 using the SEQ ID NO: 3 linker, resulting in SEQ ID NO: 20. A hexa-histidine tag was added to the N-terminus, and the fusion protein was produced by transient transfection of HEK293E cells as disclosed below.

The IL4/IL13, IL10/IL13, IL27/IL13, and IL13/IL13 fusion proteins were purified as disclosed below. Size exclusion chromatography indicated that the IL4/IL13 fusion protein containing SEQ ID NO: 16 migrated as a single peak (FIG. 18A), and the IL13/IL13 fusion protein (containing SEQ ID NO: 20) migrated as a single peak (FIG. 18B).

For IL27/IL13 (IL13/IL27-A), two peaks of recombinant protein were identified which were separately pooled after gel filtration (FIG. 18C). Pool 1 was the higher molecular weight pool. Pool 2 was of lower molecular weight, and was elected for further evaluation. Without wishing to be bound by any particular theory, pool 1 may contain multimerized and/or aggregate forms of the protein, while pool 2 may contain a pure protein (e.g., a monomer)

For IL10/IL13 (IL13/IL10), two peaks of recombinant protein were identified which were separately pooled after gel filtration (FIG. 18D). Pool 1 represents the high molecular weight pool and pool 2 the low molecular weight pool. Without wishing to be bound by any particular theory, IL10/IL13 pool 1 may contain a dimer version of the molecule, and IL10/IL13 pool 2 may contain a monomer version of IL10/IL13.

As shown in FIG. 11, purified proteins were analysed on 4-12% gradient polyacrylamide NuPage™ gels under reducing and non-reducing conditions, and bands were visualized by Coomassie protein stain.

Expression and purification of IL13-containing fusion proteins. IL13-containing fusion proteins of the disclosure were produced by transient transfection of HEK293E cells. Cells were transfected with a pUPE expression vector containing a transgene coding one of the IL13-containing fusion protein sequences. To enable purification, a hexa-histidine affinity tag was cloned at the N-terminus of each IL13-containing protein. Six days post transfection, conditioned medium containing recombinant protein was harvested by low-speed centrifugation (10 minutes, 1000×g) followed by high-speed centrifugation (10 minutes, 4000×g).

Proteins were purified via His-tag by Immobilized Metal Affinity Chromatography (IMAC). In short, the recombinant protein was bound to 0.5 ml Nickel Sepharose® excel at 20° C. Nickel Sepharose® excel containing bound protein was harvested by centrifugation and transferred into a gravity flow column. Non-specifically bound proteins were removed by washing the column with IMAC buffer (500 mM Sodium Chloride, 25 mM Tris, pH=8.2) containing 0 and 10 mM imidazol. The proteins were eluted with IMAC buffer containing 500 mM imidazol. Fractions of 2.5 ml were collected and recombinant protein-containing fractions were pooled. Conditioned medium and the unbound IMAC fraction were analyzed by LabChip® capillary electrophoresis. The IMAC pool was concentrated to 2-4 ml using an Amicon 10 kDa spin filter. Aggregates were removed by centrifugation (10 minutes 18000×g, 4° C.).

The proteins were purified further by gel filtration using a Superdex200 16/600 column that had been equilibrated in PBS. Protein containing fractions were analyzed by LabChip® capillary electrophoresis and recombinant protein containing fractions were pooled. Protein pools were sterilized by filtration over a 0.22 μm syringe filter and the product stored in 1 ml vials at −80° C.

Protein assays: Protein concentration was determined spectrophotometrically by measuring the absorbance at 280 nm (DropSense16, Trinean) and using a BCA (Thermo Scientific) protein assay. All protein assays were performed according to the manufacturer's protocols.

SDS-Page: Purified proteins were analysed on 4-12% polyacrylamide NuPage™ polyacrylamide gels under reducing and non-reducing conditions. Protein bands were visualized by Coomassie protein stain.

Example 10

Neuroprotective Effects of IL13-Containing Fusion Proteins on Paclitaxel-Induced Sensory Neuron Damage To elucidate the potential neuroprotective effect of various fusion proteins where IL13 is linked to other regulatory cytokines such as IL4, IL10, IL13, or IL27, the fusion proteins were tested in an in vitro paclitaxel-induced sensory neuron damage assay. Primary sensory neurons from mice were cultured for 24 h in the presence of paclitaxel (1 μM), and different concentrations of each fusion protein or equimolar doses of IL13 or the combination of unlinked cytokines.

Culture of DRG neurons: DRGs were cultured as described previously (Nat. Commun. 4, 1682 (2013)). Briefly, DRGs were dissected and placed on ice-cold dissection medium (HBSS w/o $Ca^{2+}$ and $Mg^{2+}$, 5 mM HEPES, and 10 mM glucose). After dissection, axons were cut and dissection medium was replaced by filtered enzyme mix (HBSS w/o $Ca^{2+}$ and $Mg^{2+}$, 5 mM HEPES, 10 mM glucose, 5 mg/ml collagenase type XI (Sigma), and 10 mg/ml Dispase (Gibco)). The DRGs were incubated in enzyme mix for 30 minutes at 37° C. and 5% $CO_2$. Subsequently, enzyme mix was inactivated with heat-inactivated fetal bovine serum (FBS, Sigma). Cells were cultured in Dulbecco's modified Eagle's medium (Gibco) containing 10% FBS (Gibco), 2 mmol/L glutamine (Gibco), 10,000 IU/ml penicillin-streptomycin (Gibco) on poly-L-lysine (0.01 mg/ml, Sigma) and laminin (0.02 mg/ml, Sigma)-coated glass coverslips in a 5% $CO_2$ incubator at 37° C. Cells were used the following 1-2 days.

Stimulation for neurite length measurement: After 24 h in culture, DRG neurons were treated with Paclitaxel (1 μM) alone (n=11) or in presence of different concentrations of IL13 fusion proteins (0.12 nM, n=6; 0.6 nM or 3 nM, n=11) or equimolar doses of the individual cytokines (n=6) for 24 h (n-values represent the number of animals for which each condition was tested). Neurites were visualised using β3-tubulin staining, whilst number of sensory neurons were determined using NeuN staining. For each animal, 2-3 wells were evaluated (cytokines: 2 wells per concentration; paclitaxel or control: 3 wells) and 5 pictures per well were taken. For each picture, the neurite length per sensory neuron was determined and averaged to a single value per animal and condition. The percentage inhibition of paclitaxel-induced neurite length loss per mouse culture of 1 mouse was calculated according the following formula (($\mu_{control}$-$\mu_{paclitaxel}$)-($\mu_{control}$-$X_{cytokine}$))/($\mu_{control}$-$\mu_{paclitaxel}$)*100 (where μ is the neurite length per neuron averaged over all samples and X is the neurite length of each individual sample).

β3-tubulin and NeuN staining: cells were fixed in 4% PFA for 10 minutes, permeabilized with PBS with 0.05% Tween-20, followed by incubation in blocking buffer (1% BSA and 5% Normal donkey serum in PBS with 0.05% Tween-20 and 0.01% triton) for 1 hour. Cells were incubated with rabbit anti-β3 tubulin (Anti-beta III Tubulin antibody-Neuronal Marker, ab18207, 1:1500, Abcam, Cambridge, UK) and NeuN (Anti-NeuN Antibody clone A60, MAB377, 1:500) Sigma Aldrich (Merck), Darmstadt, Germany) overnight at 4° C., followed by washes and incubation with AF488-conjugated donkey anti-rabbit and 568-conjugated donkey anti-mouse secondary antibodies (Thermofisher, 1:500) followed by DAPI (1:5000, Sigma) staining before sections were mounted on slides with FluorSave reagent (Millipore).

Images were taken using an Olympus IX83 microscope (Olympus). Pictures were analysed using CellSens software (Olympus) and ImageJ (NIH), using the NeuralNetrics macro (Pani G, et al. MorphoNeuroNet: An automated method for dense neurite network analysis. Cytom Part A. 2014 February; 85(2):188-99). Other plugins used were Olympus Viewer plugin (Olympus). Cell sense software was used to automatically count number of neurons based on NeuN staining. Neurite length was determined using the NeuralNetric macro in ImageJ (Fiji).

Results

Paclitaxel reduced neurite length with approximately 67% compared to control cultured sensory neurons.

FIG. 12 illustrates a comparison of the neuroprotective effect of two IL4/IL13 fusion proteins versus IL13 alone or the combination of IL4 and IL13. IL13 dose dependently inhibited the paclitaxel-induced decrease in neurite length, with a maximum of ~9% at a concentration of 3 nM (FIG. 12). The combination of IL4 and IL13 did not significantly inhibit paclitaxel-induced neurite length at any concentration tested.

The fusion protein labeled IL4/IL13 comprises SEQ ID NO: 4. The fusion protein labeled IL4/IL13$_{SKP}$ comprises SEQ ID NO: 16. IL13 is located at the C-terminal end of these constructs. IL4/IL13 dose-dependently inhibited the paclitaxel-induced reduction in neurite length, with a maximum effect of 35% at 3 nM (FIG. 12). IL4/IL13 inhibited paclitaxel-induced reduction in neurite length significantly better than IL4 and IL13 combined or IL13 alone, with ~4 fold more inhibition at a concentration of 3 nM compared to IL13 (FIG. 12). An alternative IL4/IL13 fusion protein, IL4/IL13$_{SKP}$, inhibited paclitaxel-induced reduction in neurite length to a similar extent as IL4/IL13 at all concentrations tested (FIG. 12). The IL13 protein sequence (SEQ ID NO: 14) used in IL4/IL13$_{SKP}$ (SEQ ID NO: 16) contains an additional serine N-terminally, and an arginine instead of glutamine near the C-terminal end (position 112 in SEQ ID NO: 14). Despite these protein sequence differences, both fusion proteins comprising IL4 and IL13 show the superior neuroprotective effect versus the individual IL4 and IL13 as well as the combination of IL4+IL13. Data are shown as mean±SEM. Data are analysed with a two-way ANOVA mixed-effects analysis followed by Tukey's multiple comparison test.

FIG. 13 illustrates a comparison of neuroprotective effects of two pools of IL10/IL13 fusion proteins to equimolar concentrations of IL13 alone, or the combination of IL10 and IL13. The IL10/IL13 fusion proteins comprise SEQ ID NO: 17, with IL13 located at the N-terminal end. Pools of this fusion protein are referred to as IL13/IL10$_{pool1}$ and IL13/IL10$_{pool2}$ in the figure. IL13/IL10$_{pool1}$ significantly inhibited paclitaxel-induced reduction in neurite length at all doses tested, ranging from 15% at 0.12 nM to 28% at 3 nM (FIG. 13). IL13/IL10$_{pool2}$ also concentration-dependently protected neurons from paclitaxel-induced reduction in neurite length. Importantly both IL13/IL10$_{pool1}$ and IL13/IL10$_{pool2}$ prevented paclitaxel-induced neuronal damage significantly better than IL13 or the combination of IL10 and IL13 at 3 nM (FIG. 13). Data are shown as mean±SEM. Data are analysed with a two-way ANOVA mixed-effects analysis followed by Tukey's multiple comparison test.

FIG. 14 provides a comparison of neuroprotective effects of an IL13/IL13 fusion protein and an IL27/IL13 fusion protein to IL13 alone. The IL13/IL13 fusion protein comprises SEQ ID NO: 20. The IL13/IL13 fusion protein inhibited paclitaxel-induced reduction in neurite length by ~10% at 0.12 nM, which was significantly better than IL13 at that concentration. However, with increasing concentration IL13/IL13 did not provide more neuroprotection (FIG. 14).

The IL27/IL13 fusion protein comprises SEQ ID NO: 19, with IL13 located at the N terminal end of the protein, and is referred to as IL13/IL27-A$_{pool2}$ in FIG. 14 This fusion protein includes IL13 and a secretion-competent mutein of IL27A (Müller et al., 2019). Pool 2 of IL27/IL13, generated as described above, was tested. At 0.6 nM, IL27/IL13 inhibited paclitaxel-induced neuronal damage with a maximal effect of ~21% inhibition. At this concentration, IL27/IL13 outperformed IL13. At 3 nM the neuroprotective effects of IL13 and IL27/IL13 were not significantly different. Data are shown as mean±SEM. Data are analysed with a two-way ANOVA mixed-effects analysis followed by Tukey's multiple comparison test.

These data demonstrate that multiple fusion proteins comprising IL13 and a regulatory cytokine are effective in reducing neurotoxicity, including fusion proteins comprising different IL13 sequences, different regulatory cytokines, and with IL13 at either the N-terminal or C-terminal end of the fusion protein. Multiple fusion proteins demonstrate superiority over IL13 alone, and superiority over the combination of IL13 and the regulatory cytokine.

Example 11

An IL13-Containing Fusion Protein of the Disclosure Elicits a Distinct Kinase Activity Profile Compared to a Combination of Unlinked Cytokines Animals: All animal experiments were performed in accordance with international guidelines and with prior approval from the University Medical Center Utrecht experimental animal committee. Experiments were conducted with 8-14 weeks old male and female wild type (WT) C57BL/6 mice.

Paclitaxel-induced CIPN: At day 0, 2, 4 and 6 animals were injected intraperitoneally with 8 mg/kg of Paclitaxel (diluted in Cremophor:EtOH 1:1; volume of injection 40 µl/10 g of bodyweight. At day 8, animals received i.t. injections of: IL4/IL13 fusion protein (0.3 µg), IL4+IL13 (0.15 µg each) or Vehicle. The IL4/IL13 fusion protein was a fusion protein comprising SEQ ID NO: 4.

Drugs and administration: The IL4/IL13 was produced by transient transfection of HEK293F cells with the pcDNA3.1-neo expression vector (Invitrogen; Carlsbad, CA) with dual CMV promotor. The vector contained two transgenes: cDNA coding for IL4/IL13 fusion protein and cDNA coding beta-galactoside-2, 3-sialyl-transferase to optimize glycan capping with sialic acid. The IL4/IL13 contained a 6-His tag at the N terminus and was purified through HIS-Select Nickel Affinity gel (Sigma). IL4/IL13 concentrations were determined with an IL4 ELISA kit (IL-4 Pelipair ELISA kit; Sanquin) and Bicinchoninic Acid Protein Assay (BCA Pierce Protein Assay Kit, ThermoFisher Scientific). Intrathecal (i.t.) injections of different compounds (5 µl/mouse) were performed as described before (J Neurosci 30, 2138-2149, 2010) under light isoflurane/$O_2$ anesthesia. The IL4/IL13 (0.3 µg/mouse) or equimolar doses (0.15 µg each/mouse) of recombinant human HEK-produced IL4 (Sigma) and IL13 (2bsciences) were injected intrathecally at day 8 after the first paclitaxel injection.

Kinase Activity Profiling: Animals were killed an hour after intrathecal injection of the IL4/IL13 fusion protein, IL4+IL13 or vehicle, followed by immediate DRG isolation. Lumbar DRGs were homogenized using M-PER mammalian Extraction buffer (Pierce) supplemented with phosphatase and protease inhibitor cocktails (Pierce). Protein concentration was determined using the Bradford assay (Bio-Rad). Kinase activity profiling was performed using the Tyrosine Kinase PamChip® (PTK) Array for Pamstation®12 (PamGene International B.V.). For the PTK array, 7.5 µg of protein lysate per array was used. Image quantification and statistical analysis were performed using BioNavigator® Software (PamGene International B.V.). Upstream kinase analysis was performed using BioNavigator® Software with peptide-kinase mapping using Kinexus phosphonet enrichment files (www_phosphonet.ca/).

Results

To elucidate downstream signaling in sensory neurons in an unbiased manner, PamGene kinase activity profiling was performed to assess global protein tyrosine kinases (PTK) activity in homogenates of lumbar DRGs isolated from mice with persistent paclitaxel-induced CIPN after IL4/IL13 fusion protein, IL4+IL13 (combination of unlinked cytokines), and vehicle administration. Kinomic profiles were assessed at 60 minutes after intrathecal administration of the IL4/IL13 fusion protein, the combination of cytokines, or vehicle (PBS). Naive mice (i.e. not treated with paclitaxel or IL4/IL13 fusion protein) were also included.

FIG. 15 illustrates peptides that were differentially phosphorylated based on one-way ANOVA analysis between IL4/IL13, IL4+IL13, and vehicle-treated mice compared to naive mice (untreated; no paclitaxel, no intrathecal injection). Black indicates no significant changes, while color indicates decreased phosphorylation. Analyses of the peptides that were differentially phosphorylated by PTK in the DRG homogenates of IL4/IL13-treated mice and vehicle-treated mice, indicated that in total 19 peptides were uniquely phosphorylated upon treatment with the fusion protein.

Analyses of the peptides that were differentially phosphorylated by PTK in the DRG homogenates of IL4/IL13-treated male and female mice versus IL4 plus IL13-treated mice, indicated that in both sexes the activity of different kinases is differentially affected by the IL4/IL13 compared to the combination of cytokines (FIG. 16 and FIG. 17).

In DRGs from female mice treated with the IL4/IL13 fusion protein, the activity of several kinases was reduced when compared female mice treated with the combination of IL4 and IL13 (FIG. 16). The graph shows the predicted upstream kinases inferred from the differentially phosphorylated peptide substrates on the PamChips® identified by unpaired t-test comparison between samples from IL4/IL13 fusion protein-treated females and IL4+IL13-treated females (n=3 animals per group). The top 5 predicted putative kinases affected (according to summation of sensitivity and specificity score) were: ITK, RET, TYK2, FER and ERBB4.

In male mice, unique kinase activity was predominantly increased (FIG. 17). The graph shows predicted upstream kinases that can be inferred from the differentially phosphorylated peptide substrates on the PamChips® identified by unpaired t-test comparison between samples from IL4/IL13 fusion protein-treated males and IL4+IL13-treated males (n=3 animals per group). The top 5 predicted putative kinases affected were: LTK, RYK, ALK, AXL and BLK.

These data show that IL4/IL13 uniquely regulates sets of kinases compared to the combination of unlinked IL4 plus IL13.

Example 12

Additional Fusion Proteins of the Disclosure

This example demonstrates design and generation of non-limiting examples of IL13-containing fusion proteins of the disclosure.

An IL33/IL13 fusion protein of the disclosure comprising SEQ ID NO: 6 and SEQ ID NO: 14 is designed. SEQ ID NO: 6 is joined to SEQ ID NO: 14 using the SEQ ID NO: 3 linker, resulting in SEQ ID NO: 23. The fusion protein is produced as disclosed herein. For example, a hexa-histidine tag is added to the N-terminus, and the fusion protein is produced by transient transfection of HEK293E cells as disclosed below.

A TGFβ1/IL13 fusion protein of the disclosure comprising SEQ ID NO: 21 and SEQ ID NO: 14 is designed. SEQ ID NO: 21 is joined to SEQ ID NO: 14 using the SEQ ID NO: 3 linker, resulting in SEQ ID NO: 24. The fusion protein is produced as disclosed herein. For example, a hexa-histidine tag is added to the N-terminus, and the fusion protein is produced by transient transfection of HEK293E cells as disclosed below.

A TGFβ2/IL13 fusion protein of the disclosure comprising SEQ ID NO: 22 and SEQ ID NO: 14 is designed. SEQ ID NO: 22 is joined to SEQ ID NO: 14 using the SEQ ID NO: 3 linker, resulting in SEQ ID NO: 25. The fusion protein is produced as disclosed herein. For example, a hexa-histidine tag is added to the N-terminus, and the fusion protein is produced by transient transfection of HEK293E cells as disclosed below.

Additional IL4/IL13 fusion proteins are designed wherein any one of SEQ ID NOs: 2 or 9-15 (or a variant, derivative, or fragment thereof) is joined to any one of SEQ ID NOs: 1 or 26-28 (or a variant, derivative, or fragment thereof), either directly or via a linker as disclosed herein (for example, any one of SEQ ID NOs: 3 or 37-44, or a multiple thereof). The fusion proteins are designed in both orientations, e.g., with IL4 located on the C-terminal side of IL13, or with IL4 located on the N-terminal side of IL13. The fusion proteins are produced as disclosed herein. For example, an affinity tag is added to the N-terminus and/or the C-terminus of each fusion protein, and the fusion proteins are produced by transient transfection of HEK293E cells as disclosed below.

Additional IL10/IL13 fusion proteins are designed wherein any one of SEQ ID NOs: 2 or 9-15 (or a variant, derivative, or fragment thereof) is joined to SEQ ID NOs: 5 (or a variant, derivative, or fragment thereof), either directly or via a linker as disclosed herein (for example, any one of SEQ ID NOs: 3 or 37-44, or a multiple thereof). The fusion proteins are designed in both orientations, e.g., with IL10 located on the C-terminal side of IL13, or with IL10 located on the N-terminal side of IL13. The fusion proteins are produced as disclosed herein. For example, an affinity tag is added to the N-terminus and/or the C-terminus of each fusion protein, and the fusion proteins are produced by transient transfection of HEK293E cells as disclosed below.

Additional IL27/IL13 fusion proteins are designed wherein any one of SEQ ID NOs: 2 or 9-15 (or a variant, derivative, or fragment thereof) is joined to any one of SEQ ID NOs: 18, 36, 45, or a combination thereof (or a variant, derivative, or fragment thereof), either directly or via a linker as disclosed herein (for example, any one of SEQ ID NOs: 3 or 37-44, or a multiple thereof). The fusion proteins are designed in both orientations, e.g., with IL27 located on the C-terminal side of IL13, or with IL27 located on the N-terminal side of IL13. The fusion proteins are produced as disclosed herein. For example, an affinity tag is added to the N-terminus and/or the C-terminus of each fusion protein, and the fusion proteins are produced by transient transfection of HEK293E cells as disclosed below.

Additional IL33/IL13 fusion proteins are designed wherein any one of SEQ ID NOs: 2 or 9-15 (or a variant, derivative, or fragment thereof) is joined to any one of SEQ ID NOs: 6 or 29 or 34 (or a variant, derivative, or fragment thereof), either directly or via a linker as disclosed herein (for example, any one of SEQ ID NOs: 3 or 37-44, or a multiple thereof). The fusion proteins are designed in both orientations, e.g., with IL33 located on the C-terminal side of IL13, or with IL33 located on the N-terminal side of IL13. The fusion proteins are produced as disclosed herein. For example, an affinity tag is added to the N-terminus and/or the C-terminus of each fusion protein, and the fusion proteins are produced by transient transfection of HEK293E cells as disclosed below.

Additional IL13/IL13 fusion proteins are designed wherein any one of SEQ ID NOs: 2 or 9-15 (or a variant, derivative, or fragment thereof) is joined to any one of SEQ ID NOs: 2 or 9-15 (or a variant, derivative, or fragment thereof), either directly or via a linker as disclosed herein (for example, any one of SEQ ID NOs: 3 or 37-44, or a multiple thereof). The fusion proteins are designed in both orientations, e.g., with the first IL13 located on the C-terminal side of the second IL13, or with first IL13 located on the N-terminal side of second IL13. The first IL13 and the second IL13 can be the same or different. The fusion proteins are produced as disclosed herein. For example, an affinity tag is added to the N-terminus and/or the C-terminus of each fusion protein, and the fusion proteins are produced by transient transfection of HEK293E cells as disclosed below.

Additional TGFβ1/IL13 fusion proteins are designed wherein any one of SEQ ID NOs: 2 or 9-15 (or a variant, derivative, or fragment thereof) is joined to any one of SEQ ID NOs: 7 or 21 (or a variant, derivative, or fragment thereof), either directly or via a linker as disclosed herein (for example, any one of SEQ ID NOs: 3 or 37-44, or a multiple thereof). The fusion proteins are designed in both orientations, e.g., with TGFβ1 located on the C-terminal side of IL13, or with TGFβ1 located on the N-terminal side of IL13. The fusion proteins are produced as disclosed herein. For example, an affinity tag is added to the N-terminus and/or the C-terminus of each fusion protein, and the fusion proteins are produced by transient transfection of HEK293E cells as disclosed below.

Additional TGFβ2/IL13 fusion proteins are designed wherein any one of SEQ ID NOs: 2 or 9-15 (or a variant, derivative, or fragment thereof) is joined to any one of SEQ ID NOs: 8, 22, or 35 (or a variant, derivative, or fragment thereof), either directly or via a linker as disclosed herein (for example, any one of SEQ ID NOs: 3 or 37-44, or a multiple thereof). The fusion proteins are designed in both orientations, e.g., with TGFβ2 located on the C-terminal side of IL13, or with TGFβ2 located on the N-terminal side of IL13. The fusion proteins are produced as disclosed herein. For example, an affinity tag is added to the N-terminus and/or the C-terminus of each fusion protein, and the fusion proteins are produced by transient transfection of HEK293E cells as disclosed below.

IL13-containing fusion proteins of the disclosure are produced by transient transfection of HEK293E cells. Cells are transfected with a pUPE expression vector containing a transgene coding one of the IL13-containing fusion protein sequences. To enable purification, a hexa-histidine affinity tag is cloned at the N-terminus of each IL13-containing protein. Six days post transfection, conditioned medium containing recombinant protein is harvested by low-speed centrifugation (10 minutes, 1000×g) followed by high-speed centrifugation (10 minutes, 4000×g).

Proteins are purified via His-tag by Immobilized Metal Affinity Chromatography (IMAC). In short, the recombinant protein is bound to 0.5 ml Nickel Sepharose® excel at 20° C. Nickel sepharose® excel containing bound protein is harvested by centrifugation and transferred into a gravity flow column. Non-specifically bound proteins are removed by washing the column with IMAC buffer (500 mM Sodium Chloride, 25 mM Tris, pH=8.2) containing 0 and 10 mM imidazol. The proteins are eluted with IMAC buffer containing 500 mM imidazol. Fractions of 2.5 ml are collected. Recombinant protein-containing fractions are pooled. Conditioned medium and the unbound IMAC fraction are analyzed by LabChip® capillary electrophoresis. The IMAC pool is concentrated to 2-4 ml using an Amicon 10 kDa spin filter. Aggregates are removed by centrifugation (10 minutes 18000×g, 4° C.).

The proteins are purified further by gel filtration using a Superdex200 16/600 column that has been equilibrated in PBS. Protein containing fractions are analyzed by LabChip® capillary electrophoresis and recombinant protein containing fractions are pooled. Protein pools are sterilized by filtration using a 0.22 μm syringe filter and the product stored in 1 ml vials at −80° C.

Protein assays: Protein concentration in batches is determined spectrophotometrically by measuring the absorbance at 280 nm (DropSense16, Trinean) and using a BCA (Thermo Scientific) protein assay.

SDS-Page: Purified proteins are analysed on 4-12% polyacrylamide NuPage™ polyacrylamide gels under reducing and non-reducing conditions. Protein bands are visualized by Coomassie protein stain.

Example 13

Neuroprotective Effects of Fusion Proteins of the Disclosure

Assays are conducted to assess whether the IL13-containing fusion proteins possess neuroprotective properties, e.g., inhibit paclitaxel-induced reduction of neurite length. The assays are conducted for any fusion protein disclosed herein, for example, fusion proteins comprising an IL13 and a regulatory cytokine, e.g., an IL4/IL13, IL10/IL13, IL13/IL13, IL27/IL13, IL33/IL13, TGFβ1/IL13, or TGFβ2/IL13 of the disclosure.

Culture of DRG neurons: DRGs are cultured as described previously (Nat. Commun. 4, 1682 (2013)). Briefly, DRGs are dissected and placed on ice-cold dissection medium (HBSS w/o $Ca^{2+}$ and $Mg^{2+}$, 5 mM HEPES, and 10 mM glucose). After dissection, axons are cut and dissection medium is replaced by filtered enzyme mix (HBSS without $Ca^{2+}$ and $Mg^{2+}$, 5 mM HEPES, 10 mM glucose, 5 mg/ml collagenase type XI (Sigma), and 10 mg/ml Dispase (Gibco)). The DRGs are incubated in enzyme mix for 30 minutes at 37° C. and 5% $CO_2$. Subsequently, enzyme mix is inactivated with heat-inactivated fetal bovine serum (FBS, Sigma). Cells are cultured in Dulbecco's modified Eagle's medium (Gibco) containing 10% FBS (Gibco), 2 mmol/L glutamine (Gibco), 10,000 IU/ml penicillin-streptomycin (Gibco) on poly-L-lysine (0.01 mg/ml, Sigma) and laminin (0.02 mg/ml, Sigma)-coated glass coverslips in a 5% $CO_2$ incubator at 37° C. Cells are used the following 1-2 days.

Treatments and neurite length measurement: After 24 h in culture, DRG neurons are treated with Paclitaxel (1 μM) alone, or in the presence of different concentrations of IL13 fusion proteins (e.g., 0.12 nM, 0.6 nM, or 3 nM), or equimolar doses of the individual cytokines that are present in the fusion proteins for 24 h. Neurites are visualised using β3-tubulin staining, whilst the number of sensory neurons is determined using NeuN staining. Pictures are taken and for each picture, the neurite length per sensory neuron is determined. The neurite length is averaged to a single value for each animal and condition. The percentage inhibition of paclitaxel-induced neurite length loss per mouse culture of 1 mouse is calculated according to the following formula $((\mu_{control}-\mu_{paclitaxel})-(\mu_{control}-X_{cytokine}))/(\mu_{control}-\mu_{paclitaxel})*100$ (where μ is the neurite length per neuron averaged over all samples and X is the neurite length of each individual sample).

β3-tubulin and NeuN staining: cells are fixed in 4% PFA for 10 minutes, permeabilized with PBS with 0.05% Tween-20, followed by incubation in blocking buffer (1% BSA and 5% Normal donkey serum in PBS with 0.05% Tween-20 and 0.01% triton) for 1 hour. Cells are incubated with rabbit anti-β3 tubulin (Anti-beta III Tubulin antibody-Neuronal Marker, ab18207, 1:1500, Abcam, Cambridge, UK) and NeuN (Anti-NeuN Antibody clone A60, MAB377, 1:500) Sigma Aldrich (Merck), Darmstadt, Germany) overnight at 4° C., followed by washes and incubation with AF488-conjugated donkey anti-rabbit and 568-conjugated donkey anti-mouse secondary antibodies (Thermofisher, 1:500) followed by DAPI (1:5000, Sigma) staining before sections are mounted on slides with FluorSave reagent (Millipore).

Images are taken using an Olympus IX83 microscope (Olympus). Pictures are analysed using CellSens software (Olympus) and ImageJ (NIH), using the NeuralNetrics macro (Pani G, et al. MorphoNeuroNet: An automated method for dense neurite network analysis. Cytom Part A. 2014 February; 85(2):188-99). Other plugins used are Olympus Viewer plugin (Olympus). Cell sense software is used to automatically count number of neurons based on NeuN staining. Neurite length is determined using the NeuralNetric macro in ImageJ (Fiji). The ability of IL13-containing fusion proteins of the disclosure to inhibit paclitaxel-induced reduction of neurite length is determined and compared to the combination of unlinked cytokines for each fusion protein.

Example 14

In Vivo Assessment of Fusion Proteins of the Disclosure

Assays are conducted to assess whether the IL13-containing fusion proteins can treat, for example, pain, chemotherapy-induced polyneuropathy (CIPN), pain, nerve fiber loss, and allodynia. The assays are conducted for any fusion protein disclosed herein, for example, fusion proteins comprising an IL13 and a regulatory cytokine, e.g., an IL4/IL13, IL10/IL13, IL13/IL13, IL27/IL13, IL33/113, TGFβ1/IL13, or TGFβ2/IL13 of the disclosure.

To induce transient chemotherapy-induced polyneuropathy (CIPN), paclitaxel (2 mg/kg, Cayman Chemical Company) is injected intraperitoneally into C57BL/6 mice on days 0 and 2. To induce persistent paclitaxel-induced CIPN, paclitaxel (8 mg/kg, Cayman Chemical Company) is injected intraperitoneally on day 0, 2, 4 and 6. To induce persistent oxaliplatin-induced polyneuropathy, mice receive two treatment cycles, each consisting of 5 daily intraperitoneal injections of 3 mg/kg oxaliplatin (Tocris) with a 5 days free interval. To induce inflammatory hyperalgesia, mice receive an intraplantar injection of 20 μl λ-carrageenan (2% (w/v), Sigma-Aldrich) dissolved in saline solution (NaCl 0.9%) in both hind paws. In other animals, chronic constriction injury (CCI) and spared nerve injury (SNI) models are used.

Noxious mechanical sensitivity in the hind paws is measured using von Frey hairs (Stoelting, Wood Dale, USA). Results are expressed as the 50% paw-withdrawal threshold using the up-and-down method. Thermal hyperalgesia is assessed by determining the heat withdrawal latency times using the Hargreaves test (IITC Life Science). In some experiments the length of intraepidermal nerve fibers in the paw skin at day 15 is determined by immunofluorescent staining of skin biopsies with the neuronal marker PGP9.5. All experiments are performed in a blinded manner.

IL13-containing fusion proteins are administered to mice, e.g., via intrathecal injection under light isoflurane/$O_2$ anaesthesia, or by another route as disclosed herein. The ability of IL13-containing fusion proteins of the disclosure to inhibit neuropathy, hyperalgesia, and intra-epidermal nerve fibre loss, is determined and compared to the combination of unlinked cytokines for each fusion protein.

REFERENCES

1. Breivik H, et al. Survey of chronic pain in Europe: prevalence, impact on daily life, and treatment. Eur J Pain 2006; 10:287-333.
2. Johannes C B, et al. The prevalence of chronic pain in United States adults: results of an Internet-based survey. J Pain 2010; 11:1230-9.
3. Langley P C. The prevalence, correlates and treatment of pain in the European Union. Curr Med Res Opin 2011; 27:463-80.

4. van Hecke O, et al. Chronic pain epidemiology and its clinical relevance. Br J Anaesth 2013; 111:13-8
5. Dahlhammer J, et al. Prevalence of Chronic Pain and High-Impact Chronic Pain Among Adults—United States, 2016. Morbidity and Mortality Weekly Report (MMWR) 2018; 67:1001-6
6. Breivik H, et al. The individual and societal burden of chronic pain in Europe: the case for strategic prioritisation and action to improve knowledge and availability of appropriate care. BMC Public Health 2013; 13:1229
7. Scholz J, et al. The neuropathic pain triad: neurons, immune cells and glia. Nat Neurosci 2007; 10:1361-8
8. Woolf C J, et al. Neuronal plasticity: increasing the gain in pain. Science 2000; 288:1765-9
9. Ji R-R, et al. Pain regulation by non-neuronal cells and inflammation. Science. 2016; 354:572-7
10. Chen G, et al. Microglia in Pain: Detrimental and Protective Roles in Pathogenesis and Resolution of Pain. Neuron 2018; 100:1292-311
11. Serhan C N, et al. Resolution of inflammation: state of the art, definitions and terms. FASEB J 2007; 21:325-32
12. Schaible H G. Nociceptive neurons detect cytokines in arthritis. Arthritis Res Ther 2014; 16:470
13. Raoof R, et al. Divergent roles of immune cells and their mediators in pain. Rheumatology (Oxford) 2018; 57:429-40
14. Willemen H L, et al. Monocytes/Macrophages control resolution of transient inflammatory pain. J Pain 2014; 15:496-506
15. Krukowski K, et al. CD8+ T Cells and Endogenous IL10 Are Required for Resolution of Chemotherapy-Induced Neuropathic Pain. J Neurosci 2016; 36:11074-83
16. Rijsdijk M, et al. The effects of glucocorticoids on neuropathic pain: a review with emphasis on intrathecal methylprednisolone acetate delivery. Anesth Analg 2014; 118:1097-112.
17. Rijsdijk M, et al. No beneficial effect of intrathecal methylprednisolone acetate in postherpetic neuralgia patients. Eur J Pain 2013; 17:714-23.
18. Usoskin D, et al. Unbiased classification of sensory neuron types by large-scale single-cell RNA sequencing. Nat Neurosci 2015; 18:145-53
19. Eijkelkamp N, et al. IL4-10 Fusion Protein Is a Novel Drug to Treat Persistent Inflammatory Pain. J Neurosci 2016; 36:7353-63.
20. Old E A, et al. The role of glia in the spinal cord in neuropathic and inflammatory pain. Handb Exp Pharmacol 2015; 227:145-70
21. Ji R R, et al. Glia and pain: is chronic pain a gliopathy? Pain 2013; 154 Suppl 1:S10-28.
22. Grace P M, et al. Pathological pain and the neuroimmune interface. Nat Rev Immunol 2014; 14:217-31.
23. WO 2013/070076 A1 Fusion protein comprising interleukin 4 and interleukin 10. J A G van Roon, S A Y Hartgring, C E Hack, C Louws, F P J G Lafeber (inventors).
24. Bottros M M, et al. Current perspectives on intrathecal drug delivery. J Pain Res 2014; 7:615-26
25. Steen-Louws C, et al. IL4-10 fusion protein has chondroprotective, anti-inflammatory and potentially analgesic effects in the treatment of osteoarthritis. Osteoarthritis Cartilage 2018; 26:1127-35
26. Steen-Louws C, et al. IL4-10 fusion protein: a novel immunoregulatory drug combining activities of interleukin 4 and interleukin 10. Clin Exp Immunol 2019; 195:1-9.
27. Thom G, et al. Probing a protein-protein interaction by in vitro evolution. PNAS 2006; 103:7619-24
28. Eijkelkamp N, et al. A role for Piezo2 in EPAC1-dependent mechanical allodynia. Nat Commun 2013; 4:1682
29. Chaplan S R, et al. Quantitative assessment of tactile allodynia in the rat paw. J Neurosci Methods 1994; 53:55-63
30. Toma W, et al. Effects of paclitaxel on the development of neuropathy and affective behaviors in the mouse. Neuropharmacology 2017; 117:305-15

```
SEQUENCE LISTING
SEQ ID NO: 1
Amino acid sequence of human IL4
HKCDITLQEIIKTLNSLTEQKTLCTELTVTDIFAA

SKNTTEKETFCRAATVLRQFYSHHEKDTRCLGATA

QQFHRHKQURFLKRLDRNLWGLAGLNSCPVKEANQ

STLENFLERLKTIMREKYSKCSS

SEQ ID NO: 2
Amino acid sequence of human IL13
PGPVPPSTALRELIEELVNITQNQKAPLCNGSMVW

SINLTAGMYCAALESLINVSGCSAIEKTQRMLSGF

CPHKVSAGQFSSLHVRDTKIEVAQFVKDLLLHLKK

LFREGQFN

SEQ ID NO: 3
Amino acid sequence of suitable linker
GSGGGGSGT

Amino acid sequence of an IL4/1L13
fusion protein (the linker sequence
is underlined
SEQ ID NO: 4
HKCDITLQEIIKTLNSLTEQKTLCTELTVTDIFAA

SKNTTEKETFCRAATVLRQFYSHHEKDTRCLGATA

QQFHRHKQURFLKRLDRNLWGLAGLNSCPVKEANQ

STLENFLERLKTIMREKYSKCSSGSGGGGSGTPGP

VPPSTALRELIEELVNITQNQKAPLCNGSMVWSIN

LTAGMYCAALESLINVSGCSAIEKTQRMLSGFCPH

KVSAGQFSSLHVRDTKIEVAQFVKDLLLHLKKLFR

EGQFN

SEQ ID NO: 5
Amino acid sequence of human IL10
SPGQGTQSENSCTHFPGNLPNMLRDLRDAFSRVKT

FFQMKDQLDNLLLKESLLEDFKGYLGCQALSEMIQ

FYLEEVMPQAENQDPDIKAHVNSLGENLKTLRLRL

RRCHRFLPCENKSKAVEQVKNAFNKLQEKGIYKAM

SEFDIFINYIEAYMTMKIRN

SEQ ID NO: 6
Amino acid sequence of human IL33
MKPKMKYSTNKISTAKWKNTASKALCFKLGKSQQK

AKEVCPMYFMKLRSGLMIKKEACYFRRETTKRPSL

KTGRKHKRHLVLAACQQQSTVECFAFGISGVQKYT

RALHDSSITGISPITEYLASLSTYNDQSITFALED
```

ESYEIYVEDLKKDEKKDKVLLSYYESQHPSNESGD

GVDGKMLMVTLSPTKDFWLHANNKEHSVELHKCEK

PLPDQAFFVLHNMHSNCVSFECKTDPGVFIGVKDN

HLALIKVDSSENLCTENILFKLSET

SEQ ID NO: 7
Amino acid sequence of human immature
and mature (underlined) TGFβ1:
MPPSGLRLLPLLLPLLWLLVLTPGRPAAGLSTCKT

IDMELVKRKRIEAIRGQILSKLRLASPPSQGEVPP

GPLPEAVLALYNSTRDRVAGESAEPEPEPEADYYA

KEVTRVLMVETHNEIYDKFKQSTHSIYMFFNTSEL

REAVPEPVLLSRAELRLLRLKLKVEQHVELYQKYS

NNSWRYLSNRLLAPSDSPEWLSFDVTGVVRQWLSR

GGEIEGFRLSAHCSCDSRDNTLQVDINGFTTGRRG

DLATIHGMNRPFLLLMATPLERAQHLQSSRHRRAL

DTNYCFSSTEKNCCVRQLYIDFRKDLGWKWIHEPK

GYHANFCLGPCPYIWSLDTQYSKVLALYNQHNPGA

SAAPCCVPQALEPLPIVYYVGRKPKVEQLSNMIVR

SCKCS

SEQ ID NO: 8
Amino acid sequence of human immature
and mature (underlined) TGFβ2:
MHYCVLSAFLILHLVTVALSLSTCSTLDMDQFMRK

RIEAIRGQILSKLKLTSPPEDYPEPEEVPPEVISI

YNSTRDLLQEKASRRAAACERERSDEEYYAKEVYK

IDMPPFFPSETVCPVVTTPSGSVGSLCSRQSQVLC

GYLDAIPPTFYRPYFRIVRFDVSAMEKNASNLVKA

EFRVFRLQNPKARVPEQRIELYQILKSKDLTSPTQ

RYIDSKVVKTRAEGEWLSFDVTDAVHEWLHHKDRN

LGFKISLHCPCCTFVPSNNYIIPNKSEELEARFAG

IDGTSTYTSGDQKTIKSTRKKNSGKTPHLLLMLLP

SYRLESQQTNRRKKRALDAAYCFRNVQDNCCLRP

YIDFKRDLGWKWIHEPKGYNANFCAGACPYLWSSD

TQHSRVLSLYNTINPEASASPCCVSQDLEPLTILY

YIGKTPKIEQLSNMIVKSCKCS

SEQ ID NO: 9
Amino acid sequence of human IL13
GPVPPSTALRELIEELVNITQNQKAPLCNGSMVWS

INLTAGMYCAALESLINVSGCSAIEKTQRMLSGFC

PHKVSAGQFSSLHVRDTKIEVAQFVKDLLLHLKKL

FREGQFN
Amino acid sequence of human IL13

SEQ ID NO: 10
SPGPVPPSTALRELIEELVNITQNQKAPLCNGSMV

WSINLTAGMYCAALESLINVSGCSAIEKTQRMLSG

FCPHKVSAGQFSSLHVRDTKIEVAQFVKDLLLHLK

KLFREGQFN

SEQ ID NO: 11
Amino acid sequence of human IL13
LTCLGGFASPGPVPPSTALRELIEELVNITQNQKA

PLCNGSMVWSINLTAGMYCAALESLINVSGCSAIE

KTQRMLSGFCPHKVSAGQFSSLHVRDTKIEVAQFV

KDLLLHLKKLFREGQFN

SEQ ID NO: 12
Amino acid sequence of human IL13
PGPVPPSTALRELIEELVNITQNQKAPLCNGSMVW

SINLTAGMYCAALESLINVSGCSAIEKTQRMLSGF

CPHKVSAGQFSSLHVRDTKIEVAQFVKDLLLHLKK

LFREGRFN
SEQ ID NO: 13
Amino acid sequence of human IL13
GPVPPSTALRELIEELVNITQNQKAPLCNGSMVWS

INLTAGMYCAALESLINVSGCSAIEKTQRMLSGFC

PHKVSAGQFSSLHVRDTKIEVAQFVKDLLLHLKKL

FREGRFN
Amino acid sequence of human IL13

SEQ ID NO: 14
SPGPVPPSTALRELIEELVNITQNQKAPLCNGSMV

WSINLTAGMYCAALESLINVSGCSAIEKTQRMLSG

FCPHKVSAGQFSSLHVRDTKIEVAQFVKDLLLHLK

KLFREGRFN
SEQ ID NO: 15
Amino acid sequence of human IL13
LTCLGGFASPGPVPPSTALRELIEELVNITQNQKA

PLCNGSMVWSINLTAGMYCAALESLINVSGCSAIE

KTQRMLSGFCPHKVSAGQFSSLHVRDTKIEVAQFV

KDLLLHLKKLFREGRFN

SEQ ID NO: 16
Amino acid sequence of an IL4/1L13
fusion protein
HKCDITLQEIIKTLNSLTEQKTLCTELTVTDIFAA

SKNTTEKETFCRAATVLRQFYSHHEKDTRCLGATA

QQFHRHKQURFLKRLDRNLWGLAGLNSCPVKEANQ

STLENFLERLKTIMREKYSKCSSGSGGGGSGTSPG

PVPPSTALRELIEELVNITQNQKAPLCNGSMVWSI

NLTAGMYCAALESLINVSGCSAIEKTQRMLSGFCP

HKVSAGQFSSLHVRDTKIEVAQFVKDLLLHLKKLF

REGRFN

SEQ ID NO: 17
Amino acid sequence of IL10/1L13
fusion protein
SPGPVPPSTALRELIEELVNITQNQKAPLCNGSMV

WSINLTAGMYCAALESLINVSGCSAIEKTQRMLSG

FCPHKVSAGQFSSLHVRDTKIEVAQFVKDLLLHLK

KLFREGRFNGSGGGGSGTSPGQGTQSENSCTHFPG

NLPNMLRDLRDAFSRVKTFFQMKDQLDNLLLKESL

LEDFKGYLGCQALSEMIQFYLEEVMPQAENQDPDI

KAHVNSLGENLKTLRLRLRRCHRFLPCENKSKAVE

QVKNAFNKLQEKGIYKAMSEFDIF1NYIEAYMTMKIRN

SEQ ID NO: 18
Amino acid sequence of IL27A$^{L162c}$
FPRPPGRPQLSLQELRREFTVSLHLARKLLSEVRG

QAHRFAESHLPGVNLYLLPLGEQLPDVSLTFQAWR

RLSDPERLCFISTTLQPFHALLGGLGTQGRWTNME

RMQLWAMRLDLRDLQRHLRFQVLAAGFNCPEEEEE

EEEEEEEERKGLLPGALGSALQGPAQVSWPQLLST

YRLLHSLELVLSRAVRELLLLSKAGHSVWPLGFPT

LSPQP

SEQ ID NO: 19
Amino acid sequence of IL27/1L13 fusion protein
SPGPVPPSTALRELIEELVNITQNQKAPLCNGSMV

WSINLTAGMYCAALESLINVSGCSAIEKTQRMLSG

FCPHKVSAGQFSSLHVRDTKIEVAQFVKDLLLHLK

KLFREGRFNGSGGGGSGTFPRPPGRPQLSLQELRR

EFTVSLHLARKLLSEVRGQAHRFAESHLPGVNLYL

LPLGEQLPDVSLTFQAWRRLSDPERLCFISTTLQP

FHALLGGLGTQGRWTNMERMQLWAMRLDLRDLQRH

LRFQVLAAGFNCPEEEEEEEEEEEERKGLLPGAL

GSALQGPAQVSWPQLLSTYRLLHSLELVLSRAVRE

LLLLSKAGHSVWPLGFPTLSPQP

SEQ ID NO: 20
Amino acid sequence of IL13/1L13 fusion protein
SPGPVPPSTALRELIEELVNITQNQKAPLCNGSMV

WSINLTAGMYCAALESLINVSGCSAIEKTQRMLSG

FCPHKVSAGQFSSLHVRDTKIEVAQFVKDLLLHLK

KLFREGRFNGSGGGGSGTSPGPVPPSTALRELIEE

LVNITQNQKAPLCNGSMVWSINLTAGMYCAALESL

INVSGCSAIEKTQRMLSGFCPHKVSAGQFSSLHVR

DTKIEVAQFVKDLLLHLKKLFREGRFN

SEQ ID NO: 21
Amino acid sequence of mature TGFβ1
ALDTNYCFSSTEKNCCVRQLYIDFRKDLGWKWIHE

PKGYHANFCLGPCPYIWSLDTQYSKVLALYNQHNP

GASAAPCCVPQALEPLPIVYYVGRKPKVEQLSNMI

VRSCKCS

SEQ ID NO: 22
Amino acid sequence of mature TGFβ2
ALDAAYCFRNVQDNCCLRPLYIDFKRDLGWKWIHE

PKGYNANFCAGACPYLWSSDTQHSRVLSLYNTINP

EASASPCCVSQDLEPLTILYYIGKTPKIEQLSNMI

VKSCKCS

SEQ ID NO: 23
Amino acid sequence of IL33/1L13 fusion protein
MKPKMKYSTNKISTAKWKNTASKALCFKLGKSQQK

AKEVCPMYFMKLRSGLMIKKEACYFRRETTKRPSL

KTGRKHKRHLVLAACQQQSTVECFAFGISGVQKYT

RALHDSSITGISPITEYLASLSTYNDQSITFALED

ESYEIYVEDLKKDEKKDKVLLSYYESQHPSNESGD

GVDGKMLVTLSPTKDFWLHANNKEHSVELHKCEK

PLPDQAFFVLHNMHSNCVSFECKTDPGVFIGVKDN

HLALIKVDSSENLCTENILFKLSETGSGGGGSGTS

PGPVPPSTALRELIEELVNITQNQKAPLCNGSMVW

SINLTAGMYCAALESLINVSGCSAIEKTQRMLSGF

CPHKVSAGQFSSLHVRDTKIEVAQFVKDLLLHLKK

LFREGRFN

SEQ ID NO: 24
Amino acid sequence of TGFβ1/1L13 fusion protein
ALDTNYCFSSTEKNCCVRQLYIDFRKDLGWKWIHE

PKGYHANFCLGPCPYIWSLDTQYSKVLALYNQHNP

GASAAPCCVPQALEPLPIVYYVGRKPKVEQLSNMI

VRSCKCSGSGGGGSGTSPGPVPPSTALRELIEELV

NITQNQKAPLCNGSMVWSINLTAGMYCAALESLIN

VSGCSAIEKTQRMLSGFCPHKVSAGQFSSLHVRDT

KIEVAQFVKDLLLHLKKLFREGRFN

SEQ ID NO: 25:
Amino acid sequence of TGFβ2/IL13 fusion protein
ALDAAYCFRNVQDNCCLRPLYIDFKRDLGWKWIHE

PKGYNANFCAGACPYLWSSDTQHSRVLSLYNTINP

EASASPCCVSQDLEPLTILYYIGKTPKIEQLSNMI

VKSCKCSGSGGGGSGTSPGPVPPSTALRELIEELV

NITQNQKAPLCNGSMVWSINLTAGMYCAALESLIN

VSGCSAIEKTQRMLSGFCPHKVSAGQFSSLHVRDT

KIEVAQFVKDLLLHLKKLFREGRFN

SEQ ID NO: 26
Amino acid sequence of human IL4
HKCDITLQEIIKTLNSLTEQKNTTEKETFCRAATV

LRQFYSHHEKDTRCLGATAQQFHRHKQLIRFLKRL

DRNLWGLAGLNSCPVKEANQSTLENFLERLKTIMR

EKYSKCSS

SEQ ID NO: 27
Amino acid sequence of human IL4
HKRDITLQEIIKTLNSLTEQKTLCTELTVTDIFAA

SKNTTEKETFCRAATVLRQFYSHHEKDTRCLGATA

-continued
QQFHRHKQURFLKRLDRNLWGLAGLNSCPVKEANQ

STLENFLERLKTIMREKYSKCSS

SEQ ID NO: 28
Amino acid sequence of human IL4
HKRDITLQEIIKTLNSLTEQKNTTEKETFCRAATV

LRQFYSHHEKDTRCLGATAQQFHRHKQLIRFLKRL

DRNLWGLAGLNSCPVKEANQSTLENFLERLKTIMR

EKYSKCSS

SEQ ID NO: 29
Amino acid sequence of human IL33
AFGISGVQKYTRALHDSSITGISPITEYLASLSTY

NDQSITFALEDESYEIYVEDLKKDEKKDKVLLSYY

ESQHPSNESGDGVDGKMLMVTLSPTKDFWLHANNK

EHSVELHKCEKPLPDQAFFVLHNMHSNCVSFECKT

DPGVFIGVKDNHLALIKVDSSENLCTENILFKLSE

T

SEQ ID NO: 30
Amino acid sequence of human IL33
SGVQKYTRALHDSSITGISPITEYLASLSTYNDQS

ITFALEDESYEIYVEDLKKDEKKDKVLLSYYESQH

PSNESGDGVDGKMLMVTLSPTKDFWLHANNKEHSV

ELHKCEKPLPDQAFFVLHNMHSNCVSFECKTDPGV

FIGVKDNHLALIKVDSSENLCTENILFKLSET

SEQ ID NO: 31
Amino acid sequence of human IL33
HDSSITGISPITEYLASLSTYNDQSITFALEDESY

EIYVEDLKKDEKKDKVLLSYYESQHPSNESGDGVD

GKMLMVTLSPTKDFWLHANNKEHSVELHKCEKPLP

DQAFFVLHNMHSNCVSFECKTDPGVFIGVKDNHLA

LIKVDSSENLCTENILFKLSET

SEQ ID NO: 32
Amino acid sequence of human IL33
MKPKMKYSTNKISTAKWKNTASKALCFKLGKSQQK

AKEVCPMYFMKLRSGLMIKKEACYFRRETTKRPSL

KTGRKHKRHLVLAACQQQSTVECFAFGISGVQKYT

RALHDSSITDKVLLSYYESQHPSNESGDGVDGKML

MVTLSPTKDFWLHANNKEHSVELHKCEKPLPDQAF

FVLHNMHSNCVSFECKTDPGVFIGVKDNHLALIKV

DSSENLCTENILFKLSET

SEQ ID NO: 33
Amino acid sequence of human IL33
MKPKMKYSTNKISTAKWKNTASKALCFKLGKSQQK

AKEVCPMYFMKLRSGLMIKKEACYFRRETTKRPSL

KTGISPITEYLASLSTYNDQSITFALEDESYEIYV

EDLKKDEKKDKVLLSYYESQHPSNESGDGVDGKML

MVTLSPTKDFWLHANNKEHSVELHKCEKPLPDQAF

FVLHNMHSNCVSFECKTDPGVFIGVKDNHLALIKV

-continued
DSSENLCTENILFKLSET

SEQ ID NO: 34
Amino acid sequence of human IL33
MKPKMKYSTNKISTAKWKNTASKALCFKLGNKVLL

SYYESQHPSNESGDGVDGKMLMVTLSPTKDFWLHA

NNKEHSVELHKCEKPLPDQAFFVLHNMHSNCVSFE

CKTDPGVFIGVKDNHLALIKVDSSENLCTENILFK

LSET

SEQ ID NO: 35
Amino acid sequence of immature TGFβ2
MHYCVLSAFLILHLVTVALSLSTCSTLDMDQFMRK

RIEAIRGQILSKLKLTSPPEDYPEPEEVPPEVISI

YNSTRDLLQEKASRRAAACERERSDEEYYAKEVYK

IDMPPFFPSENAIPPTFYRPYFRIVRFDVSAMEKN

ASNLVKAEFRVFRLQNPKARVPEQRIELYQILKSK

DLTSPTQRYIDSKVVKTRAEGEWLSFDVTDAVHEW

LHHKDRNLGFKISLHCPCCTFVPSNNYIIPNKSEE

LEARFAGIDGTSTYTSGDQKTIKSTRKKNSGKTPH

LLLMLLPSYRLESQQTNRRKKRALDAAYCFRNVQD

NCCLRPLYIDFKRDLGWKWIHEPKGYNANFCAGAC

PYLWSSDTQHSRVLSLYNTINPEASASPCCVSQDL

EPLTILYYIGKTPKIEQLSNMIVKSCKCS

SEQ ID NO: 36
Amino acid sequence of IL27A
FPRPPGRPQLSLQELRREFTVSLHLARKLLSEVRG

QAHRFAESHLPGVNLYLLPLGEQLPDVSLTFQAWR

RLSDPERLCFISTTLQPFHALLGGLGTQGRWTNME

RMQLWAMRLDLRDLQRHLRFQVLAAGFNLPEEEEE

EEEEEEERKGLLPGALGSALQGPAQVSWPQLLST

YRLLHSLELVLSRAVRELLLLSKAGHSVWPLGFPT

LSPQP

SEQ ID NO: 37
Linker sequence
GGGS

SEQ ID NO: 38
Linker sequence
GGGGS

SEQ ID NO: 40
Linker sequence
KESGSVSSEQLAQFRSLD

SEQ ID NO: 41
Linker sequence
EGKSSGSGSESKST

SEQ ID NO: 42
Linker sequence
GSAGSAAGSGEF

SEQ ID NO: 43
Linker sequence
EAAAK

SEQ ID NO: 44
Linker sequence
EAAAR

SEQ ID NO: 45
amino acid sequence of IL27B
RKGPPAALTLPRVQCRASRYPIAVDCSWTLPPAPN

STSPVSFIATYRLGMAARGHSWPCLQQTPTSTSCT

ITDVQLFSMAPYVLNVTAVHPWGSSSSFVPFITEH

IIKPDPPEGVRLSPLAERQLQVQWEPPGSWPFPEI

FSLKYWIRYKRQGAARFHRVGPIEATSFILRAVRP

RARYYVQVAAQDLTDYGELSDWSLPATATMSLGK

---

What is claimed is:

1. A fusion protein comprising:
   (a) a first interleukin that is IL13 and comprises the amino acid sequence of SEQ ID NO: 2 or any one of SEQ ID NOs: 9-15;
   (b) a linker; and
   (c) a second interleukin that is IL4 and comprises the amino acid sequence of SEQ ID NO: 1 or any one of SEQ ID NOs: 26-28;
   wherein a C terminus of the first interleukin is joined to an N terminus of the linker and a C terminus of the linker is joined to an N terminus of the second interleukin, or a C terminus of the second interleukin is joined to the N terminus of the linker and the C terminus of the linker is joined to an N terminus of the first interleukin.

2. The fusion protein of claim 1, wherein the linker comprises the amino acid sequence of SEQ ID NO: 3.

3. The fusion protein of claim 1, wherein the C terminus of the first interleukin is joined to the N-terminus of the linker, and the C terminus of the linker is joined to the N terminus of the second interleukin.

4. The fusion protein of claim 1, wherein the C terminus of the second interleukin is joined to the N terminus of the linker and the C-terminus of the linker is joined to the N terminus of the first interleukin.

5. The fusion protein of claim 1, wherein the fusion protein further comprises one or more chemical modifications, wherein the one or more chemical modifications comprise glycosylation, fucosylation, sialylation, or pegylation.

6. A pharmaceutical composition comprising the fusion protein of claim 1 and a pharmaceutically-acceptable excipient.

7. The pharmaceutical composition of claim 6, wherein the pharmaceutical composition is in a unit dosage form.

8. A fusion protein comprising an amino acid sequence that is SEQ ID NO: 16.

9. A fusion protein comprising:
   (a) a first cytokine that is IL13 and comprises the amino acid sequence of SEQ ID NO: 2 or any one of SEQ ID NOs: 9-15;
   (b) a second cytokine that is IL4 and comprises the amino acid sequence of SEQ ID NO: 1 or any one of SEQ ID NOs: 26-28; and:
   (c) a linker, wherein the first cytokine is joined to the second cytokine via the linker.

10. A fusion protein comprising an amino acid sequence that is SEQ ID NO: 4.

11. The fusion protein of claim 10, wherein the fusion protein consists of the amino acid sequence of SEQ ID NO: 4.

12. The fusion protein of claim 8, wherein the fusion protein consists of the amino acid sequence of SEQ ID NO: 16.

13. The fusion protein of claim 2, wherein the C terminus of the first interleukin is joined to the N-terminus of the linker, and the C terminus of the linker is joined to the N terminus of the second interleukin.

14. The fusion protein of claim 2, wherein the C terminus of the second interleukin is joined to the N terminus of the linker and the C-terminus of the linker is joined to the N terminus of the first interleukin.

15. The fusion protein of claim 1, wherein the fusion protein is glycosylated.

16. The fusion protein of claim 1, wherein the first interleukin that is IL13 comprises the amino acid sequence of SEQ ID NO: 14.

17. The fusion protein of claim 1, wherein the first interleukin that is IL13 comprises the amino acid sequence of SEQ ID NO: 2.

18. The fusion protein of claim 1, wherein the second interleukin that is IL4 comprises the amino acid sequence of SEQ ID NO: 1.

19. The fusion protein of claim 1, wherein the first interleukin that is IL13 comprises the amino acid sequence of SEQ ID NO: 14 and the second interleukin that is IL4 comprises the amino acid sequence of SEQ ID NO: 1.

20. The fusion protein of claim 1, wherein the first interleukin that is IL13 comprises the amino acid sequence of SEQ ID NO: 2 and the second interleukin that is IL4 comprises the amino acid sequence of SEQ ID NO: 1.

21. The fusion protein of claim 9, wherein the first interleukin that is IL13 comprises the amino acid sequence of SEQ ID NO: 14.

22. The fusion protein of claim 9, wherein the first interleukin that is IL13 comprises the amino acid sequence of SEQ ID NO: 2.

23. The fusion protein of claim 9, wherein the second interleukin that is IL4 comprises the amino acid sequence of SEQ ID NO: 1.

24. The fusion protein of claim 9, wherein the first interleukin that is IL13 comprises the amino acid sequence of SEQ ID NO: 14 and the second interleukin that is IL4 comprises the amino acid sequence of SEQ ID NO: 1.

25. The fusion protein of claim 9, wherein the first interleukin that is IL13 comprises the amino acid sequence of SEQ ID NO: 2 and the second interleukin that is IL4 comprises the amino acid sequence of SEQ ID NO: 1.

\* \* \* \* \*